US012630834B2

(12) United States Patent
Kudithipudi et al.

(10) Patent No.: US 12,630,834 B2
(45) Date of Patent: May 19, 2026

(54) METHODS AND COMPOSITIONS FOR REGULATING ALKALOIDS IN TOBACCO

(71) Applicant: ALTRIA CLIENT SERVICES LLC, Richmond, VA (US)

(72) Inventors: Chengalrayan Kudithipudi, Midlothian, VA (US); Rajanikanth Govindarajulu, Henrico, VA (US); Raja S. Payyavula, Henrico, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 217 days.

(21) Appl. No.: 18/365,270

(22) Filed: Aug. 4, 2023

(65) Prior Publication Data

US 2024/0132901 A1    Apr. 25, 2024
US 2024/0229054 A9    Jul. 11, 2024

Related U.S. Application Data

(60) Provisional application No. 63/395,459, filed on Aug. 5, 2022.

(51) Int. Cl.
*C12N 15/82*      (2006.01)
*A24B 13/00*      (2006.01)
*A24B 15/10*      (2006.01)
*C07K 14/415*     (2006.01)

(52) U.S. Cl.
CPC .......... *C12N 15/8243* (2013.01); *A24B 13/00* (2013.01); *A24B 15/10* (2013.01); *C07K 14/415* (2013.01)

(58) Field of Classification Search
None
See application file for complete search history.

(56) References Cited

U.S. PATENT DOCUMENTS

| | | | |
|---|---|---|---|
| 4,516,590 A | * | 5/1985 | Teng ..................... A24B 15/12 131/352 |
| 4,528,993 A | | 7/1985 | Sensabaugh et al. |
| 4,660,577 A | | 4/1987 | Sensabaugh et al. |
| 4,848,373 A | | 7/1989 | Lenkey |
| 4,897,355 A | | 1/1990 | Eppstein et al. |
| 4,946,787 A | | 8/1990 | Eppstein et al. |
| 4,987,907 A | | 1/1991 | Townend |
| 5,049,386 A | | 9/1991 | Eppstein et al. |

(Continued)

FOREIGN PATENT DOCUMENTS

| | | |
|---|---|---|
| WO | WO 91/16024 | 10/1991 |
| WO | WO 91/17424 | 11/1991 |

(Continued)

OTHER PUBLICATIONS

Agrawal et al., "RNA Interference: Biology, Mechanism, and Applications," *Microbiology and Molecular Biology Reviews,* vol. 67, No. 4, pp. 657-685 (Dec. 2003). Available online: DOI: https://doi.org/10.1128/mmbr.67.4.657-685.2003.

(Continued)

*Primary Examiner* — Amjad Abraham
(74) *Attorney, Agent, or Firm* — Arnold & Porter Kaye Scholer LLP; David R. Marsh

(57) ABSTRACT

The present disclosure relates to tobacco plants, plant parts, seeds, compositions, and methods related to modulating the expression of novel genes in tobacco to regulate alkaloid levels.

20 Claims, 32 Drawing Sheets

Specification includes a Sequence Listing.

(56) References Cited

U.S. PATENT DOCUMENTS

| | | | |
|---|---|---|---|
| 5,159,135 | A | 10/1992 | Umbeck |
| 5,188,958 | A | 2/1993 | Moloney et al. |
| 5,372,149 | A | 12/1994 | Roth et al. |
| 5,463,174 | A | 10/1995 | Moloney et al. |
| 5,538,880 | A | 7/1996 | Lundquist et al. |
| 5,550,318 | A | 8/1996 | Adams et al. |
| 5,591,616 | A | 1/1997 | Hiei et al. |
| 5,750,871 | A | 5/1998 | Moloney et al. |
| 5,824,877 | A | 10/1998 | Hinchee et al. |
| 6,153,812 | A | 11/2000 | Fry et al. |
| 6,160,208 | A | 12/2000 | Lundquist et al. |
| 6,194,636 | B1 | 2/2001 | McElroy et al. |
| 6,232,526 | B1 | 5/2001 | McElroy et al. |
| 6,384,301 | B1 | 5/2002 | Martinell et al. |
| 6,399,861 | B1 | 6/2002 | Anderson et al. |
| 8,124,851 | B2 | 2/2012 | Dewey et al. |
| 8,319,011 | B2 | 11/2012 | Xu et al. |
| 8,978,661 | B2 * | 3/2015 | Atchley ............. A24B 15/28 |
| | | | 206/256 |
| 9,187,759 | B2 | 11/2015 | Dewey et al. |
| 9,228,194 | B2 | 1/2016 | Dewey et al. |
| 9,228,195 | B2 | 1/2016 | Dewey et al. |
| 9,247,706 | B2 | 2/2016 | Dewey et al. |
| 2004/0216189 | A1 | 10/2004 | Houmard et al. |
| 2005/0178398 | A1 | 8/2005 | Breslin et al. |
| 2006/0191548 | A1 | 8/2006 | Strickland et al. |
| 2015/0152431 | A1 * | 6/2015 | Panik ............. C12N 15/8271 |
| | | | 536/23.6 |
| 2018/0119163 | A1 | 5/2018 | Kudithipudi et al. |
| 2019/0271000 | A1 | 9/2019 | de Godoy Lusso et al. |
| 2020/0029522 | A1 | 1/2020 | Kudithipudi et al. |

FOREIGN PATENT DOCUMENTS

| | | |
|---|---|---|
| WO | WO 2004/041006 A1 | 5/2004 |
| WO | WO 2011/027315 A1 | 3/2011 |
| WO | WO 2018/067985 A1 | 4/2018 |
| WO | WO 2018/237107 A1 | 12/2018 |
| WO | WO 2019/086609 A1 | 5/2019 |
| WO | WO 2019/140297 A1 | 7/2019 |
| WO | WO 2021/072241 A1 | 4/2021 |

OTHER PUBLICATIONS

Altschul et al. "Basic Local Alignment Search Tool." *Journal of Molecular Biology*, 215(3), pp. 403-410 (Oct. 1990). Available online: https://doi.org/10.1016/S0022-2836(05)80360-2.

Altschul et al., "Gapped BLAST and PSI-BLAST: a new generation of protein database search programs," *Nucleic Acids Res.*, vol. 25, No. 17, pp. 3389-3402, (Jul. 1997). Available online: https://doi.org/10.1093/nar/25.17.3389.

Bowman et al, "Revised North Carolina Grade Index for Flue-Cured Tobacco," *Tobacco Science*, vol. 32, pp. 32:39-40, (1988) (New York, USA).

Centers for Disease Control and Prevention's Protocol for Analysis of Nicotine, Total Moisture and pH in Smokeless Tobacco Products, as published in the Federal Register vol. 64, No. 55, pp. 13897-13912 (Mar. 1999)(and as amended in vol. 74, No. 4, Jan. 2009). Chapters 4B and 4C of *Tobacco, Production, Chemistry and Technology*, Davis & Nielsen, eds., Blackwell Publishing, pp. 70-103, (1999) (Oxford, UK).

Chenna et al., "Multiple sequence alignment with the Clustal series of programs," *Nucleic Acids Research* 31(13), pp. 3497-3500 (Mar. 2003). Available online: DOI: 10.1093/nar/gkg500.

Collins et al., "Determination of Nicotine Alkaloids in Tobacco Using the Autoanalyzer," *Tobacco Science*, vol. 13, pp. 79-81 (1969) (New York, USA).

"CORESTA Recommended Method No. 7: Determination of Nicotine in the Mainstream Smoke of Cigarettes by Gas Chromatographic Analysis," pp. 1-5, (1987) (updated Aug. 1991) (Paris, France).

"CORESTA Recommended Method No. 62: Determination of Nicotine in Tobacco and Tobacco Products by Gas Chromatographic Analysis," Coresta Cooperation Centre for Scientific Research Relative to Tobacco (Feb. 2005) (Version 2: Apr. 2020) (Paris, FR).

Davis et al., "A Combined Automated Procedure for the Determination of Reducing Sugars and Nicotine Alkaloids in Tobacco Products Using a New Reducing Sugar Method," *Tobacco Science* 20, pp. 139-144 (1976) (New York, USA).

Dewey et al., "Molecular genetics of alkaloid biosynthesis in *Nicotiana tabacum.*" *Phytochemistry.* vol. 94, pp. 10-27, (Oct. 2013). Available online: DOI: 10.1016/j.phytochem.2013.06.002. Epub Aug. 15, 2013. PMID: 23953973.

Goldman et al., "Female sterile tobacco plants are produced by stigma-specific cell ablation," *The EMBO Journal* vol. 13, No. 13, pp. 2976-2984 (Jul. 1994). Available online: https://doi.org/10.1002/j.1460-2075.1994.tb06596.x.

Griffiths-Jones et al., "Rfam: an RNA family database," *Nucleic Acids Research*, vol. 31, Issue 1, pp. 439-441 (Jan. 2003). Available online: https://doi.org/10.1093/nar/gkg006.

Hidalgo et al., "Bioconversion of stilbenes in genetically engineered root and cell cultures of tobacco," *Sci Rep* 7, 45331, pp. 1-11 (Mar. 2017). Available online: https://doi.org/10.1038/srep45331.

Hidalgo et al., "Tailoring tobacco hairy root metabolism for the production of stilbenes." *Sci Rep* 7, 17976, pp. 1-11 (Dec. 2017). Available online: https://doi.org/10.1038/s41598-017-18330-w.

Hibi et al., "Putrescine N-Methyltransferase in Cultured Roots of *Hyoscyamus albus,*" *Plant Physiology*, vol. 100, Issue 2, pp. 826-835, (Oct. 1992). Available online: https://doi.org/10.1104/pp.100.2.826.

Horsch et al., 1985, "A Simple and General Method for Transferring Genes into Plants," *Science: American Association for the Advancement of Science*, vol. 227, No. 4691, pp. 1229-1231 with cover page and table of contents, ISSN 0036-8075(Mar. 1985) (Washington, DC).

Kajikawa et al., Genomic Insights into the Evolution of the Nicotine Biosynthesis Pathway in Tobacco, *Plant Physiology*, vol. 174, Issue 2, pp. 999-1011 (Jun. 2017). Available online: https://doi.org/10.1104/pp.17.00070.

Katoh et al., "Specific residues at every third position of siRNA shape its efficient RNAi activity," *Nucleic Acids Res*. vol. 35, No. 4, e27, pp. 1-14. Available online: DOI: 10.1093/nar/gk11120. Epub Jan. 26, 2007. PMID: 17259216; PMCID: PMC1851635.

Khvorova et al., "Functional siRNAs and miRNAs exhibit strand bias." *Cell* vol. 115, No. 2, pp. 209-216 (Oct. 2003). Available online: https://doi.org/10.1016/S0092-8674(03)00801-8.

Kim "MicroRNA biogenesis: coordinated cropping and dicing," *Nature Rev. Mol. Cell. Biol.*, 6(5), pp. 376-385 (May 2005). Available online: DOI: https://doi.org/10.1038/nrm1644.

Langfelder et al., "WGCNA: an R package for weighted correlation network analysis," *BMC Bioinformatics* 9, 559 (Dec. 2008). Available online: https://doi.org/10.1186/1471-2105-9-559.

Larkin et al., "Clustal W and Clustal X version 2.0," *Bioinformatics* 23(21), pp. 2947-2948 (Sep. 2007). Available online: doi: 10.1093/bioinformatics/btm404.

Liu et al., "Analysis of Complementarity Requirements for Plant MicroRNA Targeting Using a Nicotiana benthamiana Quantitative Transient Assay," *The Plant Cell*, 26(2), pp. 741-753 (Feb. 2014). Available online: https://doi.org/10.1105/tpc.113.120972.

Livak et al., "Analysis of Relative Gene Expression Data Using Real-Time Quantitative PCR and the $2\text{-}\Delta\Delta C_T$ Method," *Methods*, vol. 25, Issue 4, pp. 402-408 (Dec. 2001). Available online: https://doi.org/10.1006/meth.2001.1262.

Mayo et al. Genetic transformation of tobacco NTI cells with *Agrobacterium tumefaciens, Nature Protocol*, vol. 1, No. 3, pp. 1105-1111 (Aug. 2006). Available online: DOI: 10.1038/nprot.2006.176.

Miller "Memorandum: Proposed Burley Tobacco Grade Index," Legacy Tobacco Document Library, The University of Tennessee Agricultural Experiment Station (Bates Document #523267826-523267833) (Jul. 1988) (Knoxville, USA).

Miller et al., "A Grade Index for Type 22 and 23 Fire-Cured Tobacco," *Tobacco Science*, Tobacco International 192, pp. 55-57 with cover page, (Dec. 1990) (New York, USA).

(56) References Cited

OTHER PUBLICATIONS

Official Standard Grades for Burley Tobacco (U.S. Type 31 and Foreign Type 93), effective Nov. 5, 1990 (55 F.R. 40645).

Official Standard Grades for Flue-Cured Tobacco (U.S. Types 11, 12, 13, 14 and Foreign Type 92), effective Mar. 27, 1989 (54 F.R. 7925).

Official Standard Grades for Pennsylvania Seedleaf Tobacco (U.S. Type 41), effective Jan. 8, 1965 (29 F.R. 16854).

Official Standard Grades for Ohio Cigar-Leaf Tobacco (U.S. Types 42, 43, and 44), effective Dec. 8, 1963 (28 F.R. 11719 and 28 F.R. 11926).

Official Standard Grades for Wisconsin Cigar-Binder Tobacco (U.S. Types 54 and 55), effective Nov. 20, 1969 (34 F.R. 17061).

Official Standard Grades for Georgia and Florida Shade-Grown Cigar-Wrapper Tobacco (U.S. Type 62), Effective Apr. 1971.

Reynolds, et al., "Rational siRNA design for RNA interference," *Nat Biotechnol* 22, pp. 326-330 (Mar. 2004). Available online: https://doi.org/10.1038/nbt936.

Shoji et al., "Clustered Transcription Factor Genes Regulate Nicotine Biosynthesis in Tobacco," *Plant Cell*, 22(10):3390-3409 (Oct. 2010). Available online: DOI:10.1105/tpc.110.078543.

Smith et al., "Comparison of biosequences," *Adv. Appl. Math.* vol. 2, Issue 4, pp. 482-489, (Dec. 1981). Available online: https://doi.org/10.1016/0196-8858(81)90046-4.

Thompson et al., "Clustal W: Improving the sensitivity of progressive multiple sequence alignment through sequence weighting, position-specific gap penalties and weight matrix choice," *Nucleic Acids Research* 22(22): 4673-4680 (Nov. 1994). Available online: DOI: 10.1093/nar/22.22.4673.

Tso "Seed to Smoke," Chapter 1 in Davis and Nielsen (ed.), *Tobacco: Production, Chemistry and Technology*, Blackwell Science Publishing, pp. 1-31 with cover page (Oxford, UK).

Wang et al., "More than meets the eye? Factors that affect target selection by plant miRNAs and heterochromatic siRNAs," *Curr Opin Plant Biol*. 27, pp. 118-124, (Jul. 2015). Available online: DOI: 10.1016/j.pbi.2015.06.012. Epub Jul. 31, 2015. PMID: 26246393; PMCID: PMC4732885.

Wernsman et al., "Tobacco: Chapter Seventeen" in *Principles of Cultivar Development*, vol. 2 Crop Species. W. H. Fehr (ed.), MacMillan Publishing Go., Inc., pp. 669-698, (1987) (New York, USA).

Zeng et al., "Both Natural and Designed Micro RNAs Technique Can Inhibit the Expression of Cognate mRNAs When Expressed in Human Cells," *Mol. Cell*, vol. 9, pp. 1327-1333 (Jun. 2002). Available online: https://doi.org/10.1016/S1097-2765(02)00541-5.

Zhang et al., "PowerBLAST: A New Network BLAST Application for Interactive or Automated Sequence Analysis and Annotation," *Genome Res.*, 7(6), pp. 649-656 (Apr. 1997). Available online: DOI: 10.1101/gr.7.6.649. PMID: 9199938; PMCID: PMC310664.

Zhou et al. "Production and metabolic engineering of bioactive substances in plant hairy root culture," *Appl Microbiol Biotechnol* 90, pp. 1229-1239 (Apr. 2011). Available online: https://doi.org/10.1007/s00253-011-3228-0.

Database UniProt EBI Accession No. A0A1S4BQP9_TOBAC, "SubName: Full=Uncharacterized protein LOC107810900 {ECO:0000313|RefSeq:XP_016491219.1}," accessed and printed Nov. 7, 2023, 1 page.

International Search Report and Written Opinion issued in International Patent Application No. PCT/US2023/071649, mailed Jan. 23, 2024, 17 pages.

Schachtsiek et al., "Nicotine-free, nontransgenic tobacco (*Nicotiana tabacum* L.) edited by CRISPR-Cas9." *Plant Biotechnology Journal* 17(12), pp. 2228-2230, (Dec. 2019) (electronic publication) available online: DOI: 10.1111/pbi.13193.

Biswas et al., "The Development of DNA Based Methods for the Reliable and Efficient Identification of *Nicotiana tabacum* in Tobacco and Its Derived Products," *International Journal of Analytical Chemistry*, Article ID 4352308, 6 pages, (Aug. 2016).

Korchinski et al., "Detection of *Nicotiana* DNA in Tobacco Products Using a Novel Multiplex Real-Time PCR Assay," *Journal of AOAC International*, 99(4), pp. 1038-1042 (Jul. 2016).

* cited by examiner

SEQUENCE LISTING

```
Sequence total quantity: 178
SEQ ID NO: 1            moltype = DNA  length = 1140
FEATURE                 Location/Qualifiers
source                  1..1140
                        mol_type = other DNA
                        organism = synthetic construct
SEQUENCE: 1
atgtcacatc tcactgcagc tccgccatca gaaccaccgt cggcggcggt gaattcattg   60
tacaaacaga aatcgtggtc gccggacacg tttcgcgatg aggcgtggca gcggcggaag   120
ggtacccatg gaagccgctt aaagcagcgg agcaagagcg ttaccgatga agacctcgat   180
gagctcaagg cttgtattga gttagggttt ggatttgact cgcctgaaat agatcaacga   240
ttgtctgata ctttcccggc ttatggcctt ttttacgctg ttaataaaca atatgccgac   300
accctttcga agacttcttc tttatcgtcg gtcatctcct attgcgagtc acccgctcct   360
cccggcagtc cccacaccat tgtcgatcaa ggtaattcga taaaagcctc tcctttacaa   420
tttttattcg tactcttta ttttagaatg ttctgaaatg cttaacacaa attccatttc   480
ttttgaacta tccttcactc agaaaatcca aattcattca tctaatcaaa atgaaatttg   540
attttaaatt ctaatatgaa atcctctatg tgaaattaac tttcaattat aatgtctttt   600
acaatcagta aatactactc ctatataagt taagttctat atatttaact tattgccctg   660
tcataaaaaa agagattacc agataattta accttaaaag tttgttaatg taaagaacag   720
ttgagtgcct atgggaactc tccgcccta actaaaggtc ttgagtttaa gccctatgaa   780
agaagaaact cttgatagag aatgcttccc tcatagtggt tctacgggcg gctaatctag   840
attagttgga caaatgaatt tagattaccg gatgaataga tgaaaaaga aaaaaaggat   900
```

-continued

```
gcctatgttt tatcttttgt tcaatgcaca atttagtttt gcctacaccc cttccccatt   960
ttttttgggg gggatgagtg gtggtgggga caagattcat ataaagaact atagtgttga  1020
acgtatggtt gctaatattt gcaaaaaatg aatgtaggag ataatcctca gacagtgaag  1080
acaaggttgc ggcagtgggc acaagtggtc gcttggtcag ttcgtcaatc ttcacattaa  1140

SEQ ID NO: 2              moltype = DNA   length = 2245
FEATURE                   Location/Qualifiers
source                    1..2245
                          mol_type = other DNA
                          organism = synthetic construct
SEQUENCE: 2
atggagaaaa agcagctgga tttcaatgca ccactttat cagtgaggaa aatttcatca    60
tctttatccc ctcatgagag agcaaataaa aagattatag aaagggcgcc accgaatcga   120
caacaatcac ttcctgtcaa aaaatcagat tgggaattga gtgaggtgac taaaccagta   180
gctgttccat ttatgtggga acagatccct ggaagacgaa aaggtgacaa tgaagcccga   240
gctaaccttc gagtggagtg gtcaagtagt cctaggctgc ccccgggaag attgccagag   300
actattcggt tctattcggg tgaaaggcct cgtactcaaa acatttacaa gtctccagct   360
gaaggacttc cttggattga tcatgcagct ttacttgata gcctagcgga aagtatatat   420
acaagaggag acagagcaag tgaggatgat gccaattctg atgctcctga aacattgtca   480
cctaccgaat ccttatcctt ggactgcagt gtcagtggtt tgagcggaca tcaaagttca   540
gattcaaaac catctggaac cttttccatt gactcccaaa ctagagactt tatgatgagt   600
cgattcttac ctgcagcaaa agctgttgtt ttggagacgc ctcagtatgt tcaaaaaaag   660
caagttccag tcagtactga acaacccaag ccagtacctg tggaacgaaa gccaatagtt   720
aagcagatgg agtctaaacc tgtctcatat tatagcggct atccagacga tgtaggaagt   780
gaaattgaag atgatgtgtc tgagaatcag cacaaaagac caagtaaagg gtggaaattt   840
ttccctcgga tttgtgtgaa gaattcttta tgcctattaa atccactgcc aggactaaaa   900
gtgaagacac atgttcccac accctcagct caagcagtaa agagagtttc aggaatgaaa   960
ccaaagacgc cacagagccc cacatcttat gctcatgaag tcaagagatt agctagaaaa  1020
gcttatagtg gacctcttga gaaggtaata attataattt tcctcagttt cttttttttct  1080
gtcctaagat taataagatt tatgtttgtt tctaacaatc atgttctttg cagaatactt  1140
gtgatactat aaataagcaa agatttcact ctggagtact gtctcgcgag ctgtacaaag  1200
ctgaaaatag aagtttttcc ggccaactgc ctaaccctag tgattcatgt aagctagttg  1260
gaatctctcc tggaagacgt tcaagaagtg gggctatatc tccctgtcga aatgtagcac  1320
ccccatctcc attcaatgaa ggtactaggt ttcttggtgt gccaaaggaa atggagagtc  1380
tttgggctag ccgctttgat tcattccgga aaggttgcta cactgtcaag gacaaagtac  1440
cacagcagat tggcacagga aggtttctg attcaccaag tgaagtagtt gagaaaacat  1500
tgtacataga ttctgtagat aatgtgcaaa tttcagcccg taattctgct tcttcaaagc  1560
ccaaggaatt ggtgaactcc tctggtaaga atatgaagc actggttaaa agcagtaaag  1620
tactagaaaa tatggatgcc accgctcgta tcaaggtgc caaagaccgg aatgtttcag  1680
agaaagagag caaacaggtt tttgagaagg agtcccttga tttggtggaa gcttctccca  1740
tttccatatc aacacgcaaa ggccctgctg atcatgagtc tttgaaacta aagcaaaatc  1800
ttgatacact atctggagcc ttagagtctt caaaagtgca tccctatgga aatttaggta  1860
cagaaaatga agataaccaa aatgcaaatg cccaaaaga ttctaacctt acctcctgg    1920
aatctcctat accaccaccc ttacctaaat ctccctctga atcttggctt tggcgcacgc  1980
tgccttccat ccctttgaga actccgttct caagtttgag ctccaagaag cagaataaga  2040
agtcccatgc tgatggtagt aagtgggaga ctattgtgaa aacttctaac ttgcataagg  2100
atcatgtccg ttactccgag gtaacctctt ttttcttttta taccttttga agttttctgt  2160
tgcaaatttt gatgtttact tctgctccat tttgtttgaa caggaactat atactcttgg  2220
ttcttgtcag cagagcaaag cttga                                        2245

SEQ ID NO: 3              moltype = DNA   length = 2431
FEATURE                   Location/Qualifiers
source                    1..2431
                          mol_type = other DNA
                          organism = synthetic construct
SEQUENCE: 3
atggaagtca tatctaccaa cacaaatggc tcgaccatct tcaagaatgg tgccattccc    60
atgaatggcc accagagtgg cacttccaaa cacctcaacg gctaccagaa cggcacttcc   120
aaacaccaaa acggccacca taatggcact tccgaacatc ggaacaggcca ccagaatggg   180
atttccgaac accaaaacgg ccaccagaat gggacttccg aacatcggaa cggccaccag   240
aatgggattt ccgaacacca aaacggccac cagaatggga cttccgaaca ccaaaacggc   300
caccagaatg ggacttccga acaacagaac gggacaatca gccatgacaa tggcaacgag   360
ctactgggaa actccaactc tattaagctt ggttggtttt cagagtttag cgcattatgg   420
ccaggttagt actgagaaag aaactcaaat tcatatttaa agttaaaatt gttaggctaa   480
tataagaagt tgattttctt ttagtgatta attaaaaaag gaaagagtat caaataaatt   540
ccaaaaaatg accagtaact tcgcatatta ttctacacat taatttgaaa taaatcgaat   600
tttgcaggtg aagcattctc ccttaaggtt gagaagttac tatttcaggg gaagtctgac   660
taccaagatg tcatgctctt tgaggtaaat aatattctaa tacacatgct ttaatatgaa   720
taaatacttt taatttactt ttagtttatt gcacgtgtac gtacagtcag caacatatgg   780
gaaggttttg actttggatg gagcaattca acacacagag aatggtggat ttccatacac   840
tgaaatgatt gttcatcttc cacttggttc catcccaaac ccaaaaaagg ttttgatcat   900
cggcggagga attggtttta cattattcga aatgcttcgt atcctacaa tcgaaaaaat   960
tgacattgtt gaaatcgatg acgtggtagt tgatgtaagt caaatttctt ttactcacat  1020
aaaaaaatga tttagattgc ttcttttttat ttttctaaaa gaataaatat attctctctt  1080
agttttaaac aaaattctct ttcttacagg tatctagaaa atctttccct tatctcgcag  1140
ctaatttaa tgatcctcgt gtaacccctcg ttctcggaga tggtgcgtat ttataatctc  1200
gttttgtt tatctttat ttttatttca tttaattac ctttttgtgt gtggttaatt  1260
tacccgtcat tggttctctt tcatttcagg ggctgcattt gtaaaggctg cacaagcagg  1320
atattatgat gctattatag tggactcttc tgatcccatt ggtactctat tactacttaa  1380
```

-continued

```
taccaagact aatcttattg aataagctac taataaactg taattgattt ctaaaataat    1440
ataatttcag gtccagcaaa agatttgttt gagaggccat tctttgaggc agtagccaaa    1500
gccctaaggc caggaggagt tgtatgcaca caggccgaaa gcatttggct tcatatgcat    1560
attattaagc aaatcattgc taactgtcgt caagtcttta agggctctgt caactacgct    1620
tggactactg ttccaacata tcccacgtat tttctctctc tctctcttca tctttgaaaa    1680
ttgaaaatcc tgactacttt ccttcctttg attcctcggt taaaggggcg tagatcataa    1740
gattttcaag aaatagataa tgacgtccaa gaaaaactaa cttctttta tttactattc     1800
tttttggtga caaactttat ttattatttc gttctaaaga gaaaatttat ttttatattt    1860
taaaataatt ttgtttttaa ctttatttt tacttattat atctttaata aaaaaattat     1920
agtcaaataa atattatggc cacactaaac atccaagttt ttgaaaccat aagttttaga    1980
gccaaatgag ttaatttgtt tttggtatgc gggtgcggag tcaaattatg tcacaaaaat    2040
tgtaatggag tgagcaaatt tttatttcga gtaaactttc aaggtattgt gttaaagttt    2100
tttcaactga tactaatcaa ttatgtctca accattttga tttcagtggt gtaattgggt    2160
atatgctctg ctctactgaa gggccagaag ttgacttcaa gaatccaata aatccaattg    2220
acaaagagac aactcaagtc aagtccaaat tagcacctct caagtttac aattctgatg     2280
taacttcata tctaacaatt tctttttctg ttttactgta tcttcattgt caaaatttta    2340
taattaactc ttctcaaatt atctttttt ttagattcac aaagcagcat tcattttgcc     2400
atctttcgcc agaagtatga tcgagtctta a                                   2431
```

SEQ ID NO: 4                    moltype = DNA   length = 1894
FEATURE                         Location/Qualifiers
source                          1..1894
                                mol_type = other DNA
                                organism = synthetic construct
SEQUENCE: 4
```
atggaagtca tatctaccaa cacaaatggc tctaccatct tcaagagtgg tgccattccc    60
atgaatggcc accataatgg cacttccaaa caccaaaacg gccacaagaa tgggacttcc    120
gaacaacaga acgggacaat cagccttgat aatggcaacg agctactggg aaactccaat    180
tgtattaagc ctggttggtt ttcagagttt agcgcattat ggccaggtta gtactgagaa    240
agaaactcaa atgcatattt aaagttaaaa ttgttaggct aatataagga gttgatattc    300
ttttagtgat taattaaaaa ggaaaaagta tcaaataaat tcaaaaaatg gatagtaact    360
tcgcatatta ctctacacat taatttgaaa taaatcgaat tttgcaggtg aagcattctc    420
acttaaggtt gagaagttac tgttccaggg gaagtctgac taccaagatg tcatgctctt    480
tgaggtaaat aatattttaa tacacatgct tccatttaaa ttgatacttt taatttactt    540
ttactttatt gcatgtgtac gtacagtcag caacttatgg gaaggttctg actttggatg    600
gagcaattca acacacagag aatggtggat ttccatacac tgaaatgatt gttcatcttc    660
cacttggttc catcccaaac ccaaaaaagg ttttgatcat cggcggagga attggtttta    720
cattattcga aatgcttcgt tatcctacaa tcgaaaaaat tgacattgtt gagatcgatg    780
acgtggtagt tgatgtaagt caaacttctt ttactcacat aaaaaaatgg tttagattgc    840
ttcttgttat ttttctaaaa gaatactatt tttttaaaac aaaattttct tttttacagg    900
tatctagaaa attttttccct tatctcgctg ctaattttaa cgatcctcgt gtaacccctag  960
tccttggaga tggtgcgtat ttgataatct cgcttttgtt ttatctttta tttttattgc    1020
atttaatttt tacctttgg tgtgtggtta attcacctgc cattggttct cttttcattc     1080
aggggctgca tttgtaaagg ctgcacaagc agaatattat gatgctatta tagtggactc    1140
ttctgatccc attggtactc tattacttct taataccaag actaatctta ttgaataagc    1200
tactaataaa cggtaattga tttctaaaac aatataattt caggtccagc aaaagatttg    1260
tttgagagcc cattctcttga ggcagtagct aaagccctaa ggccaggagg agttgtatgc   1320
acacaggctg aaagcatttg gcttcatatg catattatta agcaaatcat tgctaactgt    1380
cgtcaagtct ttaagggctc tgtcaactat gcttggacta ctgttccaac atatccaacg    1440
tatttttctc tctctctctc ttcctataaa attggaagtt ttgattctat aattgtcaag    1500
aaatggagaa tcagttccaa gaaaaaccaa cttctttct tttactcttc aaggtattgt     1560
gtttaatttt ttttcaactg atatgatcaa ttattttgat ttcagcggtg tgattggtta    1620
tatgctctgc tctactgaag gaccagaaat tgacttcaag aatccagtaa atccaattga    1680
caaagagaca gctcaagtca agtccaaatt agcacctctc aagttctaca actctgatgt    1740
aacttcatat ctcacaattt cttttttcct attgtactt atgttcttcg tcaaatttta     1800
taattaactc ttttcaaatt gtctttttt tttcagatt cacaaagcag cattcatttt      1860
gccatctttc gccagaagta tgatcgagtc ttaa                                1894
```

SEQ ID NO: 5                    moltype = DNA   length = 2035
FEATURE                         Location/Qualifiers
source                          1..2035
                                mol_type = other DNA
                                organism = synthetic construct
SEQUENCE: 5
```
atggaagtca tatctaccaa cacaaatggc tctactatct tcaagaatgg tgccattccc    60
atgaacggtt accagaatgg cacttccaaa caccaaaacg gccaccagaa tggcacttcc    120
gaacatcgga acgccacca gaatgggatt tccgaacacc aaaacggcca ccagaatggc     180
acttccgagc atcagaacgg ccatcagaat gggacaatca cggcgacgag cggcaacgag    240
ctacagctac tgggaagctc caactctatt aagcctggt ggttttcaga gttagcgcga     300
ttatggccag gttagtacta agaaagaaac tcaaatgcat cgtactcttg tattctgctt    360
tgcgtataat ttagatgatg gtgtttgact aagcactgag tttaaaaata aaagtttaa     420
agttaaattg ttactataga gagctatatc tttaggaact aactaaaaag gaaaaattat    480
cacataaaat tgggatgaag taagcagtta acttcgcata ttattcgaca cattaatttg    540
aaataaatcg aattttgcag gtgaagcatt ctcacttgag gagttactat tcca          600
gggaagtct gattaccaag atgtcatgct ctttgaggta attaattaat actaatagtc     660
aagctcatgt atgattatat ttaaagtggt attttcgtt tattttttaat ttattgcacg    720
tgtacgtaca gtcagcaaca tatgggaagg ttctgacttt ggatggagca attcaacaca    780
cagagaatgg tggattccaa tacactgaaa tgattgttca tcttccactt ggttccatcc    840
caaaccctaa aaaggttttg atcatcggcg gaggaattgg ttttacatta ttcgaaatgc    900
```

-continued

```
ttcgttatcc tacaatcgaa aaaattgaca ttgttgagat cgatgacgtg gtagttgatg    960
taagtcaaac ttcttttact cacataaaaa aatgatttag attcttattt ttctaaaaga   1020
attaaaacaa aatttttccgt tttacaggta tctagaaaat ttttccctta tcttgctgct   1080
aattttagcg atcctcgtgt aaccctagtc cttggagatg gtgcgtattt gataatctcg   1140
tttttatttt atctttttact tttattttat ttaattttta cctttttgtg tgtggttaat   1200
tcacctgcca ttggttcttt ttatttcagg ggctgcattt gtaaaggccg cacaagcagg   1260
atattatgat gctattatag tggactcttc tgatcccatt ggtactctat tactacttaa   1320
taccaagact attcttatta aataagctac taataaacgt aactctgata gttttctaaa   1380
ataatataat ttcaggtcca gcaaaagact tgtttgagag gccattcttt gaggcagtag   1440
ccaaagccct aaggccagga ggagttgtat gcacacaggc tgaaagcatt tggcttcata   1500
tgcatattat taagcaaatc attgctaact gtcgtcaagt ctttaagggc tctgtcaact   1560
atgcttggac tactgttcca acatatccaa cgtatttttc tctctctctt cctataaaat   1620
tggaagtttt gattctataa ttgtcaagaa atggagaatc agttccaaga aaaaccaaat   1680
tcttttcttt tactcttcaa ggtgtgttta agtttttaa actgatactg atcaattatt   1740
ttgatttcag cggtgtgatt ggttatatgc tctgttctac tgaaggacca gaagttgact   1800
tcaagaatcc agtaaatcca attgacaaag agacaactca agtcaagtcc aaattagcac   1860
ctctcaagtt ctacaactct gatgtaactt catatctcaa tttcttttttt cttattgtac   1920
tttatgttct tagtcaaatt ttataattaa ctctttttcaa attgtctttt tttttcagat   1980
tcacaaagca gcattcattt tgccatcttt cgccagaagt atgatcgagt cttaa         2035
```

SEQ ID NO: 6                moltype = DNA   length = 1732
FEATURE                     Location/Qualifiers
source                      1..1732
                            mol_type = other DNA
                            organism = synthetic construct
SEQUENCE: 6

```
atgccaaatc aaaagcaagg aagtgaacag ctacaaacac tgatgcaatc aggtcaaatt    60
tcggggtctt tgagttttaa tggggcttta actaaagaag atgaagagat gtctaggtct   120
gctctttcta ctttcaaagc taaagaagaa gaaattgaga aaaagaaat ggaagtcaaa   180
gaaagagttc aagctcagtt gggtcgggtc gaagaagaaa ctcggcgttt agccattatt   240
cgtgaggtat ctctccttttt tcttccttat tttctctttt gtttgttttt taccagttcc   300
tttttctcaa cattaatgct aattttcttg ttggggtttt aacgtaatac tggaatttaa   360
tttttaaagt tgatttttttt ttggtgagat cttgtgcatt ttttgaaat acacatatgt   420
gttggttttt cttttgattt tttgctttta ggtaggggtt tccattttgg accttgacag   480
tagaacatct ttagactact actgctacgt tatgaacaca gatttgggtt tgcatatttt   540
tataaagtta gttttaattt ttaattaggg ttaatggata attcaagata gattaagtta   600
tgccagatta tcttatcacc atcttgaaat tgggctcaac ctttttgacca gctaaaaaag   660
aaatacaaat ttctctattc ttttctattt gctttatggt ttttcctcct tttttggttg   720
ttattaaaaa aaggtttatt gaggatgaaa caggaaggag gtgggggggg ggggttggaa   780
ttatcctgaa gctaaaagat ctctgatctg tcaaaattgg tcgtttttcaa tgagggtttt   840
atgctttgct attgtttttg ccatttaata gttgaaaatg agtatgagtt ttggaaattg   900
aagtatttga gaaggttaaa atcaagatt atctcagttt ccatccaact tatgccttat   960
ttaaattcaa cttaattatc aggagctaga agcattagct gatccaaaga agaaagatgt  1020
tcaaatcgtt cggaagaaga ttgatgctgt caacaaagag ttaaaacccc tgggacagac  1080
ctgccagaag aaggtgaaat atatatgcct ctattttctt gtttttttctt tgttttttcc  1140
ccttcattag attgtatatc atataataag tacaatccta gtaataataa cccttggggg  1200
tcgtttggta caatggtggg atatcccacg ggattagtat cccaccttttt atatggaagc  1260
taatcccacc attttagtgt aaaagttatc ccgggattag ctaataccccc aaaccaaaca  1320
tgggataaag ttgatcccaa attctatccc gggattatta tccttatccc atgtaccaaa  1380
cgacccctta gagttagtta atcccaatat gtggttgaag tgttaactta tccatgaagc  1440
tcattaacga gacttttttgg atctgtgaat gcaggaaaaa gagtacaaag aagctcttga  1500
ggcgttcaat gaaaagcaca aggaaaaagt acagctaata acaagattga tggaggtgag  1560
catgagttta taatttaaaa ccagtttgta tttggaactt gtctcaacat atttgatttg  1620
cagaagctca ctgaatcttg tgtgttcaat gtacgtgcag ttggtgggtg aaagcgagaa  1680
actgcgactg aagaagttgg agctgagcaa gagcatagaa acaatacgct ga           1732
```

SEQ ID NO: 7                moltype = DNA   length = 1713
FEATURE                     Location/Qualifiers
source                      1..1713
                            mol_type = other DNA
                            organism = synthetic construct
SEQUENCE: 7

```
atggatccgt gtcctttttgt gagaatagtt atcggaaact tagccttgaa gtttccggcg    60
gaacataaac tctcctcaag tacggttttt gattgtaaat tcaagcttag aggtttctcc   120
acacaagttt caaccatctc agcttttgtt caagatccaa ttttggacaa cagaactcac   180
tcttgtttca acttgaacaa aacagaactt gacaaactgg tcgaaaaatc aactgccaaa   240
ggaaaaactt gcagcttaaa gattgaaatt tttgcacgga agaaggggat tggttgtggg   300
ttattgaatg gtgggaagct attggggagt gtaatagtgg atttaaaggg gttggaaagt   360
gatggtcgga gaggagtttgt gattcagaat gaatggtttt tggttggtgg atctagtact   420
gcagcacaat tgcatttgaa tgtgaaagct gaacctgatc caagatttgt tttccagttt   480
gatggtgaac ctgagtgtag tcctcaagtt ttttcaagtca atggcaatgt aaacaacct   540
gttttttactt gcaagttcag tttcaggaat aatggtgaca ggaatttgag atcaaggtta   600
gttttatctt ctacaattga agttgatttt ctaataatta gtagaaaaac tgatctttct   660
tgactaaaca aattcattcc ctatagtcac atggcgaaac tagtttaaac atacttgata   720
cgcagaccct gcccttcctc gtggggtaga gatgctattt tcaataatcg ctccctaacc   780
ggaacactta taggagctcc tgtgtcaatc acttccattc ctgtccttag accgtcccct   840
cgcctatata catgtataac gaattgaatt catcgagtct aaatcccaac ttcatccttc   900
ttgttggtga ttatccagct aactaacaca ttagtttttag tctatgttga ttcatatttt   960
tcttgaactc tgcatctaaa tcttggttgt tatttgtaca gatcttcact atcaaaacca  1020
```

-continued

```
agtacatcaa caagctgctt taattcttgc acatctgata aagaatcatc gccgctaaaa   1080
gagcgaaagg gatggtcaat cacaattcat gatctctctg gctcaccaat tgccgcagca   1140
tctatggtta caccatttgt cccatcacag ggttcaagta atgtcagcag atcaaacccc   1200
ggggcgtggc tcatccttcg cccaggcaac ggtacatgga agccgtgggg ccgcttagaa   1260
gcatggcaag agcgcggtgg tgacctcggt tatcgctttg aaatcatccc tgatggtgct   1320
actgatgcca taactttgtc caattcaact atcagcacca agaatggtgg gaaatttggt   1380
gtagacatca ccaatggtgc taccccattg actagtccaa acagcagctt tgactttatgc  1440
tcgggttctg gatccgggtc ggatttcggg tcagcacccg gatccgggtc gtgggcacaa   1500
ctcttgtacc gtggtttcgt gatgtcgtcc acggtggagg gtgagggaaa atgcagcaag   1560
ccagaggtgg ttgtcggggt gcagcacgtg aactgcgtgg aggatgctgc agctttcgtt   1620
gcattggcag ctgccatgga tcttagtatg gatgcttgtc agtcttttac taagaagctc   1680
cggaaaagagt tgagacagtc ggatcaagaa tga                                1713
```

SEQ ID NO: 8        moltype = DNA   length = 2086
FEATURE             Location/Qualifiers
source              1..2086
                    mol_type = other DNA
                    organism = synthetic construct
SEQUENCE: 8
```
atgtcagggt aagtggaatt ttatgaattc ccttaatttt attgtcaaat tctagtttac   60
ttgattataa ataaatgttc ctgtcgatgt catttctgtt ggtaatgatg tagacacaag   120
tgaaaactca gaagtgcaca acttaatata actatttgat cgctttacga gtagttattg   180
caacttagtc tgcaattatt tttgtatgtg tagtacatag tctatcagag tgctatttga   240
attattcttc tacgcttaaa ttaggtccta tctattggaa acagcctctc tatccacaag   300
gatggggtaa ggtctgcgta cacactaccc tccccagacc ctacggtgtg ggattatact   360
aggtatgttg ttgttgctta aattaggttc tgtgtttgct tggaatcttt ttggggttagg   420
tagcgatttg tatgtaagtg tcggataagt ttggagaatc tatagtttta gggaacctat   480
caagttcaat tcttgataat gacttgagat ggtcatcagc tctccaggaa attcttcttc   540
cattctcttt tcctctcctc cctcatcttc atccttccaa gttccatagc atctctttat   600
cagctccttc ctttgtttaa catgaatatc atgaaatctc cttccatctt tttattaagt   660
agatgtaaaa cacacgaagt agaaagactc accatgaagg ctttggttta tatggagtgu   720
cattcctttc cttgtttccg aaaattgtac aatgagccat agataacagt tctcgactaa   780
caataaaaaa aatagttctc agccagaggc ggatgtagag taccggtacc agctgaaccc   840
gctaaaatta caacaaatag tagatataaa cccataactt taaaaatatt gtgggttcaa   900
tgctaaaagt cttaaagatc ccataaatgc tggatcaact tctgttctca gctggtatca   960
gacattgtta catatcatgt aaatatttt gtttagtcct aaattttgtg aatcagctta  1020
tgttctgaaa cttaaagtca agggaggtat ctttattccc tggcaaacct tacattggac  1080
ttggtattct aagttaaact gtctcccaag tttcatgtaa tgtagcactt aatggttagg  1140
gatatccctt ccagtttgcc ttcgcggaaa ctggacatcg gtttttact tttcttccat  1200
tattcatgcc acattggaaa gttattagtt acttaatcaa ttttgctctt ttagtttttc  1260
acttccttta acttacccat aaggttctct acttaatatt cccttcgatt gtagcgagga  1320
tgttgcagtt gctgttgccg agactcctgc tccagcactt ggagagccca tggacatcat  1380
gactgctttg cagctggtgc tgaggaagtc taaggctcat ggaggcctag ctcggggact  1440
acatgaaggt gcaaaggtga ttgagaagca tgcagcacag ctttgtgtgt tagcagagga  1500
ctgcgaccag ccagattatg tcaaattggt caaagcactc tgtgctgatc acaatgtcag  1560
cttgatcaca gttccgaatg caaaaactct tggcgaatgg gctggtgtaa gtttactttg  1620
tttgccactt gctacttttt agctctaagt ggcttagagg ggtgataaaa tattaactc   1680
cgacttctct tgatgtgcat tttcatgcgt catgaatcgt tggagtatga acgttctgtc  1740
cttttctaat tcttatttt gggcccattt tacagttgtg taagattgac tctgaaggga  1800
aagcaaggaa agtggttggc tgcggctgtg ttgttgtgaa ggtatatcca tgaactacta  1860
agcatcataa tcttgttcta gcatgtatag ttcggctta tatattaaag gaaaatgact  1920
cgggctggat ttctgtctta aaaatgctga aatataaata gaacctaata agttgtggaa  1980
acagaggaga ttttccgtct tagttaatct tactatcatt ttgcaggatt atggggaaga  2040
gactgagggt ctgcatattg tccaggagta cgtaaagtcc cattaa                  2086
```

SEQ ID NO: 9        moltype = DNA   length = 1717
FEATURE             Location/Qualifiers
source              1..1717
                    mol_type = other DNA
                    organism = synthetic construct
SEQUENCE: 9
```
atgtcagggt aagcttggtg atttgtaagc tttctcatta aattcagttt tttaattcat   60
tatagtgttc aagttgctgt cttttttatt tttagtaatc tagacacgtg ataaattttg   120
tatggttttg ctgaattgct tgatccacgt taagattaga ctttcgcaagt tcaatgttca  180
aaattttctg tacctctatt agaaagagct aggcagaagt gtttcctgtc tgtagaatca   240
tgaaacaaat acattccctg gaattaaact aatatgtcat tatttcaagg gaacccaacc   300
agtagaacca tccaaaaatt gattcttttt gtaggtcatt tgaagcagaa ccaaatacaa   360
ttagcgtatg agagtttctt aattctatgt ttcagctgcc tattacatat ctatagcctt   420
tttatatata tgttgtttgt tgttagaatt acaaaaccct aaattgtcat ggtactgatg   480
cagaactgtc atatagcaaa tgttttatcc aattggttga ccactttatt ttcatggaat   540
aatggacatg ctactgtgtg tagacaaagt atcatgaaaa aatggattgg cttagctttg   600
atattccgag gttgatgag aaagaaaaat gttatgatgt caacgttctg aattagtcga   660
gtttgatgtt cttgtggcat tggctttaat accattataa tgtgacactg catggtgatt   720
tcttgttca ccaatctgt ccttgatgtg tgcctatctt tatctttagt ataaggtgta   780
ctcttacctg acagttgtat atctgtagag aggatgctgc tgttcctgtt gttgctgccg   840
agactcctgc tccagcactt ggggagccca tggacatcat gaccgctctg cagctggtgc   900
tcaggaagtc taaagctcat ggaggacttg ctcgaggact ccatgaaggt gctaaggtga   960
ttgagaagca tgctgcgcag ctttgtgtgc tagcagagga ctgcgaccag ccagactatg  1020
tcaagctggt caaagctctt tgtgctgatc acaatgtcag tttgattaca gttcccaatg  1080
```

```
caaaaactct tggcgaatgg gctggtgtaa gtaattgatc attgcttatc tatggcccca   1140
atcacagtat ctcagttgtt actatacata cttgagtagc tggttctgat gtgaaaatga   1200
aattggaatg tgcgtcttta ctagatactc catctttaa taggtgaagg gttttaggga     1260
cttgtgataa ataatactca gaatcccatg actgaagcct taactttatg ttggacctat   1320
gttattgtgt tttttgcact tgtattggag ttgaggggta tatgagtctt ctgatttaac   1380
ttgttgactc ctctttgaag tggtctgtag ttctcatttt tgtagaagtg tatcatgtaa   1440
atcgaaatat aatcactcat cgactatgat ctttcttcaa ttacagttat gcaaaattga   1500
ttctgaaggg aaagcaagga aagttgttgg ttgtggctgt gttgtcgtga aggtacgtcc   1560
tacgtatcct ctggctttaa atgaatagta cagttgataa gtttttccaat ctggaattta  1620
tactccactg taatgaattt tctaattgat tctgcaggat tatgggggaag agactgaggg  1680
tctccatatc gtccaggagt acgtgaagtc tcattaa                            1717
```

SEQ ID NO: 10           moltype = DNA   length = 1451
FEATURE                Location/Qualifiers
source                 1..1451
                       mol_type = other DNA
                       organism = synthetic construct
SEQUENCE: 10

```
atggatcctc aggctttcat taggctgtca atagggtcgc tggggttgag actgtctgga   60
acaactactt tgaacagtac aaaaacaggg ataagtgcag tctcttctcc ctgtgtgtgc   120
gagatccgtc ttcgaggttt ccctgtgcag acatcatcta ttccctatat ttcctcacct   180
gaagctacac cggatattca caacgttgca tccagctttt atcttgaaga atctgatttg   240
aaagctttac tggcacctgc cccctgtttt tatgcggctc atgcatgtct agagatagtt   300
gtttacacag gacgcaaagg aggccactgt ggtgttggta ttaagaggca gcaagttggg   360
acatttaagt tggaagtagg tcccgaatgg ggtgaaggaa aaccagccat tctgtttaat   420
ggctggatag gaattggcaa gaacaagctg gagactggaa aacctggagc ggagcttcat   480
ttgagagtga agctggaccc tgatccaaga tatgtttttcc agtttgaaga taaaacgaaa  540
ctaagccctc aaatagtgca gcttcaggga accatcaagc aacctatttt cagttgcgag   600
tttagtcagg acaggtaaat cattgttttg ctcttttacc ctttcctagg gatgagtagc   660
gtataagtag aattgaagtt ctactgttat agtctactttt ttccgggaaa cttttaagtt  720
gcttcagttc taattctaag agttgtgtgt tatgctgaac ttacagggta tctccggtag   780
atccattaaa taattttttgg tcaagttcat ttgacggttc tgaactagag gtagagaaaa  840
gagagaggaa gggatggaag gtgaagatac acgatctctc tgggtcggct gttgcagcag   900
ccttcataac aactccgttt gtgccatcaa caggttgtga ttgggtggcc aaatccaacc   960
caggagcttg gttgattgtt cgtcctgata tttgcaggcc cgaaagttgg cagccatggg   1020
gaaagcttga agcatggcgt gaacgtggga tcagagattc catttgctgt cgcttccatc   1080
ttctatcaga ggggcaggaa tgtggtggtg atcttctcat gtctgaaatc ttgatcagtg   1140
cagagaaggg tggtgagttc tacattgaca cggacagaca ggtacaagca gcagcgagtc   1200
cactgcccag tccaagaagc agcggagact ttgcagcact aagtcctgtt gcagcgcggtt  1260
ttgtcatgag ctgtcgagtg caaggggaag ggaaatgcag caaacccctc gtgcaacttg   1320
ccatgcgaca catcacctgt gtggaagatg cagccatttt catggcgctt gctgctgcag   1380
ttgatcttag cattgaggca tgcaggcctt ttcgcagaaa gctacggaga agtactcgcc   1440
attcctggtg a                                                        1451
```

SEQ ID NO: 11           moltype = DNA   length = 2282
FEATURE                Location/Qualifiers
source                 1..2282
                       mol_type = other DNA
                       organism = synthetic construct
SEQUENCE: 11

```
atggctaagg tgtgctttta caatgtgaag atgaatatgc aagtgatgtt ttgcttgttt   60
ttggtgtcac tatgtcgtga tgatgcagct gctgaagcta aacagggggat gtctcttgct  120
gcccaaaagt tcgaggttca aaagcacttg aatcgcttaa acaaacctgc aatcaaatcc   180
ataaaggtta aaattttata ccccttttt tgctccttt ttttgtgtgt cttttttgtat    240
tgatggtttc ttttggaaaa aaataacaga gcccagatgg tgatattatt gattgtgttc   300
atatgtctca ccaaccagct tttgatcatc ctttgctcaa gaatcacact gtacaggtca   360
gcctcttccc aaaaatagaa ccccttattc tgtttgtaaa aattaaacat aattcttgtg   420
ataatcttaa tgggaaaaaa gttgattttt ttgggttata gatgatgcca aattatcacc   480
cagaagggct atttcgtgat ggaaaattgt ctacagcaaa aaccaagaat gaaggttcaa   540
aatcaattac tcaactgtgg catttgaatg gaaaatgtcc agaaggaaca attccaatta   600
gaagaaccaa aaaagatgat attttaagag caagttccat gaaaagctat ggtaggaaga   660
aaaaacattc tactattcct aaaccagagt ctggtagacc tggccttgtt agccaaactg   720
gtcatcaggt acaccaaatt gttcagattt gtatagaagg aaaatcagaa gtttcattga   780
attaatggtt ttgttatctg ttggagttat tttagcatgc aatagcctat gttgaaggag   840
acaaatatta tggtgcaaaa gcaaccataa atgtttggga acctaaaatt cagcaaccca   900
atgagtttag cttgtctcag ctttggattc ttggaggttc ttttgattca gatcttaata   960
gcattgaagc tggatggcag gtactgctac ttatctttc caaattattt gcttgtttga   1020
acaattagag agtgatatta ttgtcatatt atatgtctgt atttggttgt cttgtgactt   1080
cttctttttt actttttcttg tcttttttggg gataaaaaca ggttagccca gatttgtatg  1140
gagataacaa cacaagactt tttacctact ggactgtaag ttaaatattt ttccttctaa   1200
atacagctag catacatgca taaaaaaatct aaaatcaaag agtgtgtgct atataaagtt   1260
catgtttcaa aattgaaatt ttggaaaatt atttttttgta cagagtgatg cttatcaagc   1320
cacaggctgc tacaatctgt tatgttcagg atttattcaa atcaataatg aaatagcaat   1380
gggggccacc atttccccctc tttccagcta tcatggttcc caatatgata taagcattct   1440
tgtctggaag gtaatttaat ttattggatt cacatatcat ggtttgaccc ttttcagttt   1500
acttaattct tatcaacaat tatacctcat attgtattga aaaatacacc cttgtatgtt   1560
ccacagcata ttttattgag gtgtccatta tttgcatgtg aatgcataat tgattaatta   1620
acttatgaga agacagacag aatctctgac acttgctgtt gagcccatgc tcttctttct   1680
ctatttcata aaaatctgtt ctataaaggg gagattgtaa cttgtaaagt tgcggtcatg   1740
```

-continued

```
tgttcaagcc gtggtacaat aggctcttat gttccggccc ttccctggaa cccctctta    1800
acggaagctt attataccgg accgtccttt aataaaaatc tgttctttag cttttgttat    1860
ttatcttgaa aatattttaa agtttgattt ggcttaactt ataggatcca aaagagggaa    1920
actggtggat gcaatttggg aatgactatg tattgggata ttggccaggc ttttttattt    1980
catatttaac agacagtgct tcaatgattg aatgggtgg ggaagtggtg aattcagaat    2040
cagatggact tcacaccaca actcaaatgg ggagtggcca ttttccagat gaaggttttg    2100
ggaaatcaag ctatttcagg aatatacaag tagttgatgg ttcaaataat ttgagagctc    2160
ctcaagatct tgggatttat actgaggata acaattgtta tgatgttcaa ctaggaaaaa    2220
ataatgactg ggggaactac ttttactatg gtggacctgg cagaaatcct aattgtccat    2280
ga                                                                  2282
```

SEQ ID NO: 12       moltype = DNA  length = 2377
FEATURE           Location/Qualifiers
source             1..2377
                  mol_type = other DNA
                  organism = synthetic construct
SEQUENCE: 12

```
atgtcaatag acaaaagctc aatgcaatca aaccttgatt gcttcttgga atgcaccaca    60
ccgttagtcc cttcccagtt tctaccccag gtattttttc ttcatttttc atatttataa    120
ttcaatggat gaatatgaaa tgtgatttgt tattgtatga ttgttttatg cgcagagtga    180
gattaggaat ctgaacaggt tatggcatcc atgggaaagg gagaaggttg aatattttac    240
tttggctgat ctttggaatt gttacgacga attgagtgct tatggggctg gagttcctat    300
taaaatggat acaggcgaaa ctttagttca atattacgtg ccttatcttt cagctattca    360
aatctttacc agcaggtctt ctgttaattt tctgaggtaa aattcttttg gtgctacact    420
tttttgggta tctcaatttg atcattgatt ttagggtctt ttcttgtcaa atgaatttct    480
tggtttttttt tgaaagtaat gcagcattgc ttgtttacca agttgagccg gtcaaagttt    540
gtgatggcag caaaaattct gctacttaaa gctaaatagg ctattacata gtttatgtta    600
gtaatatacg tttcccagaa gttagattat tcaaagtttg ttagttgctt gttagaaact    660
atgcttcata gttgtggact ggagataatg aagttgttca acaatttaat aattttgtag    720
ggaagagact gagtctgttt gcgagacgag ggattcgttc agtgattcgt tcagcgacga    780
gagtgaaagt gaaaagctat caagatggga tggttgttct tctgaggaag gagatagtct    840
ttggcaaatg aatgatagat ggggctatct ttattttcag tactttgaga gatctactcc    900
ttatggaaga gtcccttaa tggacaaggt tttcctcttt agacttgtta cacctttttt    960
tgtccccttt agtttctatt cccctgcttc ttaaagtctt cttttgaacc aaaatttata    1020
ctggtagcta gtgctttagg aaatgtatgt ggtagcaagt tttagttgta tatttccaat    1080
tagtttttatc tcttgtttcc tttgttatca accccttttct ttttatgaac ttcatattcg    1140
aaagaaaaag gactaactgg ggtttgtttc tgttaatagg gatgatagga atagttctta    1200
gtttgtgact tctaagtaca aatttacagg ccttaattgt gcttttttagt cccccttctc    1260
cctaaaatca ttggagataa atctattagt attgttcttt attctgtatt ctagcctaat    1320
ccggacatta tggttgactt aatcacccac tcatctttgt ttatgcaact cagagaaaat    1380
ttgaagcatt tattctttct ttatgcagta gagttctcta atgattcttt atttgataag    1440
atatataaga ttccatatga aacatgtggt ttgaactttt tagcatatat tgtttttgttt    1500
tgaacgttta tttgacacta actctgattc tttttgctcg cagattagtg gtttagctga    1560
aagataccc ggattaatgt cattgagaag tgtagatctt tcaccagcta gttggatgtc    1620
agttgcttgg tatgccagtt cttccgttct gtgcacttat ggtcatgaaa ctaatggtta    1680
actgaagtag attttatcaa gttaatgaaa tttatctggg acatgtaaaa tattgtttac    1740
ttgctccttg atgggtatta attggatcat attttccttg taatgcaacc aattttatac    1800
cacttaagtt gatcctgcat cctttttggta ttgctgactt gcttggtcgc cacagtgagt    1860
aatgaaaggg gaataaagac ggattttgtt actaacccct ttgacctgga cattataggt    1920
atccgatata tcacattcct atgggaagaa ccattaaaga cttgtcagca tgctttctca    1980
cattccacac cctttcttct tctttccaag gtattgtttg atctatccgt tggacattga    2040
atgctttttcc ctttttaatt gctatcttct gagcgaacga gtgatgaagt acagaatatt    2100
tttacactag ctaatctttt ggtcgtctcg tgcagatatg gaccttgaag atgacacgga    2160
gaatggtaaa cggaaacgaa aggaaggaga aagcatccca cttccacctt tcggtttggg    2220
cacttacaag atgcagggtg atgtgtggct ttcagacagg aaaggaaggg accaagagag    2280
gctggcatca cttttttagcg tggcggattc ttggctaaag cagttgggtg tccagcacca    2340
tgacttcaac tatttcatgg gtattcgtcg tggctga                            2377
```

SEQ ID NO: 13       moltype = DNA  length = 951
FEATURE           Location/Qualifiers
source             1..951
                  mol_type = other DNA
                  organism = synthetic construct
SEQUENCE: 13

```
atgacaaaaa ctagcaaggt gcagcgggta cctggtttgc tatcttgccg ctcaaaggtg    60
tgcaaaaaga ttcaaaagga gaaacgaccg aaatcatcag agaagaaaga tgggaaggg    120
gcaacttgct cagtttgcat ggagcatcct cacaatgcag tgctgctgct gtgctcttct    180
tatgacaagg gatgtcgtcc ttatatgtgt gccactagct gtcgtttgtc gaattgtctt    240
gagcagtaca agaaagccta tgcgaaagtc acttcaattg agggctctga accagagttg    300
ctgtcaattg atgatccaaa ttgcttgtca ggagcaggtt cttgcgctgg gaagtcggta    360
gttgaacttc tatgcccact ctgtcgtggg caggtgaagg gttggacggt tgttgaacct    420
gcacgcaagt atctaaatgc aaagaagaga acatgcatgc atgaaaattg ctcatttgtt    480
gggacataca aaaagttaag gaaacatgta aggcgggagc atccatcagc acgcccctc    540
gaagtcgaac cttcacatgc agagaaatgg aagaagcttg aacacgagag agagttgaac    600
gatgtattta gcacaatcag atcggccatg cctggggcaa ttgtaatggg agattatgta    660
atagagggta actttggagg cttccacaga aattttggat tagatgatca cctcggtgac    720
actctttta ggtcggaatc taatggcatt ccctggaatg atattgtcca ctcagatgat    780
gttttcgatg atggctatca ttcgtttgat gaggatgatt ttttcgtcaa tcattctggc    840
agtggggctg catctaatgt tttcaatagg atttctcgac ttcgtagcag gctcttattg    900
```

-continued

```
ggaagatcaa ggaggcggca acgacatcga gcgagtagca gaattcggtg a              951

SEQ ID NO: 14          moltype = DNA  length = 3966
FEATURE                Location/Qualifiers
source                 1..3966
                       mol_type = other DNA
                       organism = synthetic construct
SEQUENCE: 14
atgaggacat tgtgctccaa cttggataga aagatgggc tggaaacagt gctggaagtc       60
cccatcccag aagaaatgtt tgcttccaac aagcacaggg cacggcagag caagaattct      120
ggggtcaaat ctcacatgga caagtctgct gcttccgttt ttggtagccg aaatgctgag      180
attcaactct tgcttggcgt tgttggagct ccgttgatcc ctcatcctat ccgttgcgac      240
tactctctca acacaaaaat caacgatcat cccatagtaa gtcggagtat tgtggcagca      300
ttattttaaa gcttaaacta ttaggggtcc tttggttgct ggtagagtt atgcagctat      360
taataaagta gggagtagtt atacatgatt tagctatgta ggaattggtt atgcataatt     420
taattatata tgcagggttt agtcatgcac gatttaatta tgaagaggat atgttattta     480
tggattagta atttatgaat tgtaatgtag agattatttt ttgttcaata tttactttt      540
tttaaatata caatgtgtaa tttaaaatat atatatatgt gtggtcattt tgattgttta     600
attcatatat tataaatca tgtattaatt gttccacatt ctaccttgca taactaaac      660
atagatttgt tggttaactt atccatgtat tacttatacc tctaataaaa gcaaccaaac     720
atgatattag agggagttta gacataagaa ttgtaaaatt cccaaaaaaa aagtgaaaaa     780
aaatttaaag taaaatggta tttaaaaatt agagttgtgt ttggacatga acattatttt     840
ttgttttta tgaagttttg tgagtaatta gagtgaaaat tttgaaaaaa cacatttttg     900
gagttttca aacttccgaa aagttccaaa atgcattttc aagtgaaaaa taaaaattt       960
atgaccaaac gatgagttcg aaaaaattga aaaaatttcg gaaaaaagta aaaaatttct    1020
tatgtccaag cgggctccgt attagttata ttactcctaa tgcatgaata atttaccttg    1080
taatcagcta accccttaga gagtaaattt tttctttagt taattcaaca tgctctctca    1140
caaccggatt ctttttatg gatgattagc aacagggaga ttagaacata aaacctctac    1200
ctgtccgata tcatattgga ttgtatgacc atatcatcta aaaagtttag ttgaacatat    1260
ttttatttat ttaattggta tattttaac atgttcagga agcttcagtg gcgaaatata    1320
tagtacaaca gtacatagca gcagcagggg gagaacatgc tctaaattcc attgatagta    1380
tgtatgcaat ggggaaaata aagatggtgg cgtctgagtt tattgctgga gatgggaatgg  1440
gattgaacaa cggtaatatg atgaagatta agagtgtgaa aaatgggcct ggtgaaatgg    1500
gaggatttgt gttgtggcaa aagagacctg acctgtggag catagagctg gtggtttcag    1560
ggtgtaaaat tagtgctgga agtgatggta aagtagcctg gaggcaaact ccatggcata    1620
attcccatgc atctcgtggt cctgctaggc ctcttcgtcg ttctttacag gtactttatt    1680
tcaaatcaat gggttcaatt gaatttaata cttccagtat ggtggagcac tatgagaata    1740
gtgcaaaata aggtgtatta gtaatgcatg tgttgataat gcaagcatta gttatacaga    1800
tattatttt tatctactgt ttgatgtggt gtattaaagt tataatgcat tgcataattt     1860
ttaagagaaa tagttgttta aaaaatgtca tccatattct ctagctttaa gggtctttaa    1920
ggacaatttt atttttgacc ttactaatgc atgcattaat agcctggta ttactaatgt     1980
catagttttc tattccttac ttatacatag gataatatgt atagtttagt tatacacaga    2040
ttgaaaaat ataccaaata aggtattaat aatacataga actaatgct gcattatttt      2100
ttttctaata ccctatccca aaacaacccc gaaaagaatt aaggtatata gtgctaacaa    2160
cttttttaatc gttgaatcta tcaaagtata tatcataaat tctctcactc aatccttgaa    2220
taatggtcaa ttttccttt attagtcatg atctaaaaca agcttataac aagtgaacag     2280
gccgacaatt tctccacatg aaaatgtatc cttcttctga agggacaata attgccaaat    2340
acgtcgtttt tttctttgcc acatgatgag tgggaaggcc aagattcgtt gactgttcct    2400
actgacaact atgtatgttc ttttactttg tgtgggtcct cgtgtctgat taatctattt    2460
aactggtact tgggttttgg gaagtgtgaa atcataatca agaagatcaa aattctcttt     2520
gacgttcttt tttactttac tttggaggtg taggacctac ttatttccat ggtcattgac    2580
agctttagtt ttatctttt tctttatttc tggctctaac gggacatatc cccatgcgga    2640
cctgagttgt ccttccacca aatcaatgat tgattttatg agtactcaaa ttggcatcta    2700
ttctgaatgt gtaagaatct tagcctcaac ctctatgatc agcaatctag accaagaaat    2760
cagttctccg ttgtgaatgc gcacaaatct tagcctccat tttgaataag gagttattaa    2820
acttaatctc atatatgtgt tgagatttat attatgtttg gtttttccttt ttctcgagtg   2880
tattttataa agacaaatca catgacccat caaaatggtc agtagggcaa gcttgaaaaa    2940
tgtctaataa tcccttggtt tcattttata tgagactata cacttgaaaa cttttaacat    3000
ttatgtctac tatatttgcg atatctactt aataaaatgc attatagaca cataaatgtc    3060
tactatattt ttggatgata agtttaagg gtacctttt atatctatca aattatgtct      3120
tcttttataa aattcttgca tagtaaaata cgtcatataa gataaaatta gaaggagtaa    3180
caaactagaa gccaatatat ataaatttt tctgaagatg gtaaattcct gaactaaaaa    3240
cccccaggaa aaaataaaga taagaaatat ggaacgagta agtttgctt ttgtagaaca     3300
aattaaactg gttgaaattg aacatgttaa cagggtcttg atcccaaatc cgttgcgaat   3360
ttattctcga attccatttg tattggagag aagacggtga atatagaaga ctgttttgta   3420
ctaaagcttg aaacagagcc ctcaactctg aaagcaagaa gcagcagcaa cgttgaagta   3480
atgaggcaca ctgtttgggg ttacttcagc caacgaacag ggctcttact ccagcttgaa    3540
gacactcatc ttcttagaat caaagcccca ggaaatgatg tcttttggga aacaacaatg   3600
gactcattaa tactcgatta tcgaactctc gacggtgtta atattgcaca tggtggaaga   3660
acatctgttt ctttatttag gtttggtaag aactcagaag gactcactag gacaagaatg   3720
gaagaggttt ggaccattga agaaatcgat tttaacataa agggactatc tgcggattgt   3780
ttcttaccac ctagtgactt gaaaaaggaa gatgaagtga gtcatgatgt gaacaagaag   3840
tcaaggttgg ggttcaaggc tcgtactaat aatgctaaac taagaactgc taggaaaggt   3900
gcgtctaaaa tcatgtctat tgacgaagaa gatcttgaag attacgaagc agatgaagaa   3960
tcttga                                                                3966

SEQ ID NO: 15          moltype = DNA  length = 1022
FEATURE                Location/Qualifiers
source                 1..1022
```

-continued

```
                              mol_type = other DNA
                              organism = synthetic construct
SEQUENCE: 15
atgattattg gctctagctt ctcagaaaag taagttattc atttctttac ttttattta     60
attttttgct attggtatgt tgtgtcttca tgttatggtt tattgggtat tggggggggg    120
aggggggggg ggtgttgttt tataagggta tatagatata tgcaaagcac cagacacctt    180
aaagatttga tttttatttc tgggtagttg tgaaatttgg attttgctat catatattat    240
aaggttatat agatatatgc aaaagagagc actagatacc ttaaaagttt gaatatttct    300
ccttggtag ttttcaagat tagaagtgga gtattggcgt cacgggtaaa ttgatgcccg      360
tgaccacgag gttactagtt agagccggta aaatagcctc tcgcagaaag tcatgttaag    420
attgcgtaca atagactttt gtgatccggc tcttttttcgg acccgtgcat agcaaaaacc    480
tagtgaaccg agctttggta gttttcaaga ttggattttg atatcatatg tttatataga    540
tatatttatg caaaagagag caccagaaac attaaagatt ggattttat tttttgggta     600
attttaagaa ttggattttg tttatcatat aagtttttat aagactgaa atagcttagt     660
gggttgtgaa aagattgatg ggaaagaaga aaatttgaa gaagacaaag gagttatcag      720
tagcaatagc agaatcatca gcaatgagtg gagactctca acaacaacaa caacagatta    780
ctcctagaaa aagaggaaga ccaaggaaaa ttattgtaaa agatgaagaa gaggctactg    840
gagaaataaa gaaactcaaa ataaatgaag gtgaagaatt agaaaataaa gaagcagcag    900
aaggagaaaa gaaagaagca gaagaacaat ctgaagagga aaaaaattta cagccacaaa    960
agcagcaacc tgtagcaaag agcagagcta gaagaaaaag caagccaaga aaaagctgct    1020
aa                                                                    1022

SEQ ID NO: 16             moltype = DNA    length = 3324
FEATURE                   Location/Qualifiers
source                    1..3324
                          mol_type = other DNA
                          organism = synthetic construct
SEQUENCE: 16
atgatggcac agcatattga gattagccca ctgcttgatc aaactcctcc gaatgaagct     60
acgaaagatg aggtctctct cctctctctt cacaatcaaa cacacacata tatataagca    120
ttacctcttt gttatccaca tcatgtaacc caaattaatt aggacaatac taaaaatctt    180
gagataattt tattgaatac ctcaataatt atagcttttt cattagttaa agtcttcaat    240
aaatatagct tttttcatta gaaaaagaa tcttagctta gcggacttct ctcttttttgg     300
caaccctta aatgataatt gaacgagatt aaaaggagaa aaataatcct aaaacacaca     360
taacacctag acataattct cacttctgac tcgtctcttt cgacagtcgc cagctcgccc    420
gcggttgcta aagccttcac ccactgccgc tgcttccttc ttcgcctttg ccgtcgccag    480
tcatcaagtg gttagttctc tctccctccc ttcatctttc tctctcttag ggtccttttg    540
gtatgagtta taagtacaaa tagtgttgag ataaaaattt aatatcacct ggaataaatt    600
attacgggat taaaattagt atcgagataa cttatacctt atagatggtg ggtaattagt    660
gccgggataa catataattt cttcttagaa attatgcaat tgtcattttt aatacaacat    720
accaaacaat ggataaaaaa caataccaaa catgaaagtt tttcaaaaaa tattattttg    780
gatagaagtt tcattttata agaatgtcaa atgtttcaat tttgaaaaat aaagatatat    840
ctgtaactaa gtacattaaa atataatact ccctataaga caaattaacc aaaaacatga    900
aacttcaatt ttattcatac ctttgatcaa aaagaaaata attttatttc aaaaacatgt    960
atatttcaaa cctttttgaat aagaaataat cacaatttct taataatcaa ttactagtaa    1020
taacatttttt tgtgtttcga aaataaaatgc tatttagatt ttaagaaaat tataatattt    1080
tagcttgctt gttattattc tgcatcaaat tcatttagat gaaaatttat tcgtggaatt    1140
tccattatat aaaggggtat gcaaaggagt gtatccgtag ttgagttata ttataggat    1200
gtttaaagtg ctttactcta atgtatttgc tttatataat tgtgttgaat taactaaatc    1260
atgttactac tgattttaga agaatgaatt tgatgataaa cgtaagctcg atttaaataa    1320
gcattaattt attaattata ataacaatca tttagatttc ttttttatgt tatcttgatt    1380
atacaaatga tatacttggt taaataaaat tttccgttta accaaaaaaa ataatcacct    1440
ttctcaacat tcacctaaat agttctcttt ccttttgttt gtttgggctt ttaaggctac    1500
ttaattagct taatttgatg tatggttaag tatatattgt ccaaaaattc caggtctgta    1560
aacgtttcaa gatcgtttga tcttcttcat ttcacgtttc ttaagatagt aactatagag    1620
ttgctatcta ttactgactg cttagtcaca agtccatgtg attagaaacg aaaacacccca    1680
aaaaaatggg gaaaaaggc cgcccggtgc actaagctcc cgctatgcgc ggggtccggg      1740
taaggtcgaa ccacaagggt ctattgtacg tagtcttacc ctgtatttct gcaagaggct    1800
gtttccacgg ctcgaaccgg tgatcttcac aactttacca gttacaccaa gacttccctt    1860
caaaagaaaa actaaaaaga aaccatgttt cactaattac agatacaaga aggcgggaaa    1920
gcagattata taatcgagat aaggacagca gatcaaacaa atgaatcagc aaatcaagtc    1980
tttgatgaag gatcatctac catatttaaa gtaaatgtgg ggctatctga atcaaatcca    2040
gatgcttata ccccaaaatt gatctccatt ggtccttacc ataaccaaaa tccgagactt    2100
cgctcgatgg aaaaatataa actgcgttac cgacaacggt ttctgcagag gaaagcgtgg    2160
agagatgtgg agtattactt tagtgaaatg gagaaactaa aggatgaagc actaaagtgt    2220
tacgatgata taagggacct tgacagtaat attgttagca aattttttaga tttgctgtta    2280
cttgatggct gcttcgtggt tgagtatata cgagagtttt acgaaggggt gccagaagga    2340
gaagacaaga ttatcaacgc ggcttggatg gaatctctgg tagatcgtga cttgttgtta    2400
ctagaaaacc aacttccttt ctttatcctc gccaaactct atgagtgac taaggatcct    2460
acagacgccc cattcataca gatggtgaaa tacaactttg gtagtagttt accaaaagtg    2520
actcctaaat tcataaatgc tactgatgat gatgccgaag aaatcaaaca tttacttcaa    2580
gtagtacaca tgtgttgttg cccttcagag atgaatactg gctaactag gaatagcaga    2640
aagaaaaaag gaagtagcaa gaaaagttgt aactggaatc ctttgcgaat aggaaagtcc    2700
aaaaagaagt ttaaaactaa ggatggtgac ttatggcacg atcgcatgcg aagtgcaaca    2760
gaacttgatg aagctggaat tcgcttctct aatgttggga aaatttatag aaagttgaat    2820
aaaaacaaca aggaggatgc tataagttta tttgatatca aattcaataa gggattgctt    2880
gaaatcccctt gttttgaagt cattaatagt acgagacta tcctgagaaa tctcattgcc    2940
tacgaacaac actcctctga tgtgcatcca aaatatttca cggattatat aatttttatg    3000
gaccatctta ttaactcagg caaagatgtg aatttgcttc ggttgaacgg aattatcaga    3060
```

-continued

```
aataggatag gagatgacga agaagtggct attatgttca acaaactagg agaaggtgtc   3120
atccttcaa ctgatttctt ttacaaagtg gaatgcagaa aagtgattga gcattgtgaa    3180
aaaccatgga atgaaaacat ggcaagtttg aggcacaatt atcttaatag cccttgggcg   3240
aaaatttcaa ctgcggcagc catcattctc cttctgctca cagttgcaca aacagttcta   3300
gctttcatca gtactttaaa gtag                                          3324

SEQ ID NO: 17           moltype = DNA   length = 909
FEATURE                 Location/Qualifiers
source                  1..909
                        mol_type = other DNA
                        organism = synthetic construct
SEQUENCE: 17
atgagggact tccatcttg ttttggtgaa aatggggttc aagttgctga tgcttcttgt    60
tcagctgttg ggggtgtgac taaaaccca cagaatttag tcacatgtgt ttatcagtgt     120
aaactacttg ggaaatcttg tctgatcact attgtttgga ccaagagttt gatgggtcaa    180
tgccttagtg ttgaaattga tgatatgtct catcagtgtc tttgtaaagt tgatgtaaag   240
ccttctctct tctccaaaag aaaagggtca aggtctttag aagtaaattc ttgtaaaatt   300
gacctacact gggacttttc actaggcaag tttggatctg ggccagagcc tatagaaggg   360
tattatttag ctctagtttg caaaggacaa atggtttttgg tcattgggga tctgaggaaa   420
gaagcattta aaaagactaa tgcaactcct agttttttcaa atgcaatgtt catttctaaa   480
agagagcaca tatttgggaa gagggtattt ggtacaaagg ctcaattttg ttatacaggt   540
ccaattcatg acattacaat tgaatgtgac tctaatggca ttgacgatcc gtgtcttttg   600
gtccgtattg actctaaaac tgtaatgcaa gtgaagcatt tgcggtggaa gtttcgcggt    660
aactatactg ttttaattga tggactccct gttgaagtct tttgggatgt tcataactgg    720
ttgttcagta gcaattttgg gaatgcagtg ttcatgtttc aaacttgttt atcggccgag    780
aagttgtgga ccacacaaac tttgtcggat ctctctgtga tgccttggtc ttacacagag    840
agtttgagca attccaaatc atctggtttg ggttttttctt tggtttttgta tgtttggaag   900
aacgagtaa                                                          909

SEQ ID NO: 18           moltype = DNA   length = 2210
FEATURE                 Location/Qualifiers
source                  1..2210
                        mol_type = other DNA
                        organism = synthetic construct
SEQUENCE: 18
atggaagtca tatctaccaa cacaaatggc tctaccatct tcaagaatgg taccattccc    60
atgaacggcc accaaaatgg ctcttccgaa cacctcaacg gctaccagaa tggcatttcc    120
aaacaccaaa acgggcacca gaatggcact tccgaacatc ggaacggcca ccagaatggg   180
acatccgaac aacagaacgg gacaatcagc catgacaatg gcaacgagct actgggaagc   240
tccaactcta ttaagcctgg ttggtttttca gagtttagcg cattatggcc aggttagtat   300
taagaaagaa actcaaatgc atcgtactct tgtattttgg tttgtgtata atttataata   360
tggataaatt atgacgaagt aaactcgcat acattaattt gaaataatct aatttttgcag   420
gtgaagcatt ctcacttaag gtcgagaagt tactattcca ggggaaatct gattaccaag   480
atgtcatgct ctttgaggta attaatattc tgatacacat gctttaatct aaagtgatac   540
tttttaattta cttttagttt attgcatgtg cacgtacagt cagcaactta tgggaaggtt   600
ctgactttgg atggagcaat tcaacataca gagaatggtg gatttccata cactgaaatg   660
attgttcatc taccacttgg ttccatccca aacccaaaaa aggtttttgat catcggcgga   720
ggaattggtt ttacattatt cgaaatgctt cgttatcctt caatcgaaaa aattgacatt   780
gttgagatcg atgacgtggt agttgatgta agtcaaactt cttttaccca cataaagaaa   840
atgatttaga ttgcaattct ttttatttt ctaaaagaat aaatatattc tctcttttt     900
tttttaaaac aaaattctct ttcttacagg tatccagaaa atttttccct tatctggcag   960
ctaattttaa cgatcctcgt gtaaccctag ttctcggaga tggtgcgtat atgatagtct   1020
cgttttatat tttatttcac ttgatttttta ccttttttttg tggttaatta atcatctacc   1080
attggttctc tttaccttca ggagctgcat ttgtaaaggc tgcacaagcg ggatattatg   1140
atgctattat agtggactct tctgatccca ttggtacgct attactattt aataccaaga   1200
ctattcttat tatataagct actaagaaac taattgaata attaataaac gtaactgtaa    1260
ttgatttcta aaataatata tataaatttca ggtccagcaa aagatttgtt tgagaggcca   1320
ttctttgagg cagtagccaa agcccttagg ccaggaggag ttgtatgcac acaggctgaa   1380
agcattttggc ttcatattgca tattattaag caaatcattg ctaactgtcg tcaagtcttt   1440
aagggttctg tcaactatgc ttggacaacc gttccaacat atcccacgta ttctttttct    1500
ctctctcttc ctgtcttttt cgatgcaatg taaatttata aaattggaag tccgtttttac   1560
ttttctatag acgtagatcc taaaattgtc aagaaatgga gaattgactt acaagaaaaa   1620
tcaacttctt ttcatttact attctttttg gtgacaaact ttacttatta tttcgttcta   1680
aaatgaaaat ttattttttat attttaaaat aatttagctt taaacttttta attttacttg   1740
ttatattttt aataaaaaag atttattgtc aaataaatgt tgtggccata caataagttt    1800
caaattatgt cacaaaaatt gaaacagagt gagcaaattt ttatttcaag taaactttca    1860
aggaattgtg tttaagtttt ctcaactgat actgatcaat gatgtcttaa atattttgat    1920
ttcagcggtg tgattggtta tatgctctgc tctactgaag ggccagaagt taacttcaag   1980
aatccagtaa atccaattga caaagagaca actcaagtca agtccaaatt aggacctctc   2040
aagttctaca actctgatgt aacttcatat ctcacaattt cttttttcgt tttactgtat   2100
gttcttcatc aaattttata actaactctt ttcatattgt ctttttttttt cagattcaca   2160
aagcagcatt cattttgcca tctttcgccc gaagtatgat cgagtcttaa               2210

SEQ ID NO: 19           moltype = DNA   length = 2317
FEATURE                 Location/Qualifiers
source                  1..2317
                        mol_type = other DNA
                        organism = synthetic construct
SEQUENCE: 19
```

```
atggaagtca tatctaccaa cacaaatggc tctaccatct tcaagaatgg tgccattccc   60
atgaacggcc accaaaatgg cacttctgaa cacctcaacg gctaccagaa tggcacttcc  120
aaacaccaaa acgggcacca gaatggcact ttcgaacatc ggaacggcca ccagaatggg  180
acatccgaac aacagaacgg gacaatcagc catgacaatg gcaacgagct actgggaagc  240
tccgactcta ttaagcctgg ctggttttca gagtttagcg cattatggcc aggttagtac  300
taagaaagca actcaaatgc atcggcctct tgttgctact aaatatagag agctatcata  360
ctttttaggga ctaactaaaa aggaaagatt atcacaggga cgaagtgagc agttaacttc  420
gcatattatc agacgcatta atttgaaata atcgaatttt gcaggtgaag cattctcact  480
taaggttgag aagttactat tccaggggaa gtctgattac caagatgtca tgctctttga  540
ggtaattaat attctaatac acatgcttta atttaaagtg atactttaa tttactttta  600
gtttattgca tgtgcacgta cagtcagcaa cttatgggaa ggttctgact ttggatggag  660
caattcaaca tacagagaat ggtggatttc catacactga aatgattgtt catctaccac  720
ttggttccat cccaaaccca aaaaaggttt tgatcatcgg cggaggaatt ggtttttacat  780
tattcgaaat gcttcgttat ccttcaatcg aaaaaattga cattgttgag atcgatgacg  840
tggtagttga tgtaagtcaa acttcttta cccacataaa gaaaatgatt tagattgcaa  900
ttcttttat ttttctaaaa gaataaatat attctctttt tttttttaaa acaaaattct  960
ctttcttaca ggtatccaga aaatttttcc cttatctggc agctaatttt aacgatcctc 1020
gtgtaaccct agttctcgga gatggtgcgt atatgatagt ctcgtttat atttatttc 1080
acttgatttt tacctttttt tgtggttaat taatcatcta ccattggttc tctttacctt 1140
caggagctgc atttgtaaag gctgcacaag cgggatatta tgatgctatt atagtggact 1200
cttctgatcc cattggtacg ctattactat ttaataccaa gactattctt attaaataag 1260
ctactaagaa actaattgaa taattaataa acgtaactgt aattgatttc taaaataata 1320
tatataattt caggtccagc aaaagatttg tttgagaggc cattctttga ggcagtagcc 1380
aaagccctta ggccaggagg agttgtatgc acacaggctg aaagcatttg gcttcatatg 1440
catattatta agcaaatcat tgctaactgt cgtcaagtct ttaagggttc tgtcaactat 1500
gcttggacaa ccgttccaac atatcccacg tattctttt ctctctctct cttcctgtct 1560
ttttcgatgc aatgtaaatt tataaaattg gaagtccgtt ttacttttct atagacgtag 1620
atcctaaaat tgtcaagaaa tggagaattg acttacaaga aaaatcaact tcttttcatt 1680
tactattctt tttggtgaca aactttactt attatttcgt tctaaaatga aaatttattt 1740
ttatattta aataattta gctttaaact tttaattta cttgttatat ttttaataaa 1800
aaagatttat agtcaaataa atgttgtgac catataaaaa cctccgcatt tttaagatca 1860
taagtttcag agtcaaacga gttaatttat ttttagtatg ccggtgcgga gtcaaattat 1920
gtcataaaaa ttgaaacgga gtgagaacat tttttattcg agtaaacttt caaggtattg 1980
tgtttaattt caagtgatac tgatcaatga tgtcttaaat attttgattt cagcggtgtg 2040
atcggttata tgctctgctc tactgaaggg ccagaagttg acttcaagaa tccagtaaat 2100
ccaattgaca aagagacaac tcaagtcaag tccaaattag gacctctcaa gttctacaac 2160
tctgatgtaa cttcatatct cacaatttct ttttccgttt tactgtatgt tcttcgtcaa 2220
attttataac taactctttt catattgtct ttttttttcag attcacaaag cagcattcat 2280
tttaccatct ttcgccagaa gtatgatcga gtcttaa                          2317
```

```
SEQ ID NO: 20          moltype = DNA  length = 1443
FEATURE                Location/Qualifiers
source                 1..1443
                       mol_type = other DNA
                       organism = synthetic construct
SEQUENCE: 20
atggccaaca aggtctccaa tttctccgat ctaatccaac gtgtcactgc ttcttgcttg   60
cttcatccac tttcctctgg ccgtattgac ggcaatatct ccgatgctcg ttatagcgat  120
gaatctgaag atgacaagta cagtaccgaa gacgaagaag aaaaagaaga cccaccttat  180
gtggagactc gggaaaaatt ccagaatgtt gaggtcacaa aggaggagat aagaactgag  240
aaagtaacgt aaatggagat gctttttaggg gaagtttttg acgcggtgtc ggcagtgaag  300
acggcttacg ttagtctaca ggaggcgcat tgtccttggg atcaggataa aatgcgtgtg  360
gctgacgtgg ctgtgatatc tgaactgcgg aggcttgggg tgttgaggga acgatttcga  420
aggaatgttg gtggtggaat tagaaaaggg gactggagag ttggcgccgc tacgctgaga  480
gaagtgttga caccatatga agccaccgtg gaggaactga ggcaagaagt gaaggccaaa  540
gaaatcgaga ttgataattt gagggagaag ctgaaaacag caacaagtct tagcagcagt  600
ggtggaaaga aaagcaagtc aaaacgaaaa gttagcggta gcagtcaagc tccagttaca  660
atgtcgccgg cacctgacgt attcgaaact acagtgagct tagtaaaaga agcttcaaaa  720
tccttcacga gtttgctcct ctctttgatg cgctctgctc actgggacat tgcagcggcg  780
gtgagatcca tcgaagctgc ttcatccaac acaaacacac ccacggcaga ttctatcgtt  840
ggagccaacc atgccaaata cgcactggaa tcttatgtga accgcaaaat gttccaagga  900
ttcgatcacg agacgttcta catggatgga agcttatcat cactaatcca cccagatcaa  960
caccggcgcg attgttttac acagtacagg gacatgaaag caatggaccc aatggaactt 1020
ctgggaattc tcccccacttg cagtttcggg aacttctgtt tcaagaagta tttggccatt 1080
gtgcacccaa aaatggagga gtctctgttt ggtgatttgg agcagcggcg acaggtgttg 1140
gctgggaacc atccgaggag tcagtttat ggggagtttc ttgggctagc aaaggccgtt 1200
tggctgctgc atttgctaac cttttctttg gatcctccgc caagtcattt cgaggcgagc 1260
aaaggatctg agtttcaccc gcagtacatg gaaagtgtgg tgaagtattc catttccatg 1320
ggcataggag ggagaatggg tatgggtcta gttgtcggat ttccagttag tcccgggttt 1380
aagcttggaa atggatcggt tgttaaggct agagtttatt tagtccccaa aaatgggttt 1440
taa                                                               1443
```

```
SEQ ID NO: 21          moltype = DNA  length = 324
FEATURE                Location/Qualifiers
source                 1..324
                       mol_type = other DNA
                       organism = synthetic construct
SEQUENCE: 21
atggatcgtc taatcaactc tgacaaagat gtgaagttgt ttcgcttgaa gggaatcatc   60
```

-continued

```
agaaaccgga taggcgatga caatgaagca gctagcatct ttaacagact tggagaagga   120
gtgatccctt caactcagtt ctattacaaa gaagcatgca aaaaggtggt tgagcattgt   180
gaaaaaccat ggagtgaaag gaaggcaagt ttttggcaca attactttaa tggtccttgg   240
gtgggacttt caactgcagc tgcagtaatc ctcctttcgc tcacagttat gcaaacagtt   300
ctaactttca taagtactct ttaa                                          324

SEQ ID NO: 22          moltype = DNA  length = 953
FEATURE                Location/Qualifiers
source                 1..953
                       mol_type = other DNA
                       organism = synthetic construct
SEQUENCE: 22
atggcgatgg gaccagaaag atcgaagccg cctctacaca atttcacctt accgtgtggg   60
ctcaagtggg ggaaccaaaa gttcttaagg tgcgctaagg ttgaatccga cggacaaatc   120
tccgccattc atcgcaggtc atttgggtct gagttgatcg gacggcgccg atcaaatgat   180
cgaaaattca ggccaccgga aaagcaagat gccggtgaag gaatcggagc tgtgagagag   240
aaactcatgt ttgatctcca aacagaagct gataagataa aagacgcaat tttagagaa    300
ggtttggagg agcaacaact gtctccggcg ccggcgaaaa ctgcgactgc ggctgtatca   360
tatgccggtg aattgtccag gccgtggaac ttgaggactc ggcgtgcggc ttgtaaggag   420
cctaatggat tcgttgccgg cgccggtgcc gccggaagtg gtggtggtgg atcgaaagga   480
gggttgaaga ttgatgctta tagaactaat gctccgtcgc cgttaaggac ggaaaacaaa   540
tctccgacac ttcgaagtga ttttgccggt ggagcggccg ccggagcttc tgccagcggc   600
gagaagagac agagagtgaa gttttcggta cccctttcgc gaggagagat cgaggaggat   660
ttcatggcga tggtgggaca tagaccccct cgtagaccca agaaacgagc taaatttgtt   720
caaaagaatt tggatgtaag tcaaaaaatt tcctctctaa attgaatctt ttgatttatg   780
ataatcggac taaatagatg gaacagatat aaaagattgt aatttgcgca tagcagtagc   840
tgtaattgat aatcattttg atagtgaatt tatctatttt gcagacgtta tttccggggt   900
tgtggttgac ggaaattaca cctgacttat acaaagttcc tgaagatcag tag          953

SEQ ID NO: 23          moltype = DNA  length = 2877
FEATURE                Location/Qualifiers
source                 1..2877
                       mol_type = other DNA
                       organism = synthetic construct
SEQUENCE: 23
atggaaatta tcagtgagag aagaagaacc cgatctcaag cggctgctat tctagtggag   60
ctaaaatcca tcaattttca atcagaaaaa agacccaaag tacatgaaaa agatggtgtg   120
aaaaattttg ggaaaaggaa gcgtcgaaag ggtagtaatg tcaggagaaa aagaaaggga   180
aaatatgtac aagttgactc tgatgatgat gaagactatg tgtttgataa aagtcccaaa   240
aggagaaagc tggattatgg acacaagggg aagagttcca gctcggattt gaaggtactt   300
tccagttttc tttcgttttt ttattactct ttctgctcca ttgttatgtg atgttgtttg   360
gctggacatg gagttagaga catgtacaaa ctataagtta attatgtcat taaaggtaga   420
atgagaaagt ttaaagttaa attatttcta aatataaaaa gatttcattc tttgtgggac   480
actctaaaaa ggaaaaaatg tctcatgaat tgggacggag acagtaatat ataatgtata   540
ttatgtgtat atagctctat gtctgcgcat atacatagta tacggtgtat atgtttagta   600
tactgtgtat atatatggta tgttatgtgt attacagtgt atatgatgtg tgtgtgtgta   660
tagtagatga tgtacaaacg tatatatgt  acttttgat tgtataaat  atttgacaac   720
cttctggtgt attaacagta tagttgtatc attgttatgt agatttggga ttttttatgtt  780
caaccgagaa agcatttcac agcaagaatt gggacacaca ctaatgttga tgttgttaaa   840
ttgttgaatg cgaagttgga tgataggcag attcagatgt tcagagaaac atgcttcggg   900
cattttcttg atttgcccga tgtattggtt cagcctcaat tgatacactc gctattgctg   960
agggaggtgg ttcacgagag agaggatgag ttgtggattt cagtgaatga tgtcaggctg  1020
cgtttttgggc ttgttgagtt tgggattatc accgggttaa agtgtacggg tgatgctgat  1080
atgtgccttg atttcgacgg aacgaatcgg ttgtttgata cgtactttc  tgaacttacc  1140
agggtaccta agcaatcctt aattgactgc ttccttaata agagatggaa atccgatgag  1200
gatgcagtca acattgctgt cctatatttc atacacacat tcttgctctc cactctgaat  1260
cgtaattata tcacgaggga tgactttggg ctcgttgaga gcggtgcata tcaaacgtac  1320
ccttggggaa aagttgtctt taaagccaca ctgaagtcta ttaagggtag gttgcttggg  1380
aagccctcga tgtacaggct tcgtggatta ccattggcat tccaatgttg gttttacgag  1440
tgctgcccctt atgttaataa gaagattgct ttccgggttg atgacaaagt gccccgcata  1500
cttagttgga aagttacaaa gcagccaaac ctcaagaagt tgtcgaatgg gattttcatg  1560
cagaggcggg atcaggtaat tgggaagcag tcattttttt tatactgtgt taacatatac  1620
acttgatatt ccattaacac acacactaat gtaggatata ttttgcactt taaaagtgta  1680
tattaatggt attattctag tatattatat tgtaacattt tgctatacat gtaaaaccat  1740
tactatacca tctcagaatg gtatatctgt ggtgtaatta ttgtttatta cacattatta  1800
gttatgaatc gacgtacgtt taatctcttt tcatgctaat gtttttttat gtagtttatg  1860
ctgaggaata tttctccaac agaatttgag caaacaacac tgaatttgcc tgaatcattt  1920
gaaaatgaaa gggataatga ggtggcatct ggagatggcg ctgaagttca tcttagtgat  1980
gatgacttta gcggttcgcc gcctcaaaca agtaggaagc agacctaaaac caacctgat   2040
catcccttga acaatgatga ctggagcatc gagttaaaaa gactgagtga tggacagtcg  2100
gagttgaaga gtgagattca gatggtgcga ccacttgagc tattttagtt taacatttga  2160
atttttatac acaacagttt tttaactttg ttttttttccc ctttcactag ctcaacaagg  2220
aggttgcatc gctcaaggac tgcatggtag catcctttgc agatgctttt aaagccatca  2280
agtctctgtc gaagaaacaa agagaaaaga ttgcttccga gtgatgcac aaagtagggg   2340
ttcctttgaa tttgtgtgtg ctatttcagt atatacctga aaataatgat gtttttcatt  2400
tttgaacagc ttgatggaga aaatggccac catgacagac atggcgaaag cgattctagt  2460
gactttagta atagtgaaga caatggttgt gaaggtcaag agcatggcaa ggactctatg  2520
ggcgacaagg acaatagtga gaaagggaat gaagtagctt tgggcgatgc tgagggccgg  2580
gagacagtta gagatcctgt ggaggagggt gaaaggatgg acgtatctgc gtctccgatt  2640
```

-continued

```
cttccagata catgtgaggt ttcagaccac attacaccgg aacaaagtca tccgacacca   2700
attctagagt caccatatgt gaaccaaggc gacactggtg ttgagggttc ttccgagaag   2760
tccattttaa aaggagagca cccttttagag agcaaaattg ttgataatgt tgattatagt   2820
ttgttgtctg agtttgataa gtgggttgac gaagggatga agaaagaaag caagtaa       2877

SEQ ID NO: 24           moltype = DNA   length = 3307
FEATURE                 Location/Qualifiers
source                  1..3307
                        mol_type = other DNA
                        organism = synthetic construct
SEQUENCE: 24
atgagtagtc acgaacgccg aggcccggtg gccgtcgtcg gcagcggcgg aggtggaggt   60
ggaggtggag aactgtattg gacagccgga aattggctca atagaaccgg cagcggcggc   120
ggaggcggtt acagtcacga gagcgaacct gacttggctg ctatggttag tgattttttg   180
gaaagtagta gtgtcggtgc ggagtctcgg tatagcagtg ataatgactc tggtttctcc   240
gatctcgctc ttctcgctga taggatttcg gtgagtattc ttttgtttcc gtgtatgcat   300
attatgctta tcggattttta atttgcattc tttgtgagac acatactgca tacatagcta   360
gcttgaatag ggattttctc cagagcaatt aaagtgtgaa atggagtaat ttttgtctct   420
gtgtatagac atgtttataa ttatgcttat caaattctga ttttgcatgg tttttagagg   480
ttttagctat gaaattgatc gagtattttg gtctaggtgt atatagggag agcttgaata   540
gcgcagataa caatttttatc cagagcagtt aaagtttcag cggagcaatc ttttttctctg   600
tgtatagaca tgtttaggct gatcggcgat ccatgagtcg aagtttatga gttcctaaag   660
ctacctcaag ttaatataca ataataattg agttcatagt caattattga tagatatttt   720
gtgatttctt aaaacatgta tagagtatgg gcaaaagcta ttgggttcag gtaggttaca   780
agctaaatcc gcctctgtgt atgttgagct ttagttcaag tatttcggtc taggtgtata   840
catagcgacc ttgggtagta caaataagga tcttattctg agaaattaat gtttgaaacg   900
gagtaatcct tatatctgta tacacatatg tttatgctca tcagatcgga ttataatgtt   960
gcctgtcgat gagagatgct agagttgata ttgctcaagt agtttgatct tggtttatgt   1020
agcgagcttg gatatcgtta tagcacatac gggatttttt ccagaggatt aatgtttgag   1080
atagaatagt cggagttcca cacatatgac ggtgatggtt ttcccccata ggaataaagt   1140
ttgaattgga atgtacaaat ttcttttatt cttttttagta attttttgat aaggtaaaaa   1200
gctgtccata actggaacca atttgatgaa ttagggattc ttttagcatg acattaaaga   1260
taggaaaagag gggccataag tggtttctgc ctttgcaggt aatcaagaaa aaaatgattt   1320
gtctgaatat ctagtatttg attgctgagt aacaagctat gtatggttgg atggagggat   1380
cctgcgatgg tcatatgatg gtgaaattct ttctgtgtga cacaatattg gagattttga   1440
gtacagaatt caaaagcttt tggtgagtgt tagggagtga aaatttggggg ataatgagga   1500
gaaagctaat ggattgggaa aaggattatg cggagagtag gaaggaaagc taagaggttg   1560
agagctcgca tttagcaata gggtatttaa tttttatcag gtgtgataca agggtagtct   1620
atgtagaagc aagattgtgc gcacactaca tgggcatatg cttcatctca gttttggtgg   1680
ttgtttttaat tagagaaggt ttctcgataa gcaatagttt aaaattgcat tttatggtgg   1740
gtgagcacaa gctcctgaaa acgcaaattt ggataacccg ccggcattag caaacctact   1800
atcctgcact aaattcaggg cgggcagtac tacctttctt ccttggacat atggtatcaa   1860
cctgccatga ctttttctaag taaaagcatc actatttgta gtaggctcca atcttgattt   1920
ctcctttttt caataactat gaactaggag atggaaatga ctaggagttt tataattata   1980
gctgttggaa tatgttcgta tagcaaattt tggagtaaaa caagagctat ttctatgtcc   2040
ctttctgctt accatgcctg ttgcagacat cttctgctga aaagacttgt caatgcaacg   2100
aacttccaaa tgaaagagtc acttagagct cctagcataa gaaaacttaa gtactagctc   2160
tcatatattt gtctgctgct tcttgctgaa tcttgttacc tgcaaatttg aaccattatg   2220
tagttacaca agcactcagt ggaccagtat gaaagtgatc taacaatggt ggttcattcg   2280
ctgattcttt cgttgggcga gtcctgccat cttagcaagc ctgagacttg caatgcgagc   2340
tgcatcagat ctaatctagt gaagctccta cagtcttgcg gttatgatgc agctttgtgt   2400
tcaaccaagt ggcaggggttg tggaaagatt cctggaggta tgctttcaaa gattattact   2460
tatctgaatt cgtttcctgc atgtttgcta ccttaagatg tctaactatg aatatttctt   2520
tggcttataa agaaagtctt tcacggtgct acggtgtttt gtattacttc caatatatct   2580
atatgctggg ttccaactta gttctagtgt caatgtgtgc aaaatatgtg gcattgtcta   2640
ccatatatat tagtagattc aacaagataa tgttcccatg gaactttatc ttttgattaa   2700
aataattaac ttttcaattt tgagcgaaaa atttaccgtg gtaataacgt ctgctgaaat   2760
aaatatgaga gctggagttc tgcctgacat tgtgctactt ttcctatgtt atgaaggtga   2820
acatgagtat attgaggtga tctcacgtgg aaatgatgaa tgctctgaaa ggtacatcat   2880
tgacatcgac ttcaggagcc actttgagat tgcaagagct gtcaaatcct acaatgtggt   2940
cttgagttgt cttccaccag tgtatgttgg cacagtaaga aagcttaagc aatatcttca   3000
gactatggta gaagcagcga gatgttcgct caaacagaac tcaatgcctc ttcctccgtg   3060
gcgatccctt gcttatctgg aagccaagtg ggaatcatcc agtcaaagag tagccaactt   3120
tcaggtccaa agcagcattg gcccctctaa ttcctctcat cagcattgta ctgagctgtt   3180
gtggaggata aaatccagta ttgggtctga aatcaacgcc aaaagtttct tggttcctaa   3240
aagctgtaga aagaagcagg gactaaagat tgataaattg aggcattctt caccagtgac   3300
accgtga                                                            3307

SEQ ID NO: 25           moltype = DNA   length = 840
FEATURE                 Location/Qualifiers
source                  1..840
                        mol_type = other DNA
                        organism = synthetic construct
SEQUENCE: 25
atgcaggaag aagaatttttt ctgccctagc tttagcagct attcctcaaa tagagcggcg   60
gagattgccg ctaaaatctc cgatgaaatt gaacgcaatt ctaaggtggc ggagcaggcg   120
gaggtggaag cgaacgctgg cgaggatgat tttgaattct ctttggtatg tgaaaatcca   180
gaagcttcgg ttgggaatt cttctacgac cgtcaaatcc agcctgtttt ccccgttttc   240
aaccgcgatc tgttactaaa cgttgtttct tatgacgtag atcacaaagg cggcgttgac   300
```

```
ggcgaatcgt cggaaaatgc caatagttca atccaggttt cgttaaagga tttgttttta  360
gaagatcgcg aaccgccgtc gtcgtcgtca tcggaggtcg atgagttgga aagtgtacct  420
ccgggaacct actgtgtatg gaaaccgcag ataaccgagc cttcaccgag cagatgtaag  480
aagagtaatt caacaggatc ggcgtttaag cggtggagta ttcgagattt gatgcgtcgg  540
agtaatagcg acgggaagga cagttttgta tttttaacgc aggaaaaagg aacgaaaaac  600
gaaacttcca aaacaaagga ctcagttgag gcatcgaaag taaccggaaa attaaaggca  660
aagggaagta gtaacgtcgg agagaaggca tcttcgtcgg cggctgttta tttacggaac  720
caagcggcgg caaaggaaat ggataagaat aagaggaaat catacttacc gtatcggcaa  780
gatctggtag gtattttcgc aaatgttaac agtttaggga gaacttttcc acctttctag  840
```

SEQ ID NO: 26          moltype = DNA   length = 2254
FEATURE                Location/Qualifiers
source                 1..2254
                       mol_type = other DNA
                       organism = synthetic construct
SEQUENCE: 26

```
atggagaaaa agcagctgga tttcaatgca ccactttat cagtgaggaa aatttcatca  60
tctttatccc ctcatgagag agcaaataaa aagattatag aaagggcgcc accgaatcga  120
caacaatcac ttcctgtcaa aaaatcagat tgggaattga gtgaagtgac taaaccagta  180
gctgttccat ttatgtggga acaaatccct ggtagacgaa aagtaacaa tgatgcccga  240
gctaaccttc gagtggagtg ctcaagtagt cctaggctgc cccccggaag attgccagag  300
actattcggt tctattcggg tgaaaggcct cgtgctcaaa acatttacaa gtctccagct  360
gaaggacttc cttggattga tcatgcagct ttactggata gcctagtgga aagtatatat  420
acaagaggag acagagaaag tgaggatgat gcttattctg atgctcctga aaccttgtca  480
cctaccgaat ccttatcctt ggactgcagt gtcagtggtc tgagcggaca tcaaagttcg  540
gattcaaaac catctggaac cttttccatt gactcccaaa ctagagactt tatgatgagc  600
cgattcttac ctgcagcaaa agctgttgtt ttggagacgc ctcagtatgt tcaaaaaaag  660
caagttccag tcagtactga acaaccgaag ccagtacccg tggaacgaaa gccaacagtt  720
aagcggatgg agtctaaacc tgtctcatat tatagcggct atccagacga tgtaggaagt  780
gaaattgaag atgatgtgtc tgagaatcag cacaaaaggc caagtaaagg gtggaaattt  840
ttccctcgga tttgtgtgaa gaattcttta tgcctattaa atccactgcc aggactgaaa  900
gtgaaaacac acgttcccac accctcatct caagcagtaa agagagtttc aggattgaaa  960
ccaaagacgc cccagagtcc cacatcttat gctcatgaag tcaaaagatt agctagaaaa  1020
gcttatagtg gtcctcttga gaaggtaatc attatagttt tcctcagtta tttttttctg  1080
tcctaagatt aataagattt atgcttgttt ctaacaataa tgttctttgc agaattcttg  1140
tgatactata aataagcaaa gatttcactc tggagtactg tctcgcgagc tttacaaagc  1200
tgataataga agtttttccg gccaactacc taaccctagt gattcatgta agctagttgg  1260
aatctctcct ggaagacgtt caagaagtgg ggctatatct ccctatcgaa atgtagcacc  1320
cccatctcca ttcaatgaag gtacaaggtt tcttggtgtg ccaaaggaaa tggagagtct  1380
ttgggctagt cgctttgatt cattccggaa aggttgctac actgtcaagg acaaagtacc  1440
acagcagatt ggcacaggaa ggttttctga ttcaccaagt gaagtagttg agaaaacatt  1500
gtacatagat tctgtagata atgtgcaaat ttcagcccgt aattctgctt cttcaaaacc  1560
caaggggatta gtgaactcct ctagtaagaa tatgaagaca ctggttaaaa gcagtgtagt  1620
actagaaaat atggatgcca cggctcgtac tcaaggtgcc aagaactgga atgtttcaga  1680
gaaagagagc aaacagattg ctgaaaagga gtcccttgat ttggtggaag cttctcccgt  1740
ttccatatca actctcaaag gccctgctga tcaggagtct ttgaaactaa agcaaaatct  1800
tgatacacta tctggagcct tagagtcttc aaaagtgcat ccctatgaaa atttaggtac  1860
agaaaatgaa gataacaaaa atgcaaatga cccaaaagat tctaacctta cctccgtgga  1920
atctcctata ccaccaccct tgcctaaatc tccctctgaa tcttggcttt ggcgcacgtt  1980
gccttccatt cctttgagaa ccccattctc aagtttgagc tccaagaagc agaacaagaa  2040
gtcccacact gatggtacca agtgggagac tattgtgaaa acttctaact tgcataagga  2100
tcatgtccgt tactccgagg taacctctcc ttattttttg aagttttctg ttgcaaattt  2160
tgatgtttga gaaagtggaa ttatttactt ctgctccatt ttgtttgaac aggaactata  2220
tactcttggt tcttgtcagc agagcaaagc ttga                               2254
```

SEQ ID NO: 27          moltype = DNA   length = 2770
FEATURE                Location/Qualifiers
source                 1..2770
                       mol_type = other DNA
                       organism = synthetic construct
SEQUENCE: 27

```
atggaaaatag ctcggagctc aagaagatgc aaatgggtta cagcatttct tgttctacta  60
gcttgctcag ctgctggaca agttgaagat ggtacgcccc ttcttcttcc ctttctattt  120
taccatttcc cactttgaag atcatattat tttcataaac aaaaaatgaa atttatgctt  180
gatgggattt accaacttgg tatgagatct gatgaacaat ttcttttgtc ttcattttca  240
gcttcaatgt atgttaattt aagcatataa cacgatgatg tcatctgaag actcaaattc  300
taacattggt agaaatattt aattttaaac aatggagtag tgtatttgtt cgtaaatttt  360
gttcctctgt ctcaaacagg attattttcc tccaatttcc ggaagcaaca ttttaatatg  420
tttgtatcac atgaaaatat tgtaaagtta aattgttttt tttaaatctt aaaataacaa  480
ataaaagtta tattaataag taattatgta gttgatgttg atgatcatga ggtgttattg  540
cgacaccctc accctataag aatcatgaca atgcaggggt tatggtcctc actccacaca  600
attagaccgc tatttctatt ttgatatttt gtgtacgttt gatttacata ttataagttt  660
atttttaattt cttaatgtcg tacacattca ttaggagtga gttggtgggg gagctatagt  720
atcattacta atttcaataa ttaccattgg ttacattttt aggcctacag agttactaca  780
caggacttat ttgcataaat attccttcat aatttgtgaa agtgattacc tcagttgagt  840
gccgtgtgaa gtgaatgttc cttcatgtca tacactaatt tttggtacga ttttgaagtg  900
ggctcaataa taaatgctac cttttcttta tatgggtctt tttcacataa tgtgtgcata  960
aatatttttt catgtataat agccactaag cttaattat ttccaaaaat tagcttatga  1020
agctaagatt ttaaaaaaga gacaatattg gaaacaaaga caacgaaatc ttaactacaa  1080
```

```
tgagttgata ttgcccaagt gaaaatatat tttagttata tatcttagta aaacatttac   1140
tagtggaaac cttctctcag tgctgatagt aaagaaaaac aaaaacaacc ccatatcttt   1200
attaaattat caatccaacc ttgtggtttt gcaggtccgt tagttaacgg tgattttgag   1260
acacctccgt caggcggttt ctcttccggc gacggattct ctgatggccc tctcgtactc   1320
cctagctgga aaacaaacgg caccgtcgag ctagtgaat caggggcaaaa acaggggtggg   1380
atgatcctca tcgtaccaca aggtagacac gcagttcggc tcggaaacga cgccgagata   1440
agtcaagagc tcaaagtcga gaaaggctcc atttattcag tcacgttcag cgcggctcgc   1500
acctgcgccc agctagagtc actgaacgtg tcggttcctc cggcgtcaca gaccatcgat   1560
cttcagactc tgtataatgt ccagggctgg gattcctacg cgtgggcctt tcaagccgag   1620
gaagatgacg tgcgtgccgt tttcacaaat cctggcatgg aagatgaccc tacttgtggg   1680
cccattattg atgatattgc tatcaagaag ctttctcactc cagataagtc caaaggtaag   1740
gtcacttctg tttctttact ttcttatttg ggcccatttc cagctgttta tcacaccacg   1800
ttttggtcaa agatttgatt ctaattgaaa tatctacttg ggttttgaga aaaatttgaa   1860
tggcaaaaag aataacttaa ataaggtttg gcatagaagt actgcaaatc tcaaaattag   1920
ttttgatgtt ttcataactt ctcatattat ggagaattag gaaaaaattc agatgatcaa   1980
catgaagccg agaaataggt tcattcacct tctagctagt ttttcgacga cttttaatgca   2040
tttctcgcat ggcttgtaca tgaaactcgt gatggatgca tgaacaaaag acactctttt   2100
gatgttaaaa aaacctgaag cagaatgcaa catgtaaata actacaaatg ttgctaactt   2160
gttccttatg ttggctatcg gaacagataa tgcagtactt aatggcgact ttgaagaagg   2220
tccatggatg ttcaggaatg cttccctcgg tgttctgctt ccaaccaacc tcgacgagga   2280
aacatcatcg ctacctggtt ggatagttga atcaaatcga gcggttcggt atattgataa   2340
ttatcacttt acagttccag aagggaaaag agctatagaa ttgctttcag gaaaagaagg   2400
cattatatct cagatggttg aaaccaagcc caacaagcca tacagattga cattttttgtt   2460
gggccatgca ggggactcat gcaagcagcc actggctgtt atggcgttcg ccggtgatca   2520
ggcccaaaac atccattaca ctcccaattc caattcttca tttcagattg ctaatctgaa   2580
tttcacggct aaggcggaca ggacacgtgt tgcgttctat agtatctatt acaacacaag   2640
gagtgatgat atgagctctc tttgtgtgacc tgttgtggat gatgtgaggg ttgaagtatc   2700
tgggtctagc acagtcaagg ttttgggggtt cgggtttatg ttgtggctgt tagtcttagt   2760
attggtttaa                                                           2770
```

SEQ ID NO: 28          moltype = DNA   length = 1808
FEATURE                Location/Qualifiers
source                 1..1808
                       mol_type = other DNA
                       organism = synthetic construct
SEQUENCE: 28
```
atgagaacat tgtgtccaaa tttggacaag gcagatgggt tggagacagt tttggaggtc    60
cccataccag aggagatgtt taacaatatg ggtagcaatg gtgccttaca atggcggaat   120
atgcgcaatc ttatgagggc tcaaagtgca gacagatatt cttcttcttc tcatcatgcc   180
gctgtatcaa gtaatgatca attcatgttc ttgtttaaaa tcgttggctc tgctcttgtc   240
cctttcaag ttcaattgga ccatattgct gataacatgc ctgttaggaa tggttcaatg    300
gtaagcactc tattccttgt ttcctttct tattgaacat tcttgaatgc gattaaatct    360
taaaattgga taaatctag caatataact tgttattttt ggtaaaccat tctccaaata    420
ttgacaatta caggctttaa aaatgtaaac tgtatttgtt gtttcaagag ttttagagaa    480
acaatgtcta gttcctattt tcagtgctgc taccatttc ttgtttttgta cttgtatcta    540
aaattttgcc ctggccagat gctcttgttc aactccttag atatgaataa ggttcaagga    600
aaaaagacaa aagaaaatgt tttaactgat ttagatttca gataaaaaa ctatatatgt     660
tgaactcata actcgtacgt tatggtcatc aggaggctgc tactgctaaa tacatagtac    720
aacaatattt ggcagcatgt ggagggcagg cggcgttaaa ttcgctaaat agcatgtgtg    780
cagtagggca ggtgaagatg gctacatggg acatccatca aagtggtggt gacgccaact    840
cgaaacgcca ttgtgaggtt ggagcctttg tgctttggca gaagaaccct gacctgtggg    900
ttttagaatt ggttgtttca ggttgcaaga taagtgcagg aagtaatggg aaggttgctt    960
ggagtcagtc ttcctctact tctagtgctt caaaaggtcc tccaagaccc cttagaaggt   1020
ttttccaggt atccttttgc tgatgaaagt gttacataca cagcatttct gtaattaaat   1080
catgcctata gtctttgctt caacagaatg gagacatagt tggtacaacc aaatgcaatg   1140
aaatgagaat tctttaatat atttcggttg cttacctaga atgcatgcat aattttgatg   1200
gcaaaataaa tcatgtatct tctaatacat attcatgact ttttgcatgc tcatccaact   1260
gcttaaattg actttaaggg tcattcaaat gcgagtttat gtattttgat gaacagggct   1320
tggaccctag atcaacggcc aatttgttct tgaatgctat ttgcgttgga gaaaagacta   1380
ttaaggatga agaatgtttt attttaaaac tagaatcaag catagacatg ctcaaggcac   1440
aaagtacggc aaatacagaa gttgtccatc acacaatatt gggatacttc agccaaagga   1500
cagggcttct gattcaattt gaagacacaa aattagtaag attgaagtca ccaaaggggg   1560
atagcaatgt cttttgggaa acaagtatgg aatctatgct tgaagattat agatatattg   1620
aaggtatcaa cattgctcac agtgggaaga ctgcagcaa actttacga tatggaaaga   1680
acatagacta tagagcaaag attgaggaga cttggatgat tgaagagatt gatttcaata   1740
tatctgattt gccaatggac tgcttcttgc ctcctgctga atttgaagag caaggaatgg   1800
gttgctga                                                            1808
```

SEQ ID NO: 29          moltype = DNA   length = 1076
FEATURE                Location/Qualifiers
source                 1..1076
                       mol_type = other DNA
                       organism = synthetic construct
SEQUENCE: 29
```
atgctgcaac atctttatct tggtcaattt tctatgatgt ttcttcttct attatgttct    60
attttttgcag tattaacgac tgcagaatca tctatatacg aagtgcttga atcccatgga   120
ttgccaatgg gtttacttcc aaaaggtgtg aagaatttca cattagacaa ttcggggaaa   180
tttgtagtcc atttggatca agcttgcaat gctaaattcg agaatgagtt tcactatgat   240
aggaatgtat cgggtacaat aagttacgga cagatccatg cactttcagg aattgaggct   300
```

-continued

```
caagatttgt ttctatggtt tccagtgaag gatattcggg ttgatatacc cagttctggt   360
ttgatttact tcaacgttgg cgttgtatct aagcaattct ctttgtcttc atttgagact   420
cctagggatt gtactgctgt tcaactcacg gatcttcagg atgacatgca catagctgac   480
gctatttcta aggtctttc tcttccttga ttcagtcttt tctaagttga ccatttctg     540
ctctagtttc tatgaaactt ttgcttattt tgtttggaac aattgaagac acgttgtcca   600
gtaatttggc tacgtctgta agtccctgt aacacaggaa cttgtaccaa ggtttgaact    660
tcttcaagaa caattattcc ccaaatggat gggtgaatct aagcttggtt attttagttc    720
tgattattca agtgtatagt tctttgcatt atttggtttc tgcttcattt gttgtccaaa   780
ttgcagtact agtatttgca aaaattgcag gcagattatt gcaagcactg tcctttttct    840
gttcaatttg gatgttgtat ataaatattt tgaagctaat gaaatgttca cataatgtgc   900
tttaagtagt agtagtatat atgatatctg cttctgcatt ttgaagttca tttttgtgaa   960
agtgttccct gtttgtttat taattcttgg aatggttatt tgttgagcag agtcaatcag   1020
gggagcttcg gtacaagttt gatcagggca atatcgggag gaaggctata ttgtag        1076
```

SEQ ID NO: 30          moltype = DNA  length = 918
FEATURE                Location/Qualifiers
source                 1..918
                       mol_type = other DNA
                       organism = synthetic construct
SEQUENCE: 30
```
atgcaagctt atggtagaat gaagagagta actgacccgc ttgacgacaa agtgaaggct   60
cggatcattg ggcgtgacca gcaggaactc ggttacctca gcagcggaag cgaacacagc   120
gcccacgccg atgatgatgc ttcctgtagc ttttctactc tcatatttgg tttgcctgat   180
gatgtggcgg ccgaaaatat gtcgtcgag aatgattcag actccgacga cggagatgtg    240
tcaatgtacg agtcgacgga cgtgattgaa gatttgccaa agccagtgtt ttatagcgat   300
ctggatttgt ttcgtaattc gctggcgact aagattacta aggcactgga aatgttttcc   360
ttttcgaaat cgaataagcc aatcctgagg cgaaatgtaa tgacctatct tagggatttt   420
ggttataatg ccgctatatg caagacgaaa tgggagagtt ccggtggact taaggccgga   480
aactacgagt tccttgatgt gatccgatcg gattccggta accggatcac tcgttacttt   540
atcgacctcg attttgcggc ggagttcgag atagcaaggc ctacgaatca ctacgagcgt   600
ttatcgcaat cgttgccgag ggttttcgta ggtaaaagcg aagagttaaa gaagatgttg    660
aaggtaatga gcgacgccgg taggcgttcg ctgaaaagca aagacctcag tattcctccg    720
tggagaaaac accggttcat gcagaataag tggttaggtg cttacaaacg gacaaccaac   780
gttctcccgt cggcaaactc atcggcgttg ttgtcgccgt cgaagcagac taacgtcgct   840
aagtgccggt ccgttgggtt tagcgctgtc gccgttaacg gccgtttact ctttcccgcg   900
gcaacccgta caagatga                                                   918
```

SEQ ID NO: 31          moltype = DNA  length = 1086
FEATURE                Location/Qualifiers
source                 1..1086
                       mol_type = other DNA
                       organism = synthetic construct
SEQUENCE: 31
```
atggctagta ggaaacgaag catctcaaat gatgtagata tgcatgtcct ttacaaggaa   60
ttggatgaag cttcatgccc tgtatgcatg gatcatccac acaatgctgt tcttctcatt    120
tgtagctctc atgataaggg atgccggtca tacatttgtg atacaagtta tcgacattca    180
aattgcctgg atcgtttcaa aaaactcaga gccgaaaata gggacagtcc tcctattatg    240
acacagggaa acctggacat tgctgttgag aaccccgatg agcagttgag aaatttaagc    300
gatcgttctg ttgttcatgg aaatagtaac agagataatc acatggagat gcatgaaggt   360
actgtacaaa cttcaggtgc tgctactgta tggggaagta gtcaagaaac agcgagtgct   420
gacggctcat ctgactcaaa attgaaattg aagtgtccta tgtgccgtgg agatgtatta   480
ggctggaaag tagtggaaga agccagaaag tatctgaatt tgaagaatag aagttgctct   540
cgtgaatcat gctcattcgt tggtaactac agagaattgc gccggcatgc taggagagtt   600
cacccgacag cacgccctgc tgatattgac ccttccagac agcgagcttg gagacggctt    660
gaaagccaaa gagagtatga tgacattgtc agtgctgttc gctctgccat gcctggtgcc   720
gtcgtgcttg gagattatgt gattgagagt gggacaggc tatccggtga aagagaacga    780
ggcgcgggtg aaacagcag gtggttgagt accttcttct tgtttcagat gattggttca     840
atggacccaa tatctgaagc aagaggtggc aggtcaagag ctttgtcaag gcaccgtcgg   900
tccactggac ctttatctag gcgccgctat cttttggggtg aaaacctgct aggtctacaa   960
gacgatgacg aggatgaaga tgagcgtgat cttaacatat tgagtgacat gagtggtgac   1020
atacctacaa atccaagaag gcgtaggcgg ttgatgcggt cgaggtcaga tgaagatcag   1080
caatag                                                                1086
```

SEQ ID NO: 32          moltype = DNA  length = 2143
FEATURE                Location/Qualifiers
source                 1..2143
                       mol_type = other DNA
                       organism = synthetic construct
SEQUENCE: 32
```
atgccttttc cgatgaagat tcaacctgtt gatttcaata ccgtggaaga accgagtcga   60
tatgactcgt ttaagccggt tcaaaagtca cggttcaagc ggctattcga gaggcaattt    120
tcaggacttt tgagatcatc ggcgccgctg agaagctgg tggccggcga agagttgatt     180
tgtaataaga aggatgttgc gtccgacgag ttcgagccga gctccgtttg tttggctaaa    240
atggcacaga ctttcattga agaaggtgag gccgataaac atcggtgcaa tcggaaccga   300
aaatgcaatt gctttaactg taatggtact gacagctcag aggaggaaac tgattcactc   360
agttgcttcg gtaatcgaa tcatacttgt tgcaacgatg cttgtgaaat cctcaaggta    420
ttgcatgttc cattaatatg caattttacc ttaatttgtt gttaaaattc ttcttagagt   480
taaattaaca gtgtctgttc tttgcgtgtt tctcaaaata actccctttt tggtgtagag   540
tttggtgccg tgtccttccg ttattgaaag gaacgtttta gctgatatta caaagatcat   600
```

```
tgagaaaaac aagatgggaa agcgaaagga caatttcatc cgaaagatag ttgttgatgg   660
cctcttagct gcgggatatg atgcttcaat ctgcgagtct cgctgggaca aaactccttc   720
cactcctgcc ggtaaactca caatttcaac aacaaagatg tgctggattt ttttgcttaa   780
atctgaattg gaaactatta acttcatgct catatgtgta ctgacatata aatctcttta   840
gttttgtatg gttaaagatc tatatatatt ccagtaactg tgagatgaca tataaatctc   900
tttagttttg tatggttaaa gatctactat atatattcca gtaactgtga gagtgagaat   960
attaatttta aagtcgtcaa attattgcta aaggtattgc aatgcatctg accgaaaata  1020
gagcagaatg gatacaaaaa cttacaatga agtcaattgg ttcattcatc atataatcga  1080
tcctattatt tcgacacaga agacacatat aattgatccc aattagttcc agattaaggc  1140
ctaatagcaa gaaaacttgg tctgcaacat ggcaagttac aacttgcatt ttgtttata   1200
ttcaggctag cttaaatgga gaaacatgaa caatgaagat tcatatagcc aataccaacg  1260
tgtttgggac tgaggcatag ttgttggcta tctgcttagg ctgccttttt ttctttcttg  1320
ctattatggg gctaagaatt caacaaaaag tctgaatctt ttctacagga gcgtatgaat  1380
atgttgatgt ttgctattat ttttgggtta agatttcaac aagactctat cttttcgaca  1440
ggatcgtatg aatatattga agttgttgtg tatgaatatg ttgatgttgt ttgctattta  1500
ttgggttaag agttcaacag aagtctgaaa attttctaca ggaacgtacg agtatgttga  1560
tgtggtgatt gaaggagaaa gactactaat tgacattgat ttcagatcag agtttgaaat  1620
agcaaggtcg accaggtcct acaaatttct cctccaattg ctgcccaaca cttttgtagg  1680
caaagcggat cgccttcaga agattgttca tttgctaaca gaggctgcaa agcagagctt  1740
gaagaagaaa ggaatgcctt ttcctccatg gcgtaaagct gaatacgtga aagccaaatg  1800
gctgtcacct tacacccgta tcaaaccaac tctaatgggg gcaccaaccg tgtcaaactc  1860
tgctcccgaa actggcactg cttgcaaaac ctatcaacaa gcggtaaagg aggagtcttc  1920
agaggattct tgcggggagc tgaatctgat ttttggagag agcagccaac tcttggagaa  1980
taacgccaag agcgtgatta cctatcctct atctgcttgt gatgacgaag aaaaggatgt  2040
gatggtgcag caaggcaaac cacctgacac taaacacaag gattcaagca atggtgccag  2100
gaagataact ggtttaactt ctctgattga agaccacaca tga                    2143
```

```
SEQ ID NO: 33          moltype = DNA   length = 495
FEATURE                Location/Qualifiers
source                 1..495
                       mol_type = other DNA
                       organism = synthetic construct
SEQUENCE: 33
atgccaatgt ctttaacaag cattctctgc ttcttctttc tcttctttttc agccacaaca   60
gcttcaagaa atgagaagcc atcagcctat gaagagctgc agcgttatga cttcccaatg  120
gggattcttc caaaaggggt aaaagactat aaattaaaca ccaaaacagg tgaattctca  180
gcttatctta attccacatg cagcttcaga ttggaaaact cgtatcagct aaaattacaag  240
cctgttataa aaggggttat atcaaaaggc aggcttacaa aactgagtgg tgtaagtgtt  300
aaagtggtgt tgctatggct taacattgtt gaagttaggc gtaaaggtga gaatcttgag  360
ttctcagttg ggctcacatc ggcgaatttt ccgattgcga acttcgagga atgcccacaa  420
tgtgggtgtg gattggattg tgttagtaaa gaggagagaa agattagaca gaaggtcttt  480
gtgtcttctt cttag                                                   495
```

```
SEQ ID NO: 34          moltype = DNA   length = 419
FEATURE                Location/Qualifiers
source                 1..419
                       mol_type = other DNA
                       organism = synthetic construct
SEQUENCE: 34
atggaggagc tccgcccgag tttccggtgc tccggcgacc gaagactaga gatcgtaagc   60
ggaaaagggt tcagcagcaa ccaggtaagc gttacgcata ttaaatttcg aactcataat  120
tttttaagaac cttaaagttg aactattaag tttaaatttt agattcgcct cagcagggaa  180
gtcgggctcg ctcaccggat ctaccagtag taacgagcaa gggaacttgg ccgagccagg  240
tggcagcagc aacttcatcg tcagctaagc cctgggatt caatgatcca gagatgaaga  300
gacgaaagag aatagcaaag tacaaagtgt atactattga aggaaagttc aagacttcca  360
ttaggaatgg actgaggtgg ttcaagaata aatgctctga aatcatccat ggctattaa   419
```

```
SEQ ID NO: 35          moltype = DNA   length = 3589
FEATURE                Location/Qualifiers
source                 1..3589
                       mol_type = other DNA
                       organism = synthetic construct
SEQUENCE: 35
atggggtttt cggagaacaa tagaggatta gttctagcaa tggtgtccag cttgttcatt   60
ggaacgagtt ttatattgaa gaagaaaggt ctccggcgtg ctgctgctgc tggcactcgt  120
gcaggtctga aacgtctcta tgtgtttgtg tgtgtggtgt gttagatctt tacttcggtt  180
tattagtcaa tttactatat gaaaaggcac aaatttgttcg ctagcttaaa cttgaagtac  240
ttgtgtagat gcacaattcc agcaacttgt gttgaaaacg ctttatgtgt gatattagtg  300
acaaaatata tcaatcaact gcgcatttgg taccaaatta gttggcctc gacttaatga   360
accctctatc gaggcctgtt taatattcaa aagaatcatc acaggcagat tatttttagc  420
tgacattagt tctttatcat gacttaggac caaaaaagct ttgcgaaact catgtagaca  480
aagttacctt agtgaaagaa tatactgcat taattattct ttatttagtg aatattgcta  540
ttttacatat ctaatatcta agcatgttaa ggacattgta tctcaactta ggtgaaaatt  600
gttctgttca atttgttgta tttatgttgg ttcttctttg tttgatcaag acaatatttt  660
tttgggtgtg taattctttg ttcattaggg tctataggca ccatctggta gactatgtga  720
tagtagcaca taattactca attagagcca agcatactag gattttttaat catttaggtg  780
gtggaaacaa tatccttcag gatcactttc agttaggtat tacactgttc aggcctgtgt  840
tggaatacat aaatgatgtg ggggatgggc acgagaaaag agaagagaaa atgtagaaat  900
ctattatttg gatatgtaga gggaactgct gaagtgaaaa atatgaggtc taaaggcaaa  960
```

```
caaatcaact tcatgttttt gtgctgagtc tattgacaac ttttctagcc ccattaggtc   1020
cagccttctt ctggtagcac tggaatagcc gaattgggtt cttgacattt agtttttcttc  1080
ttcttcctgt tgtcattttc tttaatttaa accatgagta gaagattgac aaataatagt   1140
tgtctagcag actaaaacat tgcagcccca tgtgtattta ctagtagttt ttattcttat   1200
tcatgatctt gcaaacccat acataaatatg agaagaacta tctttggttg gacattctag  1260
tgggagctga agcttttatc cctgaagtac ttgtgagttt cacatgcagt aatctattcc   1320
agtacttcta gctgatgata gtttgcttgg aagtaaatgt agtttttgatt tttagatgta   1380
gtctagtgtg ccaattttct atttagtact tcaattgata gcagaacatc aaacatcgta   1440
tttagcatcc tttatcctca ttatttactc agtcaacttc aattcacctg gctaaacagt   1500
tgttgtagtt ttcactgcag gagttggaga ttatacttat ttgcttgaac ccctttggtg   1560
ggcaggcatg attacaagta agttgacata agctgtctcc ataagttaac ctcttttccag  1620
gattgtgtta cattgttctg gtgttaatgt catttggatt tggacatgca gtgattgttg   1680
gggaggcttc caattttgtg gcttatattt atgctccggc ggttcttgtg acccctcttg   1740
gcgcgttgag tataattata aggtatgatt ttgaagtctt atgagctgtt ttataactct   1800
gataaggaac tcctggtgat gtttgtgtaa ctgactttgg tgaatctgaa tagtgctctt   1860
ttggcacact ttatgttgag ggaacgatta caacggttgg gtgtggtagg atgcatattg   1920
tgcattgtag gatctgtggt aatttttata catgcacctc aggagcatat gccaacttct   1980
gtacaagaaa tctggatttt ggcaattcaa ccaggtctgg actttttgta ggttgtaaga   2040
tatttctccc tcttgcagag cttattagta atttctcctt gcttcttttg tcagcagcat   2100
ttatgattta tatagcagca acagtatcca cagtagtagc tttgatgttg cattttgggc   2160
ctcgttatgg gcagacgaac ttactggtct atttggtaat atgttcccta atgggtgcac   2220
ttacggtaat tatgttttgt tctagtctac ttccgtcatc tccttttatt ctttggtgga   2280
atttgtacaa ctacattctt gttggacatg atacagtttt gcacatgtga acattttgct   2340
agcctgttaa gatgttctgt aaaattttat tgtattttgc aggttgtcag cataaaggct   2400
attggaattg caataaaaact tactttggaa ggaattagtc agattgccta tccgcagact   2460
tggtttttttc tagctgttgc agtaatctgt gtaatcacac agttgaatta tctaaacaag   2520
gtaatgtctg tatggtactt tcccagctcg gctgagactt tcagtaatcc aatgatcact   2580
cgattacatt accttgacta gcgtgaagtc tcatttctct gaaataataa catgcctgtc   2640
ctttacgtta aaattcagaa tgcatctata ttgatgtcgt cctggcaaag catccaggac   2700
atgcatcatg catatatttg gtgtcagttc ctctgaacta aaatattgga gtagttattt   2760
ggatttatgc tcttcatgta atgatatcaa ttcttgcaca aggtgtcttt tgttaatgac   2820
atgaagataa aacatagaat caatacttga tgctaactat gctgcaatat ttttctgaag   2880
tctttaaatt atgtttctgt ttttaacttt tgtgatttgg caataaatgc tctaatttgg   2940
atcattatgt cacagacaaa taagtagagt actatgaaac tgaagccgtc cttaaatgat   3000
tcatagctct actcctaagt tgagatgaag gatactgcag ttcagattct cgtttccttt   3060
gttgctcttt cttgcatgct tgatatgtga gcagttttaa tatctgaaac gagtgctttg   3120
gttggtaatc taggaaaaag aagtttctac aatagttggt acgacttcat atcaatattt   3180
cccttatcac atgaaccttg agatgctgct tgaccattat agagcgcggt taatatgaac   3240
tgcatgctat tatgcctaat tttggttttg cagttcagca atatgcatta tatttagggg   3300
aattcacatt gcttttcttt agggtgtctg aaccattttc taacgtttat gcgtcatttg   3360
gataggcact ggatacattc aatgctgcaa ttgtttcccc aatatattat gtaatgttca   3420
ccactttgac catcattgca agcgcaataa tgttcaaggt atgttgtcag tttgaactat   3480
tcttaattgt ggtctcctat caatatgttc acggagtaaa atgtgaaccc atcatttgct   3540
tattgctttg caggactggg cgggacaaga tgctagcagc atagtatag                3589
```

```
SEQ ID NO: 36              moltype = DNA   length = 1777
FEATURE                    Location/Qualifiers
source                     1..1777
                           mol_type = other DNA
                           organism = synthetic construct
SEQUENCE: 36
atgggtacag atacagaggt agcagaaatg agttcaacac taaagcttcc tctgttttca   60
gtagagtcat cacaagagga tttagggatg ctaactcctc ttcacacttt agcttcaata   120
cctttcaaat gggaagaaga acctggaaaa cctcgtccat gcactgatct tatccctctt   180
ccaaactcca tatgtttaga accacctcct aggctttaca atatggaatt ttccaagaca   240
tcttcttctc ctacaactgt atttgatgga ccttatatta ccaacaagcc taggttttct   300
tcgtttaggt tgttgaggag ggatcgtcgt catcgtcgac aagggtcttt tgatagtact   360
actagctctg aaacaggaca acttagtact acacttgttc ttggtaacaa gaaatcggaa   420
agcaaaagct ggtggcgtcg gccgactact catcatgtta aacataatgg ctgtgagatt   480
aatagtggtt ttgtgtttcc atcttctata gattattcaa cagattgtgt tgaagaatgc   540
agcagttcca gtataaaaat ggaaacattt agaagaagtg gaagcttctc aggtcactcg   600
caagctaaga ctcacatctg ggtaagtgtc tttacaactc cactaattgt tcgttcgtaa   660
tcaatttatt atttatatgt agattttaat ttcattaatg aattttgcta ttactactgt   720
ttttcttctg tccgtctcat gtcaaattgc tctatctaag tcatgattcg tactctgcct   780
ttaacccccct tgtaattaac gtactatgat ctcaatgaac ttaggaacat tgaaagaaag   840
atgtacttac tatatagagt ctctacccta gattctttaa gaagattggc cgccccaccg   900
taggcctttt ggcatgtgtc gaggggaatt aaaaatataat atataaaagt ataaactgat   960
cttttgaatc ggcgaatgat tctgccccta aatacgccct tgcgccccac cctttccttt  1020
aagggatcaa ctgtttgttc tttgactata aaacttttcaa tcaatatatt tttagtaaaa  1080
ttcatgttac atagtttcca ttttttgttta aataaaactt gaagaataat gactgaatta  1140
ataagaatca actaactaga aataccttac agttcctttt tgtaatgagg gactaatatg   1200
aacagagaaa gtacagaact agtggggtga tagagtaatg agaaagctta attattgggg  1260
caggtgaggt tgaagaagac ggcagtgggg ctaaggaacg cctagttaac ttcactttttt  1320
aggcaatggg ggtaggtatt acacaaaccc acaaatagct gtaagcaatt atgtatcaaa   1380
atgttaaaag ctactactgt attaatagat ggggttgaat gagtaggtag atgctgtccc   1440
aagttatagg gcgtccattg tcattgcagt aaataggaaa ggggcgaagg atatgggctg   1500
tctgattgaa gctgctttgt aaaggattg ggagatatct ggagacttt ctccttagca     1560
tattttctat ccttgctctg ctatcattat cagcatttaa aatcatttgc gtgattcgtt   1620
ggatttcata attaaaactc ttctattttt ctatcagcat ttactaaact caagtattgg  1680
```

```
tcttgttgaa atcttacagg cagctatata cgagggtttc aagcaagtaa taccatggaa   1740
gaacagaaag tctaaaaagg aagcgctaat cggctaa                            1777

SEQ ID NO: 37          moltype = DNA  length = 1737
FEATURE                Location/Qualifiers
source                 1..1737
                       mol_type = other DNA
                       organism = synthetic construct
SEQUENCE: 37
atgtcagggt aagcttggtg atttgtaagc tttctcgtta atttctgttt ttttaatttc   60
ttatggtgtt caagttgctg tctttttta tttttagtag tctgcacgtt gtagaatttg    120
tatggtttgc tgaattgctt gatccacagt aagattagtc tttgcaagtt caatgttcaa   180
aattgtctgt atctctatta gaaagtgcta gccagaagta tttcctgttg cgatgcattc   240
cctggaatta aattaatctg tcattatttt gattgcttca aaggaaccca accagtagaa   300
ccatccaaaa cctggcattt cgtaggtcat ttgaagcaga accaaagaca attagccgta   360
tgacagtttc ttaactctat cttttggcca cctattatgt ctctgtagcc tatttatata   420
catattattt gttgttcgaa ttacaaaacc cctaaattgt catgctccgg atgcagagc    480
gacatatagc tagtgtttta tccaattagt ggaccacttt attttcatga aaaaatggac   540
atgttactgg atgtagacaa agtatcatga aaaaatagat tggcttagct tgcatatgga   600
catatttaag gtggatttga ttatttgctt tgatataccg agcttttctg agaaagaaac   660
ttgttgtgat gtcaacattc tgaattattc gagtttgagg tttttgtggc attggcttt   720
ataccattgt aatgtgacat tggatggtga tttcttgctt cgccaatctg gtctttgatg   780
tgtgcctatc tttaacttta gtgtaaggtg ttctctagct gacaattgtg taactgtaga   840
gaggatgctg ctgttcctgt tgtcgctgct gccgagactc ctgctccagc acttggggag   900
cccatggaca tcatgaccgc actacagctg gtgctaaaga agtctaaagc tcatggagga   960
cttgctcgag gactccatga aggtgctaag gtgattgaga agcatgctgc acagctttgt   1020
gtgctagctg aggactgtga ccagccagat tacgtcaaac tggtgaaagc actttgtgct   1080
gatcacaatg tcagtttaat tacagttccc aatgcaaaaa ctcttggcga atgggctggt   1140
gtaagtaatt ggtcattgct tatctatgac cccagttaca gtatctcagt tttttactat   1200
acacgagtag ctgtttttctg atgtgaaaat gaaattgata tgtgccttta ctagatactc   1260
catctttag aaggtgaagt gttttaggga cttgtgataa ataatactca gaatgccatg   1320
actgaagcct taacctcatg ttggactgtt tttcgcactt gtaatggagt ggaggggtac   1380
atgtgggttc tgactattaa cttgttgact cctctttgaa gtgttctgta tttctcattt   1440
ttgttgaagt gtatcatgta agtcgaaata taatcactca tcgactatga tctttcttcg   1500
attacagtta tgcaaaattg attctgaagg gaaagcaagg aaggttgttg gttgtggctg   1560
tgttgtcgtg aaggtacatc ctatttatcc tttggcttta catgagtagt atagctgata   1620
agtttccaaa ctggaattta tattccattg taatgatttt tctgattgat tctgcaggat   1680
tatggtgaag agactgaggg tctccatatc gtccaagagt acgtgaagtc tcattaa       1737

SEQ ID NO: 38          moltype = DNA  length = 2237
FEATURE                Location/Qualifiers
source                 1..2237
                       mol_type = other DNA
                       organism = synthetic construct
SEQUENCE: 38
atggggaaca gaagttcaaa tcttgataat gacaacaata tttcacgtcc aattgatact   60
ccatttaagc ttccttctcc gttgcccact tggccctcag gtactttctg tctatcaatg   120
tgtaatcttc cattatctta tcatttttgc tttactagta tctgatcact tctggtgttg   180
ttaaaggctc gcttaaagcg cgcttaattc taaagctcgg taaagcccaa gttgtgtgat   240
ttgcctcgct tagttgacgc gtgcctattt tcattgatgg gctatgtctt aagataacaa   300
cactgacaa taaatatatt tggcaaatag aaaaaaaaa ggcagtccga tgcacaaat    360
atcccgttca tgtacggtcg ggggaaagac cgcacctta ggctatgatg ttgacagtct    420
gtcctaaatac aagcattaga gggttcgagc cgtgaaacca atcattaata cttgcattag   480
aaaaagtcat ggctgaaatt ttagtgatta ttgtttgtgt tatagttata ttttcttgca   540
atacatgttt atctttttgt aaatattttg ttcattgtcg cttttctctg ctaaagccca   600
cgctttagtt gtgctttgcg cttaaagatt aatagactt tggcccttt tgtgcttttc     660
tcatttggct acttttgatca attgttctgt ttattttgat tgtttaaata ttaggtcaag   720
cctttgctac tggagttatt gatcttggag gtttagaagt gtctcaaaca tcatcattgg   780
ctaaagtttg ggctactcaa gaaagtggac cagatgatct tggagctaca ttctttgaac   840
catcaaattt accaaatggc ttctttatgc ttggatccta tagccaacct aacaatttac   900
ccctcttcgg atcggttctt gttggaaaag attcaaaagg agacgcgcta aagattccaa   960
ttgactatac acttgtatgg agtagtgaga acttgaatat caagcaggat agtgttggct   1020
atatttggct gccaattcct cctgaaggct ataaagccgt aggccacgtt gtaacaacgt   1080
cgcctcaaaa gccttctctt gacaaaattc gttgtgttcg ttctgattta accgatggt    1140
ctgaaagtga tgattggatt tggggcaata atggattgaa tgtgtattct tcaagaccaa   1200
gagacagagg aatcaatgct ttaggagtct ctactggtgc ttttgtggct tcaaataatg   1260
gaactgcaga ttcattagct tgtttgaaaa atgtcaatgc taatttatct gctatgccaa   1320
atttgaacca agttaaagca ctatttcaag cctactctcc tttgtactac ttccatcctg   1380
atgaacaata ttatccttct tctgtcactt ggttttttca gaatggagca ttattatata   1440
ccaaaggtca agaatctgca ccagttgcta ttgagtcaaa tggttcaaat cttcctcaag   1500
gtggttcaaa tgatggtgct ttttggttgg atttgccaac tgatgattcc gcgaaagatc   1560
aagtcaaaaa aggagatttg caggctgcta cagcctactt acacattaaa ccaatgtttg   1620
gcgcgacgta tactgatatt gctctgtggc tattttaccc ctttaatggc cctgctagag   1680
caaaaattga attcatgact attccattag ggaaaattgg acaacatgtc ggcgattggg   1740
aacatgttac gttaaggatt agcaacttca atggggagtt acaaggtgtg tacttttctc   1800
aacacagtgg aggaaattgg gtaagtgctc ctcagcttga attccaaaat ggtaacaaac   1860
ccgtggccta ttcatcgttg cacggtcacg cttcttatgc ccaaccagga aaaaatctgc   1920
aggggaataa caacataggc ttaagaaatg acacagcaaa agggcaaatg atggacactg   1980
gagcaaacta ttcaatagtt gctgctgaat acttaacaat tgttgagcca gcatggttga   2040
```

```
actatgctag agaatggggt ctgaaaatca gttatgatat tgcaaatgaa ctccaaaaag   2100
tggagagatt tttgccagga aaactgaaga atgctgttga gaaacttgtg aaaagtctac   2160
caaatgaggt gttgggtgag gaaggaccaa ctggacccaa gtttaaggac atgtggaatg   2220
gggatgaaag gggttaa                                                  2237

SEQ ID NO: 39              moltype = DNA   length = 492
FEATURE                    Location/Qualifiers
source                     1..492
                           mol_type = other DNA
                           organism = synthetic construct
SEQUENCE: 39
atggctttct ctcaaaagtc acaactcttg ttttgctctc tcctcttcat cttaatctcc   60
ctttctctct ccttcaatcc tagccgtcca aataaagatg atgatgtcca tgatctcctt   120
ccttcctaca atcttccaat tggacttctc ccaaataatg tgaaatccta cactctttct   180
cctaaagaca actcttttac agtccaactc acacacccctt gttatgtaca gttccaagat   240
caacttgttt actaccaaaa agaaatcaaa gggaaaatga gttatggtga ggtttctgat   300
gtctctggaa tccaagctaa gaaactgttc gtgtgggtcc ctgtaacagg gattaatgtt   360
gatgaggagt ctcatatgat tgaattccat gttgggtttt tgtctgagaa gttgcctgct   420
aaggattttg agactattcc cacttgtaag aataataagg ggtgccaaga ttctctcctt   480
tcttcaatat ga                                                       492

SEQ ID NO: 40              moltype = DNA   length = 902
FEATURE                    Location/Qualifiers
source                     1..902
                           mol_type = other DNA
                           organism = synthetic construct
SEQUENCE: 40
atgttgcttg gaaagaggcc aaggccacca atcaaaagaa caacaagcat gaaagaattc   60
accttggatc tcaacataaa cgatccttct gtagccgtta taaattatca gcccttttgat   120
cctctcaacc cctacaactt cactggtccc gtcccaatgc cctccaacgg cctagatcaa   180
cgcttaatct tgactcgcag aagatcagct gatttcgttg gaactgccca tttccttaga   240
gcttgctccc tctgcaaacg ccagttaatc cctggtcgtg acatctacat gtacaggtat   300
acagatgtat acgatttaac ttatataccc tgagaaggag agccttggcg cagttggtaa   360
agttgttacc atatgtgatc aggaggtcgc aggttcgagc cgtggaaacg gcatcttgca   420
taaatgctgt gtaagactgc gtccaataga caccttctga tcgaatcctt ctttgaacct   480
cgcgcatagc aagagcttag tgcactgggc tgccatttt aacttatact tgtttttctat   540
gttactaatt tcatttatta ttgcctatca catgtagtta tttttctaggc aatcagataa   600
taaaattaat ttattctatc aatttatagg ggttgaactc tttacatata tgtagctagc   660
tagttatttc tgtattcttt tttgttgaaa tctataataa acttatttgt ggttgttttt   720
ttttttttcag aggagatagt gctttctgca gcctagactg tagagaaaag cagatgaagc   780
aagatgaaaa gaaagagaag tatccgaagg ttgcaactag gaaaaaagtt actaactcag   840
ccgccatggc cgccgtggca agcggaacag gatccgacgc tccacctcag gccagaccgt   900
aa                                                                  902

SEQ ID NO: 41              moltype = DNA   length = 1443
FEATURE                    Location/Qualifiers
source                     1..1443
                           mol_type = other DNA
                           organism = synthetic construct
SEQUENCE: 41
atggccaaca aggtctccaa tttctccgat ctaatccaac gtgtcactgc ttcttgcttg   60
ctccatccac tttcctctgg ccgtattgac agcaatatct ccgatgctca ttacagcgat   120
gaatctgaag atgacaagta cagtaccgaa gatgaagaag aaaaaggaga cctaccttat   180
gtggagactc aggaaaaatt ccagaacgtt gaggtcacaa aggaggagat aaaaactgag   240
aaagtaactg aaatggagat gcttttaggg gaagtgttcg acgtggtgtc tgcagtgaag   300
acggcttatg ttagtctcca agaggcgcat tgtccttggg atcaggataa aatgcgtgtg   360
gctgacgtgg ctgtgatatc tgaactgcgg aggcttgggg tgttgaggga acgatttcga   420
aggaatattg gtggtggaat tagaaaaggg gactggagag tcggcgccgc tacgttgaga   480
gaagtggtca caccatatga agctaccatg gaggaactga ggcaagaagt gaaggccaaa   540
gaaatcgaga ttgataattt gagggagaag ctgaaaatgg caacaagtct tagcagcagt   600
ggtgggaaga aaagcaagtc aaagcgaaaa attagttgta gcagtcaagc tccagttgca   660
atgtcgccag cacctgacgt atttgaaact acagtgagct tagtaaaaga agcctcaaaa   720
tccttcacga gtttgctgct ctccttgatg cgctctgccc actgggacat tgcagcggct   780
gtgagatcca tcgaagctgc ttcatccaac acaaacacac cacagcagca ttcaattgtc   840
ggatccaacc atgccaaata cgcactggaa tcttacgtga accacaaaat gttccaagga   900
ttcgatcacg agacgttcta cttggacgga agcttgtcat cactgctcca cccagatcaa   960
caccggcgcg attgttttac acagtacagg gacatgaaag caatggaccc aatggaactt   1020
ctgggaattc tcccaacttg cagtttcggg aacttctgtt tcaagaagta cttggccatt   1080
gtgcacccaa aaatggagga gtctctgttt ggtgatttgg agcagcgacg acaggtgttg   1140
gcagggaacc atccgaggag tcagttctat ggggagtttc tggggctggc aaaggccgtt   1200
tggctgctgc atttgctaac cttttctttg gatcctccgc caagtcattt cgaggcaagc   1260
aaaggatcgg agtttcaccc gcagtacatg gagagtgtgg tgaagtattc aatttccatg   1320
gggataggag ggagaatggg tatgggtcta gttgttggat ttccagttag tcccgggttt   1380
aagctgggaa atggatcagt tgttaaggct agagtttatt tagtccccaa aaatgggttt   1440
taa                                                                 1443

SEQ ID NO: 42              moltype = DNA   length = 6827
FEATURE                    Location/Qualifiers
source                     1..6827
```

```
                      mol_type = other DNA
                      organism = synthetic construct
SEQUENCE: 42
atgatgggga gtggattaca gtttaatcgg agttttaacg gtgaagatcg gtttttatagt    60
gcggggaagt ttcgccggaa tgttaatcgg agttttttcta ccggcagtga ggataatctc   120
cggcgagcta agagtgatgt cgccgttatt cattccccga cgaagccgaa aatgaaagtt   180
gccgccgatg agtcgcctga tgagccggta tctgccgtgc cgccgacgga tgttctgccc   240
ccgccgcttt gtaatcttca gcggtttttg aaatctgttt ctccttcagt acctgctcaa   300
tatctatcta aggtcttaat aaattatgaa actcttttat gggttttttga ttgaagattt   360
aactattgtt tgtcggtttt tgatatgtgt tttggttgaa aatgtttgtg tttgtatggg   420
ttattcaagt gtttaaacga ttggattagt ataaaattgt acttccctcg tttgtccgaa   480
acaaaataat acctttttaa atttagaaat aatttaactc ttaaactttt ttttacaaaa   540
atgtataggt tgtttttagat cacaagtttc agtttcaaaa gtacgctttt ctttcgtaaa   600
ctctgtgcgc atcaaattga gactgaggga atattacttt agttggtatt ttcacggaga   660
atataactgt tgtttgttgt taagattata ggtttgacgg aaaatggttg cattagttta   720
aagttgtaat cttttttgctg ggtatgttga taaactgttg tttattgggt ttaaatgaaa   780
gtttaactgt ggtttgttgg taagattata ggtttttgatt gtaaaggttg tattagttta   840
aagttataat ctttactggg tatggttgaa aatttaactg ttctttattg ggtatggttg   900
aaaacttaag ttctgtttgt tgctaagatt ataggtttga ttgaaaatgg ttgtattagt   960
ttaaatttaa atcatttatt gggtatggtt gacaatttaa cttctgtttg ttgctaagat  1020
tttaggtttg attgaaagtg gttgtttttag tataaatata taatctttaa ctgctattat  1080
tgggtttgaa tgaaagttta actgtgttc gttgttaaga ttataggttt tgattgaaaa  1140
atggttgtat ttatataaat ttctaatatt ttaccgggta tgactaataa tttaactgtt  1200
ttttattggt atggttgaaa atttaactgt tgtttgttgt taatattata ggtttttgatt  1260
gaaaagtggt tgtattgata tacatttttta tcttttactg gatatgattg ataattagct  1320
gttgtcagta gggtatggtt gaaaatttta ttattttcat tgttaagaat ataggttttg  1380
agcgacaaat gtttgtgttt gtaacagaca actatgaggg gttggaggac gtgtgatgtg  1440
gagtttcagc catactttgt tcttggtgac ttatgggagt cttttagaga atggagtgca  1500
tatggagctg gagttccatt ggtgttgaat gaaggtgata gtgtagttca gtactatgtg  1560
ccctatttgt caggtattca gttgtatggt gactcgacaa aggcttcaac aaaaacaagg  1620
tatatatttg catggtttct ccttccccat ttagcctaaa cttagttttt gttactcatg  1680
gcctagtcaa attgccggcc acatcaatcg atgctctcaa tacccactg aagatgcttg  1740
ttttgtattc tctggttttc cgtgtactcc ttgatcctta tttcagttcc acaattatta  1800
ttgcgtatat ttaggctttg taagtaatga ttatttgttt ttacatgaaa tgctgataca  1860
caatagttgt ggcactaatg caaaattgtg tctaatactc tcggtcagat tatcaggact  1920
cagctaggga aaagctttgg atgatatatt atttgtgtgt ctttcacttt ccgcatgttg  1980
ttactgaagc atgtttttgcg agaaaaaatt aaacgcaata gtgatagaga aatagttcta  2040
tttgcatctt ttcaataaaa aagtggatgg caaaaagttc attccgcttt gcaatgtcat  2100
aaagttaccg aatgagcttt taggtggatt tgtgggtcat tgctataaat caaattggta  2160
cccgaatttg agatgtggct ctttaaccaa gtacttcagt ctcctttttt agatggcctc  2220
ttaacattgt tgcattcgga aacaacttct ctaccccctt ggggtaggga taaggtctgc  2280
gtacactcta ccctccctag accccacttg tgggattttta ctgggttgtt gttgttctta  2340
acattgttgc acatttcttt ggacctgtaa acttctgctt ctataagagc tgtctgatca  2400
gctacagctg ctcctaaacc ttattgttac tatctaactt agtgtttgtg gatagatgca  2460
aaacctattg cacttcacta attgaggagt ccaaagaaca cgttcaactc tcaccttagt  2520
gtatatagat ggaaataaaa cctttaccat ctcattgaca tgtgaaacag tgaaggaact  2580
tctgcattcc tgattttagt ttctttcaag tcaattattg ttttttttag aaagaattt   2640
ttgtcccact cccattatag tccttcgttg tcatacaaat agcgccctga gtaaatttat  2700
ctagaagtat gcctgcataa cgatttaggc ctgaatgagt ataaaattgt tgattttact  2760
tggtgaatgc tttttcatag gttttgatcc cttctcaacc taatattcac cttttaaaat  2820
taacttattc ttaccatact tgtagttcct tcttgaacaa tatacaactt caacatgctt  2880
ttgtttctt tttgataaga agcaaacttc ttctttttgaa gctgctgttg atgcagtcgt  2940
atgcaccatc tttggtactt tttattaata aaactttaca ttatgaaaaa aattcttatt  3000
ctactctctt catttcaatt tgtgtgtctt agtttgattg cgcacggaga ttaagaaaag  3060
taaagaagac tttaaatctt gtggtcttaa actaaagatg tgtgtaatgt accaaaaatg  3120
ccatgtggat tctgggagtt aaagaattat taaacataga aaaagacgtt cttttttgaaa  3180
caaactaaaa aggaaagcaa gacatataaa ttgaaacgga gggagtaatt ttttttcctg  3240
gataaccatg gtgtccgggc tagcttgccc gcaccttgat taattccacg gggtacctgc  3300
tacctcccac caccatagat actgggcaat tcgatctatc aaggcttcga taaatgagaa  3360
gaaatcacct agtgtttttag cctctgctgg aatttgaacg tgagacctca tgattttcaa  3420
cgccacaccc ttgggtgctc ttcttttaaa ataaactagc actaagtaaa tgctgggtaa  3480
ttacattgaa taaacttttg tacttaccca acatttttgat tcgcactcgg ttgctttcct  3540
tccctttatc tcatcttatt tcatgcaatt tgcttgctct atgcctctat cccatctaag  3600
ttttatatgt taaccaattc atgttactat tagtgaaatg tgaattgatt tgcctagtgc  3660
ctaatgaaat gacggatctc acttcgacac agctattatt tattgtcagt ttttctttt   3720
aatggttgtt gttttttcttt tattttgata aatcaaggtc ttttgttaaa aatcatggca  3780
agatggtgta actatacaaa agaaattcca ttctcaaaaa aaagaaaaga aatttcatgt  3840
gttaggcctc ttgaaaatct gtccaacttt ctatacaata aggaatttcc tttttacacc  3900
aaaagtatga gtagaataat acggagcttt ttccccagtt tttattttttt attttaataa  3960
tagggaattt ttgactagaa ttttgtttag aaatgggagt ttaggatgtg gatatgtccc  4020
tagttgctca ttcaagcagt tgaatgaaga actgatatcg ttattccgaa gtaccataaa  4080
gtgaatatta gaaacgtgtt cagtaaaaga aatatttgca ttatcagagt ctatgaaatg  4140
gatgtcctag tcattcaggc aagtagctca ttgctattcc atctattttt attggtcagc  4200
actgaaccgg gcttctcagt tgtactttgc catgttctct ctctctccct ccctccctcc  4260
ttaaacctgc ctttccctat tcacgatgtg tttttctgt aggagcagaa tatttcgtca  4320
aaggctatgg aattttcaat ttgccattct ttctgctgca tgcatctttt tgatgtcatca  4380
ttgataccat tctgctcttt cctgagacat tgttgatttc aatgcactcc ttagattgta  4440
catgggtgga caggtcggtt atagcttgaa attgtgtatt atgagtgtgt ttatgttgta  4500
aatgtgcatc attgtgtctc tttactaccc cctcacccc tcctcttttc tgaaagggtc  4560
```

-continued

```
tgaatcttga attgaagttg tttaaatttt gtatgagtaa cttttaaaaaa ctatgatatt    4620
gacttgcatt ttcttacaca gtaggcgacc aggtgaggaa agtgatagtg actatttccg    4680
ggattctagt agtgatggaa gcagtgactc tgaacatgag agacgttgct tgaattatac    4740
aagggagcag cggatgtatc atagccaaac aagtgaaagc tcccttagta ttgaccggtt    4800
atcattaaga gacaggaatg ctaccttcca agaaggattt tcaagcgatg agggtgaatc    4860
tgggtcttct cagggtgcct tgttgtttga gtatcttgag catggtcagc cttacggttg    4920
tgaacctttg gcagataagg ttggtgtttc ctccctcttc ctcaaagtag ttttcgtttg    4980
tctttcatct atggggagta atgtataagt tacccttctt gcttctttat tatatctcat    5040
attttctttt atgtttcttg ttctgtagat atctgatctt gctcaacgtt ttccggaatt    5100
aaaaacaatg agaagttgtg atctccttcc ttccagttgg atctctgtag cctggtattt    5160
tgttttttctt tgcgcatatc atatgagtgt aattttttgt atcttgaatt gtaatgctga    5220
tgtctctctt gcaggtatcc aatttaccgg atacctactg gaccaacttt aaaagctttg    5280
gacgcttgtt ttctgacctt tcattctctt catacaccca tgacaggtat ctgacagttt    5340
ctaccctaga ttgctttttgt ttttcggttg gatattacaa ctactgcttc ttacccatcc    5400
atatcactgt gtgtattctt ttcataatgt aatgtggtgt tttttgacgt ttgtctatgt    5460
attttcatct gtattagtat gtgacaatca tatatttcct taatgttctt gataaaaaaa    5520
gaaaagaaat tattcactgt caaacaaaga gtgattgacc gtatcaactt cttaaattca    5580
tcgcaatcaa tatattttac tcatttgatc cgctaataag gattcaagaa gcttccaaaa    5640
tagctacata aaagaaaaac acaatccatg tgaaagttgt gtagcgaagt ctcctcttcc    5700
tttttttaaa tttatttcgg tctcgctgaa atgaagtgga ttggagattt tcgtttgttt    5760
caaaatattt tattaggaat aagaatataa tattcttttta agcactgtgt tgtgtatctt    5820
gaagtatata gtctgaaagg aatagaatgg caagaaattg gaagttccca ttggtaattt    5880
ggtgtcatta aaagtgaggt tagaacaaga cttagtttgt gtgatgcagt gtttggtttg    5940
aatgacttac gaaacctaaa attgatttcc tccaaatttt caactttctc ttcggttgaa    6000
tttcacatgt cgtccgggaa agaaccgggg cgttaatatg ttaaagaaag ttagtcgtga    6060
aaaagatgtc caccttaatt cattaactct tttctagcat gttagaaagt caatctcttc    6120
ttgaatttag gtttttgttat tcttgagcat cctggtgaac aaattagtca tgactgtaaa    6180
aatgtttaca ttggcattaa aaataaaatc tgctctccgt ttatggtcat ggaagggaga    6240
agagttggga gggtgagagc acaggaactt aaaaatatctc ttgtttgttt cctttctttt    6300
ccctcccatg tttcacttct tttattcctt cgcctgccta cttcttcctc ctactttacg    6360
atgtgtggac aaatactatg gacctcgaaa tggtaacata acatgaggtg tgtgtaggca    6420
tattccctaa aaatggtagg tcactaataa tttaggctga aattgttcta tctggtgaag    6480
tatgtattaa attttagagt atgttacata gcttattgtg ggttgctttt ggcatttaac    6540
taaatttgtt atgttgcgag tgagttgttg aaattgcaca tggactttgt gcaggaagtc    6600
aaagtgctca tcctgcggcg gtaacatgtc cgagtgatac ggatccggtc cctaagattc    6660
cattgcctgc ttttggcctt gcttcataca agtttaaagc ctcactttgg accccaaatg    6720
gaggatctgg aagacagtta atgagctcgc ttttgcagtc tgctgaaaac tggctaacgc    6780
tgcttcaggt caatcaccca gatttcagtt cttctgcca aaggtga                 6827
```

```
SEQ ID NO: 43          moltype = DNA  length = 3439
FEATURE                Location/Qualifiers
source                 1..3439
                       mol_type = other DNA
                       organism = synthetic construct
SEQUENCE: 43
atgggttcat gtgtttcagt gcataaagac tctgaatcag ccatgaaaat tcgtcttgtt    60
tttggttctt ccaaaactga caagcttgtc actccttcac ctctcaacaa agatgatacc    120
aaagtctctg atcttcaact caaatctcaa actcctgctg ttactgcttt tcgtgacttt    180
ggtactaccc tattactctc tctttattca tttttttatt ttacaacaga aactctgtga    240
taactctgtt atattgtttg gcaatgtgga aaaaagggga aagttgctgt cttttttgaat    300
tgaaggttaa catatgtttc tggttttgaa tgtttttttga gtaattagtt tgtgttgagt    360
tgtctcacat tggttgtggg atgtgaggcc taaggttcat ttctttatat ggtaccggtg    420
acagagctag acctgtacga tttcttggtt tatcctatgt tgggctctat attatgttgt    480
ccatgcgcaa tctcacccca tgacttagct tttagagttg agttaaagtc cgttcatgcc    540
gtattagagt taagttatac ccaaagtccg tttctttacc gcgtgtcgcc atgtcatgct    600
gtattagatt cttgcctctg gtaataggtt ttgtggtgtt cctaattttt ggtattttc     660
aatttctatg agacacacgt gttatttgat tactgactat tgattatctg ggcatttgg     720
aatgtaaagg aaagttgaag aggtgttctg tttgatctga tggacattat ttttgtattt    780
tttgtgatat tagttgaata tgtgattgag ataaaattgt tgttatagga acagttaagg    840
ttggtggcct aaaaagaaac actttattat attttacaga gtagctttct attcccttttg    900
tggacttaga atattgacc aagaagctat tttcagaatc ttgaataatg ccaaaaattc      960
ttcagttgat ggggccatct gcagaacttg ttatcatggg cagggcaatt ttttaatttg    1020
tggagaaaat tattaagtta ggaacttaaa gtatcaccag aaaagaaaaa ggaaatactt    1080
agcgtaggag tataccttaa acaaaggaga tattgtagta cttctaatat tatatacaaa    1140
gtggtacttt ttagcattcc tcagctcatt acatgaattg taaagaatga gtctttgcag    1200
ccttgtaatt agtcattgga gcattctctt ttttgctggg ctgctacttt tattaaacaa    1260
atatttctta tataaaaatg tgtgtgattg ctgccactat tattttattt ttttggtaat    1320
taaagaattt tatttaccaa ttgtaatatg tacagtgaga tttcttcctc tactattaaa    1380
agccattttc actagaaaag ggtagtctgg tgcacaaggc atcccgcgtt cacgcaaggt    1440
ctgggaaagg gccggttcct taagaggtgt gatgtagaca gcctaaccta atacaagcat    1500
tagtggctgc ttccacgccc gaacccgtga cttataggtc acacggagac aaccttacca    1560
ttgttccaag gctccccttc aaaagccatc ttcactaaca ccggccaata tcacattata    1620
ccattatgca cttgacaagg acatcaatct tgctgaatat tgcctcttgc ttctgttgtt    1680
cctcttcgtc acttaaaggg aggataaatat cattaacatt tgatgattag atggtcctat    1740
ggaaatctta gttcatgtct tgattgtcgt attcatcatt atctccatgt ctaagagaat    1800
atttgagttg ttgtattaaa atattcttttg agatagttaa aactgaggtt gacatttgtt    1860
ataaaaccac tgcccttgtt tgacatatca tgttgtgggt ctacactgcc atcacttcta    1920
ctatccgtct ataataatca gcaaatagtc gacaatttttc tccttttttt ttcctaagga    1980
taaaagtaat tttaccagta ttctcggagc tttggttcaa tggttaaggt agtacattgt    2040
```

-continued

```
gtgttgtgtg gtaggcacac atcacgagtt gaagcttgct atgaatcaag tttagtgttt    2100
aatgaagaga attaaattaa ctaaataaat tttacaagta aaataaacac actgtacagc    2160
ttttagttta cctcactttt aaggaaatat gttaagttct ctgtctttct tgaatctttt    2220
ccttgtttct agcagaagat aaatgtttta caattagttt gatatggcta atggcctcag    2280
ccttctcata gttcagtttt attcatgtgg attaacaaag gttagttgag gatactaaca    2340
tcatatccac cgttatttcc gctgcatcat cttgtgttct tgaatcatct gcctaataat    2400
agcactcttt cttgaaagtc atttgtggtt tgccaatgag tgttcccaac caatctcatt    2460
tctctttatc tgtgttagat ggatttattt tggatatgat tatctggcct tctggttgaa    2520
taacgataag gacatggtgt atcctccttt tcagttttct tctttagttt ctcaaagtac    2580
cactctgatt cactgcatga aacagaggaa accgtgctaa gtgtttaaaa ttttcatgca    2640
tagtgcgtgc gtttatattt acggtggtct aatttaattg catcttttat ctgagtcaga    2700
gacatttctt tcttgtaggt agcaaggagg agaccttctt tgattcccag ccttggttgg    2760
attcagattg tgaagatgac ttcttaagcg tgaatggagg taagatcttc aatcgatggt    2820
ccgtgttatt ccatcttctc cccttttccct ttccttgtct tcataaatga gctacaaaat    2880
ggcactttat ttattgtatc cagctaacag atgtgcgttc ttcagtccaa aaccagtgtt    2940
tagaattgtc catcagccat ttcttagtta gtcgtgtata tcatcttgta tttttataat    3000
ctctctgaac ttgactccag attttacgcc atctcgtgga aatacacctg tccatccctt    3060
ggctggaaat ttaacaggga acagaacccc tgcttatttt cagcaatcat ccccaacaga    3120
taaaaagaag agattgtctg aacttttga agaaagcttg agaagcgatc tggaccaaaa    3180
tgggcaaaat gctgaagaaa aacaaaatgg tacaaacact aaaaaagaaa ctgcgtcaac    3240
tggtactcaa cttccaccaa gatccacacc tgggacacct tatgcatccg tgtgtagtag    3300
cgaaagaaca cccagtggtc tgttaaaatc tgacgtcaaa acgtcaaagt cagcacaatg    3360
ttgtcttcca aggttgctct caagtcgtag ctttaacgga aggaggagta gaatgagtcc    3420
tgcgcgtaat gttggctga                                                 3439

SEQ ID NO: 44        moltype = DNA  length = 7325
FEATURE              Location/Qualifiers
source               1..7325
                     mol_type = other DNA
                     organism = synthetic construct
SEQUENCE: 44
atgaaggatg atgaatccat accagtttca cacctacaa cacattcatc atcaaataca     60
atttcaacat attcgaagaa ttccacatct gatgccacaa tattcggtcg tggtcggtac    120
aagttctggg cattagccgc tattcttctg ctagcatttt ggtcaatgtt tactggtact    180
gttactctcc gatggtccgc cggcaacctc aacggtctct ccgattactt caatgtgcct    240
ctctccgata atctcgacgt catcgtatgg ttactatgcc ctatactttt tcttttgta     300
aataagttca tccattattg ttcaattttg actatgattt ttgcacgatc atctcactta    360
ataggtaaat acttgtaaat cttaaaaatt aatcggtaat ctagtaaatg aaggtaatta    420
atctgctatg acatgttaaa attcactgat agtgtacaaa ctctttacat tgtcagtgta    480
cgtaacttaa atgtagaaaa tatttataca atcagatcac ttaataggta atacaagtaa    540
atattttgat aagcgttaat tgatagtgaa aatggttact tactaacctg ctattatagg    600
ttaaaattca ctgatagtat aaaaaatagt atgtatgtaa cttaaatgtt tttaccattt    660
tgatacgaga agaattgtaa aattttaatt tgtaaatgag gaacaatcta gttcgattta    720
gctaggagaa ttagttaaat tgactattca taagctaaca ctggcaaata atttgggtgc    780
aggggggta cattataata gtgtttgatt tgattcttg agaaaatgat ttaatcttat    840
ttggtaggaa atggaagaga gggagaagtt ggtgaagcat atgtgggatg tgtatactaa    900
tactcctcgg atcagattgc ctaagttttg gcaggaggca ttggaggcgg cctatgaaga    960
gttaaccagt gaccttgctg atattcgaga ggctgctatc tctgagatct ctaagatgtc    1020
tctccgattt gttcatatgg agccaccacc tctgcgttca ttggttagct ctctctctct    1080
ctctctctct ctctctctct ctctctctct gtttcaatct agttatttgc tgtattctac    1140
atgtgcctgt tgatacctca atttaacctt ctgtttaggc caactgggaa ttgttgcttt    1200
tcttagtttt cgagaaccct ccagtttgct atcattataa agtattggaa agaagcgaac    1260
ccaaatggag ggtgtggatg tagaggattc atgtaactga cccaactaat ttaggattga    1320
gtcatagtag tagcagttgt tgtgcttggg aattgatcat actgcagatt ggtgtttttc    1380
atggagaagt tgcaaatcat agttcaggaa ttagttgggt gcctcttgtt cattgaaagt    1440
tgtttccttt atgttatggc ttctgagcat gctacttcga gtagttagta acagtcctta    1500
aaacctgagc tgctgttata tgaggatata ataagtttca gcaagaatcg ttttgtggaa    1560
gctaacgtcg aatatacaca acctgcaagc agcctttcat gaattagatc ttgtaggatt    1620
ttgggtgctt aggtgataga tattcggtgc aaatgcaagt agccagtata atttagtaaa    1680
tattttcaag gcatagaaat agttcagata agctgcatct gcactattga ctttgtcttg    1740
tggggttgtt gctggaactt gatcctttgt gcaaattcac tttacacatc aagaaaatgg    1800
ttggaatatt actattaatt tgaacattgc tctaaatttg cctcacaaat ttgaccttat    1860
ttgtcttgag tgtattgact tgttatgtta attgtctatt tactcgagat tccttcttgt    1920
gagttagaaa agtggatttc ccattggaaa gaacttcctc tttccaaaat tgtataattt    1980
ggtgactttt catgtcgatt aaaagaataa tgtttaatg agttactatt atattattag     2040
ggttaatatg ttgtttagaa gaaccgaagc tggtataaag attgcatata gattctaagt    2100
aacagataca gtgtcatcta cgttaatttg gctttcaaga tagattttgc cacatagaga    2160
aagaggtaat tcaggacagc ccaaaggtga aagtcaatca aagtgaggag gtagtaatat    2220
tcttcttctt gcatgtcaat gacaatgtag gattgaagtg cataagaaca gtatacatct    2280
cgatagtatc actttttctg aaattaatca ttttgaagga ataggatgga aaggaaagga    2340
ataaaaaaga aaggtattgt acctttaccg atccacatgc tatcttactt tgtttccttc    2400
tcactcatat tttcgtgatc atatctagtt gaccctttg taactcgttc agctccagtt    2460
accttctaaa cttccaaaat agagcgctgc tacactttct catcgaaaaa tttattatca    2520
tcctacatat atttatcctt atgcagatat cgggtgtgtc tatgttggtg caatccgtga    2580
tggtggtggt cataatccca ccacttctaa attttactaa aagtcttgat aggcgtgtaa    2640
acatgattat tttgcacaaa tttgaggaa agagaatgga ccccattccc tttgttggcg    2700
caagactaca actataattg tgcctcaatt tcaaacaagt tgaagtcggc tatatgaatc    2760
ctcactgacc atatcgacca tttttgatga gtcttgttgg cacatgactc gcaaaaatct    2820
cttcctccct catcatttga caaaacattt tcctccatcc tcaccatttg tcatcatgca    2880
```

-continued

```
caccatatgt tagaaaataa gaatccaaca ttgatacctt gattgttgct gctatcacaa   2940
atcaccagta agtggcatga ccaattccaa ccaactttcg tagtatactg gcatccacat   3000
aagcacttac catctaaaca ttggagcagc acatacacaa tacagaggca ccagctagat   3060
caactacttt caagttctgg aaggctgagt ggtcaatatt tagaaataac tacgtggatc   3120
tcgggtttga ctctcattat gatattcatt gtgagtccat ctgctctagc caggcggaca   3180
agattacccg cactgggttg tagcagactg tccaatggat ttagttaagg tgcgcgccca   3240
agatttggcc tggacagcac tatatttaac aagtatcaac tgtttagtcc ttttccagct   3300
ctacttgaga aatttgttcc tctgttgcat gttttgcctct gtatccaaat tctattaggg   3360
gataggagag ttatgaggac agtgaaaatc aggacgtagg aaatgttata actgtgataa   3420
tggactaaat acaaatcctt tgctctcctt ccatttccta tggggataag attgtgaagc   3480
tgattgtttt cttctcttaac ttatttcacg tttgtttaca atttccatca aattacctgc   3540
ttcttctcat aatatataga cctgaagcat tctctgatta aaacaatgaa tagatatgtc   3600
cttctcaaaa aaaaaaaaaa acaatgaaca ggtatgaagc attttacta cttttacgtg   3660
acgccctgaa ttaatgtata gtgggagaat ccgggctaat caagtaatat gcottaaaca   3720
agctttcaga tcttcaaatc atcatctcta tcacttcatt gcaattattt gggttgtcat   3780
ttagaaaaag attattctga gctctgttct gaactgctga taaaagaagt aataggcacc   3840
agtgaaaag aaaaatagga attttcttt atgttgttct gttatctcaa aatggtagaa   3900
acatgaatac agaatgtgtc tggaattcga tatctatctt cattatctct tgctggatta   3960
gtgttcgtct gtatccatga atgttaggtg attttttcccc tattgaagtt tgtgtttggc   4020
atgcaaactt cttttaaatt ttttttgcgt tttgaaattt tgcttggccg gttaattctc   4080
aaagaaaaaa aaattgagaa gcaaaagaaa gtaattttt gaacacattt ttagttgttt   4140
aaaattattt taaaaacgat tctccaaaac ttttccagaa atgcgtttca gtgccactga   4200
agtattgtta aattaaagtc cctgaggatt aacacatgga gtgcaaccta atttggactt   4260
ccctttttgt aattttttctt cgtttagttg agatttttga aatccttcat catctacaaa   4320
ctttattagt tcaaatgctt agttcttaaa cagtaattca aagtttttatt agttcaaatg   4380
cttagttctt aaacagtaat tcaaagtttg tcgagtgaaa tgcagtcaat ctattgttgc   4440
agccattcgt ctgtctgttc tgcttcttcc tatctatgca ttgttcagga atttttttc   4500
cgtaactaat ttttcttcat ttttctaaaa tccttggatg ataaaactaa attttcctct   4560
tttagtcagc agtaaacttt tatgctctgt tatggaatct ggatacctcg tgattttgtt   4620
ttacttaatg gactgtcagc attagcagct atcatttatt aaaccgaaaa ttatcctcta   4680
gctgctcctg tgcaaatgtg tgaggtctta gctgtatatt tcgtcacttg taggggttaa   4740
tgaccactct tgattatgat cattgaatag ctcagtcttt tctgtctttt cattttttatc   4800
tttaaattga gaatgcattt ttttaatcct aaatctgcct tgcctttgca tccacaatac   4860
tcgactctac ttttcggagg tgattgttat tcagtgtagg acttagtcgt ctttaagtta   4920
atatgcagtc cgggcatcaa gagaaggaaa caacttaccc acactcagtg tttgcaccaa   4980
gcaaataaat gcaagacatg tttcttggat ataaattttt atcacttaac catgcttaag   5040
tagtagatat tttcagtttg atttgaatct cttaaggttc aattgcttgg ttttgtgtaa   5100
acactgagtg ctgataagtt tcattccatc tgctttcgtg agtttcagct aatttctaac   5160
tgttgctaga gttgattata aggatgttgt catcaagtgg tggcatgata cttattgctt   5220
ctatttttca gtcttcctta cattagagag cctgcgaatt cattcgttct tggcatgaaa   5280
atcacaaagg agttagataa gtacaatatc agccattata ctttggctga atttttcctg   5340
gagttgcaaa actgcacttt agcaagttaa ctattcaagt tctgaaagca agcaaatagt   5400
ccattcagag gagtttttat gaatttttaa gggaaaattg tatcattgcc acacttgtga   5460
tcttttaagg atgatagagg atgatactac tttcagagag aaacaaagga attcagtaat   5520
gtaaagaagc atgtaactaa aagagaacag atctccacaa ctccattccc attctccttc   5580
tattcctctc tagtgaactt ttaccatccc taactcttgt tatccacctt aacatattta   5640
agtgcaggat agttacagga gaactccctt gtgagtgctt ttgtcagatg tagtaagact   5700
tatggaaaag gttacatgat acttttgtcg atctaattgt tacttatgc taaatgatcc   5760
gtggttgatc ttcatgaggg ttactgtgga tttgttgcga tgtgcctatt taggtttgac   5820
agatgaacca actgctgcta gctattactt agaaatattt ttgttatttt ttttaggtta   5880
agataatgaa ttgatttttg gtcagctgct cttagttctc tccattgtcc cttcaacctg   5940
ctcttccacc cttgttatcc tgcatttgct ccttgaacat tttcaatcat tgtaattgac   6000
atgcatgtgt gatctttca taaatcattt caggcagtaa gagaattaag tcaaaaacaa   6060
gctgaggaca aacagaggac tgcaaaagga agtaagttat gactggaaga atatcaagga   6120
tccaattttg cgtggttgcc acttatttat acaaaatata caagatgaat gaaaacatac   6180
aacaacctgc tctctggtat ttgactaaag ggagcatttg agaacacatt acattcaggt   6240
tcctcgcact tttgcaacag ggataaacat aatcaatttt ttgttacttc tacctctttt   6300
ttcccccccca tgtacccatc tccccattga aagctcatac gagtggcgga attcaacaat   6360
gtcatgattt aattatttca tgcaaagaaa ttggaagtta cttcctaggc ttttacattc   6420
gaagacccctt actaattcgt ttgtttccca cttgaaatac ccattacaca aacttgcact   6480
ggaatagaaa gattatattt agttcttgtg gtgaaacttt gtccacattt gcatttcaag   6540
tgtttgtgt agcacccagc cttatcttag gagttttctt cctgtataat tatgtgtttc   6600
ttcagatcca gtgttggaaa ctgttgatgc cctagctatt tttttatttt aaatttatgc   6660
gggaatgggtg tccgggccag cttgtgcgca tcttttttcc tttgctttttt ttaccctctt   6720
gaattcactg atcatgcaaa aggttccatt acatgcctaa ttactggctt tataatcctc   6780
ctttcttctt gactacctgg accaccttga aatttgacat gagatacaca tgaacaatca   6840
aaccaagaaa aattagatgt aaagccaaag ttactgaatt attttcttgt taaaatttta   6900
tgacttcaac caagatctct ggtgactaaa atctataagt atcatgtcat tcagaatagt   6960
cattttcgga ataatacagg tacactcttt cacactgaag caccactcac ctgtgttgct   7020
ggggcttact atagaaaata aagttgaatt tttgtcacct tttttttatca tcctgtaacc   7080
ttgatgtgat agatcatgtt aaaatgtttt ttttcctggt aaataaagaa ttttatggac   7140
acagttttca cattattatt tgatgcagca aagactcaaa gtaagcagat tgctgcccaa   7200
gtagaatcat attttgtctt aaactttcaa aacaagcata ttgacctcat ttatttgcat   7260
cagtttggct aagtgcagtc cttatggagg aaaataaaag agaagaaaaa aggggacctg   7320
attag                                                               7325
```

SEQ ID NO: 45      moltype = DNA  length = 1221
FEATURE            Location/Qualifiers
source             1..1221

```
                      mol_type = other DNA
                      organism = synthetic construct
SEQUENCE: 45
atggccgata gtgaatcgag gcaattttca cctgataagg agccatgttt tgcagaagaa    60
ctacttgact ggcagaggag ggaactgccc cgcaggtct tgtctggtca ggttgtctgg    120
gatgacgacg ctttcatccc cgaaggcgct cggagaagc acaggggttat atttcgcaga    180
atttatagga aatacttcct tcagattttt gcttcggatg ttcgtcttct ttcactactc    240
ttttattcta atcttgcatt atatgtatac acacacatca attagagctg gtcaaatttc    300
taattagagc ttacaattgt tatcactttc aacaattcca agtttttccc agttttactt    360
ttagttggct aaggctgttc ttaacattag gagtatattt ttagaaaatt agttgtttag    420
cctgcttatt gtctgagcat tcttaacaac taatttgtaa tatcccaagc tctgcccagt    480
ctgagctcct taattttgtt tagagcctta agtgtggcag acaagattat ggggcttact    540
tggttacgtg ttaaaataaa tttaggaatt catggctgtt ttggtggtac ttttagccat    600
agtgttcaag tgatttgatt agcccctgtt ctctttattt tatttagcaa atagaccaaa    660
ttctaaaaca gcatgttagc tccacaaatt aaacttcttt acttgattga atatcagctt    720
ctttgacttt cggcttcaat tatgacccct tcttgttatc gcttgagtat gaattcatga    780
ctgattggct tatttggcag ggtttcgaca ttgacatca tccgggtaaa gccaaggcag    840
ctatgcttat accatacctg gatttgaga aagaaattga cttgctgatg gaactggcta    900
accatgctat tcaggattac aacagtaaag aaaccaatgt aggcctttat tcatcttatc    960
atctttgctc tggttgaaca atctccctca ccccaagtgt ccttacagta ttttctacgt    1020
gccttgcagg tttacaaata cgaggtcttg tatgttgaaa aagtgaactt tattttggcc    1080
gaatgccgcg aattttttat gactgttaaa gttaaaaatc tcactctgcg ttcaccetaaa    1140
gaaactttc aaatccatgc atataaagga ccagatgggg agaatatttt ctgcctttgc    1200
cggagaaaat tgctggtttg a                                              1221

SEQ ID NO: 46             moltype = DNA  length = 909
FEATURE                   Location/Qualifiers
source                    1..909
                          mol_type = other DNA
                          organism = synthetic construct
SEQUENCE: 46
atgagagact ttgcttcttg tttcaatgaa tatgcagtac aagtttctga tacttcttgt    60
tctagttact caaactctgc ttgtatccct ccttctctga ttccttcaat tcaaaacact    120
gtcacttgtt tgtataaagt cactctctcc aataaaaaac aggtcttgat cacagtttca    180
tggtccaaaa caaatagtat aacacaaggc ctaagtgtac actttggtga tgatccttca    240
aatgtcttca aactcaacac gaattcgcgt cttttttagga agaaaagggg aagcaaatca    300
ctggatttgg atcatttaaa ggttgaaatt ttctgggatt tatatgcagc caggtattta    360
tcaggtcctg aaccaattga tggctattat ttactagtca aagtgattc acaacttggc    420
cttattattg gtgacatggc tgaagaagct tcattaagaa agttaaaaaa tggaactcca    480
atggccaagt tctcattggt ttcaagaaaa gaatactttt cagggaatac cctttattca    540
acaaaggctc aatttgtga caatggcaca agtcatgaca tattaattcg ttgtagcggc    600
gaaaatgaag gtctaaagca tcctgtttta tcagtttata ttgataaaaa gatggtgatt    660
agagttaaaa ggctgcaatg gaatttcagg ggaaatcaga gcatatttgt ggatggattg    720
ttggttgatc taatgtggga tgttcatgat tggttcttta atccaacatc tggttgtgca    780
ctttttatgt ttaggacaag aagtggaatg gatagcagac tgtggttaga tgataaagac    840
aaaattgctgc acaagatcc agataaagtt gagtttcat tgttgattta tgcctctaag    900
accacataa                                                           909

SEQ ID NO: 47             moltype = DNA  length = 504
FEATURE                   Location/Qualifiers
source                    1..504
                          mol_type = other DNA
                          organism = synthetic construct
SEQUENCE: 47
atggcggctt caaagagcta tttcgctgga gcaaactacc gattcctgtc gagcgagcga    60
gacgttccga tgatgagtcc tgaatcgcg ttcgaattcg atgaatcgga cctgtggaac    120
tcagcggttt cacagtcgcc ggagttccga aagtccgttc agagttcaaa aatctcgaga    180
aagcagtgcg atacgaagag ccgccgaagc ggttccgtag catcggcggc gtcattgccg    240
gtgaacgtgc cggattggtc gaagatactg aaggatgaat atagagagta tggaaggaga    300
gatagcgatg atgatgattt caacgatgag gacggcgatg atttggagaa tcggattccg    360
cctcacgagt ttttggcgaa gcagttagag aggacgagaa ttgcatcgtt ctccgtgcac    420
gaaggagttg gccgtactct caaaggtaga gatctgagta gagtcagaaa tgctatttgg    480
gagaaaactg gattccagga ttaa                                           504

SEQ ID NO: 48             moltype = DNA  length = 2534
FEATURE                   Location/Qualifiers
source                    1..2534
                          mol_type = other DNA
                          organism = synthetic construct
SEQUENCE: 48
atggaaagac ggccaaagca gagtggtgaa agaaagacaa tggagaatga agagcttgtc    60
aaatacatgt caagtttgcc aagttacctg gaaaaggggg aaaatctgca ggagaaagct    120
ttcagtgttg gcgtcctaga ttggcgtttt cttgaaaaat ggcgacga acatgtaaaa    180
gaaccttgta gaactagtgg ttgttcacca tccaccagca ataccttgtc attttcctca    240
atggagggat cttcatccaa ttctagcaga gccagaagct gctctcctgc tcgtcggagg    300
attcatcgtc ctacatcaca atcttattat gcatcaccac ctaaaggtag tcgtctttgt    360
tagatttttct cccactgatt aagggaatgg gttgttttct cctttcctta ataagtttgg    420
acaatcctca cctcgtgagc tagctttggg ggttgagtta tgcccaaggt ccaatttctt    480
aacagtcttg atgtcaaatc ctttgcagga agttatgtac agttgcaaaa ccaaaaacct    540
```

-continued

```
ggcgtaatta aatccccgga gattgagcaa cttgtctgca ggatatatca gtcttttgat    600
gagtatccac aaagaaatat gcaagaactc ggcaatgctc tacacccgcg taggactcct    660
catgttagga gatcacttga tgtagagact aagacgagaa catcacgttc caagggaaag    720
atgaagatcc aagatagaga atgtttatcg aaaggagatt ttgatgattt tgattgcata    780
gagaaacata aatcagatgt ccttcaagta ccagaacctg gccaagaaac taacagctgc    840
acaactttct gcccacctga ttcagtagtg aaagaccaga gcgcggtgaa atcaagcaga    900
cggagctttt cttgtggatt tatttctgcg ttctactatg gacagtcctc ttcagatatc    960
tctagttcca gcacccttcc tcatgatgct gatgagtcga aggtgggaca agcgagtccg   1020
atagatgcaa aggatagttg cctttcatct aagacaattc agccttcaac atattcagga   1080
aacaaattgt ccagcccacc tggaaccaat tccaaacaag agaagaaatc aactgtgatg   1140
cttaagaatc caactacact taattccgca gaatctacaa acatcagaaa ttcctctcca   1200
actcgtcaat ttagcatggc aatgggaagg attggccaga tttcaggtat aaaagatatg   1260
atcactggat cacaaggtgt caaatggcct gcagaacaat ctagtccaaa taaaactcaa   1320
agttcgtcct caattgatac aggctgtgat aaatcagaca ccactggccg agccaggact   1380
agtcctttga gaaggttgct agatccactg ctgaagccaa agacaggcaa ctctgatcac   1440
gttaaatctt caacaagacg tggtgaatct cctacgaaac gctcattgaa agtcaaattg   1500
gatttgaaga gctgtaaatc gattgatatc gacgatccac gttctaatgg cacatttgta   1560
ccatcaagat tgcaagctct cctccaagta gctgtgaaaa atggtcttcc tctattcaca   1620
tttgcagttg acaatgaagt tgacatttta gcagccacaa tgaagaaact taatccgaat   1680
ttgaaggatt acagttgctg gatttataat ttcttcaccg ttcgtgaaac aaagaaaaag   1740
agtggaaatt ggttaaatca agtagaaaaa gacagaagtc atggaattat gcctaatatc   1800
gttggaaaga tgaaggtttc tgatgttcca ttctccgaat gaatagcga gaaacttgac   1860
tcacagttta ggattacgga atttgttttg tttgctacag atcagaaagc atctgacctt   1920
cacccaaacg atgagcttgc agctattgtt gtcaaattac ccaatagaac ctccatttgt   1980
cctaatggaa gtggccatca ggatagaaac tgcagtaata cttcaacttc aggtttaaca   2040
aatccttttg aagatcttaa catgacagtt atccttcctg gtggtgcaca tagcgtacca   2100
agtaaaggcg agccttcttc actgattaac cgatggaggt caggtggatc gtgtgattgt   2160
ggtggctggg atttgggctg caaattaaga cttcttagga atcacactaa tcatcaaagg   2220
atatcaagtt gttccaaacc caaacttaat gctgcaagat ttgaactttt atcccaggtt   2280
atgatctaca taaatacaga ttatcaaaat tttacagtaa ttttcgaatg tctaatacac   2340
cattgtgaaa tctttttgtt cttgtttggc aggggggaagc acgggacagt aagcctgtct   2400
tcagcttgtc cgcattcaag gatggcatat tttcagttga attcagttct tcactgaagg   2460
ttctacaagc attctccatt tgtatagcag ttttaaatgg tagaaatcaa gaaagcttcc   2520
aaatgcaaac ttga                                                      2534

SEQ ID NO: 49           moltype = DNA  length = 1048
FEATURE                 Location/Qualifiers
source                  1..1048
                        mol_type = other DNA
                        organism = synthetic construct
SEQUENCE: 49
atgctgcaac attttgtct tggtcaattt tctgcgatgt ttcttcttct gttatgttca     60
attttgcag tattatcaac tgcagaatca tcaatatacg aagttcttga atcccatgga    120
ttgccaaggg gtttacttcc aaagggtgtg aagaatttca cattagacaa ttcggggaaa    180
tttgtggtcc atttggatca agcttgcaat gccaaattcg agaatgaatt tcactatgat    240
aggaatgtat cgggtacaat aagttatgga cagatccatg cactttcagg aattgaggct    300
caagatttgt ttctatggtt tccagtgaag gatattcggg ttgatatacc cagttctgga    360
ttgatttact tcaacgttgg cgttgtatct aagcaattct ctttgtcttc atttgagact    420
cctagggatt gtactgttgt tcaactcatg gatcttcagg atgacatgca catagctgac    480
gctgtttcta aggtctttc tctttctgga ttggttcttt tctatgttga ccattttctg    540
ctcgagtttc ttttgcttat tttgtttgga aaaattgaag acagtaattt ggctacagat    600
gtaagtccct gtaactcagg aacttgggcc aaggtttgaa cttgtctctg aaacatttat    660
tccccaaatg gattgttgaa tctaagcttg gttattttac tcaagtttat agttctttgc    720
attatttggt agctgcctca tttgttgtcc aaattgcagt actagtattt gaacaaattg    780
ctggcagatt attgcaagca ctggcctttt cttgttcaat ttggatgttg tatataaata    840
ttttgaagat aatgaaatgt tcacataatg ttctttaagt agtatatatg atatctgctt    900
ctgcattttg atgtttattt tgtgaaagtg tccactgttt gttactcct attaattatt    960
ggaatggcca tttgttgagc agagtcaatc agaggagctt cgatacaagt ttgatcaggg   1020
caatatcggg aggaaggcta tattgtag                                      1048

SEQ ID NO: 50           moltype = DNA  length = 1198
FEATURE                 Location/Qualifiers
source                  1..1198
                        mol_type = other DNA
                        organism = synthetic construct
SEQUENCE: 50
atggcttcta cagtaccggc gaagtcgaat aatccacttt acaacttcga ttttttccac     60
ttgaaatgga agaagaatca tcattcgaac aatcatcaac gtcgccgttc caacaagctg    120
tcgtcggact cttcctctcc gtcacggcac gactcgccgc taaggcactc tcagtctcag    180
tccccgatgc gtgaatccct cgcggcggcc cgtcagtctc cagtaagtga atctgctgag    240
acggcgcgta tatcgccgat gcacaattcg gctcggcggc cgcgtcagtc tccgatgcgt    300
gaatcggcac gtcagtctcc gatgcgtgat cccgttccgt cggttcaacg atcaaagcat    360
aaggtaccag agattaatgt tgtcagtagc aaagaaagca gatcgaaaat cttaattaaa    420
atccctgcca aaaacaaatc cgaagaaatt caaatcaacg aggatcaaaa tcaaaaggag    480
gcagatgagt ctcacgacga agctgcagca gctgaagaaa cagcacaaaa aacgtggaat    540
ctgagacctc ggaagccgat acacaaatca ctgaatataa acggaggagt cccatttcga    600
tccagtggat ctgcgatgca ggagatcaaa tctcaatcac cccatcacat gatgaacgtg    660
aacaagccgg aaaataatga aacccacgct gcttctgctc agaagaaggt aaaaaaggcaa    720
aggtttccca tagcgttatc cagagaagag attgatgaag atctatatgc tatgactgga    780
```

-continued

```
ttaaaagctg ctagaagacc taagaagaga gttaaagttg ttcagaaaca acttgatgta   840
agtatttatc acttttcttt ttctttctat tttgctctta tgatttctag ttatctgatg   900
atatgaattt cttttgcaga cactcttccc tggtttatgg cttgcttcaa taactcctga   960
ttcatataaa gtttgtgaaa atcttccaaa ggtagaattt actgtttgat ggatttaagt  1020
ttacactatc aatgcaatgt aacctgttat aacacgttac ttgccattta tgtaggttac  1080
aattagattt taagcgacct gattgtgcat aaaacttaac tcttgataag attagatttt  1140
catttctccc atagttttct gcgtgtatgt gacagtgtga ttttccttgc agggttag    1198
```

SEQ ID NO: 51        moltype = DNA  length = 1113
FEATURE              Location/Qualifiers
source               1..1113
                     mol_type = other DNA
                     organism = synthetic construct
SEQUENCE: 51

```
atgatgaaca accagtcctc aatctgttcc agcttaaatg aagataaagt tcacgataca   60
ccagatagct tccatcagtt acacccgaag aaagattcag attctctgga tggaagtgag  120
ttagagagtg gagatacaat ttcaacagtc gaacatctga aatcagcatt aaaagctgag  180
aggaaggctt tacattctct gtacacggag ttggaagaag agagaagtgc ttctgctgtg  240
gctgcaagtc agacaatggc tatgatcaat aggcttcaag aagagaaagc agcaatgcag  300
atggaagctt tgcaatacca aagaatgatg gaagaacaat cggagtacga tcaagaagcc  360
ttgcagctaa tgaatgagct tatggtgaag agagagaggg aaaagcaaga gttagagaaa  420
gaattggaag catataggaa aagattattg gaatatgagg caacgaggat gttgaagaga  480
agcaaggaca gtagcacatt ctcctctgag gatagtgatg gactctctat tggtttgaat  540
caagaagaag caaaggaaga tgatagcggc atgaatcata gcactcctgt tggtgcagtt  600
ataaatttgg aggaagagag aatggcgatt cttgagcagc taaaggtttt ggaggaaagg  660
cttgtcagct tggacttgga tgatgaagat gcaaaacatt ttgaggatgt taggctgatg  720
gaagattcat atcaagataa tatagaggaa gattctcatg ccaatggttt cttgaaggaa  780
atgaatggga aacatcatca tgccaaggga aagagacttc ttcctctatt tgacaaaatg  840
agtgatgaaa atggagatgg tacactaaat gccaatgggg ttcataactt tgatttagag  900
aacaagaagc tagctgtgga acaagagttg gatcatctcc atcaaaggct acaagccctt  960
gaggcagata gggagttcct aaacaactgt gtaagctcgc tgaagaaagg cgataaaggc  1020
atggatcttc ttcaggaaat cctactacat cttcgtcatc taaggaacgt tgagcttcgt  1080
gcaacaagct tcagtgatgc tgccatacta tag                                1113
```

SEQ ID NO: 52        moltype = DNA  length = 1113
FEATURE              Location/Qualifiers
source               1..1113
                     mol_type = other DNA
                     organism = synthetic construct
SEQUENCE: 52

```
atgatgaaca accagtcctc aatctgttcc agcttaaatg aagataaagt tcacgataca   60
ccagatagct tccatcagtt acacccgaag aaagattcag attctctgga tggaagtgag  120
ttagagagtg gagatacaat ttcaacagtc gaacatctga aatcagcatt aaaagctgag  180
aggaaggctt tacattctct gtacacggag ttggaagaag agagaagtgc ttctgctgtg  240
gctgcaagtc agacaatggc tatgatcaat aggcttcaag aagagaaagc agcaatgcag  300
atggaagctt tgcaatacca aagaatgatg gaagaacaat cggagtacga tcaagaagcc  360
ttgcagctaa tgaatgagct tatggtgaag agagagaggg aaaagcaaga gttagagaaa  420
gaattggaag catataggaa aagattattg gaatatgagg caacgaggat gttgaagaga  480
agcaaggaca gtagcacatt ctcctctgag gatagtgatg gactctctat tggtttgaat  540
caagaagaag caaaggaaga tgatagcggc atgaatcata gcactcctgt tggtgcagtt  600
ataaatttgg aggaagagag aatggcgatt cttgagcagc taaaggtttt ggaggaaagg  660
cttgtcagct tggacttgga tgatgaagat gcaaaacatt ttgaggatgt taggctgatg  720
gaagattcat atcaagataa tatagaggaa gattctcatg ccaatggttt cttgaaggaa  780
atgaatggga aacatcatca tgccaaggga aagagacttc ttcctctatt tgacaaaatg  840
agtgatgaaa atggagatgg tacactaaat gccaatgggg ttcataactt tgatttagag  900
aacaagaagc tagctgtgga acaagagttg gatcatctcc atcaaaggct acaagccctt  960
gaggcagata gggagttcct aaacaactgt gtaagctcgc tgaagaaagg cgataaaggc  1020
atggatcttc ttcaggaaat cctactacat cttcgtcatc taaggaacgt tgagcttcgt  1080
gcaacaagct tcagtgatgc tgccatacta tag                                1113
```

SEQ ID NO: 53        moltype = DNA  length = 2035
FEATURE              Location/Qualifiers
source               1..2035
                     mol_type = other DNA
                     organism = synthetic construct
SEQUENCE: 53

```
atgctgtggc ggaattcgac aaaattgcag ctgtgttctt catccgctag gagtcgtttg   60
ctactgattt gtcgcctcga acatcaattc atcgtcacac acaggtttgg tacttctaag  120
atcaaccttg cttcattttc tgaaaattca ttcatcgtcaa cattcagttt tgattccttg  180
agaataagca ctgaattttt actcgattgt ctgagttgat tgagtctgaa ttcgttagtc  240
gactcgaagt tgttattagt ttgaaatatt gtatgaagtt ctggtttatg aattcagttg  300
agaattttga ttgagtttca aagtgttaac tgaaagatct cattgatagc ttggtcgagg  360
ttctgtattt gctcttgttg ttggtagttg cgcatgagtt tctgaattct attggagcaa  420
agcttatgaa aattgaaaaa aaattgataa acaattgagc agatttcaaa tagctacagc  480
ttagttcttc aatccagatt gttttactga gcttcagttg ccaagttttc taatttcaag  540
ctccttgaaa cttaaagagg agtgaacaga ttttctttaa gcatcagctc gacactgccc  600
agtttttctta gccaaagtgg gattgattgt tgctgttgct agctctagaa ttgggttgga  660
atttgaatct aagtgttgaa ttgagattgg ttacaattct tgtgcacttt tggacagttt  720
tctgcacttt ttgagccaag tttagcttca gtttactgca gctttatagc ctgtttggcc  780
```

```
aagcttcttt cgaggcaaaa gcgctttttt ttgggtcaaa agtgtttttt tttctaaaat   840
taaggtgttt ggccaagctt ttgaaaggaa aaaaaagtga ttttgaggtg aagcagaagc   900
agttttgtag aagcagaaaa aagtagtttc tctccaaaag cacttttgag aaaaatacac   960
ttacaagcag gtttttaaag cttggccaaa cactaattgc tgctcagaag tacttttcaa  1020
attaattagc caaacacaaa ttgcttctca ccaaaagtac tattgagaaa agcacttttg  1080
agaaaaaaca cttctcaaaa taaactgatt tttgcagctg ggccaaacag gctattagac  1140
tttctactgt ttgatttgtt tttcagaagt tcttccctac tgaacttcta cagtttggta  1200
aactgcttag ctgctgtgaa attggttgac gttagctgat ttgagtttga tcaactattt  1260
gaaatctgct aatttgaggt tggatgtttt ggagtttagt ttggacttga gtttggcaga  1320
ggaagctcaa cagtttgaga attcatttgt gaggactaaa cattaaatgt tgttgcttac  1380
aaaaatcttg tgatagcacc tgcagttctg ccagattttg ttaatttgtc caagattaat  1440
tctgcagcag attttcagtt tctccattgt ttagttgcta aaaatctgag ttgctaccca  1500
gttctgcact agtagtactc tgcaaattat gtgttgttta agctgattgt ctgcactggt  1560
taggtttctg acatggctgc taaagtttaa atccttggac tgtttttaggg tgttattgac  1620
tgagaaaaaa accagaagaa ttttcaggca ttccagctgc agtttgaact aaatctgcag  1680
tatttgaact tgtgtttgaa gcagaaaacc agttgatctt tggggattga aaatctgtga  1740
attgaagagg cctatagctg ctgttaagtt gaattgcaaa ctgcaggttg tagttccctg  1800
ctgctacagt ttggctgcaa ttgtgaacat cttcagtagc ttgcagtcac tgatgaactt  1860
tgcatttgag ctacaacttg gagtcttttt acagaattgc gaagaagatt gctcaggaga  1920
tcaccaacag tctgcaacct tgtcagttat tgtgaggctg tccagaattg cagatttgac  1980
cagtccttac ctatgtggcc attctttgca aatccgacca attttacaaa actag         2035
```

SEQ ID NO: 54          moltype = DNA  length = 1068
FEATURE                Location/Qualifiers
source                 1..1068
                       mol_type = other DNA
                       organism = synthetic construct
SEQUENCE: 54

```
atgtttgatg actctgtatc tactgtttat tcttcaatat ggacatccat gaatagctgg    60
ttcactccca ctgtcctttt tgttcttctc aatctcatga ttggtaccat tgcttttact   120
tcttccttag ctaaccaaaa gccaaatcac cctcccaaac aagaacaaca acaagaagaa   180
caagaatact cacaaaatca cccacaacaa ccctctaaac tcattagatc tccttctatt   240
cttcaacgca tcaaatcttt aaatttctac aacaatagat ctcaagaacc tgttaaagat   300
tacaactttg acgataccca taatcaagaa accacctttg aaccacaaac acattacatt   360
ttcgaaccag ctccagaaca tactaccgta gtaccagaat ctacccagta tattttcaat   420
caatcccatc aagaaaatgc tcaaaaaaca caaacccagt acgatttcca gcaaacccat   480
ctagaaaatc tcccagatac acaaacccag tacctttttc aacacacccc cgaccaagaa   540
ctcaaaaata tggatcaaga tttccacttt cagcaaaccc atcaagaaaa tattcaagaa   600
aaatcggccc gttacattat tcaacacatc catgaacaaa aacttgataa tacagatacc   660
catttcgatt ttcagcaaac ccatgaagaa aatgaggtag aagaagagga agaagaaggt   720
gagctaaaga gcttggatga agtatacaat cagtttaaagg aacgtcacgt gagcaggagc   780
agatcagata caaatccatc ggccggtgaa gctccgataa agttgccgac gaagatgaag   840
aaatcagcaa gcatgaaatc gccatttgcg cattttgaag aggaggctat tgttgaagct   900
cgccggccgg ccactacaag ggagagaaat gtcaagacaa gcgacggaga cattaatgaa   960
gtagatgcta aagcagatga tttcatcaac aagttcaagc aacagttgaa gttacagagg  1020
ttggattcaa ttctcaggta caaggagatg attggtagag ggagctaa                1068
```

SEQ ID NO: 55          moltype = DNA  length = 1158
FEATURE                Location/Qualifiers
source                 1..1158
                       mol_type = other DNA
                       organism = synthetic construct
SEQUENCE: 55

```
atggaaattg ttgccaagtc aaaaaaacac caccattatt attctccttt cccttcttgt    60
ttccgccgcc ctttagaggt agctgccgcc gcctccgctc gtcctcttcc gccgccgccg   120
ccgccgccgc agccaccggt tgctgctaat cccaacctcg ccacctccct ctaccaaacc   180
cacctcggcc tctttgctct cacttggtct cgcaatctct tcggcagatc tttttcacatc  240
catttcctcc tcaacgattc tgatggagtt ggagctgact acaataataa tacaatctct   300
tctcctcatt tatcttccac tagtaccca tctttccacc tcaacatcaa acccttttatt   360
ttctggaaaa aacatgggtc aaaaaaagctc gacggagata acaaggttgt tcatatcttt   420
tgggatcttt ctaaatctaa atttggatct ggccctgaac ctatatcggg attttacgta   480
gctgttattg ttaacgaaga aatggttctt ctggtcggcg atttaaacaa agaagcttac   540
gctaaaaccc gagctcgaaa gccagaaaag aagcagaatc taaacccgaa tccaaaccca   600
aacctggtgc tgagaaggga acacgtatgt ggaaacaaac tctacaaaac aaaagcaaac   660
ttcggtggga aagagaaaga aatctcaatc gattgcaggt taggagaaga tccaaggctg   720
tatttcagcg tagataacaa aagggttttg caaatcaaac acttgaaatg gaaattcaga   780
ggaaatgaaa ggattgaagt tgacggagtt ccagttttgg tttcatggga tgtgtacaac   840
tggttatttg acgatgacga agatgggtat gctctgttca tgttcaaatt cgaaaaatca   900
agttacgaat atgtagctgc tgatgattac agcttaaata atggagttca attgtggtct   960
caacaatctt gtggattcgg gttcgagacg aagatgatga aaaagggtgt attacgaagc  1020
tcgagaagtt catcttcttc atctttatct tcagcatctt caacttgtag ctctgtcatg  1080
gaatgggcta gtactgaaga aaatgaattg aaaggtcctt cgggatttttc tttgctggtt  1140
tatgcttgga aaagctga                                                 1158
```

SEQ ID NO: 56          moltype = DNA  length = 715
FEATURE                Location/Qualifiers
source                 1..715
                       mol_type = other DNA
                       organism = synthetic construct

```
SEQUENCE: 56
atgtggcagt ttaacaagat atggtgccaa aatcaaagaa ttcaaattac ctattggggt    60
aagtatccaa cattgtgttg aaagagttct catacttaga caaaatcttg gatccaattg   120
gtcttctata tactatgaca attatgaatt atcaggttat caacttattt cacctgtttt   180
aggcctatta gcatacaatg ctggtgatga tatggtaact tctacaaccc cttttgagct   240
tataattcaa tctgataaaa ttccaatcac aattgatttt agcaatacaa caagactagt   300
aaatgatact agtacatctg ggataatacc attatgtgct agctttgagc gcgacggaaa   360
ggtgacacta acaaaacaag tgtcacaaaa tgtttgtgct gctaaaaaac aaggacattt   420
tggtttagta attgagtcac ctctaatgcc attgaaaaat aaaagggcaa gtaattggaa   480
attagctatt gggagcgcga ttggagctgc gttgggcgcg ttccttttag gtttgctact   540
gattgcaata tttgtgaagg tgaagaagaa agcaagaatg gaggaattgg ttagaagagc   600
atatgaagaa gaagctttac aagtttctat ggttggacat gtgagagctc caactgcagc   660
tggtactagg actgttccaa ctattgaaca tgactataat cctcataatt cttga         715

SEQ ID NO: 57          moltype = DNA  length = 2732
FEATURE                Location/Qualifiers
source                 1..2732
                       mol_type = other DNA
                       organism = synthetic construct
SEQUENCE: 57
atggatcaga tattgaacaa agtggggttcc tactggattg gtaagagagc taacaaggag    60
ctcaattccg tcggcgatga cattaacgta tgcccccttct tttccttttg cttcaatctt   120
aattatttca gattttgcta tgatctaatt tggaaattct taattatgtc tgtggaacca   180
gtaaatttta taggtttgat tgcataattt accttaatga ctaggatgtt tatcccttaa   240
tagtctgaat ttgctaaatg aaggggagtc ttggagcaat ggtaaaaacc tgtaggtcac   300
gggttcaagt cgtgcaatta gtcactgata gtaggctgcc tacatcacat ccttgagtgc   360
ggcccttccc cggaccctac gcgattgcgg gatgctttgt gcaccggcct acccccttag   420
tctgaatttg ctaaataagc tccttctagc tagatgtgga tctatgattt taagcccctc   480
agtgcgttgg ttcaatacaa aggtagtaca gatgtgcggt aggtgcacat tacgagttcg   540
aacataatag gtaaaccaag tgtgtggtta aatagtgaag gatagaggag cagtctcaat   600
atttaccaag ttccgaagtt ggaaatgact gatttttcag ttatttttaa tgaaaaagaa   660
agtgatagag aaatccgctg tttccaaaaa agaaagcagc acctaagggt gtgaggtagt   720
gaaatataac agagtgcata tgatgattcc attttgccaa ttcctttgca gtttggttat   780
caacaggtgc cactatatga tattttggtc cgtgtcatag ctaatcaacg tttaaggtta   840
aatacgactt tcatagcatg ttagaagcta atttcaaggg ggggagggg atactttcct   900
ttggcatatc ttgagatcat tcacagagtg atgacttctt aatttgggtt ctatctattt   960
ctaattaatg atccaccatt ttcttttttat accatggtat ttcaactgtt gtttattggg  1020
aaatggctct gtgactgtaa ctgggaatgc aaacacttct tcatggaaaa tggattgata  1080
accaagaagt gcggctagat ttaattttgt tggataagac tcccgcagat gcagagcgga  1140
aaagctataa tggaggcata gtactactag gttttgtcac tgacgtgcta aaattcagaa  1200
cttttttgtta gatcagtctc ttctccctca tgctgttatt cttcaagttt tattgatttt  1260
ttttataact gagatatagt tgagggctag tggcacacgg tttagaactt ggaggacaat  1320
gggctcgcct ctctactctt ctccacttaa ataccaggct tttatatgca gtagggtttg  1380
agcctcttca aaattttgt atttcctgtg tggttcctaa acaatgtcat agtagacaaa  1440
ttctagcttt tcttattgct agtctaatgc tcatgcagac ttttttgcgt ggttggcctt  1500
cgattttgat gaattgcttc tcttgttgca tttattgctt atttgcattt ccaagatcaa  1560
tataagttat tgtatacagt ggaaataaag gaacctgatg tgcgtcttct ccaccttttat  1620
tccttaaaac atgagcataa actggtcagc tgagcatccc aatgaatgta agagtgaagc  1680
tgtttactgt taatggaaga aacaaatgga aaacctttat cctcaagatg ttggtaatag  1740
ccaatagaaa ctttttatgtt ctaatatgat tataagtatt ataatgttat gatagttctt  1800
cattaaaaaa aaggtaaccg aagccactta gtgttcctgc ttctctgaat ataatgactg  1860
taattgatgg ggatatttaa aaaaaatttc cacttcagaa aaatcttgat aatgtcactt  1920
ttctagcata gcaactgaaa ccattttaga attactgtta atattactaa gtttgctaaa  1980
tttggaatta cttggagaac tcaggataag tgctgttggt tcccattagt cgtttctctg  2040
cattggattt ttctctatct ggttttttcag ttttatggt tcatactgat cttttccta  2100
tcaataatca gtcattgcaa agcagtattg aaggaggaac aaaatggctg gtgaacaagc  2160
ttaaaggttt gtgttctctt tgcataactc accatgctct tccatttttg cccccccttt  2220
tgtatgttca aaatttgcta tctgatccac tagcgtccct cgttcatctt cttgaggatt  2280
ttctacctat atcaacaagc ttaaaaagaa cttggtacaa gtcataacct ttatcttccc  2340
tggttaatct tggtttttgta ggaaaaatgc aaaagccatt gccagatctt ttgaaggagt  2400
atgatgttcc agtaggtatt ttccctcggg atgccaccaa ttacgagttt aatgaagaga  2460
caaggaagct cactgtctat ataccctctg tatgtgaagt tggttacaag gattcatctg  2520
tattacgctt ctctacagaa gttactggat ttttagaaaa aggaaagcta gctgacattg  2580
aaggaatgaa aacgaaagtg atgatgtggg taaaagttac tgccatctca tctgaaaaat  2640
ccaaggttca tttcacagct gggttgaaga aaacccggag tagggaggct tatgaggttt  2700
tgagagatgg agtagctatt gaaaaaattct aa                                2732

SEQ ID NO: 58          moltype = DNA  length = 1377
FEATURE                Location/Qualifiers
source                 1..1377
                       mol_type = other DNA
                       organism = synthetic construct
SEQUENCE: 58
atgggtgcca ttagtttctt ggacaccata ttagtcccct tgagtctttt catcacaatt    60
ggctatcatt tctatctttg gcaccacttg aagcataaac cttctcgcac caccattggt   120
atgaatatac tcaagaagag atcttggctg cgagagctca tcaagcaag tcttcctttt   180
cattctttag ttttttaattt caattaatta tttatgaaga gaaccttaga gcaacgataa   240
agttattttc atgtgactta taggttacat gttcgagcca tgaaatcaga gtgcttgcat   300
catggtaagt tgtctatgtt acaccccctta ggggttgttt ggtacgcagg atagtgagat   360
```

-continued

```
aaatttatac catcaaccaa acacagtata aatttaatct caaatttaat cctgaatatt   420
cccttatcct atcaaacttg ggattatttt atcgcacctc tcaggtggga taaagggagg   480
tggaataaat tagtccagag attacaatcc agggactata atccaggata atttagtccg   540
catagaaaat gactccttaa catacggccg tttcctgatg cgctttctga aaataactta   600
aataggtatt tgagccagct cgaaagatct ctgcttgaac acgcacaagg tggttcgtgc   660
atcgggcagt cctttatta ctaagagtct aatgaacaaa ggcggatcta aatgttgcta    720
tagggttcaa ttctgtttca actctaacta tgtatacata tacaaaaaga aaattaatct    780
tactcattct taacccgctg actctagatc ttgaataagc ctccgttgat gatttattaa    840
gtttttttt ttgtttgtgt gtggcaggga aacgagaaga aaggcacgtt agctgtacaa      900
agcttaagaa atgcactaat ggaaacaata ctcacggcaa caatcacaat gatcataact     960
ttagcattgg cagctctaac aaacaacact tacaacgtga gaaacctctt tactagtgct    1020
ttctttggat cacaaacagg gaagataatc gtgttgaaat atggctcagc aactattttc   1080
ttgttggcaa gtttcttgtg tagttctttg gcacttagtt gtttgatcga tgctaatttc   1140
ttggtcaatg cattggggga attttccata aatccaatgt atacagagac agtatttgaa   1200
agaggattta cattggcttt tgtaggggat agagtgcttt gcatggcttt tcctcttttg   1260
ttatggatgt ttggccctgt gcctgtggtt gtgtcttctt tggctttggt ttggggatta   1320
catgagcgtg attttgctgg aaatttgtca agaactatga ataagagttg tatttga      1377
```

SEQ ID NO: 59          moltype = DNA   length = 474
FEATURE                Location/Qualifiers
source                 1..474
                       mol_type = other DNA
                       organism = synthetic construct
SEQUENCE: 59

```
atgtcacatc tcactgcagc tccgccatca gaaccaccgt cggcggcggt gaattcattg    60
tacaaacaga aatcgtggtc gccggacacg tttcgcgatg gcgcgtggca gcggcggaag   120
ggtacccatg gaagccgctt aaagcagcgg agcaagagcg ttaccgatga agacctcgat   180
gagctcaagg cttgtattga gttagggttt ggatttgact cgcctgaaat agatcaacga   240
ttgtctgata cttttcccgg cttatggcctt ttttacgctg ttaataaaca atatgccgac  300
acccttttcga agacttcttc tttatcgtcg gtcatctcct attgcgagtc acccgctcct  360
cccggcagtc cccacaccat tgtcgatcaa ggagataatc ctcagacagt gaagacaagg   420
ttgcggcagt gggcacaagt ggtcgcttgg tcagttcgtc aatcttcaca ttaa          474
```

SEQ ID NO: 60          moltype = DNA   length = 2073
FEATURE                Location/Qualifiers
source                 1..2073
                       mol_type = other DNA
                       organism = synthetic construct
SEQUENCE: 60

```
atggagaaaa agcagctgga tttcaatgca ccactttat cagtgaggaa aatttcatca     60
tctttatccc ctcatgagag agcaaataaa aagattatag aaagggcgcc accgaatcga   120
caacaatcac ttcctgtcaa aaaatcagat tgggaattga gtgaggtgac taaaccagta   180
gctgttccat ttatgtggga acagatccct ggaagacgaa aaggtgacaa tgaagcccga   240
gctaaccttc gagtggagtg gtcaagtagt cctaggctgc ccccgggaag attgcccagg    300
actattcggt tctattcggg tgaaaggcct cgtactcaaa acatttacaa gtctccagct    360
gaaggacttc cttggattga tcatgcagct ttacttgata gcctagcgga aagtatatat    420
acaagaggag acagagcaag tgaggatgat gccaattcgt atgctcctga aacattgtca    480
cctaccgaat ccttatcctt ggactgcagt gtcagtggtt tgagcggaca tcaaagttca    540
gattcaaaac catctggaac cttttccatt gactcccaaa ctagagactt tatgatgagt    600
cgattcttac ctgcagcaaa agctgttgtt ttggagacgc ctcagtatgt tcaaaaaaag   660
caagttccag tcagtactga acaacccaag ccagtacctg tggaacgaaa gccaatagtt    720
aagcagatgg agtctaaacc tgtctcatat tatagcggct atccagacga tgtaggaagt    780
gaaattgaag atgatgtgtc tgagaatcag cacaaaagac caagtaaagg gtggaaattt    840
ttccctcgga tttgtgtgaa gaattcttta tgcctattaa atccactgcc aggactaaaa    900
gtgaagacac atgttcccac accctcagct caagcagtaa agagagtttc aggaatgaaa   960
ccaaagacgc cacagagccc cacatcttat gctcatgaag tcaagagatt agctagaaaa   1020
gcttatagtg gacctcttga gaagaatact tgtgatacta taaataagca aagatttcac   1080
tctggagtac tgtctcgcga gctgtacaaa gctgaaaata gaagtttttc cggccaactg   1140
cctaaccta gtgattcatg taagctagtt ggaatctctc ctggaagacg ttcaagaagt    1200
ggggctatat ctccctgtcg aaatgtagca ccccatctc cattcaatga aggtactagg    1260
tttcttggtg tgccaaagga aatggagagt ctttgggcta gccgctttga ttcattccgg   1320
aaaggttgct acactgtcaa ggacaaagta ccacagcaga ttggcacagg aaggttttct   1380
gattcaccaa gtgaagtagt tgagaaaaca ttgtacatag attctgtaga taatgtgcaa   1440
atttcagccc gtaattctgc ttcttcaaag cccaaggaat tggtgaactc ctctggtaag   1500
aatatgaagc cactggttaa aagcagtaaa gtactagaaa atatggatgc caccgctcgt   1560
actcaaggtg ccaaagaccg gaatgtttca gagaaagaga gcaaacaggt ttttgagaag    1620
gagtcccttg atttggtgga agcttctccc atttccatat caacacgcaa aggccctgct    1680
gatcatgagt cttttgaaact aaagcaaaat cttgatacac tatctggagc cttagagtct   1740
tcaaaagtgc atccctatgg aaatttaggt acagaaaatg aagataacca aaatgcaaat    1800
ggcccaaaag attctaacct tacctccttg gaatctccta taccaccacc cttacctaaa   1860
tctccctctg aatcttggct ttggcgcacg ctgccttcca tcccttttgag aactccgttc   1920
tcaagtttga gctccaagaa gcagaataag aagtcccatg ctgatggtag taagtgggag   1980
actattgtga aaacttctaa cttgcataag gatcatgtcc gttactccga ggaactatat    2040
actcttggtt cttgtcagca gagcaaagct tga                                 2073
```

SEQ ID NO: 61          moltype = DNA   length = 1260
FEATURE                Location/Qualifiers
source                 1..1260
                       mol_type = other DNA -continued

```
                                        organism = synthetic construct
SEQUENCE: 61
atggaagtca tatctaccaa cacaaatggc tcgaccatct tcaagaatgg tgccattccc   60
atgaatggcc accagagtgg cacttccaaa cacctcaacg gctaccagaa cggcacttcc  120
aaacaccaaa acggccacca taatggcact tccgaacatc ggaacggcca ccagaatggg  180
atttccgaac accaaaacgg ccaccagaat gggacttccg aacatcggaa cggccaccag  240
aatgggattt ccgaacacca aaacggccac cagaatggga cttccgaaca ccaaaacggc  300
caccagaatg ggacttccga acaacagaac gggacaatca gccatgacaa tggcaacgag  360
ctactgggaa actccaactc tattaagctt ggttggtttt cagagtttag cgcattatgg  420
ccaggtgaag cattctccct taaggttgag aagttactat ttcaggggaa gtctgactac  480
caagatgtca tgctctttga gtcagcaaca tatgggaagg ttttgacttt ggatggagca  540
attcaacaca cagagaatgg tggatttcca tacactgaaa tgattgttca tcttccactt  600
ggttccatcc caaacccaaa aaaggttttg atcatcggcg gaggaattgg ttttacatta  660
ttcgaaatgc ttcgttatcc tacaatcgaa aaaattgaca ttgttgaaat cgatgacgtg  720
gtagttgatg tatctagaaa atctttccct tatctcgcag ctaattttaa tgatcctcgt  780
gtaaccctcg ttctcggaga tggggctgca tttgtaaagg ctgcacaagc aggatattat  840
gatgctatta tagtggactc ttctgatccc attggtccag caaaagattt gtttgagagg  900
ccattctttg aggcagtagc caaagcccta aggccaggag gagttgtatg cacacaggcc  960
gaaagcattt ggcttcatat gcatattatt aagcaaatca ttgctaactg tcgtcaagtc 1020
tttaagggct ctgtcaacta cgcttggact actgttccaa catatcccac tggtgtaatt 1080
gggtatatgc tctgctctac tgaagggcca gaagttgact tcaagaatcc aataaatcca 1140
attgacaaag agacaactca agtcaagtcc aaattagcac ctctcaagtt ttacaattct 1200
gatattcaca aagcagcatt catttttgcca tctttcgcca gaagtatgat cgagtcttaa 1260

SEQ ID NO: 62              moltype = DNA  length = 1062
FEATURE                   Location/Qualifiers
source                    1..1062
                          mol_type = other DNA
                          organism = synthetic construct
SEQUENCE: 62
atggaagtca tatctaccaa cacaaatggc tctaccatct tcaagagtgg tgccattccc   60
atgaatggcc accataatgg cacttccaaa caccaaaacg gccacaagaa tgggacttcc  120
gaacaacaga acgggacaat cagccttgat aatggcaacg agctactggg aaaactccaat  180
tgtattaagc ctggttggtt ttcagagttt agcgcattat ggccaggtga agcattctca  240
cttaaggttg agaagttact gttccagggg aagtctgact accaagatgt catgctctttt  300
gagtcagcaa cttatgggaa ggttctgact ttggatggag caattcaaca cacagagaat  360
ggtggatttc catacactga aatgattgtt catcttccac ttggttccat cccaaaccca  420
aaaaaggttt tgatcatcgg cggaggaatt ggttttacat tattcgaaat gcttcgttat  480
cctacaatcg aaaaaattga cattgttgag atcgatgacg tggtagttga tgtatctaga  540
aaaatttttcc cttatctcgc tgctaatttt aacgatcctc gtgtaaccct agtccttgga  600
gatgggctg catttgtaaa ggctgcacaa gcagaatatt atgatgctat tatagtggac  660
tcttctgatc ccattggtcc agcaaaagat ttgtttgaga ggccattctt tgaggcagta  720
gctaaagccc taaggccagg aggagttgta tgcacacagg ctgaaagcat ttggcttcac  780
atgcatatta ttaagcaaat cattgctaac tgtcgtcaag tctttaaggg ctctgtcaac  840
tatgcttgga ctactgttcc aacatatcca accggtgtga ttggttatat gctctgctct  900
actgaaggac cagaaattga cttcaagaat ccagtaaatc caattgacaa agagacagct  960
caagtcaagt ccaaattagc acctctcaag ttctacaact ctgatattca caaagcagca 1020
ttcatttttgc catctttcgc cagaagtatg atcgagtctt aa                    1062

SEQ ID NO: 63              moltype = DNA  length = 1146
FEATURE                   Location/Qualifiers
source                    1..1146
                          mol_type = other DNA
                          organism = synthetic construct
SEQUENCE: 63
atggaagtca tatctaccaa cacaaatggc tctactatct tcaagaatgg tgccattccc   60
atgaacggtt accagaatgg cacttccaaa caccaaaacg gccaccagaa tggcacttcc  120
gaacatcgga acggccacca gaatgggatt ccgaacacc aaaacggcca ccagaatggc  180
acttccgagc atcagaacgg ccatcagaat gggacaatca gccatgacaa tggcaacgag  240
ctacagctac tgggaagctc caactctatt aagcctggtt ggttttcaga gtttagcgca  300
ttatggccag gtgaagcatt ctcacttaag gttgagaagt actattcca ggggaagtct  360
gattaccaag atgtcatgct ctttgagtca gcaacatatg ggaaggttct gactttggat  420
ggagcaattc aacacacaga atggtgga tttccataca ctgaaatgat tgttcatctt  480
ccacttggtt ccatcccaaa ccctaaaaag gttttgatca tcggcggagg aattggtttt  540
acattattcg aaatgcttcg ttatcctaca atcgaaaaaa ttgacattgt tgagatcgat  600
gacgtggtag ttgatgtatc tagaaaattt ttcccttatc ttgctgctaa ttttagcgat  660
cctcgtgtaa ccctagtcct tggagatggg gctgcatttg taaaggccgc acaagcagga  720
tattatgatg ctattatagt ggactcttct gatcccagaa atccagcaaa agacttgttt  780
gagaggccat tctttgaggc agtagccaaa gccctaaggc caggaggagt tgtatgcaca  840
caggctgaaa gcatttggct tcatatgcat attattaagc aaatcattgc taactgtcgt  900
caagtctttta agggctctgt caactatgct tggactactg ttccaacata tccaaccggt  960
gtgattggtt atatgctctg ttctactgaa ggaccagaag ttgacttcaa gaatccagta 1020
aatccaattg acaaagagac aactcaagtc aagtccaaat tagcacctct caagttctac 1080
aactctgata ttcacaaagc agcattcatt ttgccatctt tcgccagaag tatgatcgag 1140
tcttaa                                                            1146

SEQ ID NO: 64              moltype = DNA  length = 510
FEATURE                   Location/Qualifiers
source                    1..510
```

```
                         mol_type = other DNA
                         organism = synthetic construct
SEQUENCE: 64
atgccaaatc aaaagcaagg aagtgaacag ctacaaacac tgatgcaatc aggtcaaatt    60
tcggggtctt tgagttttaa tggggcttta actaaagaag atgaagagat gtctaggtct   120
gctctttcta cttttcaaagc taaagaagaa gaaattgaga aaaagaaaat ggaagtcaaa   180
gaaagagttc aagctcagtt gggtcgggtc gaagaagaaa ctcggcgttt agccattatt   240
cgtgaggagc tagaagcatt agctgatcca aagaagaaag atgttcaaat cgttcggaag   300
aagattgatg ctgtcaacaa agagttaaaa cccctgggac agacctgcca gaagaaggaa   360
aaagagtaca aagaagctct tgaggcgttc aatgaaaagc acaaggaaaa agtacagcta   420
ataacaagat tgatggagtt ggtgggtgaa agcgagaaac tgcgactgaa gaagttggag   480
ctgagcaaga gcatagaaac aatacgctga                                    510

SEQ ID NO: 65            moltype = DNA   length = 1308
FEATURE                  Location/Qualifiers
source                   1..1308
                         mol_type = other DNA
                         organism = synthetic construct
SEQUENCE: 65
atggatccgt gtccttttgt gagaatagtt atcggaaact tagccttgaa gtttccggcg    60
gaacataaac tctcctcaag tacggttttt gattgtaaat tcaagcttag aggtttctcc   120
acacaagttt caaccatctc agcttttgtt caagatccaa ttttggacaa cagaactcac   180
tcttgtttca acttgaacaa aacagaactc gacaaactgg tcgaaaaatc aactgccaaa   240
ggaaaaactt gcagcttaaa gattgaaatt tttgcacgga agaaggggat tggttgtggg   300
ttattgaatg gtgggaagct attggggagt gtaatagtgg atttaaaggg gttggaaagt   360
gatggtcgga gaggagttgt gattcagaat gaatgggttt tggttggtgg atctagtact   420
gcagcacaat tgcatttgaa tgtgaaagct gaacctgatc caagatttgt tttccagttt   480
gatggtgaac ctgagtgtag tcctcaagtt tttcaagtca atggcaatgt taaacaacct   540
gtttttactt gcaagttcag tttcaggaat aatggtgaca ggaatttgag atcaagatct   600
tcactatcaa aaccaagtac atcaacaagc tgctttaatt cttgcacatc tgataaagaa   660
tcatcgccgc taaaagagcg aaagggatgg tcaatcacaa ttcatgatct ctctggctca   720
ccaattgccg cagcatctat ggttacacca tttgtcccat cacagggttc aagtaatgtc   780
agcagatcaa accccggggc gtggctcatc cttcgcccag gcaacggtac atggaagccg   840
tggggccgct tagaagcatg gcaagagcgc ggtggtgacc tcggttatcg ctttgaaatc   900
atccctgatg gtgctactga tgccataact ttgtccaatt caactatcag caccaagaat   960
ggtgggaaat ttggtgtaga catcaccaat ggtgctaccc cattgactag tccaaacagc  1020
agctttgact tatgctcggg ttctggatcc gggtcggatt tcgggtcagc acccggatcc  1080
gggtcgtggg cacaactctt gtaccgtggt ttcgtgatgt cgtccacggt ggagggtgag  1140
ggaaaatgca gcaagccaga ggtggttgtc ggggtcgaac acgtgaactg cgtggaggat  1200
gctgcagctt tcgttgcatt ggcagctgcc atggatctta gtatggatgc ttgtcagtct  1260
tttactaaga agctccggaa agagttgaga cagtcggatc aagaatga               1308

SEQ ID NO: 66            moltype = DNA   length = 426
FEATURE                  Location/Qualifiers
source                   1..426
                         mol_type = other DNA
                         organism = synthetic construct
SEQUENCE: 66
atgtcaggcg aggatgttgc agttgctgtt gccgagactc ctgctccagc acttggagag    60
cccatggaca tcatgactgc tttgcagctg gtgctgagga agtctaaggc tcatggaggc   120
ctagctcggg gactacatga aggtgcaaag gtgattgaga agcatgcagc acagcttgtt   180
gtgttagcag aggactgcga ccagccagat tatgtcaaat tggtcaaagc actctgtgct   240
gatcacaatg tcagcttgat cacagttccg aatgcaaaaa ctcttggcga atgggctggt   300
ttgtgtaaga ttgactctga agggaaagca aggaaagtgg ttggctgcgg ctgtgttgtt   360
gtgaaggatt atggggaaga gactgagggt ctgcatattg tccaggagta cgtaaagtcc   420
cattaa                                                              426

SEQ ID NO: 67            moltype = DNA   length = 432
FEATURE                  Location/Qualifiers
source                   1..432
                         mol_type = other DNA
                         organism = synthetic construct
SEQUENCE: 67
atgtcaggag aggatgctgc tgttcctgtt gttgctgccg agactcctgc tccagcactt    60
ggggagccca tggacatcat gaccgctctg cagctggtgc tcaggaagtc taaagctcat   120
ggaggacttg ctcggaggact ccatgaaggt gctaaggtga ttgagaagca tgctgcgcag   180
ctttgtgtgc tagcagagga ctgcgaccag ccagactatg tcaagctggt caaagctctt   240
tgtgctgatc acaatgtcag tttgattaca gttcccaatg caaaaactct ggcgaatggg   300
gctggtttat gcaaaattga ttctgaaggg aaagcaagga agttgttgg ttgtggctgt   360
gttgtcgtga aggattatgg ggaagagact gagggtctcc atatcgtcca ggagtacgtg   420
aagtctcatt aa                                                       432

SEQ ID NO: 68            moltype = DNA   length = 1299
FEATURE                  Location/Qualifiers
source                   1..1299
                         mol_type = other DNA
                         organism = synthetic construct
SEQUENCE: 68
atggatcctc aggctttcat taggctgtca ataggtcgc tggggttgag actgtctgga     60
```

```
acaactactt tgaacagtac aaaaacaggg ataagtgcag tctcttctcc ctgtgtgtgc    120
gagatccgtc ttcgaggttt ccctgtgcag acatcatcta ttccctatat ttcctcacct    180
gaagctacac cggatattca caacgttgca tccagctttt atcttgaaga atctgatttg    240
aaagctttac tggcacctgc cccctgtttt tatgcggctc atgcatgtct agagatagtt    300
gtttacacag gacgcaaagg aggccactgt ggtgttgtta ttaagaggca gcaagttggg    360
acatttaagt tggaagtagg tcccgaatgg ggtgaaggaa aaccagccat tctgtttaat    420
ggctggatag gaattggcaa gaacaagctg gagactggaa aacctggagc ggagcttcat    480
ttgagagtga agctggaccc tgatccaaga tatgtttttcc agtttgaaga taaaacgaaa    540
ctaagccctc aaatagtgca gcttcaggga accatcaagc aacctatttt cagttgcgag    600
tttagtcagg acagggtatc tccggtagat ccattaaata attttttggtc aagttcattt    660
gacggttctg aactagaggt agagaaaaga gagaggaagg gatggaaggt gaagatacac    720
gatctctctg ggtcggctgt tgcagcagcc ttcataacaa ctccgtttgt gccatcaaca    780
ggttgtgatt gggtggccaa atccaaccca ggagcttggt tgattgttcg tcctgatatt    840
tgcaggcccg aaagttggca gccatgggga aagcttgaag catggcgtga acgtgggatc    900
agagattcca tttgctgtcg cttccatctt ctatcagagg ggcaggaatg tggtggtgat    960
cttctcatgt ctgaaatctt gatcagtgca gagaagggtg gtgagttcta cattgacacg   1020
gacagacagg tacaagcagc agcgagtcca ctgcccagtc caagaagcag cggagacttt   1080
gcagcactaa gtcctgttgc aggcggtttt gtcatgagct gtgagtgca aggggaaggg   1140
aaatgcagca aacccctcgt gcaacttgcc atgcgacaca tcacctgtgt ggaagatgca   1200
gccattttca tggcgcttgc tgctgcagtt gatcttagca ttgaggcatg caggcctttt   1260
cgcagaaagc tacggagaag tactcgccat tcctggtga                          1299
```

```
SEQ ID NO: 69            moltype = DNA   length = 1284
FEATURE                  Location/Qualifiers
source                   1..1284
                         mol_type = other DNA
                         organism = synthetic construct
SEQUENCE: 69
atggctaagg tgtgcttta caatgtgaag atgaatatgc aagtgatgtt ttgcttgttt     60
ttggtgtcac tatgtcgtga tgatgcagct gctgaagcta aacaggggat gtctcttgct    120
gcccaaaagt tcgaggttca aaagcacttg aatcgcttaa acaaacctgc aatcaaatcc    180
ataaagagcc cagatggtga tattattgat tgtgttcata tgtctcacca accagctttt    240
gatcatcctt tgctcaagaa tcacactgta cagatgatgc caaattatca cccagaaggg    300
ctatttcgtg atggaaaatt gtctacagca aaaaccaaga atgaaggttc aaaatcaatt    360
actcaactgt ggcatttgaa tggaaaatgt ccagaaggaa caattccaat tagaagaacc    420
aaaaaagatg atattttaag agcaagttcc atgaaaagct atggtaggaa gaaaaaacat    480
tctactattc ctaaaccaga gtctggtaga cctggccttg ttagccaaac tggtcatcag    540
catgcaatag cctatgttga aggagacaaa tattatggtg caaaagcaac cataaatgtt    600
tgggaaccta aaattcagca acccaatgag tttagcttgt ctcagctttg gattcttgga    660
ggttcttttg attcagatct taatagcatt gaagctggat ggcaggttag cccagatttg    720
tatggagata acaacacaag actttttacc tactggacta gtgatgctta tcaagccaca    780
ggctgctaca atctgttatg ttcaggattt attcaaatca ataatgaaat agcaatgggg    840
gccaccattt cccctctttc cagctatcat ggttcccaat atgatataag cattcttgtc    900
tggaaggatc caaaagaggg aaactggtgg atgcaatttg ggaatgacta tgtattggga    960
tattggccag gcttttatt ttcatattta acagacagtg cttcaatgat tgaatgggt    1020
ggggaagtgg tgaattcaga atcagatgga cttcacacca caactcaaat ggggagtggc   1080
cattttccag atgaaggttt tgggaaatca agctatttca ggaatataca agtagttgat   1140
ggttcaaata atttgagagc tcctcaagat cttgggattt atactgagga taacaattgt   1200
tatgatgttc aactaggaaa aaataatgac tggggggaact acttttacta tggtggacct   1260
ggcagaaatc ctaattgtcc atga                                          1284
```

```
SEQ ID NO: 70            moltype = DNA   length = 939
FEATURE                  Location/Qualifiers
source                   1..939
                         mol_type = other DNA
                         organism = synthetic construct
SEQUENCE: 70
atgtcaatag acaaaagctc aatgcaatca aaccttgatt gcttcttgga atgcaccaca     60
ccgttagtcc cttcccagtt tctaccccag agtagatta ggaatctgaa caggttatgg    120
catccatggg aaagggagaa ggttgaatat tttactttgg ctgatctttg gaattgttac    180
gacgaattga gtgcttatgg ggctggagtt cctattaaaa tggatacagg cgaaacttta    240
gttcaatatt acgtgcctta tctttcagct attcaaatct ttaccagcag gtcttctgtt    300
aattttctga gggaagagac tgagtctgtt tgcgagacga gggattcgtt cagtgattcg    360
ttcagcgacg agagtgaaag tgaaaagcta tcaagatggg atggttgttc ttctgaggaa    420
ggagatagtc tttggcaaat gaatgataga tggggctatc tttattttca gtactttgag    480
agatctactc cttatggaag agtccctta atggacaaga ttagtggttt agctgaaaga    540
taccccggat taatgtcatt gagaagtgta gatctttcac cagctagttg gatgtcagtt    600
gcttggtatc cgatatatca cattcctatg ggaagaacca ttaaagactt gtcagcatgc    660
tttctcacat tccacaccct ttcttcttct ttccaagata tggaccttga agatgacacg    720
gagaatggta aacggaaacg aaaggaagga gaaagcatcc cacttccacc tttcggtttg    780
ggcacttaca agatgcaggg tgatgtgtgg ctttcagaca ggaaaggaag ggaccaagag    840
aggctggcat cactttttag cgtggcggat tcttggctaa agcagttggg tgtccagcac    900
catgacttca actatttcat gggtattcgt cgtggctga                           939
```

```
SEQ ID NO: 71            moltype = DNA   length = 951
FEATURE                  Location/Qualifiers
source                   1..951
                         mol_type = other DNA
                         organism = synthetic construct
```

-continued

```
SEQUENCE: 71
atgacaaaaa ctagcaaggt gcagcgggta cctggtttgc tatcttgccg ctcaaaggtg    60
tgcaaaaaga ttcaaaagga gaaacgaccg aaatcatcag agaagaaaga atgggaaggg   120
gcaacttgct cagtttgcat ggagcatcct cacaatgcag tgctgctgct gtgctcttct   180
tatgacaagg gatgtcgtcc ttatatgtgt gccactagct gtcgtttgtc gaattgtctt   240
gagcagtaca agaaagccta tgcgaaagtc acttcaattg agggctctga accagagttg   300
ctgtcaattg atgatccaaa ttgcttgtca ggagcaggtt cttgcgctgg gaagtcggta   360
gttgaacttc tatgcccact ctgtcgtggg caggtgaagg gttggacggt tgttgaacct   420
gcacgcaagt atctaaatgc aaagaagaga acatgcatgc atgaaaattg ctcatttgtt   480
gggacataca aaaagttaag gaaacatgta aggcgggagc atccatcagc acgcccctc   540
gaagtcgacc cttcacatgc agagaaatgg aagaagcttg aacacgagag agagttgaac   600
gatgtattta gcacaatcag atcggccatg cctggggcaa ttgtaatggg agattatgta   660
atagagggta actttggagg cttccacaga aattttggat tagatgatca cctcggtgac   720
actcttttta ggtcggaatc taatggcatt ccctggaatg atattgtcca ctcagatgat   780
gttttcgatg atggctatca ttcgtttgat gaggatgatt ttttcgtcaa tcattctggc   840
agtggggctg catctaatgt tttcaatagg atttctcgac ttcgtagcag gctcttattg   900
ggaagatcaa ggaggcggca acgacatcga gcgagtagca gaattcggtg a           951
```

```
SEQ ID NO: 72        moltype = DNA   length = 1281
FEATURE              Location/Qualifiers
source               1..1281
                     mol_type = other DNA
                     organism = synthetic construct
SEQUENCE: 72
atgaggacat tgtgctccaa cttggataga gaagatgggc tggaaacagt gctggaagtc    60
cccatcccag aagaaatgtt tgcttccaac aagcacaggg acaggcagag caagaattct   120
ggggtcaaat ctcacatgga caagtctgct gcttccgttt ttggtagccg aaatgctgag   180
attcaactct tgcttggcgt tgtttggagct ccgttgatcc ctcatcctat ccgttgcgac   240
tactctctca acacaaaaat caacgatcat cccatagaag cttcagtggc gaaatatata   300
gtacaacagt acatagcagc agcaggggga gaacatgctc taaattccat tgatagtatg   360
tatgcaatgg ggaaaataaa gatggtggcg tctgagttta ttgctggaga tggaatggga   420
ttgaacaacg gtaatatgat gaagattaag agtgtgaaaa atgggcctgg tgaaatggga   480
ggatttgtgt tgtggcaaaa gagacctgac ctgtggagca tagagctggt ggtttcaggg   540
tgtaaaatta gtgctggaag tgatggtaaa gtagcttgga ggcaaactcc atggcataat   600
tcccatgcat ctcgtggtcc tgctaggcct cttcgtcgtt ctttacaggg tcttgatccc   660
aaatccgttg cgaatttatt ctcgaattcc atttgtattg gagagaagac ggtgaatata   720
gaagactgtt ttgtactaaa gcttgaaaca gagccctcaa ctctgaaagc aagaagcagc   780
agcaacgttg aagtaatgag gcacactgtt tggggttact tcagccaacg aacagggctc   840
ttactccagc ttgaagacac tcatcttctt agaatcaaag cccaggaaa tgatgtcttt   900
tgggaaacaa caatggactc attaatactc gattatcgaa ctctcgacg tgttaatatt   960
gcacatggtg gaagaacatc tgtttcttta tttaggtttg gtaagaactc agaaggactc  1020
actaggacaa gaatggaaga ggtttggacc attgaagaaa tcgattttaa cataaaggga  1080
ctatctgcgg attgtttctt accacctagt gacttgaaaa aggaagatga agtgagtcat  1140
gatgtgaaca agaagtcaag gttggggttc aaggctcgta ctaataatgc taaactaaga  1200
actgctagga aaggtgcgtc taaaatcatg tctattgacg aagaagatct tgaagattac  1260
gaagcagatg aagaatcttg a                                            1281
```

```
SEQ ID NO: 73        moltype = DNA   length = 378
FEATURE              Location/Qualifiers
source               1..378
                     mol_type = other DNA
                     organism = synthetic construct
SEQUENCE: 73
atgattattg gctctagctt ctcagaaaaa ttgatgggaa agaagaaaat tttgaagaag    60
acaaaggagt tatcagtagc aatagcagaa tcatcagcaa tgagtggaga ctctcaacaa   120
caacaacaac agattactcc tagaaaaaga ggaagaccaa ggaaaattat tgtaaaagat   180
gaagaagagg ctactggaga aataaagaaa ctcaaaataa atgaaggtga agaattagaa   240
aataaagaag cagcagaagg agaaaagaaa gaagcagaag aacaatctga gaggaaaaa   300
aatttacagc cacaaaagca gcaacctgta gcaaagagca gagctagaag aaaaagcaag   360
ccaagaaaaa gctgctaa                                                378
```

```
SEQ ID NO: 74        moltype = DNA   length = 1578
FEATURE              Location/Qualifiers
source               1..1578
                     mol_type = other DNA
                     organism = synthetic construct
SEQUENCE: 74
atgatggcac agcatattga gattagccca ctgcttgatc aaaactcctcc gaatgaagct    60
acgaaagatg agtcgccagc tcgcccgcgg ttgctaaagc cttcacccac tgccgctgct   120
tccttcttcg cctttgccgt cgccagtcat caagtgatac aagaaggcgg gaaagcagat   180
tatataatcg agataaggac agcagatcaa acaaatgaat cagcaaatca agtctttgat   240
gaaggatcat ctaccatatt taaagtaaat gtggggctat ctgaatcaaa tccagatgct   300
tataccccaa aattgatctc cattggtcct taccataacc aaaatccgag acttcgctcg   360
atggaaaaat ataaactgcg ttaccgacaa cggtttctgc agaggaaagc gtggagagat   420
gtggagtatt actttagtga aatggagaaa ctaaaggatg aagcactaaa gtgttacgat   480
gatataaggg accttgacag taatattgtt agcaaatttt tagatttgct gttacttgat   540
ggctgcttcg tggttgagta tatacgagag ttttacgaag gggtgccaga aggagaagac   600
aagattatca acgcggcttg gatggaatct ctggtagatc gtgacttgtt gttactagaa   660
aaccaacttc ctttctttat cctcgccaaa cttcatgaga tgactaagga tcctacagac   720
```

```
gccccattca tacagatggt gaaatacaac tttggtagta gtttaccaaa agtgactcct   780
aaattcataa atgctactga tgatgatgcc gaagaaatca aacatttact tcaagtagta   840
cacatgtgtt gttgcccttc agagatgaat actggcctaa ctaggaatag cagaaagaaa   900
aaaggaagta gcaagaaaag ttgtaactgg aatcctttgc gaataggaaa gtccaaaaag   960
aagtttaaaa ctaaggatgg tgacttatgg cacgatcgca tgcgaagtgc aacagaactt  1020
gatgaagctg gaattcgctt ctctaatgtt gggaaaattt atagaaagtt gaataaaaac  1080
aacaaggagg atgctataag tttatttgat atcaaattca ataagggatt gcttgaaatc  1140
ccttgttttg aagtcattaa tagtacggag actatcctga gaaatctcat tgcctacgaa  1200
caacactcct ctgatgtgca tccaaaatat ttcacggatt atataatttt tatggaccat  1260
cttattaact caggcaaaga tgtgaatttg cttcggttga acggaattat cagaaatagg  1320
ataggagatg acgaagaagt ggctattatg ttcaacaaac taggagaagg tgtcatccct  1380
tcaactgatt tcttttacaa agtggaatgc agaaaagtga ttgagcattg tgaaaaacca  1440
tggaatgaaa acatggcaag tttgaggcac aattatctta atagcccttg ggcgaaaatt  1500
tcaactgcgg cagccatcat tctccttctg ctcacagttg cacaaacagt tctagctttc  1560
atcagtactt taaagtag                                                1578
```

```
SEQ ID NO: 75           moltype = DNA   length = 909
FEATURE                 Location/Qualifiers
source                  1..909
                        mol_type = other DNA
                        organism = synthetic construct
SEQUENCE: 75
atgagggact tcccatcttg ttttggtgaa aatggggttc aagttgctga tgcttcttgt   60
tcagctgttg ggggtgtgac taaaaccccca cagaatttag tcacatgtgt ttatcagtgt  120
aaactacttg ggaaatcttg tctgatcact attgtttgga ccaagagttt gatgggtcaa  180
tgccttagtg ttgaaattga tgatatgtct catcagtgtc tttgtaaagt tgatgtaaag  240
ccttctctct tctccaaaag aaaagggtca aggtctttag aagtaaattc ttgtaaaatt  300
gacctacact gggacttttc actaggcaag tttggatctg ggccagagcc tatagaaggg  360
tattatttag ctctagtttg caaaggacaa atggtttttgg tcattgggga tctgaggaaa  420
gaagcattta aaaagactaa tgcaactcct agttttttcaa atgcaatgtt catttctaaa  480
agagagcaca tatttgggaa gagggtattt ggtacaaagg ctcaattttg ttatacaggt  540
ccaattcatg acattacaat tgaatgtgac tctaatggca ttgacgatcc gtgtcttttg  600
gtccgtattg actctaaaac tgtaatgcaa gtgaagcatt tgcggtggaa gtttcgcggt  660
aactatactg ttttaattga tggactccct gttgaagtct tttgggatgt tcataactgg  720
ttgttcagta gcaattttgg gaatgcagtg ttcatgtttc aaacttgttt atcggccgag  780
aagttgtgga ccacacaaac tttgtcggat ctctctgtga tgccttggtc ttacacagag  840
agtttgagca attccaaatc atctggtttg ggttttttctt tggtttttgta tgtttggaag  900
aacgagtaa                                                          909
```

```
SEQ ID NO: 76           moltype = DNA   length = 1128
FEATURE                 Location/Qualifiers
source                  1..1128
                        mol_type = other DNA
                        organism = synthetic construct
SEQUENCE: 76
atggaagtca tatctaccaa cacaaatggc tctaccatct tcaagaatgg taccattccc   60
atgaacggcc accaaaatgg ctcttccgaa cacctcaacg gctaccagaa tggcatttcc  120
aaacaccaaa acgggcacca gaatggcact tccgaacatc ggaacggcca ccagaatggg  180
acatccgaac aacagaacgg gacaatcagc catgacaatg gcaacgagct actgggaagc  240
tccaactcta ttaagcctgg ttggtttttca gagtttagcg cattatggcc aggtgaagca  300
ttctcactta aggtcgagaa gttactattc caggggaaat ctgattacca agatgtcatg  360
ctctttgagt cagcaactta tgggaaggtt ctgactttgg atggagcaat tcaacataca  420
gagaatggtg gatttccata cactgaaatg attgttcatc taccacttgg ttccatccca  480
aacccaaaaa aggttttgat catcggcgga ggaattggtt ttacattatt cgaaatgctt  540
cgttatcctt caatcgaaaa aattgacatt gttgagatcg atacgtggt agttgatgta  600
tccagaaaat ttttcccttta tctggcagct aattttaacg atcctcgtgt aaccctagtt  660
ctcggagatg gagctgcatt tgtaaaggct gcacaagcgg gatattatga tgctattata  720
gtggactctt ctgatcccat tggtccagca aaagatttgt ttgagaggcc attctttgag  780
gcagtagcca aagcccttag gccaggagga gttgtatgca caggctga aagcatttgg  840
cttcatatgc atattattaa gcaaatcatt gctaactgtc gtcaagtctt taagggttct  900
gtcaactatg cttggacaac cgttccaaca tatcccaccg gtgtgattgg ttatatgctc  960
tgctctactg aagggccaga agttaacttc aagaatccag taaatccaat tgacaaagag 1020
acaactcaag tcaagtccaa attaggacct ctcaagttct acaactctga tattcacaaa 1080
gcagcattca tttttgccatc tttcgcccga agtatgatcg agtcttaa             1128
```

```
SEQ ID NO: 77           moltype = DNA   length = 1128
FEATURE                 Location/Qualifiers
source                  1..1128
                        mol_type = other DNA
                        organism = synthetic construct
SEQUENCE: 77
atggaagtca tatctaccaa cacaaatggc tctaccatct tcaagaatgg tgccattccc   60
atgaacggcc accaaaatgg cacttctgaa cacctcaacg gctaccagaa tggcacttcc  120
aaacaccaaa acgggcacca gaatggcact tcgaacatc ggaacggcca ccagaatggg  180
acatccgaac aacagaacgg gacaatcagc catgacaatg gcaacgagct actgggaagc  240
tccgactcta ttaagcctgg ctggtttttca gagtttagcg cattatggcc aggtgaagca  300
ttctcactta aggttgagaa gttactattc caggggaagt ctgattacca agatgtcatg  360
ctctttgagt cagcaactta tgggaaggtt ctgactttgg atggagcaat tcaacataca  420
gagaatggtg gatttccata cactgaaatg attgttcatc taccacttgg ttccatccca  480
```

```
aacccaaaaa aggttttgat catcggcgga ggaattggtt ttacattatt cgaaatgctt   540
cgttatcctt caatcgaaaa aattgacatt gttgagatcg atgacgtggt agttgatgta   600
tccagaaaat ttttcccttac tctggcagct aattttaacg atcctcgtgt aaccctagtt   660
ctcgagatgt gagctgcatt tgtaaaggct gcacaagcgg gatattatga tgctattata   720
gtggactctt ctgatcccat tggtccagca aaagatttgt ttgagaggcc attctttgag   780
gcagtagcca aagcccttag gccaggagga gttgtatgca cacaggctga aagcatttgt   840
cttcatatgc atattattaa gcaaatcatt gctaactgtc gtcaagtctt taagggttct   900
gtcaactatg cttggacaac cgttccaaca tatcccaccg gtgtgatcgg ttatatgctc   960
tgctctactg aagggccaga agttgacttc aagaatccaa taaatccaat tgacaaagag   1020
acaactcaag tcaagtccaa attaggacct ctcaagttct acaactctga tattcacaaa   1080
gcagcattca tttaccatc ttttcgccaga agtatgatcg agtcttaa             1128
```

```
SEQ ID NO: 78              moltype = DNA  length = 1443
FEATURE                    Location/Qualifiers
source                     1..1443
                           mol_type = other DNA
                           organism = synthetic construct
SEQUENCE: 78
atggccaaca aggtctccaa tttctccgat ctaatccaac gtgtcactgc ttcttgcttg   60
cttcatccac tttcctctgg ccgtattgac ggcaatatct ccgatgctcg ttatagcgat   120
gaatctgaag atgacaagta cagtaccgaa gacgaagaag aaaaagaaga cccacccttat   180
gtggagactc gggaaaaatt ccagaatgtt gaggtcacaa aggaggagat aagaactgag   240
aaagtaactg aaatggagat gctttttaggg gaagtttttg acgcggtgtc ggcagtgaag   300
acggcttacg ttagtctaca ggaggcgcat tgtccttggg atcaggataa aatgcgtgtg   360
gctgacgtgg ctgtgatatc tgaactgcgg aggcttgggg tgttgaggga acgatttcga   420
aggaatgttg gtggtggaat tagaaaaggg gactggagga ttggcgccgc tacgctgaga   480
gaagtggtgg caccatatga agccaccgtg gaggaactga ggcaagaagt gaaggccaaa   540
gaaatcgaga ttgataattt gagggagaag ctgaaaacag caacaagtct tagcagcagt   600
ggtggaaaga aaagcaagtc aaaacgaaaa gttagcggta gcagtcaagc tccagttaca   660
atgtcgccgg cacctgacgt attcgaaact acagtgagct tagtaaaaga agcttcaaaa   720
tccttcacga gtttgctcct ctctttgatg cgctctgctc actgggacat tgcagcggcg   780
gtgagatcca tcgaagctgc ttcatccaac acaaacacac ccacggcaga ttctatcgtt   840
ggagccaacc atgccaaata cgcactggaa tcttatgtga accgcaaaat gttccaagga   900
ttcgatcacg agacgttcta catggatgga agcttatcat cactaatcca cccagatcaa   960
caccggcgcg attgtttttac acagtacagg gacatgaaag caatggaccc aatggaactt   1020
ctgggaattc tcccccacttg cagtttcggg aacttctgtt tcaagaagta tttggccatt   1080
gtgcacccaa aaatggagga gtctctgttt ggtgatttgg agcagcggcg acaggtgttg   1140
gctgggaacc atccgaggag tcagtttttat ggggagtttc ttgggctagc aaaggccgtt   1200
tggctgctgc atttgctaac ctttttcttg gatcctccgc caagtcattt cgaggcgagc   1260
aaaggatctg agtttcaccc gcagtacatg gaaagtgtgg tgaagtattc catttccatg   1320
ggcataggag ggagaatggg tatgggtcta gttgtcggat ttccagttag tcccgggtt   1380
aagcttggaa atggatcggt tgttaaggct agagtttatt tagtccccaa aaatgggttt   1440
taa                                                                1443
```

```
SEQ ID NO: 79              moltype = DNA  length = 324
FEATURE                    Location/Qualifiers
source                     1..324
                           mol_type = other DNA
                           organism = synthetic construct
SEQUENCE: 79
atggatcgtc taatcaactc tgacaaagat gtgaagttgt ttcgcttgaa gggaatcatc   60
agaaaccgga taggcgatga caatgaagca gctagcatct ttaacagact tggagaagga   120
gtgatccctt caactcagtt ctattacaaa gaagcatgca aaaaggtggt tgagcattgt   180
gaaaaaccat ggagtgaaag gaaggcaagt ttttggcaca attactttaa tggtccttgg   240
gtgggacttt caactgcagc tgcagtaatc ctcctttcgc tcacagttat gcaaacagtt   300
ctaactttca taagtactct ttaa                                         324
```

```
SEQ ID NO: 80              moltype = DNA  length = 804
FEATURE                    Location/Qualifiers
source                     1..804
                           mol_type = other DNA
                           organism = synthetic construct
SEQUENCE: 80
atggcgatgg gaccagaaag atcgaagccg cctctacaca atttcacctt accgtgtggg   60
ctcaagtggg ggaaccaaaa gttcttaagg tgcgctaagg ttgaatccga cggacaaatc   120
tccgccattc atcgcaggtc atttgggtct gagttgatcg gacggcgccg atcaaatgat   180
cgaaaattca ggccaccgga aaagcaagat gccggtgaag gaatcggagc tgtgagagag   240
aaactcatgt ttgatctcca aacagaagct gataagataa aagacgcaat ttttagagaa   300
ggtttggagg agcaacaact gtctccggcg ccggcgaaaa ctgcgactgc ggctgtatca   360
tatgccggtg aattgtccag gccgtggaac ttgaggactc ggcgtgcggc ttgtaaggag   420
cctaatggat tcgttgccgg cgccggtgcc gccggaagtg gtggtggtgg atcgaaagga   480
gggttgaaga ttgatgctta tagaaactaa tgctccgtcgc cgttaaggac ggaaaacaaa   540
tctccgacac ttcgaagtga ttttgccggt ggagcggccg ccggagcttc tgccagcggc   600
gagaagaac agagagtgaa gttttcggta cccctttcgc gaggagagat cgaggaggat   660
ttcatggcga tggtgggaca tagacccct cgtagaccca agaaacgagc taaatttgtt   720
caaaagaatt tggatacgtt attttccgggg ttgtggttga cggaaattac acctgactta   780
tacaaagttc ctgaagatca gtag                                         804
```

```
SEQ ID NO: 81              moltype = DNA  length = 1956
```

-continued

```
FEATURE               Location/Qualifiers
source                1..1956
                      mol_type = other DNA
                      organism = synthetic construct
SEQUENCE: 81
atggaaatta tcagtgagag aagaagaacc cgatctcaag cggctgctat tctagtggag  60
ctaaatcca tcaattttca atcagaaaaa agacccaaag tacatgaaaa agatggtgtg  120
aaaaattttg ggaaaaggaa gcgtcgaaag ggtagtaatg tcaggagaaa aaagaaggga  180
aaatatgtac aagttgactc tgatgatgat gaagactatg tgtttgataa aagtcccaaa  240
aggagaaagc tggattatgg acacaagggg aagagttcca gctcggattt gaagatttgg  300
gatttttatg ttcaaccgag aaagcatttc acagcaagaa ttgggacaca cactaatgtt  360
gatgttgtta aattgttgaa tgcgaagttg gatgataggc agattcagat gttcagagaa  420
acatgcttcg ggcattttct tgatttgccc gatgtattgg ttcagcctca attgatacac  480
tcgctattgc tgagggaggt ggttcacgag agagagggat agttgtggat ttcagtgaat  540
gatgtcaggc tgcgttttgg gcttgttgag tttgggatta tcaccgggtt aaagtgtacg  600
ggtgatgctg atatgtgcct tgatttcgac ggaacgaatc ggttgtttga tacgtacttt  660
tctgaactta ccagggtacc taagcaatcc ttaattgact gcttccttaa taagagatgg  720
aaatccgatg aggatgcagt caacattgct gtcctatatt tcatacacac attcttgctc  780
tccactctga atcgtaatta tatcacgagg gatgactttg ggctcgttga gagcggtgca  840
tatcaaacgt acccttgggg aaaagttgtc tttaaagcca cactgaagtc tattaagggt  900
aggttgcttg ggaagccctc gatgtacagg cttcgtggat taccattggc attccaatgt  960
tggttttacg agtgctgccc ttatgttaat aagaagattg ctttccgggt tgatgacaaa  1020
gtgccccgca tacttagttg gaaagttaca aagcagccaa acctcaagaa gttgtcgaat  1080
gggatttttca tgcagaggcg ggatcagttt atgctgagga atatttctcc aacagaattt  1140
gagcaaacaa cactgaattt gcctgaatca tttgaaaatg aaagggataa tgaggtggca  1200
tctggagatg gcgctgaagt tcatcttagt gatgatgact ttagcggttc gccgcctcaa  1260
acaagtagga agcagcctaa aaccaaacct gatcatccct tgaacaatga tgactggagc  1320
atcgagttaa aaagactgag tgatggacag tcggagttga agagtgagat tcagatgctc  1380
aacaaggagg ttgcatcgct caaggactgc atggtagcat cctttgcaga tgctttttaaa  1440
gccatcaagt ctctgtcgaa gaaacaaaga gaaaagattg cttccgagct tgatggagaa  1500
aatggccacc atgacagaca tggcgaaagc gattctagtg actttagtaa tagtgaagac  1560
aatggttgtg aaggtcaaga gcatggcaag gactctatgg gcgacaagga caatagtgag  1620
aaagggaatg aagtagcttt gggcgatgct gagggccggg agacagttag agatcctgtg  1680
gaggagggtg aaaggatgga cgtatctgcg tctccgattc ttccagatac atgtgaggtt  1740
tcagaccaca ttacaccgga acaaagtcat ccgacaccaa ttctagagtc accatatgtg  1800
aaccaaggcg acactggtgt tgagggttct tccgagaagt ccatttttaaa aggagagcac  1860
cctttagaga gcaaaattgt tgataatgtt gattatagtt tgttgtctga gtttgataag  1920
tgggttgacg aagggatgaa gaaagaaagc aagtaa  1956

SEQ ID NO: 82            moltype = DNA   length = 897
FEATURE               Location/Qualifiers
source                1..897
                      mol_type = other DNA
                      organism = synthetic construct
SEQUENCE: 82
atgagtagtc acgaacgccg aggcccggtg gccgtcgtcg gcagcggcgg ttacagtcac  60
gagagcgaac ctgacttggc tgctatggtt agtgattttt tggaaagtag tagtgtcggt  120
gcggagtctc ggtatagcag tgataatgac tctggtttct ccgatctcgc tcttctcgct  180
gataggattt cgttacacaa gcactcagtg gaccagtatg aaagtgatct aacaatggtg  240
gttcattcgc tgattctttc gttgggcgag tcctgccatc ttagcaagcc tgagacttgc  300
aatgcgagct gcatcagatc taatctagtg aagctcctac agtcttgcgg ttatgatgca  360
gctttgtgtt caaccaagtg gcagggttgt ggaaagattc ctggaggtga acatgagtat  420
attgaggtga tctcacgtgg aaatgatgga tgctctgaaa ggtacatcat tgacatcgac  480
ttcaggagcc actttgagat tgcaagagct gtcaaatcct acaatgtggt cttgagttgt  540
cttccaccag tgtatgttgg cacagtaaga aagcttaagc aatatcttca gactatggta  600
gaagcagcga gatgttcgct caaacagaac tcaatgcctc ttcctccgtg gcgatccctt  660
gcttatctgg aagccaagtg ggaatcatcc agtcaaagag tagccaactt tcaggtccaa  720
agcagcattg gcccctctaa ttcctctcat cagcattgta ctgagctgtt gtggaggata  780
aaatccagta ttgggtctga aatcaacgcc aaaagtttct tggttcctaa aagctgtaga  840
aagaagcagg gactaaagat tgataaattg aggcattctt caccagtgac accgtga  897

SEQ ID NO: 83            moltype = DNA   length = 840
FEATURE               Location/Qualifiers
source                1..840
                      mol_type = other DNA
                      organism = synthetic construct
SEQUENCE: 83
atgcaggaag aagaattttt ctgccctagc tttagcagct attcctcaaa tagagcggcg  60
gagattgccg ctaaaatctc cgatgaaatt gaacgcaatt ctaaggtggc ggagcaggcg  120
gaggtggaag cgaacgctgg cgaggatgat tttgaattct ctttggtatg tgaaaatcca  180
gaagcttcgg ttgggaatt cttctacgac cgtcaaatcc agcctgtttt ccccgttttc  240
aaccgcgatc tgttactaaa cgttgtttct tatgacgtag atcacaaagg cggcgttgac  300
ggcgaatcgt cggaaaatgc caatagttca atccaggttt cgttaaagga tttgttttta  360
gaagatcgcg aaccgccgtc gtcgtcgtca tcggaggtcg atgagttgga aagtgtacct  420
ccgggaacct actgtgtatg aaaccgcgca ataaccgagc cttcaccgag cagatgtaag  480
aagagtaatt caacaggatc ggcgtttaag cggtggagta ttcgagattt gatgcgtcgg  540
agtaatagcg acgggaagga cagttttgta tttttaacgc aggaaaaagg aacgaaaaac  600
gaaacttcca aaacaaagga ctcagttgag gcatcgaaag taaccggaaa attaaaggca  660
aagggaagta gtaacgtcgg agagaaggca tcttcgtcgg cggctgttta tttacggaac  720
```

-continued

```
caagcggcgg caaaggaaat ggataagaat aagaggaaat catacttacc gtatcggcaa   780
gatctggtag gtattttcgc aaatgttaac agtttaggga gaacttttcc acctttctag   840

SEQ ID NO: 84           moltype = DNA  length = 2073
FEATURE                 Location/Qualifiers
source                  1..2073
                        mol_type = other DNA
                        organism = synthetic construct
SEQUENCE: 84
atggagaaaa agcagctgga tttcaatgca ccacttttat cagtgaggaa aatttcatca   60
tctttatccc ctcatgagag agcaaataaa aagattatag aaagggcgcc accgaatcga   120
caacaatcac ttcctgtcaa aaaatcagat tgggaattga gtgaagtgac taaaccagta   180
gctgttccat ttatgtggga acaaatccct ggtagacgaa aagtaacaa tgatgcccga    240
gctaaccttc gagtggagtg ctcaagtagt cctaggctgc cccccggaag attgccagag   300
actattcggt tctattcggg tgaaaggcct cgtgctcaaa acatttacaa gtctccagct   360
gaaggacttc cttggattga tcatgcagct ttactggata gcctagtgga aagtatatat   420
acaagaggag acagagaaag tgaggatgat gcttattctg atgctcctga aaccttgtca   480
cctaccgaat ccttatcctt ggactgcagt gtcagtggtc tgagcggaca tcaaagttcg   540
gattcaaaac catctggaac ctttttccatt gactcccaaa ctagagactt tatgatgagc   600
cgattcttac ctgcagcaaa agctgttgtt ttggagacgc ctcagtatgt tcaaaaaaag   660
caagttccag tcagtactga acaaccgaag ccagtacccg tggaacgaaa gccaacagtt   720
aagcggatgg agtctaaacc tgtctcatat tatagcggct atccagacga tgtaggaagt   780
gaaattgaag atgatgtgtc tgagaatcag cacaaaaggc caagtaaagg gtggaaattt   840
ttccctcgga tttgtgtgaa gaattcttta tgcctattaa atccactgcc aggactgaaa   900
gtgaaaacac acgttcccac accctcatct caagcagtaa agagagtttc aggattgaaa   960
ccaaagacgc cccagagtcc cacatcttat gctcatgaag tcaaaagatt agctagaaaa   1020
gcttatagtg gtcctcttga gaagaattct tgtgatacta taaataagca aagatttcac   1080
tctggagtac tgtctcgcga gctttacaaa gctgataata gaagtttttc cggccaacta   1140
cctaacccta gtgattcatg taagctagtt ggaatctctc ctggaagacg ttcaagaagt   1200
ggggctatat ctccctatcg aaatgtagca ccccatcctc cattcaatga agttacaagg   1260
tttcttggtg tgccaaagga aatggagagt ctttgggcta gtcgctttga ttcattccgg   1320
aaaggttgct acactgtcaa ggacaaagta ccacagcaga ttggcacagg aaggttttct   1380
gattcaccaa gtgaagtagt tgagaaaaca ttgtacatag attctgtaga taatgtgcaa   1440
atttcagccc gtaattctgc ttcttcaaaa cccaagggat tagtgaactc ctctagtaag   1500
aatatgaaga cactggttaa aagcagtgta gtactagaaa atatggatgc cacggctcgt   1560
actcaaggtg ccaagaactg gaatgtttca gagaaagaga gcaaacagat tgctgaaaag   1620
gagtcccttg atttggtgga agcttctccc gtttccatat caactctcaa aggccctgct   1680
gatcaggagt ctttgaaact aaagcaaaat cttgatacac tatctggagc cttagagtct   1740
tcaaaagtgc atccctatgg aaatttaggt acagaaaatg agataacaa aaaatgcaaat   1800
gacccaaaag attctaacct tacctccgtg gaatctccta taccaccacc cttgcctaaa   1860
tctccctctg aatcttggct ttggcgcacg ttgccttcca ttcctttgag aacccattc    1920
tcaagtttga gctccaagaa gcagaacaag aagtcccaca ctgatggtac caagtgggag   1980
actattgtga aaacttctaa cttgcataag gatcatgtcc gttactccga ggaactatat   2040
actcttggtt cttgtcagca gagcaaagct tga                                2073

SEQ ID NO: 85           moltype = DNA  length = 1176
FEATURE                 Location/Qualifiers
source                  1..1176
                        mol_type = other DNA
                        organism = synthetic construct
SEQUENCE: 85
atggaaatag ctcggagctc aagaagatgc aaatgggtta cagcatttct tgttctacta   60
gcttgctcag ctgctggaca agttgaagat ggtccgttag ttaacggtga ttttgagaca   120
cctccgtcag gcggtttctc ttccggcgac ggattctctg atggccctct cgtactccct   180
agctggaaaa caaacggcac cgtcgagcta gtggaatcag ggcaaaaaca gggtgggatg   240
atcctcatcg taccacaagg tagacacgca gttcggctcg gaaacgacgc cgagataagt   300
caagagctca aagtcgagaa aggctccatt tattcagtca cgttcagcgc ggctcgcacc   360
tgcgcccagc tagagtcact gaacgtgtcg gttcctccgg cgtcacagac catcgatctt   420
cagactctgt ataatgtcca gggctgggat tcctacgcgt gggcctttca agccggagaa   480
gatgacgtgc gtgccgtttt cacaaatcct ggcatggaag atgaccctac ttgtgggccc   540
attattgatg atattgctat caagaagctt ttcactccag ataagtccaa agataatgca   600
gtacttaatg gcgactttga agaaggtcca tggatgttca ggaatgcttc cctcggtgtt   660
ctgcttccaa ccaacctcga cgaggaaaca tcatcgctac ctggttggat agttgaatca   720
aatcgagcgg ttcggtatat tgataattat cactttacag ttccagaagg gaaaagagct   780
atagaattgc tttcaggaaa agaaggcatt atatctcaga tggttgaaac caagcccaac   840
aagccataca gattgacatt tttgttgggc catgcagggg actcatgcaa gcagccactg   900
gctgttatg cgttcgccgg tgatcaggcc caaaacatcc attacactcc caattccaat    960
tcttcattc agattgctaa tctgaatttc acggctaagg cggacaggac acgtgttgcg    1020
ttctatagta tctattacaa cacaaggagt gatgatatga gctctctttg tggacctgt     1080
gtggatgatg tgagggttga agtatctggg tctagcacag tcaaggtttt ggggtcggg     1140
tttatgttgt ggctgttagt cttagtattg gtttaa                             1176

SEQ ID NO: 86           moltype = DNA  length = 1128
FEATURE                 Location/Qualifiers
source                  1..1128
                        mol_type = other DNA
                        organism = synthetic construct
SEQUENCE: 86
atgagaacat tgtgtccaaa tttggacaag gcagatgggt tggagacagt tttggaggtc   60
```

-continued

```
cccataccag aggagatgtt taacaatatg ggtagcaatg gtgccttaca atggcggaat   120
atgcgcaatc ttatgagggc tcaaagtgca gacagatatt cttcttcttc tcatcatgcc   180
gctgtatcaa gtaatgatca attcatgttc ttgtttaaaa tcgttggctc tgctcttgtc   240
ccttttcaag ttcaattgga ccatattgct gataacatgc ctgttaggaa tggttcaatg   300
gaggctgcta ctgctaaata catagtacaa caatatttgg cagcatgtgg agggcaggcg   360
gcgttaaatt cgctaaatag catgtgtgca gtagggcagg tgaagatggc tacatgggac   420
atccatcaaa gtggtggtga cgccaactcg aaacgccatt gtgaggttgg agcctttgtg   480
ctttggcaga agaaccctga cctgtgggtt ttagaattgg ttgtttcagg ttgcaagata   540
agtgcaggaa gtaatgggaa ggttgcttgg agtcagtctt cctctacttc tagtgcttca   600
aaaggtcctc caagacccct tagaaggttt ttccagggct tggaccctag atcaacggcc   660
aatttgttct tgaatgctat ttgcgttgga gaaaagacta ttaaggatga agaatgtttt   720
attttaaaac tagaatcaag catagacatg ctcaaggcac aaagtacggc aaatacagaa   780
gttgtccatc acacaatatt gggatacttc agccaaagga cagggcttct gattcaattt   840
gaagacacaa aattagtaag attgaagtca ccaaaggggg atagcaatgt cttttgggaa   900
acaagtatgg aatctatgct tgaagattat agatatattg aaggtatcaa cattgctcac   960
agtgggaaga ctgcagcaac aatttacaga tatggaaaga acatagacta tagagcaaag   1020
attgaggaga cttggatgat tgaagagatt gatttcaata tatctgattt gccaatggac   1080
tgcttcttgc ctcctgctga atttgaagag caaggaatgg gttgctga              1128
```

SEQ ID NO: 87          moltype = DNA   length = 558
FEATURE                Location/Qualifiers
source                 1..558
                       mol_type = other DNA
                       organism = synthetic construct SEQUENCE: 87
```
atgctgcaac atctttatct tggtcaattt tctatgatgt ttcttcttct attatgttct   60
attttttgcag tattaacgac tgcagaatca tctatatacg aagtgcttga atcccatgga   120
ttgccaatgg gtttacttcc aaaaggtgtg aagaatttca cattagacaa ttcggggaaa   180
tttgtagtcc atttggatca agcttgcaat gctaaattcg agaatgagtt tcactatgat   240
aggaatgtat cgggtacaat aagttacgga cagatccatg cactttcagg aattgaggct   300
caagatttgt ttctatggtt tccagtgaag gatattcggg ttgatatacc cagttctggt   360
ttgatttact tcaacgttgg cgttgtatct aagcaattct ctttgtcttc atttgagact   420
cctagggatt gtactgctgt tcaactcacg gatcttcagg atgacatgca catagctgac   480
gctatttcta agagtcaatc aggggagctt cggtacaagt ttgatcaggg caatatcggg   540
aggaaggcta tattgtag                                              558
```

SEQ ID NO: 88          moltype = DNA   length = 918
FEATURE                Location/Qualifiers
source                 1..918
                       mol_type = other DNA
                       organism = synthetic construct SEQUENCE: 88
```
atgcaagctt atggtagaat gaagagagta actgacccgc ttgacgacaa agtgaaggct   60
cggatcattg ggcgtgacca gcaggaactc ggttacctca gcagcggaag cgaacacagc   120
gcccacgccg atgatgatgc ttcctgtagc ttttctactc tcatatttgg tttgcctgat   180
gatgtggcgg ccgaaaatat gtcgtcggag aatgattcag actccgacga cggagatgtg   240
tcaatgtacg agtcgacgga cgtgattgaa gatttgccaa agccagtgtt ttatagcgat   300
ctggatttgt ttcgtaattc gctggcgact aagattacta aggcactgga aatgtttttcc   360
ttttcgaaat cgaataagcc aatcctgagg cgaaatgtaa tgacctatct tagggatttt   420
ggttataatg ccgctatatg caagacgaaa tgggagagtt ccggtggact taaggccgga   480
aactacgagt tccttgatgt gatccgatcg gattccgata accggatcac tcgttacttt   540
atcgacctcg attttgcggc ggagttcgag atagcaaggc ctacgaatca ctacgagcgt   600
ttatcgcaat cgttgccgag ggttttcgta ggtaaaagcg aagagttaaa gaagatgttg   660
aaggtaatga gcgacgccgg taggcgttcg ctgaaaagca aagacctcag tattcctccg   720
tggagaaaac accggttcat gcagaataag tggttaggtg cttacaaacg gacaaccaac   780
gttctcccgt cggcaaactc atcggcgttg ttgtcgccgt cgaagcagac taacgtcgct   840
aagtgccggt ccgttgggtt tagcgctgtc gccgttaacg gccgtttact ctttcccgcg   900
gcaacccgta caagatga                                              918
```

SEQ ID NO: 89          moltype = DNA   length = 1086
FEATURE                Location/Qualifiers
source                 1..1086
                       mol_type = other DNA
                       organism = synthetic construct SEQUENCE: 89
```
atggctagta ggaaacgaag catctcaaat gatgtagata tgcatgtcct ttacaaggaa   60
ttggatgaag cttcatgccc tgtatgcatg gatcatccac acaatgctgt tcttctcatt   120
tgtagctctc atgataaggg atgccggtca tacatttgtg atacaagtta tcgacattca   180
aattgcctgg atcgtttcaa aaaactcaga gccgaaaata gggacagtcc tcctattatg   240
acacagggaa acctggacat tgctgttgag aaccccgatg agcagttgag aaatttaagc   300
gatcgttctg ttgttcatgg aaatagtaac agagataatc acatggagat gcatgaaggt   360
actgtacaaa cttcaggtgc tgctactgta tggggaagta gtcaagaaac agcgagtgct   420
gacggctcat ctgactcaaa attgaaattg aagtgtccta tgtgccgtgg agatgtatta   480
ggctgaaaag tagtggaaga agccagaaag tatctgaatt tgaagaatag aagttgctct   540
cgtgaatcat gctcattcgt tggtaactac agagaattgc gccggcatgc taggagagtt   600
cacccgacag cacgccctgc tgatattgac ccttccagac agcgagcttg agacggcttt   660
gaaagccaaa gagagtatga tgacattgtc agtgctgttc gctctgccat gcctggtgcc   720
gtcgtgcttg gagattatgt gattgagagt ggagacaggc tatccggtga aagagaacga   780
ggcgcgggtg gaaacagcag gtggttgagt accttcttct tgtttcagat gattggttca   840
```

-continued

```
atggacccaa tatctgaagc aagaggtggc aggtcaagag ctttgtcaag gcaccgtcgg    900
tccactggac ctttatctag gcgccgctat ctttgggggtg aaaacctgct aggtctacaa    960
gacgatgacg aggatgaaga tgagcgtgat cttaacatat tgagtgacat gagtggtgac   1020
atacctacaa atccaagaag gcgtaggcgg ttgatgcggt cgaggtcaga tgaagatcag   1080
caatag                                                              1086

SEQ ID NO: 90            moltype = DNA   length = 1212
FEATURE                  Location/Qualifiers
source                   1..1212
                         mol_type = other DNA
                         organism = synthetic construct
SEQUENCE: 90
atgccttttc cgatgaagat tcaacctgtt gatttcaata ccgtggaaga accgagtcga    60
tatgactcgt ttaagccggt tcaaaagtca cggttcaagc ggctattcga gaggcaattt    120
tcaggacttt tgagatcatc ggcgccgctg gagaagctgg tggccggcga agagttgatt    180
tgtaataaga aggatgttgc gtccgacgag ttcgagccga gctccgtttg tttggctaaa    240
atggtacaga ctttcattga agaaggtgag gccgataaac atcggtgcaa tcggaaccga    300
aaatgcaatt gctttaactg taatggtact gacagctcag aggaggaaac tgattcactc    360
agttgcttcg gtgaatcgaa tcatacttgt tgcaacgatg cttgtgaaat cctcaagagt    420
ttggtgccgt gtccttccgt tattgaaagg aacgttttag ctgatattac aaagatcatt    480
gagaaaaaca agatgggaaa gcgaaaggac aatttcatcc gaaagatagt tgttgatggc    540
ctcttagctg cgggatatga tgcttcaatc tgcgagtctc gctgggacaa aactccttcc    600
actcctgccg gaacgtacga gtatgttgat gtggtgattg aaggagaaag actactaatt    660
gacattgatt tcagatcaga gtttgaaata gcaaggtcga ccaggtccta caaatttctc    720
ctccaattgc tgcccaacac ttttgtaggc aaagcggatc gccttcagaa gattgttcat    780
ttgctaacag aggctgcaaa gcagagcttg aagaagaaag catggccttt tcctccatgg    840
cgtaaagctg aatacgtgaa agccaaatgc ctgtcacctt acaccgtat caaaccaact    900
ctaatggggg caccaaccgt gtcaaactct gctcccgaaa ctggcactgc ttgcaaaacc    960
tatcaacaag cggtaaagga ggagtcttca gaggattctt gcggggagct gaatctgatt   1020
tttggagaga gcagccaact cttggagaat aacgccaaga gcgtgattac ctatcctcca   1080
tctgcttgtg atgacgaaga aaaggatgtg atggtgcagc aaggcaaacc acctgacact   1140
aaacacaagg attcaagcaa tggtgccagg aagataactg gtttaacttc tctgattgaa   1200
gaccacacat ga                                                       1212

SEQ ID NO: 91            moltype = DNA   length = 495
FEATURE                  Location/Qualifiers
source                   1..495
                         mol_type = other DNA
                         organism = synthetic construct
SEQUENCE: 91
atgccaatgt ctttaacaag cattctctgc ttcttctttc tcttctttttc agccacaaca    60
gcttcaagaa atgagaagcc atcagcctat gaagagctgc agcgttatga cttcccaatg    120
gggattcttc caaaagggggt aaaagactat aaattaaaca ccaaaacagg tgaattctca    180
gcttatctta attccacatg cagcttcaga ttggaaaact cgtatcagct aaattacaag    240
cctgttataa aaggggttat atcaaaaggc aggcttacaa aactgagtgg tgtaagtgtt    300
aaagtggtgt gctatggct taacattgtt gaagttaggc gtaaaggtga gaatcttgag    360
ttctcagttg ggctcacatc ggcgaatttt ccgattgaga acttcgagga atgcccacaa    420
tgtgggtgtg gattggattg tgttagtaaa gaggagagaa agattagaca gaaggtcttt    480
gtgtcttctt cttag                                                    495

SEQ ID NO: 92            moltype = DNA   length = 327
FEATURE                  Location/Qualifiers
source                   1..327
                         mol_type = other DNA
                         organism = synthetic construct
SEQUENCE: 92
atggaggagc tccgcccgag tttccggtgc tccggcgacc gaagactaga gatcgtaagc    60
ggaaaagggt tcagcagcaa ccagggaagt cgggctcgct caccggatct accagtagta    120
acgagcaagg gaacttggcc gagccaggtg gcagcagcca cttcatcgtc agctaagccc    180
tgggggattca atgatccaga gatgaagaga cgaaagagaa tagcaaagta caaagtgtat    240
actattgaag gaaagttcaa gacttccatt aggaatggac tgaggtggtt caagaataaa    300
tgctctgaaa tcatccatgg ctattaa                                       327

SEQ ID NO: 93            moltype = DNA   length = 828
FEATURE                  Location/Qualifiers
source                   1..828
                         mol_type = other DNA
                         organism = synthetic construct
SEQUENCE: 93
atggggtttt cggagaacaa tagaggatta gttctagcaa tggtgtccag cttgttcatt    60
ggaacgagtt ttatattgaa gaagaaaggt ctccggcgtg ctgctgctgc tggcactcgt    120
gcaggagttg gagattatac ttatttgctt gaacccctttt ggtgggcagg catgattaca    180
atgattgttg gggaggcttc caatttttgtg gcttatattt atgctccggc ggttcttgtg    240
acccctcttg gcgcgttgag tataattata agtgctcttt tggcacactt tatgttgagg    300
gaacgattac aacggttggg tgtggtagga tgcatattgt gcattgtagg atctgtggta    360
attttttatac atgcacctca ggagcatatg ccaacttctg tacaagaaat ctggatttttg    420
gcaattcaac cagcatttat gatttatata gcagcaacag tatccacagt agtagctttg    480
atgttgcatt ttgggcctcg ttatgggcag acgaacttac tggtctattt ggtaatatgt    540
tccctaatgg gtgcacttac ggttgtcagc ataaaggcta ttggaattgc aataaaacttt    600
```

-continued

```
actttggaag gaattagtca gattgcctat ccgcagactt ggtttttct agctgttgca   660
gtaatctgtg taatcacaca gttgaattat ctaaacaagg cactggatac attcaatgct   720
gcaattgttt ccccaatata ttatgtaatg ttcaccactt tgaccatcat tgcaagcgca   780
ataatgttca aggactgggc gggacaagat gctagcagca tagtatag               828

SEQ ID NO: 94              moltype = DNA   length = 699
FEATURE                    Location/Qualifiers
source                     1..699
                           mol_type = other DNA
                           organism = synthetic construct
SEQUENCE: 94
atgggtacag atacagaggt agcagaaatg agttcaacac taaagcttcc tctgttttca   60
gtagagtcat cacaagagga tttagggatg ctaactcctc ttcacacttt agcttcaata   120
cctttcaaat gggaagaaga acctggaaaa cctcgtccat gcactgatct tatccctctt   180
ccaaactcca tatgtttaga accacctcct aggctttaca atatggaatt ttccaagaca   240
tcttcttctc ctacaactgt atttgatgga ccttatatta ccaacaagcc taggttttct   300
tcgtttaggt tgttgaggag ggatcgtcgt catcgtcgac aagggtcttt tgatagtact   360
actagctctg aaacaggaca acttagtact acacttgttc ttggtaacaa gaaatcggaa   420
agcaaaagct ggtggcgtcg gccgactact catcatgtta aacataatgg ctgtgagatt   480
aatagtggtt ttgtgtttcc atcttctata gattattcaa cagattgtgt tgaagaatgc   540
agcagttcca gtataaaaat ggaaacattt agaagaagtg gaagcttctc aggtcactcg   600
caagctaaga ctcacatctg ggcagctata tacgagggtt tcaagcaagt aataccatgg   660
aagaacagaa agtctaaaaa ggaagcgcta atcggctaa                         699

SEQ ID NO: 95              moltype = DNA   length = 435
FEATURE                    Location/Qualifiers
source                     1..435
                           mol_type = other DNA
                           organism = synthetic construct
SEQUENCE: 95
atgtcaggag aggatgctgc tgttcctgtt gtcgctgctg ccgagactcc tgctccagca   60
cttggggagc ccatggacat catgaccgca ctacagctgg tgctaaagaa gtctaaagct   120
catgaggac ttgctcgagg actccatgaa ggtgctaagg tgattgagaa gcatgctgca   180
cagctttgtg tgctagctga ggactgtgac cagccagatt acgtcaaact ggtgaaagca   240
ctttgtgctg atcacaatgt cagtttaatt acagttccca atgcaaaaac tcttggcgaa   300
tgggctggtt tatgcaaaat tgattctgaa gggaaagcaa ggaaggttgt tggttgtggc   360
tgtgttgtcg tgaaggatta tggtgaagag actgagggtc tccatatcgt ccaagagtac   420
gtgaagtctc attaa                                                    435

SEQ ID NO: 96              moltype = DNA   length = 1623
FEATURE                    Location/Qualifiers
source                     1..1623
                           mol_type = other DNA
                           organism = synthetic construct
SEQUENCE: 96
atggggaaca gaagttcaaa tcttgataat gacaacaata tttcacgtcc aattgatact   60
ccatttaagc ttccttctcc gttgcccact tggccctcag gtcaagcctt tgctactgga   120
gttattgatc ttggaggttt agaagtgtct caaacatcat cattggctaa agtttggggct   180
actcaagaaa gtggaccaga tgatcttgga gctacattct ttgaaccatc aaatttacca   240
aatggcttct ttatgcttgg atcctatagc caacctaaca atttaccccct cttcggatcg   300
gttcttgttg gaaaagattc aaaaggagac gcgctaaaga ttccaattga ctatacactt   360
gtatggagta gtgagaactt gaatatcaag caggatagtg ttggctatat ttggctgcca   420
attcctcctg aaggctataa agccgtaggc cacgttgtaa caacgtcgcc tcaaaagcct   480
tctcttgaca aaattcgttg tgttcgttct gatttaaccg atgtgtctga aagtgatgat   540
tggattttggg gcaataatgg attgaatgtg tattcttcaa gaccaagaga cagaggaatc   600
aatgctttag gagtctctac tggtgctttt gtggcttcaa ataatgaac tgcagattca   660
ttagcttgtt tgaaaaatgt caatgctaat ttatctgcta tgccaaattt gaaccaagtt   720
aaagcactat ttcaagccta ctctcctttg tactacttcc atcctgatga acaatattat   780
ccttcttctg tcacttggtt ttttcagaat ggagcattat tatataccaa aggtcaagaa   840
tctgcaccag ttgctattga gtcaaatggt tcaaatcttc ctcaaggtgg ttcaaatgat   900
ggtgcttttt ggttggattt gccaactgat gattccgcga aagatcaagt caaaaaagga   960
gatttgcagg ctgctacagc ctacttacac attaaaccaa tgtttggcgc gacgtatact   1020
gatattgctc tgtggctatt ttacccctttt aatggccctg ctagagcaaa aattgaattc   1080
atgactattc cattagggaa aattggacaa catgtcgcg atgttggaac a tgttacgtta   1140
aggattagca acttcaatgg ggagttacaa ggtgtgtact tttctcaaca cagtggagga   1200
aattgggtaa gtgcttctca gcttgaattc caaaatggta acaaaaccgt ggcctattca   1260
tcgttgcacg gtcacgcttc ttatgcccaa ccaggaaaaa atctgcaggg gaataacaac   1320
ataggcttaa gaaatgacac agcaaaaggg caaatgatgg acactggagc aaactattca   1380
atagttgctg ctgaatactt aacaattgtt gagccagcat ggttgaacta tgctagagaa   1440
tggggtctga aaatcagtta tgatattgca aatgaactcc aaaaagtgga gagatttttg   1500
ccaggaaaac tgaagaatgc tgttgagaaa cttgtgaaaa gtctaccaaa tgaggtgttg   1560
ggtgaggaag gaccaactgg acccaagttt aaggacatgt ggaatgggga tgaaaggggt   1620
taa                                                                 1623

SEQ ID NO: 97              moltype = DNA   length = 492
FEATURE                    Location/Qualifiers
source                     1..492
                           mol_type = other DNA
                           organism = synthetic construct
```

```
SEQUENCE: 97
atggctttct ctcaaaagtc acaactcttg ttttgctctc tcctcttcat cttaatctcc  60
ctttctctct ccttcaatcc tagccgtcca aataaagatg atgatgtcca tgatctcctt 120
ccttcctaca atcttccaat tggacttctc ccaaataatg tgaaatccta cactctttct 180
cctaaagaca actctttttac agtccaactc acacacccct gttatgtaca gttccaagat 240
caacttgttt actaccaaaa agaaatcaaa gggaaaatga gttatggtga ggtttctgat 300
gtctctggaa tccaagctaa gaaactgttc gtgtgggtcc ctgtaacagg gattaatgtt 360
gatgaggagt ctcatatgat tgaattccat gttgggtttt tgtctgagaa gttgcctgct 420
aaggattttg agactattcc cacttgtaag aataataagg ggtgccaaga ttctctcctt 480
tcttcaatat ga                                                     492

SEQ ID NO: 98          moltype = DNA  length = 468
FEATURE                Location/Qualifiers
source                 1..468
                       mol_type = other DNA
                       organism = synthetic construct
SEQUENCE: 98
atgttgcttg gaaagaggcc aaggccacca atcaaaagaa caacaagcat gaaagaattc  60
accttggatc tcaacataaa cgatccttct gtagccgtta taaattatca gcccttttgat 120
cctctcaacc cctacaactt cactggtccc gtcccaatgc cctccaacgg cctagatcaa 180
cgcttaatct tgactcgcag aagatcagct gatttcgttg gaactgccca tttccttaga 240
gcttgctccc tctgcaaacg ccagttaatc cctggtcgtg acatctacat gtacagagga 300
gatagtgctt tctgcagcct agactgtaga gaaaagcaga tgaagcaaga tgaaaagaaa 360
gagaagtatc cgaaggttgc aactaggaaa aaagttacta actcagccgc catggccgcc 420
gtggcaagcg gaacaggatc cgacgctcca cctcaggcca gaccgtaa              468

SEQ ID NO: 99          moltype = DNA  length = 1443
FEATURE                Location/Qualifiers
source                 1..1443
                       mol_type = other DNA
                       organism = synthetic construct
SEQUENCE: 99
atggccaaca aggtctccaa tttctccgat ctaatccaac gtgtcactgc ttcttgcttg  60
ctccatccac tttcctctgg ccgtattgac agcaatatct ccgatgctca ttacagcgat 120
gaatctgaag atgacaagta cagtaccgaa gatgaagaag aaaaaggaga cctaccttat 180
gtggagactc aggaaaaatt ccagaacgtt gaggtcacaa aggaggagat aaaaactgag 240
aaagtaactg aaatggagat gcttttaggg gaagtgttcg acgtggtgtc tgcagtgaag 300
acggcttatg ttagtctcca agaggcgcat tgtccttggg atcaggataa aatgcgtgtg 360
gctgacgtgg ctgtgatatc tgaactgcgg aggcttgggg tgttgaggga acgatttcga 420
aggaatattg gtggtggaat tagaaaaggg gactggagag tcggcgccgc tacgttgaga 480
gaagtggtgg caccatatga agctaccatg gaggaactga ggcaagaagt gaaggccaaa 540
gaaatcgaga ttgataattt gagggagaag ctgaaaatgg caacaagtct tagcagcagt 600
ggtggaaaga aaagcaagtc aaagcgaaaa attagttgta gcagtcaagc tccagttgca 660
atgtcgccag cacctgacgt atttgaaact acagtgagct tagtaaaaga agcctcaaaa 720
tccttcacga gtttgctgct ctccttgatg cgctctgccc actgggacat tgcagcggct 780
gtgagatcca tcgaagctgc ttcatccaac acaaacacac ccacagcaga ttcaattgtc 840
ggatccaacc atgccaaata cgcactggaa tcttacgtga accacaaaat gttccaagga 900
ttcgatcacg agacgttcta cttggacgga agcttgtcat cactgctcca cccagatcaa 960
caccggcgcg attgttttac acagtacagg gacatgaaag caatgggccc aatggaactt 1020
ctgggaattc tcccaacttg cagtttcggg aacttctgtt tcaagaagta cttggccatt 1080
gtgcacccaa aaatggagga gtctctgttt ggtgatttgg agcagcgacg acaggtgttg 1140
gcagggaacc atccgaggag tcagttctat ggggagtttc tggggctggc aaaggccgtt 1200
tggctgctgc atttgctaac cttttctttg gatcctccgc caagtcattt cgaggcaagc 1260
aaaggatcgg agtttcaccc gcagtacatg gagagtgtgg tgaagtattc aatttccatg 1320
gggataggag ggagaatggg tatgggtcta gttgttggat ttccagttag tcccgggttt 1380
aagctgggaa atggatcagt tgttaaggct agagtttatt tagtccccaa aaatgggttt 1440
taa                                                              1443

SEQ ID NO: 100         moltype = DNA  length = 1233
FEATURE                Location/Qualifiers
source                 1..1233
                       mol_type = other DNA
                       organism = synthetic construct
SEQUENCE: 100
atgatgggga gtggattaca gtttaatcgg agttttaacg gtgaagatcg gttttatagt  60
gcggggaagt ttcgccggaa tgttaatcgg agtttttcta ccggcagtga ggataatctc 120
cggcgagcta agagtgatgt cgccgttatt cattccccga cgaagccgaa aatgaaagtt 180
gccgccgatg agtcgcctga tgagccggta tctgccgtgc cgccgacgga tgttctgccc 240
ccgccgcttt gtaatcttca gcggttttg aaatctgttt ctccttcagt acctgctcaa 300
tatctatcta agacaactat gaggggttgg aggacgtgtg atgtggagtt tcagccatac 360
tttgttcttg gtgacttatg ggagtctttt agagaatgga gtgcatatgg agctggagtt 420
ccattggtgt tgaatgaagg tgatagtgta gttcagtact atgtgcccta tttgtcaggt 480
attcagttgt atggtgactc gacaaaggct tcaacaaaaa caagtaggcg accaggtgag 540
gaaagtgata gtgactattt ccgggattct agtagtgatg gaagcagtga ctctgaacat 600
gagagacgtt gcttgaatta tacaaggag cagcggatgt atcatagcca aacaagtgaa 660
agctccctta gtattgaccg gttatcatta agagacagga atgctacctt ccaagaagga 720
tttttcaagcg atgagggtga atctgggtct tctcagggtg ccttgttgtt tgagtatctt 780
gagcatggtc agccttacgg ttgtgaacct ttggcagata agatatctga tcttgctcaa 840
cgtttttccgg aattaaaaac aatgagaagt tgtgatctcc ttccttccag ttggatctct 900
```

-continued

```
gtagcctggt atccaattta ccggatacct actggaccaa cttttaaaagc tttggacgct   960
tgttttctga cctttcattc tcttcataca cccatgacag gaagtcaaag tgctcatcct  1020
gcggcggtaa catgtccgag tgatacggat ccggtcccta agattccatt gcctgctttt  1080
ggccttgctt catacaagtt taaagcctca ctttggaccc caaatggagg atctggaaga  1140
cagttaatga gctcgctttt gcagtctgct gaaaactggc taacgctgct tcaggtcaat  1200
cacccagatt tcagtttctt ctgccaaagg tga                                1233

SEQ ID NO: 101          moltype = DNA   length = 681
FEATURE                 Location/Qualifiers
source                  1..681
                        mol_type = other DNA
                        organism = synthetic construct
SEQUENCE: 101
atgggttcat gtgtttcagt gcataaagac tctgaatcag ccatgaaaat tcgtcttgtt    60
tttggttctt ccaaaactga caagcttgtc actccttcac ctctcaacaa agatgatacc   120
aaagtctctg atcttcaact caaatctcaa actcctgctg ttactgcttt tcgtgacttt   180
ggtagcaagg aggagacctt ctttgattcc cagccttggt tggattcaga ttgtgaagat   240
gacttcttaa gcgtgaatgg agattttacg ccatctcgtg gaaatacacc tgtccatccc   300
ttggctggaa atttaacagg gaacagaacc cctgcttatt ttcagcaatc atccccaaca   360
gataaaaaga agagattgtc tgaacttttt gaagaaagct tgagaagcga tctgaccaa    420
aatgggcaaa atgctgaaga aaaacaaaat ggtacaaaca ctaaaaaaga aactgcgtca   480
actggtactc aacttccacc aagatccaca cctgggacac cttatgcatc cgtgtgtagt   540
agcgaaagaa cacccagtgg tctgttaaaa tctgacgtca aaacgtcaaa gtcagcacaa   600
tgttgtcttc caaggttgct ctcaagtcgt agctttaacg gaaggaggag tagaatgagt   660
cctgcgcgta atgttggctg a                                              681

SEQ ID NO: 102          moltype = DNA   length = 600
FEATURE                 Location/Qualifiers
source                  1..600
                        mol_type = other DNA
                        organism = synthetic construct
SEQUENCE: 102
atgaaggatg atgaatccat accagtttca cacctacaa cacattcatc atcaaataca     60
atttcaacat attcgaagaa ttccacatct gatgccacaa ttcggtcg tggtcggtac     120
aagttctggg cattagccgc tattcttctg ctagcatttt ggtcaatgtt tactggtact   180
gttactctcc gatggtccgc cggcaacctc aacggtctct ccgattactt caatgtgcct   240
ctctccgata atctcgacgt catcgaaatg gaagagaggg agaagttggt gaagcatatg   300
tgggatgtgt atactaatac tcctcggatc agattgccta agttttggca ggaggcattc   360
gaggcggcct atgaagagtt aaccagtgac cttgctgata ttcgagaggc tgctatctct   420
gagatctcta agatgtctct ccgatttgtt catatggagc caccacctct gcgttcattg   480
gcagtaagag aattaagtca aaaacaagct gaggacaaac agaggactgc aaaaggaatt   540
tggctaagtg cagtccttat ggaggaaaat aaaagagaag aaaaaagggg acctgattag   600

SEQ ID NO: 103          moltype = DNA   length = 549
FEATURE                 Location/Qualifiers
source                  1..549
                        mol_type = other DNA
                        organism = synthetic construct
SEQUENCE: 103
atggccgata gtgaatcgag gcaatttcca cctgataagg agccatgttt tgcagaagaa    60
ctacttgact ggcagaggag ggaactgccc cgcaggttct tgtctggtca ggttgtctgg   120
gatgacgacg ctttcatccc cgaaggcgct tcggagaagc acagggttat atttcgcaga   180
atttatagga aatacttcct tcagattttt gcttcggatg gtttcgacat tgacatctat   240
ccgggtaaag ccaaggcagc tatgcttata ccatacctgg attttgagaa agaaattgac   300
ttgctgatgg aactggctaa ccatgctatt caggattaca acagtaaaga aaccaatgtt   360
tacaaatacg aggtcttgta tgttgaaaaa gtgaacttta ttttggccga atgccgcgaa   420
tttttttatga ctgttaaagt taaaaatctc actctgcgtt cacctaaaga aacttttcaa   480
atccatgcat ataaaggacc agatggggag aatattttct gcctttgccg gagaaaattg   540
ctggtttga                                                            549

SEQ ID NO: 104          moltype = DNA   length = 909
FEATURE                 Location/Qualifiers
source                  1..909
                        mol_type = other DNA
                        organism = synthetic construct
SEQUENCE: 104
atgagagact ttgcttcttg tttcaatgaa tatgcagtac aagtttctga tacttcttgt    60
tctagttact caaactctgc ttgtatccct ccttctctga ttccttcaat tcaaaacact   120
gtcacttgtt tgtataaagt cactctctcc aataaaaaac aggtcttgat cacagtttca   180
tggtccaaaa caaatagtat aacacaaggc ctaagtgtac actttggtga tgatccttca   240
aatgtcttca aactcaacac gaattcgcgt ctttttagga gaaaaggg aagcaaatca    300
ctggatttgg atcatttaaa ggttgaaatt ttctgggatt tatatgcagc caggtattta   360
tcaggtcctg aaccaattga tggctattat ttactagtca aagttgattc acaacttggc   420
cttattattg gtgacatggc tgaagaagct tcattaagaa agttaaaaaa tggaactcca   480
atggccaagt tctcattggt ttcaagaaaa gaatactttt cagggaatac cctttattca   540
acaaaggctc aattttgtga caatggcaca agtcatgaca tattaattcg ttgtagcggc   600
gaaaatgaag gtctaaagca tcctgtttta tcagtttata ttgataaaaa gatggtgatt   660
agagttaaaa ggctgcaatg gaatttcagg ggaaatcaga gcatatttgt ggatggattg   720
ttggttgatc taatgtggga tgttcatgat tggtctttta tccaacatc tggttgtgca   780
```

-continued

```
ctttttatgt ttaggacaag aagtggaatg gatagcagac tgtggttaga tgataaagac  840
aaattgctgc acaaagatcc agataaagtt gagttttcat tgttgattta tgcctctaag  900
accacataa                                                          909

SEQ ID NO: 105          moltype = DNA  length = 504
FEATURE                 Location/Qualifiers
source                  1..504
                        mol_type = other DNA
                        organism = synthetic construct
SEQUENCE: 105
atggcggctt caaagagcta tttcgctgga gcaaactacc gattcctgtc gagcgagcga  60
gacgttccga tgatgagtcc tgaatctgcg ttcgaattcg atgaatcgga cctgtggaac  120
tcagcggttt cacagtcgcc ggagttccga aagtccgttc agagttcaaa aatctcgaga  180
aagcagtgcg atacgaagag ccgccgaagc ggttccgtag catcggcggc gtcattgccg  240
gtgaacgtgc cggattggtc gaagatactg aaggatgaat atagagagta tggaaggaga  300
gatagcgatg atgatgattt caacgatgag gacggcgatg atttggagaa tcggattccg  360
cctcacgagt ttttggcgaa gcagttagag aggacgagaa ttgcatcgtt ctccgtgcac  420
gaaggagttg gccgtactct caaaggtaga gatctgagta gagtcagaaa tgctatttgg  480
gagaaaactg gattccagga ttaa                                         504

SEQ ID NO: 106          moltype = DNA  length = 2277
FEATURE                 Location/Qualifiers
source                  1..2277
                        mol_type = other DNA
                        organism = synthetic construct
SEQUENCE: 106
atggaaagac ggccaaagca gagtggtgaa agaaagacaa tggagaatga agagcttgtc  60
aaatacatgt caagtttgcc aagttacctg gaaaaggggg aaaatctgca ggagaaagct  120
ttcagtgttg gcgtcctaga ttggcgtttt cttgaaaaat ggcgacacga acatgtaaaa  180
gaaccttgta gaactagtgg ttgttcacca tccaccagca ataccttgtc attttcctca  240
atggagggat cttcatccaa ttctagcaga gccagaagct gctctcctgc tcgtcggagg  300
attcatcgtc ctacatcaca atcttattat gcatcaccac ctaaaggaag ttatgtacag  360
ttgcaaaacc aaaaacctgg cgtaattaaa tccccggaga ttgagcaact tgtctgcagg  420
atatatcagt cttttgatga gtatccacaa agaaatatgc aagaactcgg caatgctcta  480
cacccgcgta ggactcctca tgttaggaga tcacttgatg tagagactaa gacgagaaca  540
tcacgttcca agggaaagat gaagatccaa gatagagaat gtttatcgaa aggagatttt  600
gatgatttg attgcataga gaaacataaa tcagatgtcc ttcaagtacc agaacctggc  660
caagaaacta acagctgcac aactttctgc ccacctgatt cagtagtgaa agaccagagc  720
gcggtgaaat caagcagacg gagctttct tgtggattta tttctgcgtt ctactatgga  780
cagtcctctt cagatatctc tagttccagc acccttcctc atgatgctga tgagtcgaag  840
gtgggacaag cgagtccgat agatgcaaag gatagttgcc tttcatctaa gacaattcag  900
ccttcaacat attcaggaaa caaattgtcc agcccacctg gaaccaattc caaacaagag  960
aagaaatcaa ctgtgatgct taagaatcca actacactta attccgcaga atctacaaac  1020
atcagaaatt cctctccaac tcgtcaattt agcatggcaa tgggaaggat tggccagatt  1080
tcaggtataa aagatatgat cactggatca caaggtgtca aatggcctgc agaacaatct  1140
agtccaaata aaactcaaag ttcgtcctca attgatacag gctgtgataa atcagacacc  1200
actggccgag ccaggactag tcctttgaga aggttgctag atccactgct gaagccaaag  1260
acaggcaact ctgatcacgt taaatcttca acaagacgtg gtgaatctcc tacgaaacgc  1320
tcattgaaag tcaaattgga tttgaagagc tgtaaatcga ttgatatcga cgatccacgt  1380
tctaatggca catttgtacc atcaagattg caagctctcc tccaagtagc tgtgaaaaat  1440
ggtcttcctc tattcacatt tgcagttgac aatgaagttg acattttagc agccacaatg  1500
aagaaactta atccgaattt gaaggattac agttgctgga tttataattt cttcaccgtt  1560
cgtgaaacaa agaaaaagag tggaaattgg ttaaatcaag tagaaaaaga cagaagtcat  1620
ggaattatgc ctaatatcgt tggaaagatg aaggtttctg atgttccatt ctccgaattg  1680
aataggcaga aacttgactc acagtttagg attacggaat ttgttttgct tgctacagat  1740
cagaaagcat ctgaccttca cccaaacgat gagcttgcag ctattgttgt caaattaccc  1800
aatagaacct ccatttgtcc taatggaagt ggccatcagg atagaaactg cagtaatact  1860
tcaacttcag gttaacaaa tccttttgaa gatcttaaca tgacagttat ccttcctggt  1920
ggtgcacata gcgtaccaag taaaggcgag ccttcttcac tgattaaccg atggaggtca  1980
ggtggatcgt gtgattgtgg tggctgggat ttgggctgca aattaagact tcttaggaat  2040
cacactaatc atcaaaggat atcaagttgt tccaaaccca aacttaatgc tgcaagattt  2100
gaacttttat cccaggggga agcacgggac agtaagcctg tcttcagctt gtccgcattc  2160
aaggatggca tattttcagt tgaattcagt tcttcactga aggttctaca agcattctcc  2220
atttgtatag cagtttttaaa tggtagaaat caagaaagct tccaaatgca aacttga     2277

SEQ ID NO: 107          moltype = DNA  length = 558
FEATURE                 Location/Qualifiers
source                  1..558
                        mol_type = other DNA
                        organism = synthetic construct
SEQUENCE: 107
atgctgcaac atttttgtct tggtcaattt tctgcgatgt ttcttcttct gttatgttca  60
attttttgcag tattatcaac tgcagaatca tcaatatacg aagttcttga atcccatgga  120
ttgccaaggg gtttacttcc aaagggtgtg aagaattca cattagacaa ttcggggaaa  180
tttgtggtcc atttggatca agcttgcaat gccaaattcg agaatgaatt tcactatgat  240
aggaatgtat cgggtacaat aagttatgga cagatccatg cactttcagg aattgaggct  300
caagatttgt ttctatggtt tccagtgaag gatattcggg ttgatatacc cagttctgga  360
ttgatttact tcaacgttgg cgttgtatct aagcaattct ctttgtcttc atttgagact  420
cctagggatt gtactgttgt tcaactcatg gatcttcagg atgacatgca catagctgac  480
```

-continued

```
gctgtttcta agagtcaatc agaggagctt cgatacaagt ttgatcaggg caatatcggg   540
aggaaggcta tattgtag                                                 558

SEQ ID NO: 108        moltype = DNA  length = 915
FEATURE               Location/Qualifiers
source                1..915
                      mol_type = other DNA
                      organism = synthetic construct
SEQUENCE: 108
atggcttcta cagtaccggc gaagtcgaat aatccacttt acaacttcga ttttcccac    60
ttgaaatgga agaagaatca tcattcgaac aatcatcaac gtcgccgttc caacaagctg   120
tcgtcggact cttcctctcc gtcacggcac gactcgccgc taaggcactc tcagtctcag   180
tccccgatgc gtgaatccct cgcggcggcg cgtcagtctc cagtaagtga atctgctgag   240
acggcgcgta tatcgccgat gcacaattcg gctgcggcgg cgcgtcagtc tccgatgcgt   300
gaatcggcac gtcagtctcc gatgcgtgat cccgttccgt cggttcaacg atcaaagcat   360
aagtaccag agattaatgt tgtcagtagc aaagaaagca gatcgaaaat cttaattaaa    420
atccctcgca aaaacaaatc cgaagaaatt caaatcaacg aggatcaaaa tcaaaaggag   480
gcagatgagt ctcacgacga agctgcagca gctgaagaaa cagcacaaaa aacgtggaat   540
ctgagacctc ggaagccgat acacaaatca ctgaatataa acggaggagt cccatttcga   600
tccagtggat ctgcgatgca ggagatcaaa tctcaatcac cccatcacat gatgaacgtg   660
aacaagccgg aaaataatga aacccacgct gcttctgctc agaagaaggt aaaaaggcaa   720
aggttttcca tagcgttatc cagagaagag attgatgaag atctatatgc tatgactgga   780
ttaaaagctg ctagaagacc taagaagaga gttaaagttg ttcagaaaca acttgataca   840
ctcttccctg gtttatggct tgcttcaata actcctgatt catataaagt ttgtgaaaat   900
cttccaaagg gttag                                                    915

SEQ ID NO: 109        moltype = DNA  length = 1113
FEATURE               Location/Qualifiers
source                1..1113
                      mol_type = other DNA
                      organism = synthetic construct
SEQUENCE: 109
atgatgaaca accagtcctc aatctgttcc agcttaaatg aagataaagt tcacgataca    60
ccagatagct tccatcagtt acacccgaag aaagattcag attctctgga tggaagtgag   120
ttagagagtg gagatacaat ttcaacagtc gaacatctga aatcagcatt aaaagctgag   180
aggaaggctt tacattctct gtacacggag ttggaagaag agagaagtgc ttctgctgtg   240
gctgcaagtc agacaatggc tatgatcaat aggcttcaag aagagaaagc agcaatgcag   300
atggaagctt tgcaatacca aagaatgatg gaagaacaat cggagtacga tcaagaagcc   360
ttgcagctaa tgaatgagct tatggtgaag agagagaggg aaaagcaaga gttagagaaa   420
gaattggaag catataggaa aagattattg gaatatgagg caacgaggat gttgaagaga   480
agcaaggaca gtagcacatt ctcctctgag gatagtgatg gactctctat tggtttgaat   540
caagaagaag caaaggaaga tgatagcggc atgaatcata gcactcctgt tggtgcagtt   600
ataaatttgg aggaagagag aatggcgatt cttgagcagc taaaggtttt ggaggaaagg   660
cttgtcagct tggacttgga tgatgaagat gcaaaacatt ttgaggatgt taggctgatg   720
gaagattcat atcaagataa tatagaggaa gattctcatg ccaatggttt cttgaaggaa   780
atgaatggga aacatcatca tgccaaggga aagagacttc ttcctctatt tgacaaaatg   840
agtgatgaaa atggagatgg tacactaaat gccaatgggt ttcataactt tgatttagag   900
aacaagaagc tagctgtgga acaagagttg gatcatctcc atcaaaggct acaagccctt   960
gaggcagata gggagttcct aaacaactgt gtaagctcgc tgaagaaagg cgataaaggc  1020
atggatcttc ttcaggaaat cctactacat cttcgtcatc taaggaacgt tgagcttcgt  1080
gcaacaagct tcagtgatgc tgccatacta tag                              1113

SEQ ID NO: 110        moltype = DNA  length = 1113
FEATURE               Location/Qualifiers
source                1..1113
                      mol_type = other DNA
                      organism = synthetic construct
SEQUENCE: 110
atgatgaaca accagtcctc aatctgttcc agcttaaatg aagataaagt tcacgataca    60
ccagatagct tccatcagtt acacccgaag aaagattcag attctctgga tggaagtgag   120
ttagagagtg gagatacaat ttcaacagtc gaacatctga aatcagcatt aaaagctgag   180
aggaaggctt tacattctct gtacacggag ttggaagaag agagaagtgc ttctgctgtg   240
gctgcaagtc agacaatggc tatgatcaat aggcttcaag aagagaaagc agcaatgcag   300
atggaagctt tgcaatacca aagaatgatg gaagaacaat cggagtacga tcaagaagcc   360
ttgcagctaa tgaatgagct tatggtgaag agagagaggg aaaagcaaga gttagagaaa   420
gaattggaag catataggaa aagattattg gaatatgagg caacgaggat gttgaagaga   480
agcaaggaca gtagcacatt ctcctctgag gatagtgatg gactctctat tggtttgaat   540
caagaagaag caaaggaaga tgatagcggc atgaatcata gcactcctgt tggtgcagtt   600
ataaatttgg aggaagagag aatggcgatt cttgagcagc taaaggtttt ggaggaaagg   660
cttgtcagct tggacttgga tgatgaagat gcaaaacatt ttgaggatgt taggctgatg   720
gaagattcat atcaagataa tatagaggaa gattctcatg ccaatggttt cttgaaggaa   780
atgaatggga aacatcatca tgccaaggga aagagacttc ttcctctatt tgacaaaatg   840
agtgatgaaa atggagatgg tacactaaat gccaatgggt ttcataactt tgatttagag   900
aacaagaagc tagctgtgga acaagagttg gatcatctcc atcaaaggct acaagccctt   960
gaggcagata gggagttcct aaacaactgt gtaagctcgc tgaagaaagg cgataaaggc  1020
atggatcttc ttcaggaaat cctactacat cttcgtcatc taaggaacgt tgagcttcgt  1080
gcaacaagct tcagtgatgc tgccatacta tag                              1113

SEQ ID NO: 111        moltype = DNA  length = 435
```

-continued

```
FEATURE              Location/Qualifiers
source               1..435
                     mol_type = other DNA
                     organism = synthetic construct
SEQUENCE: 111
atgctgtggc ggaattcgac aaaaattgcag ctgtgttctt catccgctag gagtcgtttg    60
ctactgattt gtcgcctcga acatcaattc atcgtcacac acagaaaacc agttgatctt   120
tggggattga aaatctgtga attgaagagg cctatagctg ctgttaagtt gaattgcaaa   180
ctgcaggttg tagttccctg ctgctacagt ttggctgcaa ttgtgaacat cttcagtagc   240
ttgcagtcac tgatgaactt tgcatttgag ctacaacttg gagtcttttt acagaattgt   300
gaagaagatt gctcaggaga tcaccaacag tctgcaacct tgtcagttat tgtgaggctg   360
tccagaattg cagatttgac cagtccttac ctatgtggcc attctttgca aatccgacca   420
attttacaaa actag                                                     435

SEQ ID NO: 112          moltype = DNA   length = 1068
FEATURE              Location/Qualifiers
source               1..1068
                     mol_type = other DNA
                     organism = synthetic construct
SEQUENCE: 112
atgtttgatg actctgtatc tactgtttat tcttcaatat ggacatccat gaatagctgg    60
ttcactccca ctgtcctttt tgttcttctc aatctcatga ttggtaccat tgcttttact   120
tcttccttag ctaaccaaaa gccaaatcac cctcccaaac aagaacaaca acaagaagaa   180
caagaatact cacaaaatca cccacaacaa ccctctaaac tcattagatc tccttctatt   240
cttcaacgca tcaaatcttt aaatttctac aacaatagat ctcaagaacc tgttaaagat   300
tacaactttg acgataccca taatcaagaa accacctttg aaccacaaac acattacatt   360
ttcgaaccag ctccagaaca tactaccgta gtaccagaat ctacccagta tattttcaat   420
caatcccatc aagaaaatgc tcaaaaaaca caaacccagt acgatttcca gcaaacccat   480
ctagaaaatc tcccagatac acaaacccag tacctttttc aacacacccc cgaccaagaa   540
ctcaaaaata tggatcaaga tttccacttt cagcaaaccc atcaagaaaa tattcaagaa   600
aaatcggccc gttacattat tcaacacatc catgaacaaa aacttgataa tacagatacc   660
catttcgatt ttcagcaaac ccatgaagaa aatgaggtag aagaagagga agaagaaggt   720
gagctaaaga gcttggatga agtatacaat cagttaaagg aacgtcacgt gagcaggagc   780
agatcagata caaatccatc ggccggtgaa gctccgataa agttgccgac gaagatgaag   840
aaatcagcaa gcatgaaatc gccatttgcg cattttgaag aggaggctat tgttgaagct   900
cgccggccgg ccactacaag ggagagaaat gtcaagacaa gcgacggaga cattaatgaa   960
gtagatgcta aagcagatga tttcatcaac aagttcaagc aacagttgaa gttacagagg  1020
ttggattcaa ttctcaggta caaggagatg attggtagag ggagctaa                1068

SEQ ID NO: 113          moltype = DNA   length = 1158
FEATURE              Location/Qualifiers
source               1..1158
                     mol_type = other DNA
                     organism = synthetic construct
SEQUENCE: 113
atggaaattg ttgccaagtc aaaaaaacac caccattatt attctccttt cccttcttgt    60
ttccgccgcc ctttagaggt agctgccgcc gcctccgctc gtcctcttcc gccgccgccg   120
ccgccgccgc agccaccggt tgctgctaat cccaacctcg ccacctccct ctaccaaacc   180
cacctcggcc tctttgctct cacttggtct cgcaatctct tcggcagatc ttttcacatc   240
catttcctcc tcaacgattc tgatggagtt ggagctgact acaataataa tacaatctct   300
tctcctcatt tatcttccac tagtacccca tctttccacc tcaacatcaa accctttatt   360
ttctggaaaa aacatgggtc aaaaaaagctc gacggagata acaaggttgt tcatatcttt   420
tgggatcttt ctaaatctaa atttggatct ggccctgaac ctatatctgg attttacgta   480
gctgttattg ttaacgaaga aatggttctt ctggtcggcg atttaaacaa agaagcttac   540
gctaaaaccc gagctcgaaa gccagaaaag aagcagaatc taaacccgaa tccaaaccca   600
aacctggtgc tgagaaggga acacgtatgt ggaaacaaac tctacaaaac aaaagcaaac   660
ttcggtggga aagagaaaga aatctcaatc gattgcaggt taggagaaga tccaaggctg   720
tatttcagcg tagataacaa aagggttttg caaatcaaac acttgaaatg gaaattcaga   780
ggaaatgaaa ggattgaagt tgacggagtt ccagttttgg tttcatggga tgtgtacaac   840
tggttatttg acgatgacga agatgggtat gctctgttca tgttcaaatt cgaaaaatca   900
agttacgaat atgtagatgc tgatgattac agcttaaata atggagttca attgtggtct   960
caacaatctt gtggattcgg gttcgagacg aagatgatga aaaagggtgt attacgaagc  1020
tcgagaagtt catcttcttc atctttatct tcagcatctt caacttgtag ctctgtcatg  1080
gaatgggcta gtactgaaga aaatgaattg aaaggtcctt cgggattttc tttgctggtt  1140
tatgcttgga aaagctga                                                 1158

SEQ ID NO: 114          moltype = DNA   length = 591
FEATURE              Location/Qualifiers
source               1..591
                     mol_type = other DNA
                     organism = synthetic construct
SEQUENCE: 114
atgtggcagt ttaacaagat atggtgccaa aatcaaagaa ttcaaattac ctattggggc    60
ctattagcat acaatgctgg tgatgatatg gtaacttcta caaccccttt tgagcttata   120
attcaatctg ataaaattcc aatcacaatt gatttttagca atacaacaag actagtaaat   180
gatactagta catctgggat aataccatta tgtgctagct ttgagcgcga cggaaaggtg   240
acactaacaa aacaagtgtc acaaaatgtt tgtgctgcta aaaaacaagg acatttcggt   300
ttagtaattg agtcacctct aatgccattg aaaaataaaa gggcaagtaa ttggaaatta   360
gctattggga gcgcgattgg agctgcgttg ggcgcgttcc tttttaggttt gctactgatt   420
```

-continued

```
gcaatatttg tgaaggtgaa gaagaaagca agaatggagg aattggttag aagagcatat   480
gaagaagaag ctttacaagt ttctatggtt ggacatgtga gagctccaac tgcagctggt   540
actaggactg ttccaactat tgaacatgac tataatcctc ataattcttg a            591

SEQ ID NO: 115              moltype = DNA   length = 513
FEATURE                    Location/Qualifiers
source                     1..513
                           mol_type = other DNA
                           organism = synthetic construct
SEQUENCE: 115
atggatcaga tattgaacaa agtgggttcc tactggattg gtaagagagc taacaaggag   60
ctcaattccg tcggcgatga cattaactca ttgcaaagca gtattgaagg aggaacaaaa   120
tggctggtga acaagcttaa aggaaaaatg caaaagccat tgccagatct tttgaaggag   180
tatgatgttc cagtaggtat tttccctcgg gatgccaaca attacgagtt taatgaagag   240
acaaggaagc tcactgtcta tataccctct gtatgtgaag ttggttacaa ggattcatct   300
gtattacgct tctctacaga agttactgga tttttagaaa aaggaaagct agctgacatt   360
gaaggaatga aaacgaaagt gatgatgtgg gtaaaagtta ctgccatctc atctgaaaaa   420
tccaaggttc atttcacagc tgggttgaag aaaacccgga gtagggaggc ttatgaggtt   480
ttgagagatg gagtagctat tgaaaaattc taa                                 513

SEQ ID NO: 116              moltype = DNA   length = 675
FEATURE                    Location/Qualifiers
source                     1..675
                           mol_type = other DNA
                           organism = synthetic construct
SEQUENCE: 116
atgggtgcca ttagtttctt ggacaccata ttagtcccct tgagtctttt catcacaatt   60
ggctatcatt tctatctttg gcaccacttg aagcataaac cttctcgcac caccattggt   120
atgaatatac tcaagaagag atcttggctg cgagagctca atcaaggaaa cgagaagaaa   180
ggcacgttag ctgtacaaag cttaagaaat gcactaatgg aaacaatact cacggcaaca   240
atcacaatga tcataacttt agcattggca gctctaacaa acaacactta caacgtgaga   300
aacctcttta ctagtgcttt cttttggatca caaacaggga agataatcgt gttgaaatat   360
ggctcagcaa ctattttctt gttggcaagt ttcttgtgta gttctttggc acttagttgt   420
ttgatcgatg ctaattttctt ggtcaatgca ttgggggaat tttccataaa tccaatgtat   480
acagagacag tatttgaaag aggatttaca ttggcttttg tagggggatag agtgctttgc   540
atggctttttc ctcttttgtt atggatgtttt ggccctgtgc ctgtggttgt gtcttctttg   600
gctttggttt ggggattaca tgagcgtgat tttgctggaa atttgtcaag aactatgaat   660
aagagttgta tttga                                                     675

SEQ ID NO: 117              moltype = AA   length = 157
FEATURE                    Location/Qualifiers
source                     1..157
                           mol_type = protein
                           organism = synthetic construct
SEQUENCE: 117
MSHLTAAPPS EPPSAAVNSL YKQKSWSPDT FRDEAWQRRK GTHGSRLKQR SKSVTDEDLD   60
ELKACIELGF GFDSPEIDQR LSDTFPAYGL FYAVNKQYAD TLSKTSSLSS VISYCESPAP   120
PGSPHTIVDQ GDNPQTVKTR LRQWAQVVAW SVRQSSH                              157

SEQ ID NO: 118              moltype = AA   length = 690
FEATURE                    Location/Qualifiers
source                     1..690
                           mol_type = protein
                           organism = synthetic construct
SEQUENCE: 118
MEKKQLDFNA PLLSVRKISS SLSPHERANK KIIERAPPNR QQSLPVKKSD WELSEVTKPV   60
AVPFMWEQIP GRRKGDNEAR ANLRVEWSSS PRLPPGRLPE TIRFYSGERP RTQNIYKSPA   120
EGLPWIDHAA LLDSLAESIY TRGDRASEDD ANSDAPETLS PTESLSLDCS VSGLSGHQSS   180
DSKPSGTFSI DSQTRDFMMS RFLPAAKAVV LETPQYVQKK QVPVSTEQPK PVPVERKPIV   240
KQMESKPVSY YSGYPDDVGS EIEDDVSENQ HKRPSKGWKF FPRICVKNSL CLLNPLPGLK   300
VKTHVPTPSA QAVKRVSGMK PKTPQSPTSY AHEVKRLARK AYSGPLEKNT CDTINKQRFH   360
SGVLSRELYK AENRSFSGQL PNPSDSCKLV GISPGRRSRS GAISPCRNVA PPSPFNEGTR   420
FLGVPKEMES LWASRFDSFR KGCYTVKDKV PQQIGTGRFS DSPSEVVEKT LYIDSVDNVQ   480
ISARNSASSK PKELVNSSGK NMKPLVKSSK VLENMDATAR TQGAKDRNVS EKESKQVFEK   540
ESLDLVEASP ISISTRKGPA DHESLKLKQN LDTLSGALES SKVHPYGNLG TENEDNQNAN   600
GPKDSNLTSL ESPIPPPLPK SPSESWLWRT LPSIPLRTPF SSLSSKKQNK KSHADGSKWE   660
TIVKTSNLHK DHVRYSEELY TLGSCQQSKA                                     690

SEQ ID NO: 119              moltype = AA   length = 419
FEATURE                    Location/Qualifiers
source                     1..419
                           mol_type = protein
                           organism = synthetic construct
SEQUENCE: 119
MEVISTNTNG STIFKNGAIP MNGHQSGTSK HLNGYQNGTS KHQNGHHNGT SEHRNGHQNG   60
ISEHQNGHQN GTSEHRNGHQ NGISEHQNGH QNGTSEHQNG HQNGTSEQQN GTISHDNGNE   120
LLGNSNSIKL GWFSEFSALW PGEAFSLKVE KLLFQGKSDY QDVMLFESAT YGKVLTLDGA   180
IQHTENGGFP YTEMIVHLPL GSIPNPKKVL IIGGGIGFTL FEMLRYPTIE KIDIVEIDDV   240
VVDVSRKSFP YLAANFNDPR VTLVLGDGAA FVKAAQAGYY DAIIVDSSDP IGPAKDLFER   300
```

-continued

```
PFFEAVAKAL RPGGVVCTQA ESIWLHMHII KQIIANCRQV FKGSVNYAWT TVPTYPTGVI   360
GYMLCSTEGP EVDFKNPINP IDKETTQVKS KLAPLKFYNS DIHKAAFILP SFARSMIES     419

SEQ ID NO: 120            moltype = AA  length = 381
FEATURE                   Location/Qualifiers
source                    1..381
                          mol_type = protein
                          organism = synthetic construct
SEQUENCE: 120
MEVISTNTNG STIFKNGAIP MNGYQNGTSK HQNGHQNGTS EHRNGHQNGI SEHQNGHQNG   60
TSEHQNGHQN GTISHDNGNE LQLLGSSNSI KPGWFSEFSA LWPGEAFSLK VEKLLFQGKS   120
DYQDVMLFES ATYGKVLTLD GAIQHTENGG FPYTEMIVHL PLGSIPNPKK VLIIGGGIGF   180
TLFEMLRYPT IEKIDIVEID DVVVDVSRKF FPYLAANFSD PRVTLVLGDG AAFVKAAQAG   240
YYDAIIVDSS DPIGPAKDLF ERPFFEAVAK ALRPGGVVCT QAESIWLHMH IIKQIIANCR   300
QVFKGSVNYA WTTVPTYPTG VIGYMLCSTE GPEVDFKNPV NPIDKETTQV KSKLAPLKFY   360
NSDIHKAAFI LPSFARSMIE S                                            381

SEQ ID NO: 121            moltype = AA  length = 381
FEATURE                   Location/Qualifiers
source                    1..381
                          mol_type = protein
                          organism = synthetic construct
SEQUENCE: 121
MEVISTNTNG STIFKNGAIP MNGYQNGTSK HQNGHQNGTS EHRNGHQNGI SEHQNGHQNG   60
TSEHQNGHQN GTISHDNGNE LQLLGSSNSI KPGWFSEFSA LWPGEAFSLK VEKLLFQGKS   120
DYQDVMLFES ATYGKVLTLD GAIQHTENGG FPYTEMIVHL PLGSIPNPKK VLIIGGGIGF   180
TLFEMLRYPT IEKIDIVEID DVVVDVSRKF FPYLAANFSD PRVTLVLGDG AAFVKAAQAG   240
YYDAIIVDSS DPIGPAKDLF ERPFFEAVAK ALRPGGVVCT QAESIWLHMH IIKQIIANCR   300
QVFKGSVNYA WTTVPTYPTG VIGYMLCSTE GPEVDFKNPV NPIDKETTQV KSKLAPLKFY   360
NSDIHKAAFI LPSFARSMIE S                                            381

SEQ ID NO: 122            moltype = AA  length = 169
FEATURE                   Location/Qualifiers
source                    1..169
                          mol_type = protein
                          organism = synthetic construct
SEQUENCE: 122
MPNQKQGSEQ LQTLMQSGQI SGSLSFNGAL TKEDEEMSRS ALSTFKAKEE EIEKKKMEVK   60
ERVQAQLGRV EEETRRLAII REELEALADP KKKDVQIVRK KIDAVNKELK PLGQTCQKKE   120
KEYKEALEAF NEKHKEKVQL ITRLMELVGE SEKLRLKKLE LSKSIETIR               169

SEQ ID NO: 123            moltype = AA  length = 435
FEATURE                   Location/Qualifiers
source                    1..435
                          mol_type = protein
                          organism = synthetic construct
SEQUENCE: 123
MDPCPFVRIV IGNLALKFPA EHKLSSSTVF DCKFKLRGFS TQVSTISAFV QDPILDNRTH   60
SCFNLNKTEL DKLVEKSTAK GKTCSLKIEI FARKKGIGCG LLNGGKLLGS VIVDLKGLES   120
DGRRGVVIQN EWVLVGGSST AAQLHLNVKA EPDPRFVFQF DGEPECSPQV FQVNGNVKQP   180
VFTCKFSFRN NGDRNLRSRS SLSKPSTSTS CFNSCTSDKE SSPLKERKGW SITIHDLSGS   240
PIAAASMVTP FVPSQGSSNV SRSNPGAWLI LRPGNGTWKP WGRLEAWQER GGDLGYRFEI   300
IPDGATDAIT LSNSTISTKN GGKFGVDITN GATPLTSPNS SFDLCSGSGS GSDFGSAPGS   360
GSWAQLLYRG FVMSSTVEGE GKCSKPEVVV GVQHVNCVED AAAFVALAAA MDLSMDACQS   420
FTKKLRKELR QSDQE                                                  435

SEQ ID NO: 124            moltype = AA  length = 141
FEATURE                   Location/Qualifiers
source                    1..141
                          mol_type = protein
                          organism = synthetic construct
SEQUENCE: 124
MSGEDVAVAV AETPAPALGE PMDIMTALQL VLRKSKAHGG LARGLHEGAK VIEKHAAQLC   60
VLAEDCDQPD YVKLVKALCA DHNVSLITVP NAKTLGEWAG LCKIDSEGKA RKVVGCGCVV   120
VKDYGEETEG LHIVQEYVKS H                                            141

SEQ ID NO: 125            moltype = AA  length = 143
FEATURE                   Location/Qualifiers
source                    1..143
                          mol_type = protein
                          organism = synthetic construct
SEQUENCE: 125
MSGEDAAVPV VAAETPAPAL GEPMDIMTAL QLVLRKSKAH GGLARGLHEG AKVIEKHAAQ   60
LCVLAEDCDQ PDYVKLVKAL CADHNVSLIT VPNAKTLGEW AGLCKIDSEG KARKVVGCGC   120
VVVKDYGEET EGLHIVQEYV KSH                                          143

SEQ ID NO: 126            moltype = AA  length = 432
FEATURE                   Location/Qualifiers
source                    1..432
```

-continued

```
                           mol_type = protein
                           organism = synthetic construct
SEQUENCE: 126
MDPQAFIRLS IGSLGLRLSG TTTLNSTKTG ISAVSSPCVC EIRLRGFPVQ TSSIPYISSP    60
EATPDIHNVA SSFYLEESDL KALLAPAPCF YAAHACLEIV VYTGRKGGHC GVGIKRQQVG   120
TFKLEVGPEW GEGKPAILFN GWIGIGKNKL ETGKPGAELH LRVKLDPDPR YVFQFEDKTK   180
LSPQIVQLQG TIKQPIFSCE FSQDRVSPVD PLNNFWSSSF DGSELEVEKR ERKGWKVKIH   240
DLSGSAVAAA FITTPFVPST GCDWVAKSNP GAWLIVRPDI CRPESWQPWG KLEAWRERGI   300
RDSICCRFHL LSEGQECGGD LLMSEILISA EKGGEFYIDT DRQVQAAASP LPSPRSSGDF   360
AALSPVAGGF VMSCRVQGEG KCSKPLVQLA MRHITCVEDA AIFMALAAAV DLSIEACRPF   420
RRKLRRSTRH SW                                                      432

SEQ ID NO: 127          moltype = AA  length = 427
FEATURE                 Location/Qualifiers
source                  1..427
                        mol_type = protein
                        organism = synthetic construct
SEQUENCE: 127
MAKVCFYNVK MNMQVMFCLF LVSLCRDDAA AEAKQGMSLA AQKFEVQKHL NRLNKPAIKS    60
IKSPDGDIID CVHMSHQPAF DHPLLKNHTV QMMPNYHPEG LFRDGKLSTA KTKNEGSKSI   120
TQLWHLNGKC PEGTIPIRRT KKDDILRASS MKSYGRKKKH STIPKPESGR PGLVSQTGHQ   180
HAIAYVEGDK YYGAKATINV WEPKIQQPNE FSLSQLWILG GSFDSDLNSI EAGWQVSPDL   240
YGDNNTRLFT YWTSDAYQAT GCYNLLCSGF IQINNEIAMG ATISPLSSYH GSQYDISILV   300
WKDPKEGNWW MQFGNDYVLG YWPGFLFSYL TDSASMIEWG GEVVNSESDG LHTTTQMGSG   360
HFPDEGFGKS SYFRNIQVVD GSNNLRAPQD LGIYTEDNNC YDVQLGKNND WGNYFYYGGP   420
GRNPNCP                                                            427

SEQ ID NO: 128          moltype = AA  length = 312
FEATURE                 Location/Qualifiers
source                  1..312
                        mol_type = protein
                        organism = synthetic construct
SEQUENCE: 128
MSIDKSSMQS NLDCFLECTT PLVPSQFLPQ SEIRNLNRLW HPWEREKVEY FTLADLWNCY    60
DELSAYGAGV PIKMDTGETL VQYYVPYLSA IQIFTSRSSV NFLREETESV CETRDSFSDS   120
FSDESESEKL SRWDGCSSEE GDSLWQMNDR WGYLYFQYFE RSTPYGRVPL MDKISGLAER   180
YPGLMSLRSV DLSPASWMSV AWYPIYHIPM GRTIKDLSAC FLTFHTLSSS FQDMDLEDDT   240
ENGKRKRKEG ESIPLPPFGL GTYKMQGDVW LSDRKGRDQE RLASLFSVAD SWLKQLGVQH   300
HDFNYFMGIR RG                                                      312

SEQ ID NO: 129          moltype = AA  length = 316
FEATURE                 Location/Qualifiers
source                  1..316
                        mol_type = protein
                        organism = synthetic construct
SEQUENCE: 129
MTKTSKVQRV PGLLSCRSKV CKKIQKEKRP KSSEKKEWEG ATCSVCMEHP HNAVLLLCSS    60
YDKGCRPYMC ATSCRLSNCL EQYKKAYAKV TSIEGSEPEL LSIDDPNCLS GAGSCAGKSV   120
VELLCPLCRG QVKGWTVVEP ARKYLNAKKR TCMHENCSFV GTYKKLRKHV RREHPSARPL   180
EVDPSHAEKW KKLEHERELN DVFSTIRSAM PGAIVMGDYV IEGNFGGFHR NFGLDDHLGD   240
TLFRSESNGI PWNDIVHSDD VFDDGYHSFD EDDFFVNHSG SGAASNVFNR ISRLRSRLLL   300
GRSRRRQRHR ASSRIR                                                  316

SEQ ID NO: 130          moltype = AA  length = 426
FEATURE                 Location/Qualifiers
source                  1..426
                        mol_type = protein
                        organism = synthetic construct
SEQUENCE: 130
MRTLCSNLDR EDGLETVLEV PIPEEMFASN KHRARQSKNS GVKSHMDKSA ASVFGSRNAE    60
IQLLLGVVGA PLIPHPIRCD YSLNTKINDH PIEASVAKYI VQQYIAAAGG EHALNSIDSM   120
YAMGKIKMVA SEFIAGDGMG LNNGNMMKIK SVKNGPGEMG GFVLWQKRPD LWSIELVVSG   180
CKISAGSDGK VAWRQTPWHN SHASRGPARP LRRSLQGLGP KSVANLFSNS ICIGEKTVNI   240
EDCFVLKLET EPSTLKARSS SNVEVMRHTV WGYFSQRTGL LLQLEDTHLL RIKAPGNDVF   300
WETTMDSLIL DYRTLDGVNI AHGGRTSVSL FRFGKNSEGL TRTRMEEVWT IEEIDFNIKG   360
LSADCFLPPS DLKKEDEVSH DVNKKSRLGF KARTNNAKLR TARKGASKIM SIDEEDLEDY   420
EADEES                                                            426

SEQ ID NO: 131          moltype = AA  length = 125
FEATURE                 Location/Qualifiers
source                  1..125
                        mol_type = protein
                        organism = synthetic construct
SEQUENCE: 131
MIIGSSFSEK LMGKKKILKK TKELSVAIAE SSAMSGDSQQ QQQQITPRKR GRPRKIIVKD    60
EEEATGEIKK LKINEGEELE NKEAAEGEKK EAEEQSEEEK NLQPQKQQPV AKSRARRKSK   120
PRKSC                                                             125

SEQ ID NO: 132          moltype = AA  length = 525
```

```
FEATURE             Location/Qualifiers
source              1..525
                    mol_type = protein
                    organism = synthetic construct
SEQUENCE: 132
MMAQHIEISP LLDQTPPNEA TKDESPARPR LLKPSPTAAA SFFAFAVASH QVIQEGGKAD    60
YIIEIRTADQ TNESANQVFD EGSSTIFKVN VGLSESNPDA YTPKLISIGP YHNQNPRLRS   120
MEKYKLRYRQ RFLQRKAWRD VEYYFSEMEK LKDEALKCYD DIRDLDSNIV SKFLDLLLLD   180
GCFVVEYIRE FYEGVPEGED KIINAAWMES LVDRDLLLLE NQLPFFILAK LHEMTKDPTD   240
APFIQMVKYN FGSSLPKVTP KFINATDDDA EEIKHLLQVV HMCCCPSEMN TGLTRNSRKK   300
KGSSKKSCNW NPLRIGKSKK KFKTKDGDLW HDRMRSATEL DEAGIRFSNV GKIYRKLNKN   360
NKEDAISLFD IKFNKGLLEI PCFEVINSTE TILRNLIAYE QHSSDVHPKY FTDYIIFMDH   420
LINSGKDVNL LRLNGIIRNR IGDDEEVAIM FNKLGEGVIP STDFFYKVEC RKVIEHCEKP   480
WNENMASLRH NYLNSPWAKI STAAAIILLL LTVAQTVLAF ISTLK                   525

SEQ ID NO: 133     moltype = AA  length = 302
FEATURE             Location/Qualifiers
source              1..302
                    mol_type = protein
                    organism = synthetic construct
SEQUENCE: 133
MRDFPSCFGE NGVQVADASC SAVGGVTKTP QNLVTCVYQC KLLGKSCLIT IVWTKSLMGQ    60
CLSVEIDDMS HQCLCKVDVK PSLFSKRKGS RSLEVNSCKI DLHWDFSLGK FGSGPEPIEG   120
YYLALVCKGQ MVLVIGDLRK EAFKKTNATP SFSNAMFISK REHIFGKRVF GTKAQFCYTG   180
PIHDITIECD SNGIDDPCLL VRIDSKTVMQ VKHLRWKFRG NYTVLIDGLP VEVFWDVHNW   240
LFSSNFGNAV FMFQTCLSAE KLWTTQTLSD LSVMPWSYTE SLSNSKSSGL GFSLVLYVWK   300
NE                                                                 302

SEQ ID NO: 134     moltype = AA  length = 375
FEATURE             Location/Qualifiers
source              1..375
                    mol_type = protein
                    organism = synthetic construct
SEQUENCE: 134
MEVISTNTNG STIFKNGTIP MNGHQNGSSE HLNGYQNGIS KHQNGHQNGT SEHRNGHQNG    60
TSEQQNGTIS HDNGNELLGS SNSIKPGWFS EFSALWPGEA FSLKVEKLLF QGKSDYQDVM   120
LFESATYGKV LTLDGAIQHT ENGGFPYTEM IVHLPLGSIP NPKKVLIIGG GIGFTLFEML   180
RYPSIEKIDI VEIDDVVVDV SRKFFPYLAA NFNDPRVTLV LGDGAAFVKA AQAGYYDAII   240
VDSSDPIGPA KDLFERPFFE AVAKALRPGG VVCTQAESIW LHMHIIKQII ANCRQVFKGS   300
VNYAWTTVPT YPTGVIGYML CSTEGPEVNF KNPVNPIDKE TTQVKSKLGP LKFYNSDIHK   360
AAFILPSFAR SMIES                                                   375

SEQ ID NO: 135     moltype = AA  length = 375
FEATURE             Location/Qualifiers
source              1..375
                    mol_type = protein
                    organism = synthetic construct
SEQUENCE: 135
MEVISTNTNG STIFKNGAIP MNGHQNGTSE HLNGYQNGTS KHQNGHQNGT FEHRNGHQNG    60
TSEQQNGTIS HDNGNELLGS SDSIKPGWFS EFSALWPGEA FSLKVEKLLF QGKSDYQDVM   120
LFESATYGKV LTLDGAIQHT ENGGFPYTEM IVHLPLGSIP NPKKVLIIGG GIGFTLFEML   180
RYPSIEKIDI VEIDDVVVDV SRKFFPYLAA NFNDPRVTLV LGDGAAFVKA AQAGYYDAII   240
VDSSDPIGPA KDLFERPFFE AVAKALRPGG VVCTQAESIW LHMHIIKQII ANCRQVFKGS   300
VNYAWTTVPT YPTGVIGYML CSTEGPEVDF KNPVNPIDKE TTQVKSKLGP LKFYNSDIHK   360
AAFILPSFAR SMIES                                                   375

SEQ ID NO: 136     moltype = AA  length = 480
FEATURE             Location/Qualifiers
source              1..480
                    mol_type = protein
                    organism = synthetic construct
SEQUENCE: 136
MANKVSNFSD LIQRVTASCL LHPLSSGRID GNISDARYSD ESEDDKYSTE DEEEKEDPPY    60
VETREKFQNV EVTKEEIRTE KVTEMEMLLG EVFDAVSAVK TAYVSLQEAH CPWDQDKMRV   120
ADVAVISELR RLGVLRERFR RNVGGGIRKG DWRVGAATLR EVVAPYEATV EELRQEVKAK   180
EIEIDNLREK LKTATSLSSS GGKKSKSKRK VSGSSQAPVT MSPAPDVFET TVSLVKEASK   240
SFTSLLLSLM RSAHWDIAAA VRSIEAASSN TNTPTADSIV GANHAKYALE SYVNRKMFQG   300
FDHETFYMDG SLSSLIHPDQ HRRDCFTQYR DMKAMDPMEL LGILPTCSFG NFCFKKYLAI   360
VHPKMEESLF GDLEQRRQVL AGNHPRSQFY GEFLGLAKAV WLLHLLTFSL DPPPSHFEAS   420
KGSEFHPQYM ESVVKYSISM GIGGRMGMGL VVGFPVSPGF KLGNGSVVKA RVYLVPKNGF   480

SEQ ID NO: 137     moltype = AA  length = 107
FEATURE             Location/Qualifiers
source              1..107
                    mol_type = protein
                    organism = synthetic construct
SEQUENCE: 137
MDRLINSDKD VKLFRLKGII RNRIGDDNEA ASIFNRLGEG VIPSTQFYYK EACKKVVEHC    60
EKPWSERKAS FWHNYFNGPW VGLSTAAAVI LLSLTVMQTV LTFISTL                107
```

-continued

```
SEQ ID NO: 138            moltype = AA   length = 267
FEATURE                   Location/Qualifiers
source                    1..267
                          mol_type = protein
                          organism = synthetic construct
SEQUENCE: 138
MAMGPERSKP PLHNFTLPCG LKWGNQKFLR CAKVESDGQI SAIHRRSFGS ELIGRRRSND    60
RKFRPPEKQD AGEGIGAVRE KLMFDLQTEA DKIKDAIFRE GLEEQQLSPA PAKTATAAVS   120
YAGELSRPWN LRTRRAACKE PNGFVAGAGA AGSGGGSKG  GLKIDAYRTN APSPLRTENK   180
SPTLRSDFAG GAAAGASASG EKRQRVKFSV PLSRGEIEED FMAMVGHRPP RRPKKRAKFV   240
QKNLDTLFPG LWLTEITPDL YKVPEDQ                                       267

SEQ ID NO: 139            moltype = AA   length = 651
FEATURE                   Location/Qualifiers
source                    1..651
                          mol_type = protein
                          organism = synthetic construct
SEQUENCE: 139
MEIISERRRT RSQAAAILVE LKSINFQSEK RPKVHEKDGV KNFGKRKRRK GSNVRRKKKG    60
KYVQVDSDDD EDYVFDKSPK RRKLDYGHKG KSSSSDLKIW DFYVQPRKHF TARIGTHTNV   120
DVVKLLNAKL DDRQIQMFRE TCFGHFLDLP DVLVQPQLIH SLLLREVVHE REDELWISVN   180
DVRLRFGLVE FGIITGLKCT GDADMCLDFD GTNRLFDTYF SELTRVPKQS LIDCFLNKRW   240
KSDEDAVNIA VLYFIHTFLL STLNRNYITR DDFGLVESGA YQTYPWGKVV FKATLKSIKG   300
RLLGKPSMYR LRGLPLAFQC WFYECCPYVN KKIAFRVDDK VPRILSWKVT KQPNLKKLSN   360
GIFMQRRDQF MLRNISPTEF EQTTLNLPES FENERDNEVA SGDGAEVHLS DDDFSGSPPQ   420
TSRKQPKTKP DHPLNNDDWS IELKRLSDGQ SELKSEIQML NKEVASLKDC MVASFADAFK   480
AIKSLSKKQR EKIASELDGE NGHHDRHGES DSSDFSNSED NGCEGQEHGK DSMGDKDNSE   540
KGNEVALGDA EGRETVRDPV EEGERMDVSA SPILPDTCEV SDHITPEQSH PTPILESPYV   600
NQGDTGVEGS SEKSILKGEH PLESKIVDNV DYSLLSEFDK WVDEGMKKES K           651

SEQ ID NO: 140            moltype = AA   length = 298
FEATURE                   Location/Qualifiers
source                    1..298
                          mol_type = protein
                          organism = synthetic construct
SEQUENCE: 140
MSSHERRGPV AVVGSGGYSH ESEPDLAAMV SDFLESSSVG AESRYSSDND SGFSDLALLA    60
DRISLHKHSV DQYESDLTMV VHSLILSLGE SCHLSKPETC NASCIRSNLV KLLQSCGYDA   120
ALCSTKWQGC GKIPGGEHEY IEVISRGNDG CSERYIIDID FRSHFEIARA VKSYNVVLSC   180
LPPVYVGTVR KLKQYLQTMV EAARCSLKQN SMPLPPWRSL AYLEAKWESS SQRVANFQVQ   240
SSIGPSNSSH QHCTELLWRI KSSIGSEINA KSFLVPKSCR KKQGLKIDKL RHSSPVTP     298

SEQ ID NO: 141            moltype = AA   length = 279
FEATURE                   Location/Qualifiers
source                    1..279
                          mol_type = protein
                          organism = synthetic construct
SEQUENCE: 141
MQEEEFFCPS FSSYSSNRAA EIAAKISDEI ERNSKVAEQA EVEANAGEDD FEFSLVCENP    60
EASVGEFFYD RQIQPVFPVF NRDLLLNVVS YDVDHKGGVD GESSENANSS IQVSLKDLFL   120
EDREPPSSSS SEVDELESVP PGTYCVWKPQ ITEPSPSRCK KSNSTGSAFK RWSIRDLMRR   180
SNSDGKDSFV FLTQEKGTKN ETSKTKDSVE ASKVTGKLKA KGGSSNVGEKA SSSAAVYLRN  240
QAAAKEMDKN KRKSYLPYRQ DLVGIFANVN SLGRTFPPF                          279

SEQ ID NO: 142            moltype = AA   length = 690
FEATURE                   Location/Qualifiers
source                    1..690
                          mol_type = protein
                          organism = synthetic construct
SEQUENCE: 142
MEKKQLDFNA PLLSVRKISS SLSPHERANK KIIERAPPNR QQSLPVKKSD WELSEVTKPV    60
AVPFMWEQIP GRRKGNNDAR ANLRVECSSS PRLPPGRLPE TIRFYSGERP RAQNIYKSPA   120
EGLPWIDHAA LLDSLVESIY TRGDRESEDD AYSDAPETLS PTESLSLDCS VSGLSGHQSS   180
DSKPSGTFSI DSQTRDFMMS RFLPAAKAVV LETPQYVQKK QVPVSTEQPK PVPVERKPTV   240
KRMESKPVSY YSGYPDDVGS EIEDDVSENQ HKRPSKGWKF FPRICVKNSL CLLNPLPGLK   300
VKTHVPTPSS QAVKRVSGLK PKTPQSPTSY AHEVKRLARK AYSGPLEKNS CDTINKQRFH   360
SGVLSRELYK ADNRSFSGQL PNPSDSCKLV GISPGRRSRS GAISPYRNVA PPSPFNEGTR   420
FLGVPKEMES LWASRFDSFR KGCYTVKDKV PQQIGTGRFS DSPSEVVEKT LYIDSVDNVQ   480
ISARNSASSK PKGLVNSSSK NMKTLVKSSV VLENMDATAR TQGAKNWNVS EKESKQIAEK   540
ESLDLVEASP VSISTLKGPA DQESLKLKQN LDTLSGALES SKVHPYGNLG TENEDNKNAN   600
DPKDSNLTSV ESPIPPPLPK SPSESWLWRT LPSIPLRTPF SSLSSKKQNK KSHTDGTKWE   660
TIVKTSNLHK DHVRYSEELY TLGSCQQSKA                                    690

SEQ ID NO: 143            moltype = AA   length = 391
FEATURE                   Location/Qualifiers
source                    1..391
                          mol_type = protein
                          organism = synthetic construct
```

-continued

```
SEQUENCE: 143
MEIARSSRRC KWVTAFLVLL ACSAAGQVED GPLVNGDFET PPSGGFSSGD GFSDGPLVLP    60
SWKTNGTVEL VESGQKQGGM ILIVPQGRHA VRLGNDAEIS QELKVEKGSI YSVTFSAART   120
CAQLESLNVS VPPASQTIDL QTLYNVQGWD SYAWAFQAEE DDVRAVFTNP GMEDDPTCGP   180
IIDDIAIKKL FTPDKSKDNA VLNGDFEEGP WMFRNASLGV LLPTNLDEET SSLPGWIVES   240
NRAVRYIDNY HFTVPEGKRA IELLSGKEGI ISQMVETKPN KPYRLTFLLG HAGDSCKQPL   300
AVMAFAGDQA QNIHYTPNSN SSFQIANLNF TAKADRTRVA FYSIYYNTRS DDMSSLCGPV   360
VDDVRVEVSG SSTVKVLGFG FMLWLLVLVL V                                  391

SEQ ID NO: 144           moltype = AA   length = 375
FEATURE                  Location/Qualifiers
source                   1..375
                         mol_type = protein
                         organism = synthetic construct
SEQUENCE: 144
MRTLCPNLDK ADGLETVLEV PIPEEMFNNM GSNGALQWRN MRNLMRAQSA DRYSSSSHHA    60
AVSSNDQFMF LFKIVGSALV PFQVQLDHIA DNMPVRNGSM EAATAKYIVQ QYLAACGGQA   120
ALNSLNSMCA VGQVKMATWD IHQSGGDANS KRHCEVGAFV LWQKNPDLWV LELVVSGCKI   180
SAGSNGKVAW SQSSSTSSAS KGPPRPLRRF FQGLDPRSTA NLFLNAICVG EKTIKDEECF   240
ILKLESSIDM LKAQSTANTE VVHHTILGYF SQRTGLLIQF EDTKLVRLKS PKGDSNVFWE   300
TSMESMLEDY RYIEGINIAH SGKTAATIYR YGKNIDYRAK IEETWMIEEI DFNISDLPMD   360
CFLPPAEFEE QGMGC                                                    375

SEQ ID NO: 145           moltype = AA   length = 185
FEATURE                  Location/Qualifiers
source                   1..185
                         mol_type = protein
                         organism = synthetic construct
SEQUENCE: 145
MLQHLYLGQF SMMFLLLLCS IFAVLTTAES SIYEVLESHG LPMGLLPKGV KNFTLDNSGK    60
FVVHLDQACN AKFENEFHYD RNVSGTISYG QIHALSGIEA QDLFLWFPVK DIRVDIPSSG   120
LIYFNVGVVS KQFSLSSFET PRDCTAVQLT DLQDDMHIAD AISKSQSGEL RYKFDQGNIG   180
RKAIL                                                               185

SEQ ID NO: 146           moltype = AA   length = 305
FEATURE                  Location/Qualifiers
source                   1..305
                         mol_type = protein
                         organism = synthetic construct
SEQUENCE: 146
MQAYGRMKRV TDPLDDKVKA RIIGRDQQEL GYLSSGSEHS AHADDDASCS FSTLIFGLPD    60
DVAAENMSSE NDSDSDDGDV SMYESTDVIE DLPKPVFYSD LDLFRNSLAT KITKALEMFS   120
FSKSNKPILR RNVMTYLRDF GYNAAICKTK WESSGGLKAG NYEFLDVIRS DSGNRITRYF   180
IDLDFAAEFE IARPTNHYER LSQSLPRVFV GKSEELKKML KVMSDAGRRS LKSKDLSIPP   240
WRKHRFMQNK WLGAYKRTTN VLPSANSSAL LSPSKQTNVA KCRSVGFSAV AVNGRLLFPA   300
ATRTR                                                               305

SEQ ID NO: 147           moltype = AA   length = 361
FEATURE                  Location/Qualifiers
source                   1..361
                         mol_type = protein
                         organism = synthetic construct
SEQUENCE: 147
MASRKRSISN DVDMHVLYKE LDEASCPVCM DHPHNAVLLI CSSHDKGCRS YICDTSYRHS    60
NCLDRFKKLR AENRDSPPIM TQGNLDIAVE NPDEQLRNLS DRSVVHGNSN RDNHMEMHEG   120
TVQTSGAATV WGSSQETASA DGSSDSKLKL KCPMCRGDVL GWKVVEEARK YLNLKNRSCS   180
RESCSFVGNY RELRRHARRV HPTARPADID PSRQRAWRRL ESQREYDDIV SAVRSAMPGA   240
VVLGDYVIES GDRLSGERER GAGGNSRWLS TFFLFQMIGS MDPISEARGG RSRALSRHRR   300
STGPLSRRRY LWGENLLGLQ DDDEDEDERD LNILSDMSGD IPTNPRRRRR LMRSRSDEDQ   360
Q                                                                   361

SEQ ID NO: 148           moltype = AA   length = 403
FEATURE                  Location/Qualifiers
source                   1..403
                         mol_type = protein
                         organism = synthetic construct
SEQUENCE: 148
MPFPMKIQPV DFNTVEEPSR YDSFKPVQKS RFKRLFERQF SGLLRSSAPL EKLVAGEELI    60
CNKKDVASDE FEPSSVCLAK MVQTFIEEGE ADKHRCNRNR KCNCFNCNGT DSSEEETDSL   120
SCFGESNHTC CNDACEILKS LVPCPSVIER NVLADITKII EKNKMGKRKD NFIRKIVVDG   180
LLAAGYDASI CESRWDKTPS TPAGTYEYVD VVIEGERLLI DIDFRSEFEI ARSTRSYKFL   240
LQLLPNTFVG KADRLQKIVH LLTEAAKQSL KKKGMPFPPW RKAEYVKAKW LSPYTRIKPT   300
LMGAPTVSNS APETGTACKT YQQAVKEESS EDSCGELNLI FGESSQLLEN NAKSVITYPL   360
SACDDEEKDV MVQQGKPPDT KHKDSSNGAR KITGLTSLIE DHT                     403

SEQ ID NO: 149           moltype = AA   length = 164
FEATURE                  Location/Qualifiers
source                   1..164
                         mol_type = protein
```

-continued

```
                          organism = synthetic construct
SEQUENCE: 149
MPMSLTSILC FFFLFFSATT ASRNEKPSAY EELQRYDFPM GILPKGVKDY KLNTKTGEFS   60
AYLNSTCSFR LENSYQLNYK PVIKGVISKG RLTKLSGVSV KVVLLWLNIV EVRRKGENLE  120
FSVGLTSANF PIENFEECPQ CGCGLDCVSK EERKIRQKVF VSSS                  164

SEQ ID NO: 150           moltype = AA   length = 108
FEATURE                  Location/Qualifiers
source                   1..108
                         mol_type = protein
                         organism = synthetic construct
SEQUENCE: 150
MEELRPSFRC SGDRRLEIVS GKGFSSNQGS RARSPDLPVV TSKGTWPSQV AAATSSSAKP   60
WGFNDPEMKR RKRIAKYKVY TIEGKFKTSI RNGLRWFKNK CSEIIHGY              108

SEQ ID NO: 151           moltype = AA   length = 275
FEATURE                  Location/Qualifiers
source                   1..275
                         mol_type = protein
                         organism = synthetic construct
SEQUENCE: 151
MGFSENNRGL VLAMVSSLFI GTSFILKKKG LRRAAAAGTR AGVGDYTYLL EPLWWAGMIT   60
MIVGEASNFV AYIYAPAVLV TPLGALSIII SALLAHFMLR ERLQRLGVVG CILCIVGSVV  120
IFIHAPQEHM PTSVQEIWIL AIQPAFMIYI AATVSTVVAL MLHFGPRYGQ TNLLVYLVIC  180
SLMGALTVVS IKAIGIAIKL TLEGISQIAY PQTWFFLAVA VICVITQLNY LNKALDTFNA  240
AIVSPIYYVM FTTLTIIASA IMFKDWAGQD ASSIV                           275

SEQ ID NO: 152           moltype = AA   length = 232
FEATURE                  Location/Qualifiers
source                   1..232
                         mol_type = protein
                         organism = synthetic construct
SEQUENCE: 152
MGTDTEVAEM SSTLKLPLFS VESSQEDLGM LTPLHTLASI PFKWEEEPGK PRPCTDLIPL   60
PNSICLEPPP RLYNMEFSKT SSSPTTVFDG PYITNKPRFS SFRLLRRDRR HRRQGSFDST  120
TSSETGQLST TLVLGNKKSE SKSWWRRPTT HHVKHNGCEI NSGFVFPSSI DYSTDCVEEC  180
SSSSIKMETF RRSGSFSGHS QAKTHIWAAI YEGFKQVIPW KNRKSKKEAL IG         232

SEQ ID NO: 153           moltype = AA   length = 144
FEATURE                  Location/Qualifiers
source                   1..144
                         mol_type = protein
                         organism = synthetic construct
SEQUENCE: 153
MSGEDAAVPV VAAAETPAPA LGEPMDIMTA LQLVLKKSKA HGGLARGLHE GAKVIEKHAA   60
QLCVLAEDCD QPDYVKLVKA LCADHNVSLI TVPNAKTLGE WAGLCKIDSE GKARKVVGCG  120
CVVVKDYGEE TEGLHIVQEY VKSH                                       144

SEQ ID NO: 154           moltype = AA   length = 540
FEATURE                  Location/Qualifiers
source                   1..540
                         mol_type = protein
                         organism = synthetic construct
SEQUENCE: 154
MGNRSSNLDN DNNISRPIDT PFKLPSPLPT WPSGQAFATG VIDLGGLEVS QTSSLAKVWA   60
TQESGPDDLG ATFFEPSNLP NGFFMLGSYS QPNNLPLFGS VLVGKDSKGD ALKIPIDYTL  120
VWSSENLNIK QDSVGYIWLP IPPEGYKAVG HVVTTSPQKP SLDKIRCVRS DLTDVSESDD  180
WIWGNNGLNV YSSRPRDRGI NALGVSTGAF VASNNGTADS LACLKNVNAN LSAMPNLNQV  240
KALFQAYSPL YYFHPDEQYY PSSVTWFFQN GALLYTKGQE SAPVAIESNG SNLPQGGSND  300
GAFWLDLPTD DSAKDQVKKG DLQAATAYLH IKPMFGATYT DIALWLFYPF NGPARAKIEF  360
MTIPLGKIGQ HVGDWEHVTL RISNFNGELQ GVYFSQHSGG NWVSASQLEF QNGNKPVAYS  420
SLHGHASYAQ PGKNLQGNNN IGLRNDTAKG QMMDTGANYS IVAAEYLTIV EPAWLNYARE  480
WGLKISYDIA NELQKVERFL PGKLKNAVEK LVKSLPNEVL GEEGPTGPKF KDMWNGDERG  540

SEQ ID NO: 155           moltype = AA   length = 163
FEATURE                  Location/Qualifiers
source                   1..163
                         mol_type = protein
                         organism = synthetic construct
SEQUENCE: 155
MAFSQKSQLL FCSLLFILIS LSLSFNPSRP NKDDDVHDLL PSYNLPIGLL PNNVKSYTLS   60
PKDNSFTVQL THPCYVQFQD QLVYYQKEIK GKMSYGEVSD VSGIQAKKLF VWVPVTGINV  120
DEESHMIEFH VGFLSEKLPA KDFETIPTCK NNKGCQDSLL SSI                  163

SEQ ID NO: 156           moltype = AA   length = 155
FEATURE                  Location/Qualifiers
source                   1..155
                         mol_type = protein
                         organism = synthetic construct
```

```
SEQUENCE: 156
MLLGKRPRPP IKRTTSMKEF TLDLNINDPS VAVINYQPFD PLNPYNFTGP VPMPSNGLDQ   60
RLILTRRRSA DFVGTAHFLR ACSLCKRQLI PGRDIYMYRG DSAFCSLDCR EKQMKQDEKK   120
EKYPKVATRK KVTNSAAMAA VASGTGSDAP PQARP                             155

SEQ ID NO: 157          moltype = AA  length = 480
FEATURE                 Location/Qualifiers
source                  1..480
                        mol_type = protein
                        organism = synthetic construct
SEQUENCE: 157
MANKVSNFSD LIQRVTASCL LHPLSSGRID SNISDAHYSD ESEDDKYSTE DEEEKGDLPY   60
VETQEKFQNV EVTKEEIKTE KVTEMEMLLG EVFDVVSAVK TAYVSLQEAH CPWDQDKMRV   120
ADVAVISELR RLGVLRERFR RNIGGGIRKG DWRVGAATLR EVVAPYEATM EELRQEVKAK   180
EIEIDNLREK LKMATSLSSS GGKKSKSKRK ISCSSQAPVA MSPAPDVFET TVSLVKEASK   240
SFTSLLLSLM RSAHWDIAAA VRSIEAASSN TNTPTADSIV GSNHAKYALE SYVNHKMFQG   300
FDHETFYLDG SLSSLLHPDQ HRRDCFTQYR DMKAMDPMEL LGILPTCSFG NFCFKKYLAI   360
VHPKMEESLF GDLEQRRQVL AGNHPRSQFY GEFLGLAKAV WLLHLLTFSL DPPPSHFEAS   420
KGSEFHPQYM ESVVKYSISM GIGGRMGMGL VVGFPVSPGF KLGNGSVVKA RVYLVPKNGF   480

SEQ ID NO: 158          moltype = AA  length = 410
FEATURE                 Location/Qualifiers
source                  1..410
                        mol_type = protein
                        organism = synthetic construct
SEQUENCE: 158
MMGSGLQFNR SFNGEDRFYS AGKFRRNVNR SFSTGSEDNL RRAKSDVAVI HSPTKPKMKV   60
AADESPDEPV SAVPPTDVLP PPLCNLQRFL KSVSPSVPAQ YLSKTTMRGW RTCDVEFQPY   120
FVLGDLWESF REWSAYGAGV PLVLNEGDSV VQYYVPYLSG IQLYGDSTKA STKTSRRPGE   180
ESDSDYFRDS SSDGSSDSEH ERRCLNYTRE QRMYHSQTSE SSLSIDRLSL RDRNATFQEG   240
FSSDEGESGS SQGALLFEYL EHGQPYGCEP LADKISDLAQ RFPELKTMRS CDLLPSSWIS   300
VAWYPIYRIP TGPTLKALDA CFLTFHSLHT PMTGSQSAHP AAVTCPSDTD PVPKIPLPAF   360
GLASYKFKAS LWTPNGGSGR QLMSSLLQSA ENWLTLLQVN HPDFSFFCQR             410

SEQ ID NO: 159          moltype = AA  length = 226
FEATURE                 Location/Qualifiers
source                  1..226
                        mol_type = protein
                        organism = synthetic construct
SEQUENCE: 159
MGSCVSVHKD SESAMKIRLV FGSSKTDKLV TPSPLNKDDT KVSDLQLKSQ TPAVTAFRDF   60
GSKEETFFDS QPWLDSDCED DFLSVNGDFT PSRGNTPVHP LAGNLTGNRT PAYFQQSSPT   120
DKKKRLSELF EESLRSDLDQ NGQNAEEKQN GTNTKKETAS TGTQLPPRST PGTPYASVCS   180
SERTPSGLLK SDVKTSKSAQ CCLPRLLSSR SFNGRRSRMS PARNVG                 226

SEQ ID NO: 160          moltype = AA  length = 199
FEATURE                 Location/Qualifiers
source                  1..199
                        mol_type = protein
                        organism = synthetic construct
SEQUENCE: 160
MKDDESIPVS TPTTHSSSNT ISTYSKNSTS DATIFGRGRY KFWALAAILL LAFWSMFTGT   60
VTLRWSAGNL NGLSDYFNVP LSDNLDVIEM EEREKLVKHM WDVYTNTPRI RLPKFWQEAF   120
EAAYEELTSD LADIREAAIS EISKMSLRFV HMEPPPLRSL AVRELSQKQA EDKQRTAKGI   180
WLSAVLMEEN KREEKRGPD                                               199

SEQ ID NO: 161          moltype = AA  length = 182
FEATURE                 Location/Qualifiers
source                  1..182
                        mol_type = protein
                        organism = synthetic construct
SEQUENCE: 161
MADSESRQFS PDKEPCFAEE LLDWQRRELP RRFLSGQVVW DDDAFIPEGA SEKHRVIFRR   60
IYRKYFLQIF ASDGFDIDIY PGKAKAAMLI PYLDFEKEID LLMELANHAI QDYNSKETNV   120
YKYEVLYVEK VNFILAECRE FFMTVKVKNL TLRSPKETFQ IHAYKGPDGE NIFCLCRRKL   180
LV                                                                 182

SEQ ID NO: 162          moltype = AA  length = 302
FEATURE                 Location/Qualifiers
source                  1..302
                        mol_type = protein
                        organism = synthetic construct
SEQUENCE: 162
MRDFASCFNE YAVQVSDTSC SSYSNSACIP PSLIPSIQNT VTCLYKVTLS NKKQVLITVS   60
WSKTNSITQG LSVHFGDDPS NVFKLNTNSR LFRKKRGSKS LDLDHLKVEI FWDLYAARYL   120
SGPEPIDGYY LLVKVDSQLG LIIGDMAEEA SLRKLKNGTP MAKFSLVSRK EYFSGNTLYS   180
TKAQFCDNGT SHDILIRCSG ENEGLKHPVL SVYIDKKMVI RVKRLQWNFR GNQSIFVDGL   240
LVDLMWDVHD WFFNPTSGCA LFMFRTRSGM DSRLWLDDKD KLLHKDPDKV EFSLLIYASK   300
TT                                                                 302
```

-continued

```
SEQ ID NO: 163            moltype = AA   length = 167
FEATURE                   Location/Qualifiers
source                    1..167
                          mol_type = protein
                          organism = synthetic construct
SEQUENCE: 163
MAASKSYFAG ANYRFLSSER DVPMMSPESA FEFDESDLWN SAVSQSPEFR KSVQSSKISR   60
KQCDTKSRRS GSVASAASLP VNVPDWSKIL KDEYREYGRR DSDDDDFNDE DGDDLENRIP  120
PHEFLAKQLE RTRIASFSVH EGVGRTLKGR DLSRVRNAIW EKTGFQD                167

SEQ ID NO: 164            moltype = AA   length = 758
FEATURE                   Location/Qualifiers
source                    1..758
                          mol_type = protein
                          organism = synthetic construct
SEQUENCE: 164
MERRPKQSGE RKTMENEELV KYMSSLPSYL EKGENLQEKA FSVGVLDWRF LEKWRHEHVK   60
EPCRTSGCSP STSNTLSFSS MEGSSSNSSR ARSCSPARRR IHRPTSQSYY ASPPKGSYVQ  120
LQNQKPGVIK SPEIEQLVCR IYQSFDEYPQ RNMQELGNAL HPRRTPHVRR SLDVETKTRT  180
SRSKGKMKIQ DRECLSKGDF DDFDCIEKHK SDVLQVPEPG QETNSCTTFC PPDSVVKDQS  240
AVKSSRRSFS CGFISAFYYG QSSSDISSSS TLPHDADESK VGQASPIDAK DSCLSSKTIQ  300
PSTYSGNKLS SPPGTNSKQE KKSTVMLKNP TTLNSAESTN IRNSSPTRQF SMAMGRIGQI  360
SGIKDMITGS QGVKWPAEQS SPNKTQSSSS IDTGCDKSDT TGRARTSPLR RLLDPLLKPK  420
TGNSDHVKSS TRRGESPTKR SLKVKLDLKS CKSIDIDDPR SNGTFVPSRL QALLQVAVKN  480
GLPLFTFAVD NEVDILAATM KKLNPNLKDY SCWIYNFFTV RETKKKSGNW LNQVEKDRSH  540
GIMPNIVGKM KVSDVPFSEL NRQKLDSQFR ITEFVLFATD QKASDLHPND ELAAIVVKLP  600
NRTSICPNGS GHQDRNCSNT STSGLTNPFE DLNMTVILPG GAHSVPSKGE PSSLINRWRS  660
GGSCDCGGWD LGCKLRLLRN HTNHQRISSC SKPKLNAARF ELLSQGEARD SKPVFSLSAF  720
KDGIFSVEFS SSLKVLQAFS ICIAVLNGRN QESFQMQT                          758

SEQ ID NO: 165            moltype = AA   length = 185
FEATURE                   Location/Qualifiers
source                    1..185
                          mol_type = protein
                          organism = synthetic construct
SEQUENCE: 165
MLQHFCLGQF SAMFLLLLCS IFAVLSTAES SIYEVLESHG LPRGLLPKGV KNFTLDNSGK   60
FVVHLDQACN AKFENEFHYD RNVSGTISYG QIHALSGIEA QDLFLWFPVK DIRVDIPSSG  120
LIYFNVGVVS KQFSLSSFET PRDCTVVQLM DLQDDMHIAD AVSKSQSEEL RYKFDQGNIG  180
RKAIL                                                              185

SEQ ID NO: 166            moltype = AA   length = 304
FEATURE                   Location/Qualifiers
source                    1..304
                          mol_type = protein
                          organism = synthetic construct
SEQUENCE: 166
MASTVPAKSN NPLYNFDFSH LKWKKNHHSN NHQRRRSNKL SSDSSSPSRH DSPLRHSQSQ   60
SPMRESLAAA RQSPVSESAE TARISPMHNS AAAARQSPMR ESARQSPMRD PVPSVQRSKH  120
KVPEINVVSS KESRSKILIK IPRKNKSEEI QINEDQNQKA ADESHDEAAA AEETAQKTWN  180
LRPRKPIHKS LNINGGVPFR SSGSAMQEIK SQSPHHMMNV NKPENNETHA ASAQKKVKRQ  240
RFSIALSREE IDEDLYAMTG LKAARRPKKR VKVVQKQLDT LFPGLWLASI TPDSYKVCEN  300
LPKG                                                               304

SEQ ID NO: 167            moltype = AA   length = 370
FEATURE                   Location/Qualifiers
source                    1..370
                          mol_type = protein
                          organism = synthetic construct
SEQUENCE: 167
MMMNQSSICS SLNEDKVHDT PDSFHQLHPK KDSDSLDGSE LESGDTISTV EHLKSALKAE   60
RKALHSLYTE LEEERSASAV AASQTMAMIN RLQEEKAAMQ MEALQYQRMM EEQSEYDQEA  120
LQLMNELMVK REREKQELEK ELEAYRKRLL EYEATRMLKR SKDSSTFSSE DSDGLSIGLN  180
QEEAKEDDSG MNHSTPVGAV INLEEERMAI LEQLKVLEER LVSLDLDDED AKHFEDVRLM  240
EDSYQDNIEE DSHANGFLKE MNGKHHHAKG KRLLPLFDKM SDENGDGTLN ANGVHNFDLE  300
NKKLAVEQEL DHLHQRLQAL EADREFLNNC VSSLKKGDKG MDLLQEILLH LRHLRNVELR  360
ATSFSDAAIL                                                         370

SEQ ID NO: 168            moltype = AA   length = 370
FEATURE                   Location/Qualifiers
source                    1..370
                          mol_type = protein
                          organism = synthetic construct
SEQUENCE: 168
MMMNQSSICS SLNEDKVHDT PDSFHQLHPK KDSDSLDGSE LESGDTISTV EHLKSALKAE   60
RKALHSLYTE LEEERSASAV AASQTMAMIN RLQEEKAAMQ MEALQYQRMM EEQSEYDQEA  120
LQLMNELMVK REREKQELEK ELEAYRKRLL EYEATRMLKR SKDSSTFSSE DSDGLSIGLN  180
QEEAKEDDSG MNHSTPVGAV INLEEERMAI LEQLKVLEER LVSLDLDDED AKHFEDVRLM  240
```

-continued

```
EDSYQDNIEE DSHANGFLKE MNGKHHHAKG KRLLPLFDKM SDENGDGTLN ANGVHNFDLE    300
NKKLAVEQEL DHLHQRLQAL EADREFLNNC VSSLKKGDKG MDLLQEILLH LRHLRNVELR    360
ATSFSDAAIL                                                          370

SEQ ID NO: 169           moltype = AA   length = 144
FEATURE                  Location/Qualifiers
source                   1..144
                         mol_type = protein
                         organism = synthetic construct
SEQUENCE: 169
MLWRNSTKLQ LCSSSARSRL LLICRLEHQF IVTHRKPVDL WGLKICELKR PIAAVKLNCK     60
LQVVVPCCYS LAAIVNIFSS LQSLMNFAFE LQLGVFLQNC EEDCSGDHQQ SATLSVIVRL    120
SRIADLTSPY LCGHSLQIRP ILQN                                          144

SEQ ID NO: 170           moltype = AA   length = 355
FEATURE                  Location/Qualifiers
source                   1..355
                         mol_type = protein
                         organism = synthetic construct
SEQUENCE: 170
MFDDSVSTVY SSIWTSMNSW FTPTVLFVLL NLMIGTIAFT SSLANQKPNH PPKQEQQQEE     60
QEYSQNHPQQ PSKLIRSPSI LQRIKSLNFY NNRSQEPVKD YNFDDTHNQE TTFEPQTHYI    120
FEPAPEHTTV VPESTQYIFN QSHQENAQKT QTQYDFQQTH LENLPDTQTQ YLFQHTPDQE    180
LKNMDQDFHF QQTHQENIQE KSARYIIQHI HEQKLDNTDT HFDFQQTHEE NEVEEEEEEG    240
ELKSLDEVYN QLKERHVSRS RSDTNPSAGE APIKLPTKMK KSASMKSPFA HFEEEAIVEA    300
RRPATTRERN VKTSDGDINE VDAKADDFIN KFKQQLKLQR LDSILRYKEM IGRGS         355

SEQ ID NO: 171           moltype = AA   length = 385
FEATURE                  Location/Qualifiers
source                   1..385
                         mol_type = protein
                         organism = synthetic construct
SEQUENCE: 171
MEIVAKSKKH HHYYSPFPSC FRRPLEVAAA ASARPLPPPP PPPQPPVAAN PNLATSLYQT     60
HLGLFALTWS RNLFGRSFHI HFLLNDSDGV GADYNNNTIS SPHLSSTSTP SFHLNIKPFI    120
FWKKHGSKKL DGDNKVVHIF WDLSKSKFGS GPEPISGFYV AVIVNEEMVL LVGDLNKEAY    180
AKTRARKPEK KQNLNPNPNP NLVLRREHVC GNKLYKTKAN FGGKEKEISI DCRLGEDPRL    240
YFSVDNKRVL QIKHLKWKFR GNERIEVDGV PVLVSWDVYN WLFDDDEDGY ALFMFKFEKS    300
SYEYVAADDY SLNNGVQLWS QQSCGFGFET KMMKKGVLRS SRSSSSSSLS SASSTCSSVM    360
EWASTEENEL KGPSGFSLLV YAWKS                                         385

SEQ ID NO: 172           moltype = AA   length = 196
FEATURE                  Location/Qualifiers
source                   1..196
                         mol_type = protein
                         organism = synthetic construct
SEQUENCE: 172
MWQFNKIWCQ NQRIQITYWG LLAYNAGDDM VTSTTPFELI IQSDKIPITI DFSNTTRLVN     60
DTSTSGIIPL CASFERDGKV TLTKQVSQNV CAAKKQGHFG LVIESPLMPL KNKRASNWKL    120
AIGSAIGAAL GAFLLGLLLI AIFVKVKKKA RMEELVRRAY EEEALQVSMV GHVRAPTAAG    180
TRTVPTIEHD YNPHNS                                                   196

SEQ ID NO: 173           moltype = AA   length = 170
FEATURE                  Location/Qualifiers
source                   1..170
                         mol_type = protein
                         organism = synthetic construct
SEQUENCE: 173
MDQILNKVGS YWIGKRANKE LNSVGDDINS LQSSIEGGTK WLVNKLKGKM QKPLPDLLKE     60
YDVPVGIFPR DATNYEFNEE TRKLTVYIPS VCEVGYKDSS VLRFSTEVTG FLEKGKLADI    120
EGMKTKVMMW VKVTAISSEK SKVHFTAGLK KTRSREAYEV LRDGVAIEKF              170

SEQ ID NO: 174           moltype = AA   length = 224
FEATURE                  Location/Qualifiers
source                   1..224
                         mol_type = protein
                         organism = synthetic construct
SEQUENCE: 174
MGAISFLDTI LVPLSLFITI GYHFYLWHHL KHKPSRTTIG MNILKKRSWL RELNQGNEKK     60
GTLAVQSLRN ALMETILTAT ITMIITLALA ALTNNTYNVR NLFTSAFFGS QTGKIIVLKY    120
GSATIFLLAS FLCSSLALSC LIDANFLVNA LGEFSINPMY TETVFERGFT LAFVGDRVLC    180
MAFPLLLWMF GPVPVVVSSL ALVWGLHERD FAGNLSRTMN KSCI                    224

SEQ ID NO: 175           moltype = DNA   length = 3155
FEATURE                  Location/Qualifiers
source                   1..3155
                         mol_type = other DNA
                         organism = synthetic construct
SEQUENCE: 175
```

```
aagcttccag aaggtaatta tccaagatgt agcatcaaga atccaatgtt tacgggaaaa    60
actatggaag tattatgtga gctcagcaag aagcagatca atatgcggca catatgcaac   120
ctatgttcaa aaatgaagaa tgtacagata caagatccta tactgccaga atacgaagaa   180
gaatacgtag aaattgaaaa agaagaacca ggcgaagaaa agaatcttga agacgtaagc   240
actgacgaca acaatgaaaa gaagaagata aggtcggtga ttgtgaaaga gacatagagg   300
acacatgtaa ggtggaaaat gtaagggcgg aaagtaacct tatcacaaag gaatcttatc   360
ccccactact tatcctttta tattttttccg tgtcattttt gcccttgagt tttcctatat   420
aaggaaccaa gttcggcatt tgtgaaaaca agaaaaaatt tggtgtaagc tattttcttt   480
gaagtactga ggatacaact tcagagaaat ttgtaagttt gtggatcctg caggctagcg   540
tgcactctag actcgacgaa ctgacgagct cgaatttccc cgatcgttca aacatttggc   600
aataaagttt cttaagattg aatcctgttg ccggtcttgc gatgattatc atataatttc   660
tgttgaatta cgttaagcat gtaataatta acatgtaatg catgacgtta tttatgagat   720
gggttttat gattagagtc ccgcaattat acatttaata cgcgatagaa aacaaaatat   780
agcgcgcaaa ctatgataaa ttatcgcgcg cggtgtcatc tatgttacta gatcgggaat   840
tcctcgagca actattttta tgtatgcaag agtcagcata tgtataattg attcagaatc   900
gttttgacga gttcggatgt agtagtagcc attatttaat gtacatacta atcgtgaata   960
gtgaatatga tgaaacattg tatcttattg tataaatatc cataaacaca tcatgaaaga  1020
cactttcttt cacggtctga attaattatg atacaattct aatagaaaac gaattaaatt  1080
acgttgaatt gtatgaaatc taattgaaca agccaaccac gacgacgact aacgttgcct  1140
ggattgactc ggtttaagtt aaccactaaa aaaacggagc tgtcatgtaa cacgcggatc  1200
gagcaggtca cagtcatgaa gccatcaaag caaaagaact aatccaaggg ctgagatgat  1260
taattagttt aaaaattagt taacacgagg gaaaaggctg tctgacagcc aggtcacgtt  1320
atctttacct gtggtcgaaa tgattcgtgt ctgtcgattt taattatttt tttgaaaggc  1380
cgaaaataaa gttgtaagag ataaacccgc ctatataaat tcatatattt tcctctccgc  1440
tttgaattgt ctcgttgtcc tcctcacttt catcagccgt tttgaatctc cggcgacttg  1500
acagagaaga acaaggaaga agactaagag agaaagtaag agataatcca ggagattcat  1560
tctccgtttt gaatcttcct caatctcatc ttcttccgct ctttcttttcc aaggtaatag  1620
gaactttctg gatctacttt atttgctgga tctcgatctt gtttttctcaa tttccttgag  1680
atctggaatt cgtttaattt ggatctgtga acctccacta aatcttttgg ttttactaga  1740
atcgatctaa gttgaccgat cagttagctc gattatagct accagaattt ggcttgacct  1800
tgatggagag atccatgttc atgttacctg ggaaatgatt tgtatatgtg aattgaaatc  1860
tgaactgttg aagttagatt gaatctgaac actgtcaatg ttagattgaa tctgaacact  1920
gtttaaggtt agatgaagtt tgtgtataga ttcttcgaaa cttttaggatt tgtagtgtcg  1980
tacgttgaac agaaagctat ttctgattca atcagggttt atttgactgt attgaactct  2040
ttttgtgtgt ttgcagctca taaaaggtac caaacaatga ttgaacaaga tggattgcac  2100
gcaggttctc cggccgcttg ggtggagagg ctattcggct atgactgggc acaacagaca  2160
atcggctgct ctgatgccgc cgtgttccgg ctgtcagcgc aggggcgccc ggttcttttt  2220
gtcaagaccg acctgtccgg tgccctgaat gaactgcagg acgaggcagc gcggctatcg  2280
tggctggcca cgacgggcgt tccttgcgca gctgtgctcg acgttgtcac tgaagcggga  2340
agggactggc tgctattggg cgaagtgccg gggcaggatc tcctgtcatc tcaccttgct  2400
cctgccgaga aagtatccat catggctgat gcaatgcggc ggctgcatac gcttgatccg  2460
gctacctgcc cattcgacca ccaagcgaaa catcgcatcg agcgagcacg tactcggatg  2520
gaagccggtc ttgtcgatca ggatgatctg gacgaagagc atcaggggct cgcgccagcc  2580
gaactgttcg ccaggctcaa ggcgcgcatg cccgacggcg aggatctcgt cgtgacccat  2640
ggcgatgcct gcttgccgaa tatcatggtg gaaaatggcc gcttttctgg attcatcgac  2700
tgtggccggc tgggtgtggc ggaccgctat caggacatag cgttggctac ccgtgatatt  2760
gctgaagagc ttggcggcga atgggctgac cgcttcctcg tgctttacgg tatcgccgct  2820
cccgattcgc agcgcatcgc cttctatcgc cttcttgacg agttcttttg agcgggactc  2880
tggcgatcgc cccgatcgtt caaacatttg gcaataaagt ttcttaagat tgaatcctgt  2940
tgccggtctt gcgatgatta tcatataatt tctgttgaat tacgttaagc atgtaataat  3000
taacatgtaa tgcatgacgt tatttatgag atggggtttt atgattagag tcccgcaatt  3060
atacatttaa tacgcgcgca aaaacaaaat atagcgcgca aactaggata aattatcgcg  3120
cgcggtgtca tctatgttac tagatcggga ctagt                              3155

SEQ ID NO: 176          moltype = DNA  length = 465
FEATURE                 Location/Qualifiers
source                  1..465
                        mol_type = other DNA
                        organism = synthetic construct
SEQUENCE: 176
atggctccag ctaaagctga tccgtccaaa aaatctgacc ccaaggcaca ggcagctaag    60
gttgccaagc ctgtcaagtc aggatcaacc ttgaagaaaa agtcacaaaa gataaggaca   120
aaagttacat tccaccgacc taagactttg aagaaggata gaaaccccaa gtaccctcgt   180
attagtgcac ctggaaggaa caaacttgat cagtatggga ttctaaagta tccccctcacc   240
acagagtctg caatgaagaa gattgaggac aacaacaccc ttgttttcat tgtggacatc   300
aaggctgata aaaagaagat taaggatgcc gtgaagaaga tgtatgacat tcagacaaag   360
aaagtcaata cccttaattag gcctgatggg acgaagaaag catatgtgag gttgactcct   420
gactatgatg ctttggacgt tgccaacaaa attggaatca tctaa                   465

SEQ ID NO: 177          moltype = DNA  length = 22
FEATURE                 Location/Qualifiers
source                  1..22
                        mol_type = other DNA
                        organism = synthetic construct
SEQUENCE: 177
aaagaagatt aaggatgccg tg                                              22

SEQ ID NO: 178          moltype = DNA  length = 22
FEATURE                 Location/Qualifiers
```

-continued

```
source              1..22
                    mol_type = other DNA
                    organism = synthetic construct
SEQUENCE: 178
gcatcatagt caggagtcaa cc                                            22
```

METHODS AND COMPOSITIONS FOR REGULATING ALKALOIDS IN TOBACCO

CROSS-REFERENCE TO RELATED APPLICATION

This application claims the benefit of U.S. Provisional Application No. 63/395,459, filed on Aug. 5, 2022, the contents of which are incorporated herein by reference in its entirety.

FIELD

The present disclosure relates to tobacco plants, plant parts, seeds, compositions, and methods related to modulating the expression of novel genes in tobacco to regulate alkaloid levels.

INCORPORATION OF SEQUENCE LISTING

A sequence listing conforming to the rules of WIPO Standard ST.26 is hereby incorporated by reference in its entirety. Said sequence listing has been filed as an electronic document via PatentCenter encoded as XML in UTF-8 text. The electronic document is named "P34753US01_SL.xml", and is 341,150 bytes in size (measured in MS-Windows®) and created on Jul. 26, 2023.

A listing of nucleic acid sequences and amino acid sequences is provided in Table 1.

TABLE 1

| Nucleic acid sequences and amino acid sequences | | |
| --- | --- | --- |
| SEQ ID NO | Sequence Description | Sequence Type |
| 1 | g12941 | Nucleic Acid |
| 2 | g14663 | Nucleic Acid |
| 3 | g20986 | Nucleic Acid |
| 4 | g20989a | Nucleic Acid |
| 5 | g20989b | Nucleic Acid |
| 6 | g22648 | Nucleic Acid |
| 7 | g23499 | Nucleic Acid |
| 8 | g26597 | Nucleic Acid |
| 9 | g31004 | Nucleic Acid |
| 10 | g31698 | Nucleic Acid |
| 11 | g31724 | Nucleic Acid |
| 12 | g44455 | Nucleic Acid |
| 13 | g44587 | Nucleic Acid |
| 14 | g47147 | Nucleic Acid |
| 15 | g49713 | Nucleic Acid |
| 16 | g52130 | Nucleic Acid |
| 17 | g57292 | Nucleic Acid |
| 18 | g59464 | Nucleic Acid |
| 19 | g59465 | Nucleic Acid |
| 20 | g60786 | Nucleic Acid |
| 21 | g62380 | Nucleic Acid |
| 22 | g62763 | Nucleic Acid |
| 23 | g66085 | Nucleic Acid |
| 24 | g66301 | Nucleic Acid |
| 25 | g68242 | Nucleic Acid |
| 26 | g69182 | Nucleic Acid |
| 27 | g69391 | Nucleic Acid |
| 28 | g71598 | Nucleic Acid |
| 29 | g74738 | Nucleic Acid |
| 30 | g74782 | Nucleic Acid |
| 31 | g74912 | Nucleic Acid |
| 32 | g75157 | Nucleic Acid |
| 33 | g75446 | Nucleic Acid |
| 34 | g75500 | Nucleic Acid |
| 35 | g76096 | Nucleic Acid |
| 36 | g77018 | Nucleic Acid |
| 37 | g77780 | Nucleic Acid |
| 38 | g78265 | Nucleic Acid |
| 39 | g78408 | Nucleic Acid |

TABLE 1-continued

| Nucleic acid sequences and amino acid sequences | | |
| --- | --- | --- |
| SEQ ID NO | Sequence Description | Sequence Type |
| 40 | g79607 | Nucleic Acid |
| 41 | g79774 | Nucleic Acid |
| 42 | g82124 | Nucleic Acid |
| 43 | g82252 | Nucleic Acid |
| 44 | g82744 | Nucleic Acid |
| 45 | g83936 | Nucleic Acid |
| 46 | g86315 | Nucleic Acid |
| 47 | g86407 | Nucleic Acid |
| 48 | g86563 | Nucleic Acid |
| 49 | g89013 | Nucleic Acid |
| 50 | g91123 | Nucleic Acid |
| 51 | g91334 | Nucleic Acid |
| 52 | g91336 | Nucleic Acid |
| 53 | g91411 | Nucleic Acid |
| 54 | g92376 | Nucleic Acid |
| 55 | g92662 | Nucleic Acid |
| 56 | g93191 | Nucleic Acid |
| 57 | g95317 | Nucleic Acid |
| 58 | g95400 | Nucleic Acid |
| 59 | g12941 | Nucleic Acid |
| 60 | g14663 | Nucleic Acid |
| 61 | g20986 | Nucleic Acid |
| 62 | g20989a | Nucleic Acid |
| 63 | g20989b | Nucleic Acid |
| 64 | g22648 | Nucleic Acid |
| 65 | g23499 | Nucleic Acid |
| 66 | g26597 | Nucleic Acid |
| 67 | g31004 | Nucleic Acid |
| 68 | g31698 | Nucleic Acid |
| 69 | g31724 | Nucleic Acid |
| 70 | g44455 | Nucleic Acid |
| 71 | g44587 | Nucleic Acid |
| 72 | g47147 | Nucleic Acid |
| 73 | g49713 | Nucleic Acid |
| 74 | g52130 | Nucleic Acid |
| 75 | g57292 | Nucleic Acid |
| 76 | g59464 | Nucleic Acid |
| 77 | g59465 | Nucleic Acid |
| 78 | g60786 | Nucleic Acid |
| 79 | g62380 | Nucleic Acid |
| 80 | g62763 | Nucleic Acid |
| 81 | g66085 | Nucleic Acid |
| 82 | g66301 | Nucleic Acid |
| 83 | g68242 | Nucleic Acid |
| 84 | g69182 | Nucleic Acid |
| 85 | g69391 | Nucleic Acid |
| 86 | g71598 | Nucleic Acid |
| 87 | g74738 | Nucleic Acid |
| 88 | g74782 | Nucleic Acid |
| 89 | g74912 | Nucleic Acid |
| 90 | g75157 | Nucleic Acid |
| 91 | g75446 | Nucleic Acid |
| 92 | g75500 | Nucleic Acid |
| 93 | g76096 | Nucleic Acid |
| 94 | g77018 | Nucleic Acid |
| 95 | g77780 | Nucleic Acid |
| 96 | g78265 | Nucleic Acid |
| 97 | g78408 | Nucleic Acid |
| 98 | g79607 | Nucleic Acid |
| 99 | g79774 | Nucleic Acid |
| 100 | g82124 | Nucleic Acid |
| 101 | g82252 | Nucleic Acid |
| 102 | g82744 | Nucleic Acid |
| 103 | g83936 | Nucleic Acid |
| 104 | g86315 | Nucleic Acid |
| 105 | g86407 | Nucleic Acid |
| 106 | g86563 | Nucleic Acid |
| 107 | g89013 | Nucleic Acid |
| 108 | g91123 | Nucleic Acid |
| 109 | g91334 | Nucleic Acid |
| 110 | g91336 | Nucleic Acid |
| 111 | g91411 | Nucleic Acid |
| 112 | g92376 | Nucleic Acid |
| 113 | g92662 | Nucleic Acid |
| 114 | g93191 | Nucleic Acid |
| 115 | g95317 | Nucleic Acid |

TABLE 1-continued

| Nucleic acid sequences and amino acid sequences | | |
|---|---|---|
| SEQ ID NO | Sequence Description | Sequence Type |
| 116 | g95400 | Nucleic Acid |
| 117 | g12941 | Amino Acid |
| 118 | g14663 | Amino Acid |
| 119 | g20986 | Amino Acid |
| 120 | g20989a | Amino Acid |
| 121 | g20989b | Amino Acid |
| 122 | g22648 | Amino Acid |
| 123 | g23499 | Amino Acid |
| 124 | g26597 | Amino Acid |
| 125 | g31004 | Amino Acid |
| 126 | g31698 | Amino Acid |
| 127 | g31724 | Amino Acid |
| 128 | g44455 | Amino Acid |
| 129 | g44587 | Amino Acid |
| 130 | g47147 | Amino Acid |
| 131 | g49713 | Amino Acid |
| 132 | g52130 | Amino Acid |
| 133 | g57292 | Amino Acid |
| 134 | g59464 | Amino Acid |
| 135 | g59465 | Amino Acid |
| 136 | g60786 | Amino Acid |
| 137 | g62380 | Amino Acid |
| 138 | g62763 | Amino Acid |
| 139 | g66085 | Amino Acid |
| 140 | g66301 | Amino Acid |
| 141 | g68242 | Amino Acid |
| 142 | g69182 | Amino Acid |
| 143 | g69391 | Amino Acid |
| 144 | g71598 | Amino Acid |
| 145 | g74738 | Amino Acid |
| 146 | g74782 | Amino Acid |
| 147 | g74912 | Amino Acid |
| 148 | g75157 | Amino Acid |
| 149 | g75446 | Amino Acid |
| 150 | g75500 | Amino Acid |
| 151 | g76096 | Amino Acid |
| 152 | g77018 | Amino Acid |
| 153 | g77780 | Amino Acid |
| 154 | g78265 | Amino Acid |
| 155 | g78408 | Amino Acid |
| 156 | g79607 | Amino Acid |
| 157 | g79774 | Amino Acid |
| 158 | g82124 | Amino Acid |
| 159 | g82252 | Amino Acid |
| 160 | g82744 | Amino Acid |
| 161 | g83936 | Amino Acid |
| 162 | g86315 | Amino Acid |
| 163 | g86407 | Amino Acid |
| 164 | g86563 | Amino Acid |
| 165 | g89013 | Amino Acid |
| 166 | g91123 | Amino Acid |
| 167 | g91334 | Amino Acid |
| 168 | g91336 | Amino Acid |
| 169 | g91411 | Amino Acid |
| 170 | g92376 | Amino Acid |
| 171 | g92662 | Amino Acid |
| 172 | g93191 | Amino Acid |
| 173 | g95317 | Amino Acid |
| 174 | g95400 | Amino Acid |
| 175 | Expression construct | Nucleic acid |
| 176 | Tobacco eukaryotic translation elongation factor 1 alpha (EF1α) | Nucleic acid |
| 177 | Tobacco eukaryotic translation elongation factor 1 alpha (EF1α) | Nucleic acid |
| 178 | Tobacco eukaryotic translation | Nucleic acid |

TABLE 1-continued

| Nucleic acid sequences and amino acid sequences | | |
|---|---|---|
| SEQ ID NO | Sequence Description | Sequence Type |
| | elongation factor 1 alpha (EF1α) | |

BACKGROUND

Four major alkaloids are found in tobacco: nicotine, nornicotine, anabasine, and anatabine. Nicotine is the predominant alkaloid, usually accounting for more than 90% of the total alkaloids in commercial tobacco cultivars. Nicotine biosynthesis occurs predominantly in tobacco roots. Tobacco plants then transport nicotine through the vascular bundle to leaves where nicotine is then stored in the vacuoles. Cumulative levels of nicotine and related alkaloids in tobacco leaves depend on biosynthesis and transport, both of which can be influenced by environmental conditions, phytohormones, developmental status, and gene regulatory factors.

Methods and compositions for modulating novel tobacco genes to modulate alkaloid levels in tobacco are provided herein.

SUMMARY

In one aspect, this disclosure provides a modified tobacco plant, or part thereof, comprising at least one non-natural mutation in an endogenous nucleic acid sequence, where the endogenous nucleic acid sequence encodes a polypeptide comprising an amino acid sequence at least 80% identical or similar to an amino acid sequence selected from the group consisting of SEQ ID NOs: 117-174.

In one aspect, this disclosure provides a modified tobacco plant, or part thereof, comprising a recombinant DNA construct comprising a heterologous promoter operably linked to a nucleic acid encoding at least one small RNA molecule capable of binding to and reducing the expression of an endogenous nucleic acid sequence encoding a polypeptide at least 80% identical or similar to an amino acid sequence selected from the group consisting of SEQ ID NOs: 117-174.

In one aspect, this disclosure provides a modified tobacco plant, or part thereof, comprising a recombinant DNA construct comprising a heterologous promoter operably linked to a nucleic acid sequence encoding a polypeptide comprising an amino acid sequence at least 80% identical or similar to an amino acid sequence selected from the group consisting of SEQ ID NOs: 117-174.

In one aspect, this disclosure provides a method of producing a modified tobacco plant, the method comprising: (a) inducing a non-natural mutation in at least one tobacco cell in an endogenous nucleic acid sequence encoding a polypeptide comprising an amino acid sequence at least 80% identical or similar to an amino acid sequence selected from the group consisting of SEQ ID NOs: 117-174; (b) selecting at least one tobacco cell comprising the non-natural mutation from step (a); and (c) regenerating at least one modified tobacco plant from the at least one tobacco cell selected in step (b).

In one aspect, this disclosure provides a method of producing a modified tobacco plant, the method comprising: (a) introducing a recombinant DNA construct to at least one tobacco cell, where the recombinant DNA construct comprises a heterologous promoter operably linked to a nucleic acid encoding at least one small RNA molecule capable of binding to and reducing the expression of an endogenous nucleic acid sequence encoding a polypeptide at least 80% identical or similar to an amino acid sequence selected from the group consisting of SEQ ID NOs: 117-174; (b) selecting at least one tobacco cell comprising the recombinant DNA construct; and; (c) regenerating at least one modified tobacco plant from the at least one tobacco cell selected in step (b).

In one aspect, this disclosure provides a method of producing a modified tobacco plant, the method comprising: (a) introducing a recombinant DNA construct to at least one tobacco cell, where the recombinant DNA construct comprises a heterologous promoter operably linked to a nucleic acid sequence encoding a polypeptide comprising an amino acid sequence at least 80% identical or similar to an amino acid sequence selected from the group consisting of SEQ ID NOs: 117-174; (b) selecting at least one tobacco cell comprising the recombinant DNA construct; and (c) regenerating at least one modified tobacco plant from the at least one tobacco cell selected in step (b).

In one aspect, this disclosure provides a method comprising preparing a tobacco product using cured tobacco material from a modified tobacco plant, where the modified tobacco plant comprises a non-natural mutation in an endogenous nucleic acid sequence, where the endogenous nucleic acid sequence encodes a polypeptide comprising an amino acid sequence at least 80% identical or similar to an amino acid sequence selected from the group consisting of SEQ ID NOs: 117-174.

In one aspect, this disclosure provides a method comprising preparing a tobacco product using cured tobacco material from a modified tobacco plant, where the modified tobacco plant comprises a recombinant DNA construct, and where the recombinant DNA construct comprises a heterologous promoter operably linked to a nucleic acid sequence encoding at least one small RNA molecule capable of binding to and reducing the expression of an endogenous nucleic acid sequence encoding a polypeptide at least 80% identical or similar to an amino acid sequence selected from the group consisting of SEQ ID NOs: 117-174.

In one aspect, this disclosure provides a method comprising preparing a tobacco product using cured tobacco material from a modified tobacco plant, where the modified tobacco plant comprises a recombinant DNA construct, and where the recombinant DNA construct comprises a heterologous promoter operably linked to a nucleic acid sequence encoding a polypeptide comprising an amino acid sequence at least 80% identical or similar to an amino acid sequence selected from the group consisting of SEQ ID NOs: 117-174.

In one aspect, this disclosure provides a method comprising transforming a tobacco cell with a recombinant DNA construct, where the recombinant DNA construct comprises a heterologous promoter operably linked to a nucleic acid sequence encoding at least one small RNA molecule capable of binding to and reducing the expression of an endogenous nucleic acid sequence encoding a polypeptide at least 80% identical or similar to an amino acid sequence selected from the group consisting of SEQ ID NOs: 117-174.

In one aspect, this disclosure provides a method comprising transforming a tobacco cell with a recombinant DNA construct, where the recombinant DNA construct comprises a heterologous promoter operably linked to a nucleic acid sequence encoding a polypeptide comprising an amino acid sequence at least 80% identical or similar to an amino acid sequence selected from the group consisting of SEQ ID NOs: 117-174.

In one aspect, this disclosure provides a method for producing a modified tobacco plant, the method comprising: (a) crossing at least one tobacco plant of a first tobacco variety with at least one tobacco plant of a second tobacco variety to produce at least one progeny tobacco seed, where the at least one tobacco plant of the first tobacco variety comprises a non-natural mutation in an endogenous nucleic acid sequence, where the endogenous nucleic acid sequence encodes a polypeptide comprising an amino acid sequence at least 80% identical or similar to an amino acid sequence selected from the group consisting of SEQ ID NOs: 117-174, where the non-natural mutation is not present in the endogenous nucleic acid sequence in a control tobacco plant of the first tobacco variety; and; (b) selecting for at least one progeny tobacco seed, or a plant germinated therefrom, where the at least one tobacco seed or plant germinated therefrom comprises the non-natural mutation.

In one aspect, this disclosure provides a method for producing a modified tobacco plant, the method comprising: (a) crossing at least one tobacco plant of a first tobacco variety with at least one tobacco plant of a second tobacco variety to produce at least one progeny tobacco seed, where the at least one tobacco plant of the first tobacco variety comprises a recombinant DNA construct, where the recombinant DNA construct comprises a heterologous promoter operably linked to a nucleic acid sequence encoding at least one small RNA molecule capable of binding to and reducing the expression of an endogenous nucleic acid sequence encoding a polypeptide at least 80% identical or similar to an amino acid sequence selected from the group consisting of SEQ ID NOs: 117-174, where the recombinant DNA construct is not present in the endogenous nucleic acid sequence in a control tobacco plant of the same variety; and; (b) selecting for at least one progeny tobacco seed, or a plant germinated therefrom, where the at least one tobacco seed or plant germinated therefrom comprises the recombinant DNA construct.

In one aspect, this disclosure provides a method for producing a modified tobacco plant, the method comprising: (a) crossing at least one tobacco plant of a first tobacco variety with at least one tobacco plant of a second tobacco variety to produce at least one progeny tobacco seed, where the at least one tobacco plant of the first tobacco variety comprises a recombinant DNA construct, where the recombinant DNA construct comprises a heterologous promoter operably linked to a nucleic acid sequence encoding a polypeptide comprising an amino acid sequence at least 80% identical or similar to an amino acid sequence selected from the group consisting of SEQ ID NOs: 117-174, where the recombinant DNA construct is not present in the nucleic acid sequence in a control tobacco plant of the first tobacco variety; and (b) selecting for at least one progeny tobacco seed, or a plant germinated therefrom, where the at least one tobacco seed or plant germinated therefrom comprises the recombinant DNA construct.

In one aspect, this disclosure provides a modified tobacco plant, or part thereof, comprising at least one non-natural mutation in an endogenous nucleic acid sequence that modulates the expression or functional activity of a gene, where the gene encodes a polypeptide comprising an amino acid sequence at least 80% identical or similar to an amino acid sequence selected from the group consisting of SEQ ID NOs: 117-174.

BRIEF DESCRIPTION OF THE DRAWINGS

FIG. 4 depicts relative expression of g95400 (SEQ ID NO: 58). FIG. 5 depicts relative expression of g82124 (SEQ ID NO: 42). FIG. 6 depicts relative expression of g23499 (SEQ ID NO: 7). FIG. 7 depicts relative expression of g69182 (SEQ ID NO: 26). FIG. 8 depicts relative expression of g14663 (SEQ ID NO: 2). FIG. 9 depicts relative expression of g71598 (SEQ ID NO: 28). FIG. 10 depicts relative expression of g74782 (SEQ ID NO: 30).

FIG. 11 depicts relative expression of g92662 (SEQ ID NO: 55). FIG. 12 depicts relative expression of g91334 (SEQ ID NO: 51). FIG. 13 depicts relative expression of g93191 (SEQ ID NO: 56). FIG. 14 depicts relative expression of g74738 (SEQ ID NO: 29). FIG. 15 depicts relative expression of g66301 (SEQ ID NO: 24). FIG. 16 depicts relative expression of g86407 (SEQ ID NO: 47).

Figure 1:
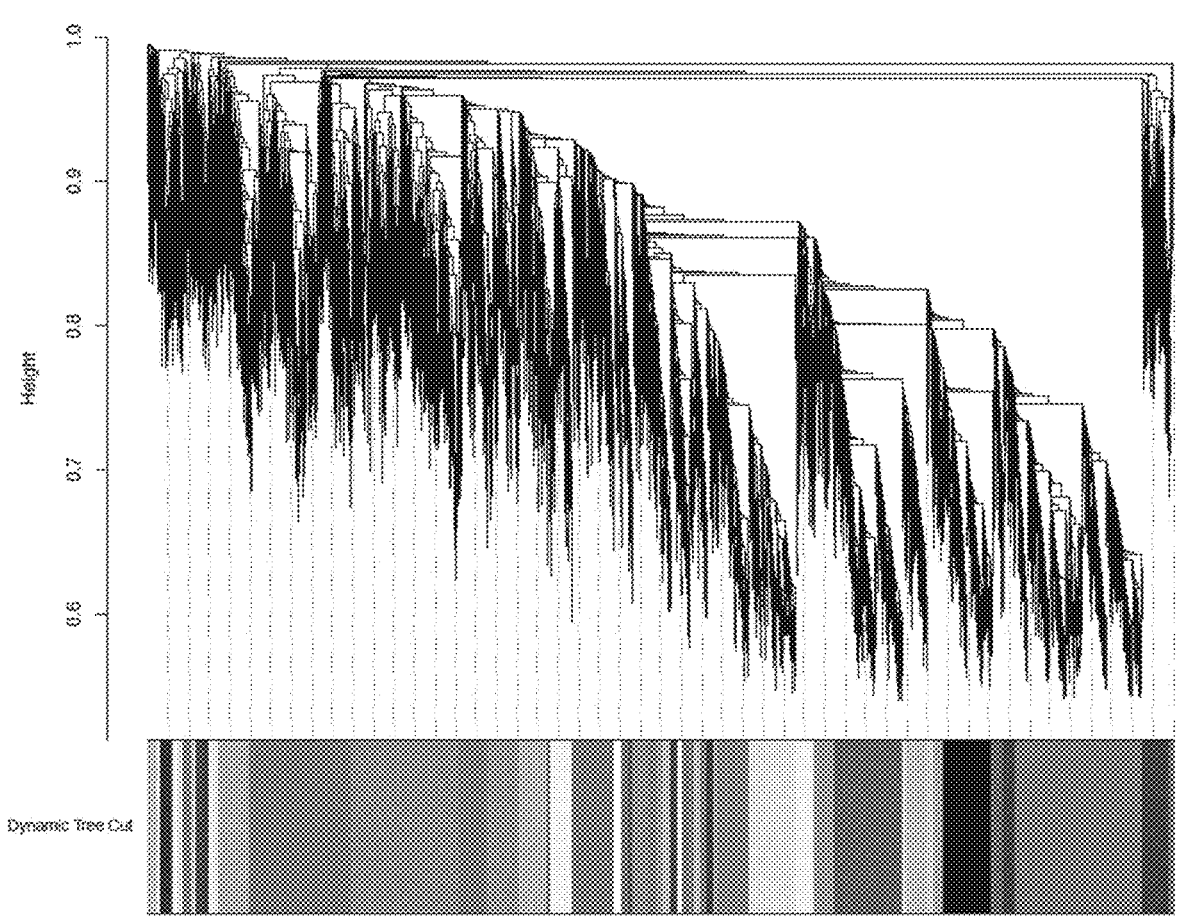
FIG. 1 depicts clustering of genes based on dissimilarity of topological overlap measurement. The bars at the bottom of the figure indicate different network modules.

For FIGS. 17, 18, 22, 25, 26, 29, 30, 33, 34, 37, 38, 41, 42, 45, 46, 49, 50, 53, 54, 57, and 58, error bars represent the range of observed data.

DETAILED DESCRIPTION

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York).

Any references cited herein, including, e.g., all patents, published patent applications, and non-patent publications, are incorporated herein by reference in their entirety.

When a grouping of alternatives is presented, any and all combinations of the members that make up that grouping of alternatives is specifically envisioned. For example, if an item is selected from a group consisting of A, B, C, and D, the inventors specifically envision each alternative individually (e.g., A alone, B alone, etc.), as well as combinations such as A, B, and D; A and C; B and C; etc. The term "and/or" when used in a list of two or more items means any one of the listed items by itself or in combination with any one or more of the other listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

When a range of numbers is provided herein, the range is understood to inclusive of the edges of the range as well as any number between the defined edges of the range. For example, "between 1 and 10" includes any number between 1 and 10, as well as the number 1 and the number 10.

When the term "about" is used in reference to a number, it is understood to mean plus or minus 10%. For example, "about 100" would include from 90 to 110.

As used herein, the singular form "a," "an," and "the" include plural references unless the context clearly dictates otherwise. For example, the term "a compound" or "at least one compound" may include a plurality of compounds, including mixtures thereof.

Any tobacco plant, or part thereof, provided herein is specifically envisioned for use with any method provided herein. Similarly, any modified tobacco plant, or part thereof, is specifically envisioned for use with any method provided herein. Any nucleic acid sequence, amino acid sequence, or other composition provided herein is specifically envisioned for use with any method provided herein.

Tobacco plants typically produce alkaloids at levels between 2% and 4% of their total dry weight. Nicotine is a major alkaloid compound in tobacco plants, and it often accounts for approximately 95% of the total alkaloid content of the plants. The remaining pool of alkaloids primarily comprises other structurally-related alkaloids such as anabasine, anatabine, and nornicotine.

Nicotine is synthesized in roots via one of two primary metabolic pathways: the pyridine nicotine biosynthesis pathway and the pyrrolidine nicotine biosynthesis pathway.

In the pyridine nicotine biosynthesis pathway, quinolinate synthetase (QS) produces quinolinic acid, and the conversion of quinolinic acid to nicotinic acid mono-nucleotide (NAMN) is catalyzed by quinolinate phosphoribosyl-transferase (QPT). NAMN can be converted into nicotinic acid either directly by a NAMN glycohydrolase, or through a multi-step process involving the synthesis and degradation of nicotine adenine dinucleotide (NAD). Further reduction of nicotinic acid subsequently forms 3,6-dihydronicotinic acid.

In the pyrrolidine nicotine biosynthesis pathway, the decarboxylation of amino acids (e.g., arginine) is required to form putrescine, and methylation of putrescine to N-methylputrescine is catalyzed by N-methyltransferase (PMT). N-methylputrescine is then oxidized by a diamine oxidase and cyclized spontaneously to the N-methyl-$\Delta^1$-pyrrolinium cation. This N-methyl-$\Delta^1$-pyrrolinium cation is then coupled with 3,6-dihydronicotinic acid or another nicotinic acid intermediate to form nicotine. However, the exact substrate and enzymes involved in these reactions remains unknown.

Here, novel genes involved in the biosynthesis of nicotine or other alkaloids in tobacco are provided.

In an aspect, this disclosure provides a modified tobacco plant, or part thereof, comprising at least one non-natural mutation in an endogenous nucleic acid sequence, where the endogenous nucleic acid sequence encodes a polypeptide comprising an amino acid sequence at least 80% identical or similar to an amino acid sequence selected from the group consisting of SEQ ID NOs: 117-174. In another aspect, this disclosure provides a modified tobacco plant, or part thereof, comprising at least one non-natural mutation in an endogenous nucleic acid sequence at least 80% identical to a nucleotide sequence selected from the group consisting of SEQ ID NOs: 1-58. In another aspect, this disclosure provides a modified tobacco plant, or part thereof, comprising at least one non-natural mutation in an endogenous nucleic acid sequence at least 80% identical to a nucleotide sequence selected from the group consisting of SEQ ID NOs: 59-116. In another aspect, this disclosure provides a modified tobacco plant, or part thereof, comprising at least one non-natural mutation in an endogenous nucleic acid sequence selected from the group consisting of SEQ ID NOs: 1-116.

In an aspect, this disclosure provides a modified tobacco plant, or part thereof, comprising a recombinant DNA construct comprising a heterologous promoter operably linked to a nucleic acid encoding at least one small RNA molecule capable of binding to and reducing the expression of an endogenous nucleic acid sequence encoding a polypeptide at least 80% identical or similar to an amino acid sequence selected from the group consisting of SEQ ID NOs: 117-174. In another aspect, this disclosure provides a modified tobacco plant, or part thereof, comprising a recombinant DNA construct comprising a heterologous promoter operably linked to a nucleic acid encoding at least one small RNA molecule capable of binding to and reducing the expression of an endogenous nucleic acid sequence at least 80% identical to a nucleic acid sequence selected from the group consisting of SEQ ID NOs: 1-58. In yet another aspect, this disclosure provides a modified tobacco plant, or part thereof, comprising a recombinant DNA construct comprising a heterologous promoter operably linked to a nucleic acid encoding at least one small RNA molecule capable of binding to and reducing the expression of an endogenous nucleic acid sequence at least 80% identical to a nucleic acid sequence selected from the group consisting of SEQ ID NOs: 59-116.

In an aspect, this disclosure provides a modified tobacco plant, or part thereof, comprising a recombinant DNA construct comprising a heterologous promoter operably linked to a nucleic acid sequence encoding a polypeptide comprising an amino acid sequence at least 80% identical or similar to an amino acid sequence selected from the group consisting of SEQ ID NOs: 117-174. In another aspect, this disclosure provides a modified tobacco plant, or part thereof, comprising a recombinant DNA construct comprising a heterologous promoter operably linked to a nucleic acid sequence at least 80% identical to a nucleic acid sequence selected from the group consisting of SEQ ID NOs: 1-58. In another aspect, this disclosure provides a modified tobacco plant, or part thereof, comprising a recombinant DNA construct comprising a heterologous promoter operably linked to a nucleic acid sequence at least 80% identical to a nucleic acid sequence selected from the group consisting of SEQ ID NOs: 59-116.

In an aspect, this disclosure provides a modified tobacco plant, or part thereof, comprising at least one non-natural mutation in an endogenous nucleic acid sequence that modulates the expression or activity of a gene, where the gene encodes a polypeptide comprising an amino acid sequence at least 80% identical or similar to an amino acid sequence selected from the group consisting of SEQ ID NOs: 117-174. In another aspect, this disclosure provides a modified tobacco plant, or part thereof, comprising at least one non-natural mutation in an endogenous nucleic acid sequence that modulates the expression or activity of a gene, where the gene encodes an RNA sequence at least 80% identical or complementary to a nucleic acid sequence selected from the group consisting of SEQ ID NOs: 59-116. In an aspect, an endogenous nucleic acid sequence encodes a transcription factor that is capable of biding to a nucleic acid sequence encoding the gene. As used herein, a "transcription factor" refers to a protein that controls the rate of transcription of a gene from DNA to messenger RNA by binding to a specific DNA sequence of the gene. Without being limited by any scientific theory, if a transcription factor is bound to a gene, it turns on, or enhances, transcription of the gene as compared to transcription in the absence of the transcription factor. In another aspect, an endogenous nucleic acid sequence encodes a repressor that is capable of binding to a nucleic acid sequence encoding the gene. As used herein, a "repressor" refers to a protein that inhibits the transcription of a gene from DNA to messenger RNA by binding to a specific DNA sequence of the gene. Without being limited by any scientific theory, if a repressor is bound to a gene, it turns off, or reduces, transcription of the gene as compared to transcription in the absence of the repressor. In a further aspect, an endogenous nucleic acid sequence encodes a protein that generates a precursor required for the polypeptide encoded by the gene to function. As a non-limiting example of a precursor, quinolate synthase produces quinolinic acid, which is a precursor required for quinolinate phosphoribosyltransferase to function. In an aspect, a gene comprises a nucleic acid sequence at least 80% identical or similar to SEQ ID NOs: 1-58.

In an aspect, this disclosure provides a modified tobacco plant, or part thereof, comprising (a) a genetic modification in a gene; or (b) a genetic modification targeting the gene; where the genetic modification downregulates the expression or activity of the gene, where the gene encodes an amino acid sequence having at least 80% identity or similarity to an amino acid sequence selected from the group consisting of SEQ ID NOs: 117-174. In another aspect, this disclosure provides a modified tobacco plant, or part thereof, comprising (a) a genetic modification in a gene; or (b) a genetic modification targeting the gene; where the genetic modification downregulates the expression or activity of the gene, where the gene encodes a nucleic acid sequence having at least 80% identity to a polynucleotide sequence selected from the group consisting of SEQ ID NOs: 1-58. In another aspect, this disclosure provides a modified tobacco plant, or part thereof, comprising (a) a genetic modification in a gene; or (b) a genetic modification targeting the gene; where the genetic modification downregulates the expression or activity of the gene, where the gene encodes a nucleic acid sequence having at least 80% identity to a polynucleotide sequence selected from the group consisting of SEQ ID NOs: 59-116. In another aspect, this disclosure provides a modified tobacco plant, or part thereof, comprising (a) a genetic modification in a gene; or (b) a genetic modification targeting the gene; where the genetic modification downregulates the expression or activity of the gene, where the gene encodes a nucleic acid sequence having at least 80% identity to a polynucleotide sequence selected from the group consisting of SEQ ID NOs: 1-116.

As used herein, a "genetic modification" refers to a change in the genetic makeup of a plant or plant genome. A genetic modification can be introduced by methods including, but not limited to, mutagenesis, genome editing, genetic transformation, or a combination thereof. A genetic modification includes, for example, a mutation (e.g., a non-natural mutation) in a gene or a transgene targeting a gene (e.g., an arginine decarboxylase (ADC) transgene targets an ADC gene). As used here, "targeting" refers to either directly upregulating or directly downregulating the expression or activity of a gene. As used here, "directly", in the context of a transgene impacting the expression or activity of a gene, refers to the impact being exerted over the gene via a physical contact or chemical interaction between the gene (e.g., a promoter region or a UTR region) or a product encoded therein (e.g., a mRNA molecule or a polypeptide) and a product encoded by the transgene (e.g., a small RNA molecule or a protein such as a transcription factor or a dominant negative polypeptide variant). In an aspect, a transgene impacts the expression or activity of a target gene without involving a transcription factor (e.g., the transgene does not encode a transcription factor and/or does not suppress the expression or activity of a transcription factor that in turn regulates the target gene).

Mutations

As used herein, "modified," in the context of a plant, refers to a plant comprising a genetic alteration introduced for certain purposes and beyond natural polymorphisms. Without being limiting, a modified plant can comprise a non-natural mutation or a recombinant DNA construct. In an aspect, a modified tobacco plant comprises a non-natural mutation. In another aspect, a modified tobacco plant comprises a recombinant DNA construct. In another aspect, a modified tobacco plant comprises a genetic modification.

As used herein, a "mutation" refers to an inheritable genetic modification introduced into a gene to alter the expression or activity of a product encoded by a reference sequence of the gene. A mutation in a certain gene, such as, for example, an arginine decarboxylase (ADC) is referred to as an ADC mutant. Such a modification can be in any sequence region of a gene, for example, in a promoter, 5'untranslated region (UTR), exon, intron, 3'-UTR, or terminator region. In an aspect, a mutation reduces, inhibits, or eliminates the expression or activity of a gene product. In another aspect, a mutation increases, elevates, strengthens, or augments the expression or activity of a gene product.

In an aspect, mutations are not natural polymorphisms that exist in a particular tobacco variety or cultivar. In an aspect, a mutation is a "non-natural" or "non-naturally occurring" mutation. As used herein, a "non-natural" or "non-naturally occurring" mutation refers to a non-spontaneous mutation generated via human intervention, and does not correspond to a spontaneous mutation generated without human intervention. Non-limiting examples of human intervention include mutagenesis (e.g., chemical mutagenesis, ionizing radiation mutagenesis) and targeted genetic modifications (e.g., CRISPR-based methods, TALEN-based methods, zinc finger-based methods). Non-natural mutations and non-naturally occurring mutations do not include spontaneous mutations that arise naturally (e.g., via aberrant DNA replication in a germ line of a plant).

In an aspect, mutations are not natural polymorphisms that exist in a particular tobacco variety or cultivar. It will be appreciated that, when identifying a mutation, the reference DNA sequence should be from the same variety of tobacco. For example, if a modified tobacco plant comprising a mutation is from the variety TN90, then the endogenous reference sequence must be the endogenous TN90 sequence, not a homologous sequence from a different tobacco variety (e.g., K326). Similarly, if a modified tobacco cell comprising a mutation is a TN90 cell, then the endogenous reference sequence must be the endogenous TN90 sequence, not a homologous sequence from a tobacco cell from a different tobacco variety (e.g., K326).

In an aspect, a tobacco plant, or part thereof, is homozygous for at least one non-natural mutation. In another aspect, a tobacco plant, or part thereof, is heterozygous for at least one non-natural mutation. In another aspect, a tobacco plant, or part thereof, is homozygous for an introduced recombinant DNA construct. In another aspect, a tobacco plant, or part thereof, is hemizygous for an introduced recombinant DNA construction. In a further aspect, a tobacco plant, or part thereof, is heterozygous for an introduced recombinant DNA construct.

In an aspect, a mutation provided herein creates a dominant allele of the mutated locus. Dominant alleles are alleles that mask the contribution of a second allele at the same locus. A dominant allele can be a "dominant negative allele" or a "dominant positive allele." Dominant negative alleles, or antimorphs, are alleles that act in opposition to normal allelic function. A dominant negative allele typically does not function normally and either directly inhibits the activity of a wild-type protein (e.g., through dimerization) or inhibits the activity of a second protein that is required for the normal function of the wild-type protein (e.g., an activator or a downstream component of a pathway). For example, a dominant negative allele abrogates or reduces the normal function of an allele in a heterozygous or homozygous state. Dominant positive alleles can increase normal gene function (e.g., a hypermorph) or provide new functions for a gene (e.g., a neomorph). A semi-dominant allele occurs when penetrance of a linked phenotype in individuals heterozygous for the allele is less than that which is observed in individuals homozygous for the allele.

In an aspect, a mutation provided herein creates a dominant negative allele of the mutated locus. In another aspect, a mutation provided herein creates a dominant positive allele of a mutated locus.

As used herein, "inducing" a mutation refers to generating a mutation in a polynucleotide sequence via human intervention. Many suitable methods for inducing mutations in tobacco are known in the art. Non-limiting examples of such methods include use of chemical mutagens, use of irradiation, use of nucleases, use of transposons, and use of *Agrobacterium*. In an aspect, inducing a mutation comprises the use of an agent selected from the group consisting of a chemical mutagen, irradiation, a transposon, *Agrobacterium*, and a nuclease.

In an aspect, inducing a mutation comprises the use of a chemical mutagen. In an aspect, a chemical mutagen comprises ethyl methanesulfonate (EMS).

In another aspect, inducing a mutation comprises the use of irradiation. In an aspect, irradiation comprises gamma rays, X-rays, ionizing radiation, or fast neutrons.

In an aspect, inducing a mutation comprises the use of a transposon. In another aspect, inducing a mutation comprises the use of *Agrobacterium*.

In a further aspect, inducing a mutation comprises the use of a nuclease. In an aspect, a nuclease is selected from the group consisting of a meganuclease, a zinc-finger nuclease, a transcription activator-like effector nuclease, a CRISPR/Cas9 nuclease, a CRISPR/Cpf1 nuclease, a CRISPR/CasX nuclease, a CRISPR/CasY nuclease, and a Csm1 nuclease. In an aspect, inducing a mutation comprises the use of a CRISPR/Cas9 nuclease. In an aspect, inducing a mutation comprises the use of a CRISPR/Cpf1 nuclease. In an aspect, inducing a mutation comprises the use of a CRISPR/CasX nuclease. In an aspect, inducing a mutation comprises the use of a CRISPR/CasY nuclease. In an aspect, inducing a mutation comprises the use of a Csm1 nuclease.

Several types of mutations are known in the art. In an aspect, a mutation comprises an insertion. An "insertion" refers to the addition of one or more nucleotides or amino acids to a given polynucleotide or amino acid sequence, respectively, as compared to an endogenous reference polynucleotide or amino acid sequence. In another aspect, a mutation comprises a deletion. A "deletion" refers to the removal of one or more nucleotides or amino acids to a given polynucleotide or amino acid sequence, respectively, as compared to an endogenous reference polynucleotide or amino acid sequence. In another aspect, a mutation comprises a substitution. A "substitution" refers to the replacement of one or more nucleotides or amino acids to a given polynucleotide or amino acid sequence, respectively, as compared to an endogenous reference polynucleotide or amino acid sequence. In another aspect, a mutation comprises an inversion. An "inversion" refers to when a segment of a polynucleotide or amino acid sequence is reversed end-to-end. A "duplication" refers to when a segment of a polynucleotide or amino acid sequence is repeated. The repeated segment can immediately follow the original segment, or it can be separated from the original segment by one or more nucleotides or amino acids. In an aspect, a mutation provided herein comprises a mutation selected from the group consisting of an insertion, a deletion, a substitution, a duplication, and an inversion.

In an aspect, a non-natural mutation comprises a mutation selected from the group consisting of a substitution, a deletion, an insertion, a duplication, and an inversion of one or more nucleotides relative to an endogenous nucleic acid sequence selected from the group consisting of SEQ ID NOs: 1-116.

In an aspect, a non-natural mutation comprises a mutation selected from the group consisting of a substitution, a deletion, an insertion, a duplication, and an inversion of one or more nucleotides relative to an endogenous nucleic acid sequence encoding an amino acid sequence selected from the group consisting of SEQ ID NOs: 117-174.

In an aspect, a non-natural mutation comprises one or more mutation types selected from the group consisting of a nonsense mutation, a missense mutation, a frameshift mutation, a splice-site mutation, and any combinations thereof. As used herein, a "nonsense mutation" refers to a mutation to a nucleic acid sequence that introduces a premature stop codon to an amino acid sequence by the nucleic acid sequence. As used herein, a "missense mutation" refers to a mutation to a nucleic acid sequence that causes a substitution within the amino acid sequence encoded by the nucleic acid sequence. As used herein, a "frameshift mutation" refers to an insertion or deletion to a nucleic acid sequence that shifts the frame for translating the nucleic acid sequence to an amino acid sequence. A "splice-site mutation" refers to a mutation in a nucleic acid sequence that causes an intron to be retained for protein translation, or, alternatively, for an exon to be excluded from protein translation. Splice-site mutations can cause nonsense, missense, or frameshift mutations.

Mutations in coding regions of genes (e.g., exonic mutations) can result in a truncated protein or polypeptide when a mutated messenger RNA (mRNA) is translated into a protein or polypeptide. In an aspect, this disclosure provides a mutation that results in the truncation of a protein or polypeptide. As used herein, a "truncated" protein or polypeptide comprises at least one fewer amino acid as compared to an endogenous control protein or polypeptide. For example, if endogenous Protein A comprises 100 amino acids, a truncated version of Protein A can comprise between 1 and 99 amino acids. In an aspect, a non-natural mutation results in a truncation of a polypeptide.

Without being limited by any scientific theory, one way to cause a protein or polypeptide truncation is by the introduction of a premature stop codon in an mRNA transcript of an endogenous gene. In an aspect, this disclosure provides a mutation that results in a premature stop codon in an mRNA transcript of an endogenous gene. As used herein, a "stop codon" refers to a nucleotide triplet within an mRNA transcript that signals a termination of protein translation. A "premature stop codon" refers to a stop codon positioned earlier (e.g., on the 5'-side) than the normal stop codon position in an endogenous mRNA transcript. Without being limiting, several stop codons are known in the art, including "UAG," "UAA," "UGA," "TAG," "TAA," and "TGA."

In an aspect, a mutation provided herein comprises a null mutation. As used herein, a "null mutation" refers to a mutation that confers a complete loss-of-function for a protein encoded by a gene comprising the mutation, or, alternatively, a mutation that confers a complete loss-of-function for a small RNA encoded by a genomic locus. A null mutation can cause lack of mRNA transcript production, a lack of small RNA transcript production, a lack of protein function, or a combination thereof.

A mutation provided herein can be positioned in any part of an endogenous gene. In an aspect, a mutation provided herein is positioned within an exon of an endogenous gene. In another aspect, a mutation provided herein is positioned within an intron of an endogenous gene. In a further aspect, a mutation provided herein is positioned within a 5'-UTR of an endogenous gene. In still another aspect, a mutation provided herein is positioned within a 3'-UTR of an endogenous gene. In yet another aspect, a mutation provided herein is positioned within a promoter of an endogenous gene. In yet another aspect, a mutation provided herein is positioned within a terminator of an endogenous gene. In an aspect, a non-natural mutation provided herein comprises a mutation in a sequence region selected from the group consisting of a promoter, a 5'-UTR, a 3'-UTR, an exon, an intron, and a terminator.

The screening and selection of mutagenized tobacco plants can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454) enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.
Nucleic Acids and Amino Acids As used herein, an "endogenous" nucleic acid sequence refers to a nucleic acid sequence that occurs naturally in the genome of an organism. Endogenous nucleic acid sequences do not include heterologous sequences inserted into a genome via deliberate human intervention. Similarly, endogenous amino acid sequences are sequences that exist naturally via translation of an endogenous nucleic acid molecule. In an aspect, a nucleic acid sequence provided herein is an endogenous nucleic acid sequence.

As used herein, "heterologous" refers to a sequence (nucleic acid or amino acid) that originates from a foreign species, or, if from the same species, is substantially modified from its native form in composition and/or genomic locus by deliberate human intervention. The term also is applicable to nucleic acid constructs, also referred to herein as "polynucleotide constructs" or "nucleotide constructs." In this manner, a "heterologous" nucleic acid construct is intended to mean a construct that originates from a foreign species, or, if from the same species, is substantially modified from its native form in composition and/or genomic locus by deliberate human intervention. Heterologous nucleic acid constructs include, but are not limited to, recombinant nucleotide constructs that have been introduced into a plant or plant part thereof, for example, via transformation methods or subsequent breeding of a transgenic plant with another plant of interest.

As used herein, a "gene" refers to a polynucleotide that can produce a functional unit (e.g., without being limiting, for example, a protein, or a small RNA molecule). A gene can comprise a promoter, an enhancer sequence, a leader sequence, a transcriptional start site, a transcriptional stop site, a polyadenylation site, one or more exons, one or more introns, a 5'-UTR, a 3'-UTR, or any combination thereof. A "gene sequence" can comprise a polynucleotide sequence encoding a promoter, an enhancer sequence, a leader sequence, a transcriptional start site, a transcriptional stop site, a polyadenylation site, one or more exons, one or more introns, a 5'-UTR, a 3'-UTR, or any combination thereof. In one aspect, a gene encodes a small RNA molecule or a precursor thereof. In another aspect, a gene encodes a protein.

The terms "percent identity" or "percent identical" as used herein in reference to two or more nucleotide or amino acid sequences is calculated by (i) comparing two optimally aligned sequences (nucleotide or amino acid) over a window of comparison (the "alignable" region or regions), (ii) determining the number of positions at which the identical nucleic acid base (for nucleotide sequences) or amino acid residue (for proteins and polypeptides) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present application, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

When percentage of sequence identity is used in reference to amino acids it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity can be adjusted upwards to correct for the conservative nature of the substitution. Sequences that differ by such conservative substitutions are said to have "sequence similarity" or "similarity."

For optimal alignment of sequences to calculate their percent identity, various pair-wise or multiple sequence alignment algorithms and programs are known in the art, such as ClustalW or Basic Local Alignment Search Tool® (BLAST™), etc., that can be used to compare the sequence identity or similarity between two or more nucleotide or amino acid sequences. Although other alignment and comparison methods are known in the art, the alignment and percent identity between two sequences (including the percent identity ranges described above) can be as determined by the ClustalW algorithm, see, e.g., Chenna et al., "Multiple sequence alignment with the Clustal series of programs," *Nucleic Acids Research* 31: 3497-3500 (2003); Thompson et al., "Clustal W: Improving the sensitivity of progressive multiple sequence alignment through sequence weighting, position-specific gap penalties and weight matrix choice," *Nucleic Acids Research* 22: 4673-4680 (1994); Larkin M A et al., "Clustal W and Clustal X version 2.0," *Bioinformatics* 23: 2947-48 (2007); and Altschul et al. "Basic local alignment search tool." *J. Mol. Biol.* 215:403-410 (1990), the entire contents and disclosures of which are incorporated herein by reference.

The terms "percent complementarity" or "percent complementary" as used herein in reference to two nucleotide sequences is similar to the concept of percent identity but refers to the percentage of nucleotides of a query sequence that optimally base-pair or hybridize to nucleotides a subject sequence when the query and subject sequences are linearly arranged and optimally base paired without secondary folding structures, such as loops, stems or hairpins. Such a percent complementarity can be between two DNA strands, two RNA strands, or a DNA strand and a RNA strand. The "percent complementarity" can be calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences can be determined based on the known pairings of nucleotide bases, such as G-C, A-T, and A-U, through hydrogen binding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present application, when two sequences (query and subject) are optimally base-paired (with allowance for mismatches or non-base-paired nucleotides), the "percent complementarity" for the query sequence is equal to the number of base-paired positions between the two sequences divided by the total number of positions in the query sequence over its length, which is then multiplied by 100%.

The use of the term "polynucleotide" or "nucleic acid molecule" is not intended to limit the present disclosure to polynucleotides comprising deoxyribonucleic acid (DNA). For example, ribonucleic acid (RNA) molecules are also envisioned. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like. In an aspect, a nucleic acid molecule provided herein is a DNA molecule. In another aspect, a nucleic acid molecule provided herein is an RNA molecule. In an aspect, a nucleic acid molecule provided herein is single-stranded. In another aspect, a nucleic acid molecule provided herein is double-stranded. A nucleic acid molecule can encode a polypeptide or a small RNA.

As used herein, a "recombinant nucleic acid" refers to a nucleic acid molecule formed by laboratory methods of genetic recombination, such as, without being limiting, molecular cloning. Similarly, a "recombinant DNA construct" refers to a DNA molecule formed by laboratory methods of genetic recombination.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In one aspect, this disclosure provides methods of detecting recombinant nucleic acids and polypeptides in plant cells. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, NY).

In an aspect, a nucleic acid sequence provided herein is at least 70% identical or complementary to a sequence selected from the group consisting of SEQ ID NOs: 1-116. In another aspect, a nucleic acid sequence provided herein is at least 75% identical or complementary to a sequence selected from the group consisting of SEQ ID NOs: 1-116. In another aspect, a nucleic acid sequence provided herein is at least 80% identical or complementary to a sequence selected from the group consisting of SEQ ID NOs: 1-116. In another aspect, a nucleic acid sequence provided herein is at least 85% identical or complementary to a sequence selected from the group consisting of SEQ ID NOs: 1-116. In another aspect, a nucleic acid sequence provided herein is at least 88% identical or complementary to a sequence selected from the group consisting of SEQ ID NOs: 1-116. In another aspect, a nucleic acid sequence provided herein is at least 90% identical or complementary to a sequence selected from the group consisting of SEQ ID NOs: 1-116. In another aspect, a nucleic acid sequence provided herein is at least 91% identical or complementary to a sequence selected from the group consisting of SEQ ID NOs: 1-116. In another aspect, a nucleic acid sequence provided herein is at least 92% identical or complementary to a sequence selected from the group consisting of SEQ ID NOs: 1-116. In another aspect, a nucleic acid sequence provided herein is at least 93% identical or complementary to a sequence selected from the group consisting of SEQ ID NOs: 1-116. In another aspect, a nucleic acid sequence provided herein is at least 94% identical or complementary to a sequence selected from the group consisting of SEQ ID NOs: 1-116. In another aspect, a nucleic acid sequence provided herein is at least 95% identical or complementary to a sequence selected from the group consisting of SEQ ID NOs: 1-116. In another aspect, a nucleic acid sequence provided herein is at least 96% identical or complementary to a sequence selected from the group consisting of SEQ ID NOs: 1-116. In another aspect, a nucleic acid sequence provided herein is at least 97% identical or complementary to a sequence selected from the group consisting of SEQ ID NOs: 1-116. In another aspect, a nucleic acid sequence provided herein is at least 98% identical or complementary to a sequence selected from the group consisting of SEQ ID NOs: 1-116. In another aspect, a nucleic acid sequence provided herein is at least 99% identical or complementary to a sequence selected from the group consisting of SEQ ID NOs: 1-116. In another aspect, a nucleic acid sequence provided herein is 100% identical or complementary to a sequence selected from the group consisting of SEQ ID NOs: 1-116.

In an aspect, an endogenous nucleic acid sequence provided herein is at least 70% identical or complementary to a sequence selected from the group consisting of SEQ ID NOs: 1-116. In another aspect, an endogenous nucleic acid sequence provided herein is at least 75% identical or complementary to a sequence selected from the group consisting of SEQ ID NOs: 1-116. In another aspect, an endogenous nucleic acid sequence provided herein is at least 80% identical or complementary to a sequence selected from the group consisting of SEQ ID NOs: 1-116. In another aspect, an endogenous nucleic acid sequence provided herein is at least 85% identical or complementary to a sequence selected from the group consisting of SEQ ID NOs: 1-116. In another aspect, an endogenous nucleic acid sequence provided herein is at least 88% identical or complementary to a sequence selected from the group consisting of SEQ ID NOs: 1-116. In another aspect, an endogenous nucleic acid sequence provided herein is at least 90% identical or complementary to a sequence selected from the group consisting of SEQ ID NOs: 1-116. In another aspect, an endogenous nucleic acid sequence provided herein is at least 91% identical or complementary to a sequence selected from the group consisting of SEQ ID NOs: 1-116. In another aspect, an endogenous nucleic acid sequence provided herein is at least 92% identical or complementary to a sequence selected from the group consisting of SEQ ID NOs: 1-116. In another aspect, an endogenous nucleic acid sequence provided herein is at least 93% identical or complementary to a sequence selected from the group consisting of SEQ ID NOs: 1-116. In another aspect, an endogenous nucleic acid sequence provided herein is at least 94% identical or complementary to a sequence selected from the group consisting of SEQ ID NOs: 1-116. In another aspect, an endogenous nucleic acid sequence provided herein is at least 95% identical or complementary to a sequence selected from the group consisting of SEQ ID NOs: 1-116. In another aspect, an endogenous nucleic acid sequence provided herein is at least 96% identical or complementary to a sequence selected from the group consisting of SEQ ID NOs: 1-116. In another aspect, an endogenous nucleic acid sequence provided herein is at least 97% identical or complementary to a sequence selected from the group consisting of SEQ ID NOs: 1-116. In another aspect, an endogenous nucleic acid sequence provided herein is at least 98% identical or complementary to a sequence selected from the group consisting of SEQ ID NOs: 1-116. In another aspect, an endogenous nucleic acid sequence provided herein is at least 99% identical or complementary to a sequence selected from the group consisting of SEQ ID NOs: 1-116. In another aspect, an endogenous nucleic acid sequence provided herein is 100% identical or complementary to a sequence selected from the group consisting of SEQ ID NOs: 1-116.

As used herein, the term "polypeptide" refers to a chain of at least two covalently linked amino acids. Polypeptides can be encoded by polynucleotides provided herein. Proteins provided herein can be encoded by nucleic acid molecules provided herein. Proteins can comprise polypeptides provided herein. As used herein, a "protein" refers to a chain of amino acid residues that is capable of providing structure or enzymatic activity to a cell.

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

In an aspect, an amino acid sequence provided herein is at least 70% identical or similar to an amino acid sequence selected from the group consisting of SEQ ID NOs: 117-174. In another aspect, an amino acid sequence provided herein is at least 75% identical or similar to an amino acid sequence selected from the group consisting of SEQ ID NOs: 117-174. In another aspect, an amino acid sequence provided herein is at least 80% identical or similar to an amino acid sequence selected from the group consisting of SEQ ID NOs: 117-174. In another aspect, an amino acid sequence provided herein is at least 85% identical or similar to an amino acid sequence selected from the group consisting of SEQ ID NOs: 117-174. In another aspect, an amino acid sequence provided herein is at least 88% identical or similar to an amino acid sequence selected from the group consisting of SEQ ID NOs: 117-174. In another aspect, an amino acid sequence provided herein is at least 90% identical or similar to an amino acid sequence selected from the group consisting of SEQ ID NOs: 117-174. In another aspect, an amino acid sequence provided herein is at least 91% identical or similar to an amino acid sequence selected from the group consisting of SEQ ID NOs: 117-174. In another aspect, an amino acid sequence provided herein is at least 92% identical or similar to an amino acid sequence selected from the group consisting of SEQ ID NOs: 117-174. In another aspect, an amino acid sequence provided herein is at least 93% identical or similar to an amino acid sequence selected from the group consisting of SEQ ID NOs: 117-174. In another aspect, an amino acid sequence provided herein is at least 94% identical or similar to an amino acid sequence selected from the group consisting of SEQ ID NOs: 117-174. In another aspect, an amino acid sequence provided herein is at least 95% identical or similar to an amino acid sequence selected from the group consisting of SEQ ID NOs: 117-174. In another aspect, an amino acid sequence provided herein is at least 96% identical or similar to an amino acid sequence selected from the group consisting of SEQ ID NOs: 117-174. In another aspect, an amino acid sequence provided herein is at least 97% identical or similar to an amino acid sequence selected from the group consisting of SEQ ID NOs: 117-174. In another aspect, an amino acid sequence provided herein is at least 98% identical or similar to an amino acid sequence selected from the group consisting of SEQ ID NOs: 117-174. In another aspect, an amino acid sequence provided herein is at least 99% identical or similar to an amino acid sequence selected from the group consisting of SEQ ID NOs: 117-174. In another aspect, an amino acid sequence provided herein is 100% identical or similar to an amino acid sequence selected from the group consisting of SEQ ID NOs: 117-174.

In an aspect, a nucleic acid sequence provided herein encodes a polypeptide comprising an amino acid sequence at least 70% identical or similar to an amino acid sequence selected from the group consisting of SEQ ID NOs: 117-174. In an aspect, a nucleic acid sequence provided herein encodes a polypeptide comprising an amino acid sequence at least 75% identical or similar to an amino acid sequence selected from the group consisting of SEQ ID NOs: 117-174. In an aspect, a nucleic acid sequence provided herein encodes a polypeptide comprising an amino acid sequence at least 80% identical or similar to an amino acid sequence selected from the group consisting of SEQ ID NOs: 117-174. In an aspect, a nucleic acid sequence provided herein encodes a polypeptide comprising an amino acid sequence at least 85% identical or similar to an amino acid sequence selected from the group consisting of SEQ ID NOs: 117-174. In an aspect, a nucleic acid sequence provided herein encodes a polypeptide comprising an amino acid sequence at least 88% identical or similar to an amino acid sequence selected from the group consisting of SEQ ID NOs: 117-174. In an aspect, a nucleic acid sequence provided herein encodes a polypeptide comprising an amino acid sequence at least 90% identical or similar to an amino acid sequence selected from the group consisting of SEQ ID NOs: 117-174. In an aspect, a nucleic acid sequence provided herein encodes a polypeptide comprising an amino acid sequence at least 91% identical or similar to an amino acid sequence selected from the group consisting of SEQ ID NOs: 117-174. In an aspect, a nucleic acid sequence provided herein encodes a polypeptide comprising an amino acid sequence at least 92% identical or similar to an amino acid sequence selected from the group consisting of SEQ ID NOs: 117-174. In an aspect, a nucleic acid sequence provided herein encodes a polypeptide comprising an amino acid sequence at least 93% identical or similar to an amino acid sequence selected from the group consisting of SEQ ID NOs: 117-174. In an aspect, a nucleic acid sequence provided herein encodes a polypeptide comprising an amino acid sequence at least 94% identical or similar to an amino acid sequence selected from the group consisting of SEQ ID NOs: 117-174. In an aspect, a nucleic acid sequence provided herein encodes a polypeptide comprising an amino acid sequence at least 95% identical or similar to an amino acid sequence selected from the group consisting of SEQ ID NOs: 117-174. In an aspect, a nucleic acid sequence provided herein encodes a polypeptide comprising an amino acid sequence at least 96% identical or similar to an amino acid sequence selected from the group consisting of SEQ ID NOs: 117-174. In an aspect, a nucleic acid sequence provided herein encodes a polypeptide comprising an amino acid sequence at least 97% identical or similar to an amino acid sequence selected from the group consisting of SEQ ID NOs: 117-174. In an aspect, a nucleic acid sequence provided herein encodes a polypeptide comprising an amino acid sequence at least 98% identical or similar to an amino acid sequence selected from the group consisting of SEQ ID NOs: 117-174. In an aspect, a nucleic acid sequence provided herein encodes a polypeptide comprising an amino acid sequence at least 99% identical or similar to an amino acid sequence selected from the group consisting of SEQ ID NOs: 117-174. In an aspect, a nucleic acid sequence provided herein encodes a polypeptide comprising an amino acid sequence 100% identical or similar to an amino acid sequence selected from the group consisting of SEQ ID NOs: 117-174.

In an aspect, an endogenous nucleic acid sequence provided herein encodes a polypeptide comprising an amino acid sequence at least 70% identical or similar to an amino acid sequence selected from the group consisting of SEQ ID NOs: 117-174. In an aspect, an endogenous nucleic acid sequence provided herein encodes a polypeptide comprising an amino acid sequence at least 75% identical or similar to an amino acid sequence selected from the group consisting of SEQ ID NOs: 117-174. In an aspect, an endogenous nucleic acid sequence provided herein encodes a polypeptide comprising an amino acid sequence at least 80% identical or similar to an amino acid sequence selected from the group consisting of SEQ ID NOs: 117-174. In an aspect, an endogenous nucleic acid sequence provided herein encodes a polypeptide comprising an amino acid sequence at least 85% identical or similar to an amino acid sequence selected from the group consisting of SEQ ID NOs: 117-174. In an aspect, an endogenous nucleic acid sequence provided herein encodes a polypeptide comprising an amino acid sequence at least 88% identical or similar to an amino acid sequence selected from the group consisting of SEQ ID NOs: 117-174. In an aspect, an endogenous nucleic acid sequence provided herein encodes a polypeptide comprising an amino acid sequence at least 90% identical or similar to an amino acid sequence selected from the group consisting of SEQ ID NOs: 117-174. In an aspect, an endogenous nucleic acid sequence provided herein encodes a polypeptide comprising an amino acid sequence at least 91% identical or similar to an amino acid sequence selected from the group consisting of SEQ ID NOs: 117-174. In an aspect, an endogenous nucleic acid sequence provided herein encodes a polypeptide comprising an amino acid sequence at least 92% identical or similar to an amino acid sequence selected from the group consisting of SEQ ID NOs: 117-174. In an aspect, an endogenous nucleic acid sequence provided herein encodes a polypeptide comprising an amino acid sequence at least 93% identical or similar to an amino acid sequence selected from the group consisting of SEQ ID NOs: 117-174. In an aspect, an endogenous nucleic acid sequence provided herein encodes a polypeptide comprising an amino acid sequence at least 94% identical or similar to an amino acid sequence selected from the group consisting of SEQ ID NOs: 117-174. In an aspect, an endogenous nucleic acid sequence provided herein encodes a polypeptide comprising an amino acid sequence at least 95% identical or similar to an amino acid sequence selected from the group consisting of SEQ ID NOs: 117-174. In an aspect, an endogenous nucleic acid sequence provided herein encodes a polypeptide comprising an amino acid sequence at least 96% identical or similar to an amino acid sequence selected from the group consisting of SEQ ID NOs: 117-174. In an aspect, an endogenous nucleic acid sequence provided herein encodes a polypeptide comprising an amino acid sequence at least 97% identical or similar to an amino acid sequence selected from the group consisting of SEQ ID NOs: 117-174. In an aspect, an endogenous nucleic acid sequence provided herein encodes a polypeptide comprising an amino acid sequence at least 98% identical or similar to an amino acid sequence selected from the group consisting of SEQ ID NOs: 117-174. In an aspect, an endogenous nucleic acid sequence provided herein encodes a polypeptide comprising an amino acid sequence at least 99% identical or similar to an amino acid sequence selected from the group consisting of SEQ ID NOs: 117-174. In an aspect, an endogenous nucleic acid sequence provided herein encodes a polypeptide comprising an amino acid sequence 100% identical or similar to an amino acid sequence selected from the group consisting of SEQ ID NOs: 117-174.

Promoters

As commonly understood in the art, the term "promoter" refers to a DNA sequence that contains an RNA polymerase binding site, a transcription start site, and/or a TATA box and assists or promotes the transcription and expression of an associated transcribable polynucleotide sequence and/or gene (or transgene). A promoter can be synthetically produced, varied, or derived from a known or naturally occurring promoter sequence or other promoter sequence. A promoter can also include a chimeric promoter comprising a combination of two or more heterologous sequences. A promoter of the present application can thus include variants of promoter sequences that are similar in composition, but not identical to, other promoter sequence(s) known or provided herein.

Promoters that drive expression in all or most tissues of the plant are referred to as "constitutive" promoters. In an aspect, a constitutive promoter is selected from the group consisting of a Cauliflower Mosaic Virus 35S promoter, a ubiquitin promoter, an actin promoter, an opine promoter, and an alcohol dehydrogenase promoter.

Promoters that drive expression during certain periods or stages of development are referred to as "developmental" promoters.

Promoters that drive enhanced expression in certain tissues of an organism relative to other tissues of the organism are referred to as "tissue-preferred" promoters. Thus, a "tissue-preferred" promoter causes relatively higher or preferential expression in a specific tissue(s) of a plant, but with lower levels of expression in other tissue(s) of the plant. As a non-limiting example, a root tissue-preferred promoter exhibits higher activity in root tissue, but may also exhibit activity, albeit at lower levels, in additional tissues such as stem, leaves, and floral tissues. A "tissue-specific" promoter causes expression only in a specific tissue. As a non-limiting example, a root tissue-specific promoter drives expression only in root tissue. In an aspect, a tissue-specific promoter is a root tissue-specific promoter. In another aspect, a tissue-preferred promoter is a root tissue-preferred promoter.

In an aspect, a root tissue-preferred promoter is a cassava vein mosaic virus (CsVMV) promoter.

An "inducible" promoter is a promoter that initiates transcription in response to an environmental stimulus such as heat, cold, drought, light, or other stimuli, such as wounding or chemical application.

In an aspect, a promoter provided herein is a constitutive promoter. In another aspect, a promoter provided herein is an inducible promoter. In a further aspect, a promoter provided herein is a developmental promoter. In another aspect, a promoter is a tissue-preferred or tissue-specific promoter. In a further aspect, a promoter is selected from the group consisting of a constitutive promoter, a tissue-preferred promoter, a tissue-specific promoter, and an inducible promoter.

In an aspect, this disclosure provides a heterologous promoter. In another aspect, this disclosure provides a promoter that is operably linked to a heterologous polynucleotide. In another aspect, this disclosure provides a polynucleotide sequence that is operably linked to a heterologous promoter.

As used herein, "operably linked" refers to a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous. In an aspect, a promoter provided herein is operably linked to a heterologous nucleic acid molecule.

Small RNA Molecules

In an aspect, a nucleic acid molecule provided herein is a small RNA molecule. In another aspect, a nucleic acid molecule encodes a small RNA molecule.

As used herein, a "small RNA molecule" refers to a non-coding RNA molecule of between 16 nucleotides and 50 nucleotides in length. In an aspect, a small RNA molecule comprises between 16 nucleotides and 40 nucleotides. In another aspect, a small RNA molecule comprises between 16 nucleotides and 30 nucleotides. In another aspect, a small RNA molecule comprises between 18 nucleotides and 50 nucleotides. In another aspect, a small RNA molecule comprises between 18 nucleotides and 40 nucleotides. In another aspect, a small RNA molecule comprises between 18 nucleotides and 30 nucleotides. In another aspect, a small RNA molecule comprises between 18 nucleotides and 25 nucleotides. In another aspect, a small RNA molecule comprises between 20 nucleotides and 28 nucleotides. In another aspect, a small RNA molecule comprises between 20 nucleotides and 24 nucleotides. In another aspect, a small RNA molecule comprises between 21 nucleotides and 23 nucleotides. In another aspect, a small RNA molecule comprises 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

In an aspect, a small RNA molecule is selected from the group consisting of a double-stranded RNA, a small interfering RNA (siRNA), a trans-acting siRNA, and a microRNA (miRNA).

miRNAs are generally of between about 19 to about 25 nucleotides (commonly about 20-24 nucleotides in plants), that guide cleavage in trans of target transcripts, negatively regulating the expression of genes involved in various regulation and development pathways. In some cases, miRNAs serve to guide in-phase processing of siRNA primary transcripts.

It is appreciated in the art that, in plants, miRNAs and targeted nucleic acids often do not share perfect complementarity (although miRNAs and targeted nucleic acids can have perfect complementarity). miRNAs and their targets can have several mismatches between them while still enabling the miRNA to reduce the expression and/or function of the target gene. See, for example, Liu et al., *Plant Cell,* 26:741-753 (2014) and Wang et al., *Curr. Opin. Plant Biol.,* 27:118-124 (2015).

In an aspect, a small RNA molecule comprises 100% complementarity with a nucleic acid molecule comprising a sequence selected from the group consisting of SEQ ID NOs: 1-58. In an aspect, a small RNA molecule comprises at least 95% complementarity over 21 consecutive nucleotides of a nucleic acid molecule comprising a sequence selected from the group consisting of SEQ ID NOs: 1-58. In an aspect, a small RNA molecule comprises at least 90% complementarity over 21 consecutive nucleotides of a nucleic acid molecule comprising a sequence selected from the group consisting of SEQ ID NOs: 1-58. In an aspect, a small RNA molecule comprises at least 85% complementarity over 21 consecutive nucleotides of a nucleic acid molecule comprising a sequence selected from the group consisting of SEQ ID NOs: 1-58. In an aspect, a small RNA molecule comprises at least 95% complementarity over 20 consecutive nucleotides of a nucleic acid molecule comprising a sequence selected from the group consisting of SEQ ID NOs: 1-58. In an aspect, a small RNA molecule comprises at least 90% complementarity over 20 consecutive nucleotides of a nucleic acid molecule comprising a sequence selected from the group consisting of SEQ ID NOs: 1-58. In an aspect, a small RNA molecule comprises at least 85% complementarity over 20 consecutive nucleotides of a nucleic acid molecule comprising a sequence selected from the group consisting of SEQ ID NOs: 1-58. In an aspect, a small RNA molecule comprises at least 95% complementarity over 19 consecutive nucleotides of a nucleic acid molecule comprising a sequence selected from the group consisting of SEQ ID NOs: 1-58. In an aspect, a small RNA molecule comprises at least 90% complementarity over 19 consecutive nucleotides of a nucleic acid molecule comprising a sequence selected from the group consisting of SEQ ID NOs: 1-58. In an aspect, a small RNA molecule comprises at least 85% complementarity over 19 consecutive nucleotides of a nucleic acid molecule comprising a sequence selected from the group consisting of SEQ ID NOs: 1-58.

Many microRNA genes (MIR genes) have been identified and made publicly available in a database ("miRBase", available online at microrna[dot]sanger[dot]ac[dot]uk/sequences; also see Griffiths-Jones et al. (2003) Nucleic Acids Res., 31:439-441). MIR genes have been reported to occur in intergenic regions, both isolated and in clusters in the genome, but can also be located entirely or partially within introns of other genes (both protein-coding and non-protein-coding). For a review of miRNA biogenesis, see Kim (2005) Nature Rev. Mol. Cell. Biol., 6:376-385. Transcription of MIR genes can be, at least in some cases, under promotional control of a MIR gene's own promoter. The primary transcript, termed a "pri-miRNA", can be quite large (several kilobases) and can be polycistronic, containing one or more pre-miRNAs (fold-back structures containing a stem-loop arrangement that is processed to the mature miRNA) as well as the usual 5' "cap" and polyadenylated tail of an mRNA.

Maturation of a mature miRNA from its corresponding precursors (pri-miRNAs and pre-miRNAs) differs significantly between animals and plants. For example, in plant cells, microRNA precursor molecules are believed to be largely processed to the mature miRNA entirely in the nucleus, whereas in animal cells, the pri-miRNA transcript is processed in the nucleus by the animal-specific enzyme Drosha, followed by export of the pre-miRNA to the cytoplasm where it is further processed to the mature miRNA. Mature miRNAs in plants are typically 21 nucleotides in length.

Transgenic expression of miRNAs (whether a naturally occurring sequence or an artificial sequence) can be employed to regulate expression of the miRNA's target gene or genes. Inclusion of a miRNA recognition site in a transgenically expressed transcript is also useful in regulating expression of the transcript. Recognition sites of miRNAs have been validated in all regions of an mRNA, including the 5' untranslated region, coding region, and 3' untranslated region, indicating that the position of the miRNA target site relative to the coding sequence may not necessarily affect suppression. Because miRNAs are important regulatory elements in eukaryotes, transgenic suppression of miRNAs is useful for manipulating biological pathways and responses. Finally, promoters of MIR genes can have very specific expression patterns (e.g., cell-specific, tissue-specific, temporally specific, or inducible), and thus are useful in recombinant constructs to induce such specific transcription of a DNA sequence to which they are operably linked. Various utilities of miRNAs, their precursors, their recognition sites, and their promoters are described in detail in U.S. Patent Application Publication 2006/0200878 A1, incorporated by reference herein. Non-limiting examples of these utilities include: (1) the expression of a native miRNA or miRNA precursor sequence to suppress a target gene; (2) the expression of an artificial miRNA or miRNA precursor sequence to suppress a target gene; (3) expression of a transgene with a miRNA recognition site, where the transgene is suppressed when the mature miRNA is expressed; (4) expression of a transgene driven by a miRNA promoter.

Designing an artificial miRNA sequence can be as simple as substituting sequence that is complementary to the intended target for nucleotides in the miRNA stem region of the miRNA precursor, as demonstrated by Zeng et al. (2002) Mol. Cell, 9:1327-1333. One non-limiting example of a general method for determining nucleotide changes in the native miRNA sequence to produce the engineered miRNA precursor includes the following steps: (a) Selecting a unique target sequence of at least 18 nucleotides specific to the target gene, e.g., by using sequence alignment tools such as BLAST (see, for example, Altschul et al. (1990) J. Mol. Biol., 215:403-410; Altschul et al. (1997) Nucleic Acids Res., 25:3389-3402), for example, of both tobacco cDNA and genomic DNA databases, to identify target transcript orthologues and any potential matches to unrelated genes, thereby avoiding unintentional silencing of non-target sequences; (b) Analyzing the target gene for undesirable sequences (e.g., matches to sequences from non-target species), and score each potential 19-mer segment for GC content, Reynolds score (see Reynolds et al. (2004) Nature Biotechnol., 22:326-330), and functional asymmetry characterized by a negative difference in free energy (".DELTA..DELTA.G" or "AAG") (see Khvorova et al. (2003) Cell, 115:209-216). Preferably 19-mers are selected that have all or most of the following characteristics: (1) a Reynolds score>4, (2) a GC content between about 40% to about 60%, (3) a negative AAG, (4) a terminal adenosine, (5) lack of a consecutive run of 4 or more of the same nucleotide; (6) a location near the 3' terminus of the target gene; (7) minimal differences from the miRNA precursor transcript. Positions at every third nucleotide in an siRNA have been reported to be especially important in influencing RNAi efficacy and an algorithm, "siExplorer" is publicly available at rna[dot]chem[dot]t[dot]u-tokyo[dot]ac[dot]jp/siexplorer.htm (see Katoh and Suzuki (2007) Nucleic Acids Res., 10.1093/nar/gkl1120); (c) Determining the reverse complement of the selected 19-mers to use in making a modified mature miRNA. The additional nucleotide at position 20 is preferably matched to the selected target sequence, and the nucleotide at position 21 is preferably chosen to either be unpaired to prevent spreading of silencing on the target transcript or paired to the target sequence to promote spreading of silencing on the target transcript; and (d) transforming the artificial miRNA into a plant.

Without being limited by any scientific theory, it is appreciated in the art that an RNAi knockdown of a candidate gene (e.g., via the use of an artificial miRNA or an siRNA) and a mutation (e.g., missense or nonsense mutations) in the same candidate gene can both cause reduction of expression and/or decreased protein activity and can cause identical or similar phenotypes in plants. See, for example, Agrawal et al., Microbiology and Molecular Biology Reviews, 67:657-685 (2003).

In an aspect, a small RNA provided herein comprises at nucleic acid sequence at least 75% identical or complementary to a nucleic acid sequence selected from the group consisting of SEQ ID NOs: 1-116. In an aspect, a small RNA provided herein comprises at nucleic acid sequence at least 80% identical or complementary to a nucleic acid sequence selected from the group consisting of SEQ ID NOs: 1-116. In an aspect, a small RNA provided herein comprises at nucleic acid sequence at least 85% identical or complementary to a nucleic acid sequence selected from the group consisting of SEQ ID NOs: 1-116. In an aspect, a small RNA provided herein comprises at nucleic acid sequence at least 90% identical or complementary to a nucleic acid sequence selected from the group consisting of SEQ ID NOs: 1-116. In an aspect, a small RNA provided herein comprises at nucleic acid sequence at least 95% identical or complementary to a nucleic acid sequence selected from the group consisting of SEQ ID NOs: 1-116. In an aspect, a small RNA provided herein comprises at nucleic acid sequence at least 96% identical or complementary to a nucleic acid sequence selected from the group consisting of SEQ ID NOs: 1-116. In an aspect, a small RNA provided herein comprises at nucleic acid sequence at least 97% identical or complementary to a nucleic acid sequence selected from the group consisting of SEQ ID NOs: 1-116. In an aspect, a small RNA provided herein comprises at nucleic acid sequence at least 98% identical or complementary to a nucleic acid sequence selected from the group consisting of SEQ ID NOs: 1-116. In an aspect, a small RNA provided herein comprises at nucleic acid sequence at least 99% identical or complementary to a nucleic acid sequence selected from the group consisting of SEQ ID NOs: 1-116. In an aspect, a small RNA provided herein comprises at nucleic acid sequence 100% identical or complementary to a nucleic acid sequence selected from the group consisting of SEQ ID NOs: 1-116.

In an aspect, a small RNA provided herein comprises at nucleic acid sequence at least 75% complementary to a nucleic acid sequence selected from the group consisting of SEQ ID NOs: 59-116. In an aspect, a small RNA provided herein comprises at nucleic acid sequence at least 80% complementary to a nucleic acid sequence selected from the group consisting of SEQ ID NOs: 59-116. In an aspect, a small RNA provided herein comprises at nucleic acid sequence at least 85% identical or complementary to a nucleic acid sequence selected from the group consisting of SEQ ID NOs: 59-116. In an aspect, a small RNA provided herein comprises at nucleic acid sequence at least 90% identical or complementary to a nucleic acid sequence selected from the group consisting of SEQ ID NOs: 59-116. In an aspect, a small RNA provided herein comprises at nucleic acid sequence at least 95% identical or complementary to a nucleic acid sequence selected from the group consisting of SEQ ID NOs: 59-116. In an aspect, a small RNA provided herein comprises at nucleic acid sequence at least 96% identical or complementary to a nucleic acid sequence selected from the group consisting of SEQ ID NOs: 59-116. In an aspect, a small RNA provided herein comprises at nucleic acid sequence at least 97% identical or complementary to a nucleic acid sequence selected from the group consisting of SEQ ID NOs: 59-116. In an aspect, a small RNA provided herein comprises at nucleic acid sequence at least 98% identical or complementary to a nucleic acid sequence selected from the group consisting of SEQ ID NOs: 59-116. In an aspect, a small RNA provided herein comprises at nucleic acid sequence at least 99% identical or complementary to a nucleic acid sequence selected from the group consisting of SEQ ID NOs: 59-116. In an aspect, a small RNA provided herein comprises at nucleic acid sequence 100% identical or complementary to a nucleic acid sequence selected from the group consisting of SEQ ID NOs: 59-116.

In an aspect, a small RNA provided herein comprises a nucleic acid sequence at least 88.7% identical or complementary to at least 18 contiguous nucleotides of a nucleic acid sequence selected from the group consisting of SEQ ID NOs: 1-116. In another aspect, a small RNA provided herein comprises a nucleic acid sequence at least 94.3% identical or complementary to at least 18 contiguous nucleotides of a nucleic acid sequence selected from the group consisting of SEQ ID NOs: 1-116. In another aspect, a small RNA provided herein comprises a nucleic acid sequence 100% identical or complementary to at least 18 contiguous nucleotides of a nucleic acid sequence selected from the group consisting of SEQ ID NOs: 1-116. In another aspect, a small RNA provided herein comprises a nucleic acid sequence at least 85% identical or complementary to at least 20 contiguous nucleotides of a nucleic acid sequence selected from the group consisting of SEQ ID NOs: 1-116. In another aspect, a small RNA provided herein comprises a nucleic acid sequence at least 90% identical or complementary to at least 20 contiguous nucleotides of a nucleic acid sequence selected from the group consisting of SEQ ID NOs: 1-116. In another aspect, a small RNA provided herein comprises a nucleic acid sequence at least 95% identical or complementary to at least 20 contiguous nucleotides of a nucleic acid sequence selected from the group consisting of SEQ ID NOs: 1-116. In another aspect, a small RNA provided herein comprises a nucleic acid sequence 100% identical or complementary to at least 20 contiguous nucleotides of a nucleic acid sequence selected from the group consisting of SEQ ID NOs: 1-116.

In an aspect, a small RNA molecule provided herein is capable of binding to and reducing the expression of a nucleic acid sequence encoding a polypeptide at least 70% identical or similar to an amino acid sequence selected from the group consisting of SEQ ID NOs: 117-174. In an aspect, a small RNA molecule provided herein is capable of binding to and reducing the expression of a nucleic acid sequence encoding a polypeptide at least 75% identical or similar to an amino acid sequence selected from the group consisting of SEQ ID NOs: 117-174. In an aspect, a small RNA molecule provided herein is capable of binding to and reducing the expression of a nucleic acid sequence encoding a polypeptide at least 80% identical or similar to an amino acid sequence selected from the group consisting of SEQ ID NOs: 117-174. In an aspect, a small RNA molecule provided herein is capable of binding to and reducing the expression of a nucleic acid sequence encoding a polypeptide at least 85% identical or similar to an amino acid sequence selected from the group consisting of SEQ ID NOs: 117-174. In an aspect, a small RNA molecule provided herein is capable of binding to and reducing the expression of a nucleic acid sequence encoding a polypeptide at least 88% identical or similar to an amino acid sequence selected from the group consisting of SEQ ID NOs: 117-174. In an aspect, a small RNA molecule provided herein is capable of binding to and reducing the expression of a nucleic acid sequence encoding a polypeptide at least 90% identical or similar to an amino acid sequence selected from the group consisting of SEQ ID NOs: 117-174. In an aspect, a small RNA molecule provided herein is capable of binding to and reducing the expression of a nucleic acid sequence encoding a polypeptide at least 91% identical or similar to an amino acid sequence selected from the group consisting of SEQ ID NOs: 117-174. In an aspect, a small RNA molecule provided herein is capable of binding to and reducing the expression of a nucleic acid sequence encoding a polypeptide at least 92% identical or similar to an amino acid sequence selected from the group consisting of SEQ ID NOs: 117-174. In an aspect, a small RNA molecule provided herein is capable of binding to and reducing the expression of a nucleic acid sequence encoding a polypeptide at least 93% identical or similar to an amino acid sequence selected from the group consisting of SEQ ID NOs: 117-174. In an aspect, a small RNA molecule provided herein is capable of binding to and reducing the expression of a nucleic acid sequence encoding a polypeptide at least 94% identical or similar to an amino acid sequence selected from the group consisting of SEQ ID NOs: 117-174. In an aspect, a small RNA molecule provided herein is capable of binding to and reducing the expression of a nucleic acid sequence encoding a polypeptide at least 95% identical or similar to an amino acid sequence selected from the group consisting of SEQ ID NOs: 117-174. In an aspect, a small RNA molecule provided herein is capable of binding to and reducing the expression of a nucleic acid sequence encoding a polypeptide at least 96% identical or similar to an amino acid sequence selected from the group consisting of SEQ ID NOs: 117-174. In an aspect, a small RNA molecule provided herein is capable of binding to and reducing the expression of a nucleic acid sequence encoding a polypeptide at least 97% identical or similar to an amino acid sequence selected from the group consisting of SEQ ID NOs: 117-174. In an aspect, a small RNA molecule provided herein is capable of binding to and reducing the expression of a nucleic acid sequence encoding a polypeptide at least 98% identical or similar to an amino acid sequence selected from the group consisting of SEQ ID NOs: 117-174. In an aspect, a small RNA molecule provided herein is capable of binding to and reducing the expression of a nucleic acid sequence encoding a polypeptide at least 99% identical or similar to an amino acid sequence selected from the group consisting of SEQ ID NOs: 117-174. In an aspect, a small RNA molecule provided herein is capable of binding to and reducing the expression of a nucleic acid sequence encoding a polypeptide 100% identical or similar to an amino acid sequence selected from the group consisting of SEQ ID NOs: 117-174.

In an aspect, a small RNA molecule provided herein is capable of binding to and reducing the expression of a nucleic acid sequence at least 70% identical to nucleic acid sequence selected from the group consisting of SEQ ID NOs: 1-116, or an RNA transcribed therefrom. In an aspect, a small RNA molecule provided herein is capable of binding to and reducing the expression of a nucleic acid sequence at least 75% identical to nucleic acid sequence selected from the group consisting of SEQ ID NOs: 1-116, or an RNA transcribed therefrom. In an aspect, a small RNA molecule provided herein is capable of binding to and reducing the expression of a nucleic acid sequence at least 80% identical to nucleic acid sequence selected from the group consisting of SEQ ID NOs: 1-116, or an RNA transcribed therefrom. In an aspect, a small RNA molecule provided herein is capable of binding to and reducing the expression of a nucleic acid sequence at least 85% identical to nucleic acid sequence selected from the group consisting of SEQ ID NOs: 1-116, or an RNA transcribed therefrom. In an aspect, a small RNA molecule provided herein is capable of binding to and reducing the expression of a nucleic acid sequence at least 88% identical to nucleic acid sequence selected from the group consisting of SEQ ID NOs: 1-116, or an RNA transcribed therefrom. In an aspect, a small RNA molecule provided herein is capable of binding to and reducing the expression of a nucleic acid sequence at least 90% identical to nucleic acid sequence selected from the group consisting of SEQ ID NOs: 1-116, or an RNA transcribed therefrom. In an aspect, a small RNA molecule provided herein is capable of binding to and reducing the expression of a nucleic acid sequence at least 91% identical to nucleic acid sequence selected from the group consisting of SEQ ID NOs: 1-116, or an RNA transcribed therefrom. In an aspect, a small RNA molecule provided herein is capable of binding to and reducing the expression of a nucleic acid sequence at least 92% identical to nucleic acid sequence selected from the group consisting of SEQ ID NOs: 1-116, or an RNA transcribed therefrom. In an aspect, a small RNA molecule provided herein is capable of binding to and reducing the expression of a nucleic acid sequence at least 93% identical to nucleic acid sequence selected from the group consisting of SEQ ID NOs: 1-116, or an RNA transcribed therefrom. In an aspect, a small RNA molecule provided herein is capable of binding to and reducing the expression of a nucleic acid sequence at least 94% identical to nucleic acid sequence selected from the group consisting of SEQ ID NOs: 1-116, or an RNA transcribed therefrom. In an aspect, a small RNA molecule provided herein is capable of binding to and reducing the expression of a nucleic acid sequence at least 95% identical to nucleic acid sequence selected from the group consisting of SEQ ID NOs: 1-116, or an RNA transcribed therefrom. In an aspect, a small RNA molecule provided herein is capable of binding to and reducing the expression of a nucleic acid sequence at least 96% identical to nucleic acid sequence selected from the group consisting of SEQ ID NOs: 1-116, or an RNA transcribed therefrom. In an aspect, a small RNA molecule provided herein is capable of binding to and reducing the expression of a nucleic acid sequence at least 97% identical to nucleic acid sequence selected from the group consisting of SEQ ID NOs: 1-116, or an RNA transcribed therefrom. In an aspect, a small RNA molecule provided herein is capable of binding to and reducing the expression of a nucleic acid sequence at least 98% identical to nucleic acid sequence selected from the group consisting of SEQ ID NOs: 1-116, or an RNA transcribed therefrom. In an aspect, a small RNA molecule provided herein is capable of binding to and reducing the expression of a nucleic acid sequence at least 99% identical to nucleic acid sequence selected from the group consisting of SEQ ID NOs: 1-116, or an RNA transcribed therefrom. In an aspect, a small RNA molecule provided herein is capable of binding to and reducing the expression of a nucleic acid sequence 100% identical to nucleic acid sequence selected from the group consisting of SEQ ID NOs: 1-116, or an RNA transcribed therefrom.

As used herein, "capable of binding to" is synonymous with "capable of hybridizing to." In an aspect, a first nucleic acid molecule that is capable of binding to a second nucleic acid molecule binds to the second nucleic acid molecule. As used herein, a first nucleic acid molecule can "hybridize" a second nucleic acid molecule via non-covalent interactions (e.g., Watson-Crick base-pairing) in a sequence-specific, antiparallel manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine pairing with thymine, adenine pairing with uracil, and guanine (G) pairing with cytosine (C) [DNA, RNA]. In addition, it is also known in the art that for hybridization between two RNA molecules (e.g., dsRNA), guanine base pairs with uracil. For example, G/U base-pairing is partially responsible for the degeneracy (i.e., redundancy) of the genetic code in the context of tRNA anti-codon base-pairing with codons in mRNA. In the context of this disclosure, a guanine of a protein-binding segment (dsRNA duplex) of a subject DNA-targeting RNA molecule is considered complementary to an uracil, and vice versa. As such, when a G/U base-pair can be made at a given nucleotide position a protein-binding segment (dsRNA duplex) of a subject DNA-targeting RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer nucleotides) the position of mismatches becomes important (see Sambrook et al.). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides). Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST® programs (basic local alignment search tools) and PowerBLAST programs known in the art (see Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

Reduced Expression/Activity

In an aspect, a small RNA molecule reduces the expression of any nucleic acid sequence to which it is capable of binding. In another aspect, a non-natural mutation provided herein reduces the expression of the mutated nucleic acid sequence as compared to the non-mutated nucleic acid sequence in a control plant grown under comparable conditions.

Reduced expression of an endogenous nucleic acid sequence can be measured using any suitable method known in the art. Non-limiting examples of measuring expression include quantitative reverse transcriptase polymerase chain reaction (qRT-PCR), RNA blot (e.g., a Northern blot), RNA sequencing. Differences in expression can be described as an absolute quantification or a relative quantification. See, for example, Livak and Schmittgen, *Methods,* 25:402-408

(2001). If an endogenous nucleic acid sequence encodes a protein, changes in expression can be inferred by examining the accumulation of the encoded protein. Non-limiting examples of measuring protein accumulation include Western blots and enzyme-linked immunosorbent assays (ELISAs).

In an aspect, a reduction in expression is measured using qRT-PCR. In another aspect, a reduction in expression is measured using an RNA blot. In another aspect, a reduction in expression is measured using RNA sequencing. In a further aspect, a reduction in expression is measured using a Western blot. In yet a further aspect, a reduction in expression is measured using an ELISA.

In an aspect, a non-natural mutation in a nucleic acid sequence selected from the group consisting of SEQ ID NOs: 1-116 results in a reduced level of expression of the nucleic acid sequence as compared to the nucleic acid sequence lacking the non-natural mutation in a control plant grown under comparable conditions. In an aspect, a non-natural mutation in a nucleic acid sequence encoding an amino acid sequence selected from the group consisting of SEQ ID NOs: 117-174 results in a reduced level of expression of the nucleic acid sequence as compared to the nucleic acid sequence lacking the non-natural mutation in a control plant grown under comparable conditions.

In an aspect, a reduction in expression comprises a reduction of at least 1% as compared to expression in the same tissue of a control plant grown under comparable conditions. In another aspect, a reduction in expression comprises a reduction of at least 5% as compared to expression in the same tissue of a control plant grown under comparable conditions. In another aspect, a reduction in expression comprises a reduction of at least 10% as compared to expression in the same tissue of a control plant grown under comparable conditions. In another aspect, a reduction in expression comprises a reduction of at least 25% as compared to expression in the same tissue of a control plant grown under comparable conditions. In another aspect, a reduction in expression comprises a reduction of at least 50% as compared to expression in the same tissue of a control plant grown under comparable conditions. In another aspect, a reduction in expression comprises a reduction of at least 75% as compared to expression in the same tissue of a control plant grown under comparable conditions. In another aspect, a reduction in expression comprises a reduction of at least 90% as compared to expression in the same tissue of a control plant grown under comparable conditions. In another aspect, a reduction in expression comprises a reduction of at least 95% as compared to expression in the same tissue of a control plant grown under comparable conditions.

In an aspect, a reduction in expression comprises a reduction of between 1% and 99% as compared to expression in the same tissue of a control plant grown under comparable conditions. In another aspect, a reduction in expression comprises a reduction of between 1% and 90% as compared to expression in the same tissue of a control plant grown under comparable conditions. In another aspect, a reduction in expression comprises a reduction of between 1% and 75% as compared to expression in the same tissue of a control plant grown under comparable conditions. In another aspect, a reduction in expression comprises a reduction of between 1% and 50% as compared to expression in the same tissue of a control plant grown under comparable conditions. In another aspect, a reduction in expression comprises a reduction of between 1% and 25% as compared to expression in the same tissue of a control plant grown under comparable conditions. In another aspect, a reduction in expression comprises a reduction of between 25% and 90% as compared to expression in the same tissue of a control plant grown under comparable conditions. In another aspect, a reduction in expression comprises a reduction of between 50% and 90% as compared to expression in the same tissue of a control plant grown under comparable conditions. In another aspect, a reduction in expression comprises a reduction of between 25% and 75% as compared to expression in the same tissue of a control plant grown under comparable conditions.

In an aspect, a reduction in expression comprises a statistically significant reduction as compared to expression in the same tissue of a control plant grown under comparable conditions. One of ordinary skill in the art would recognize that any level of reduction is envisioned, so long as the level of reduction has been determined to be statistically significant using an accepted statistical hypothesis test. As a non-limiting example, a Student's t-test is one statistical hypothesis test that can be used to determine if a reduction in expression between a modified plant and a control plant is statistically significant. As used herein, "statistically significant" refers to a p-value of less than or equal to 0.05.

In an aspect, a non-natural mutation results in a reduced level of activity by a protein or polypeptide encoded by a nucleic acid sequence provided herein as compared to the activity of a control plant grown under comparable conditions. In another aspect, a non-natural mutation in an endogenous nucleic acid sequence selected from the group consisting of SEQ ID NOs: 1-116 reduces the level of activity by a protein or polypeptide encoded by the nucleic acid sequence as compared to activity of a protein or polypeptide encoded by the endogenous nucleic acid sequence in a control tobacco plant when grown under comparable conditions, where the nucleic acid sequence lacks the non-natural mutation in the control tobacco plant. In another aspect, a non-natural mutation in an endogenous nucleic acid sequence, where the endogenous nucleic acid sequence encodes an amino acid sequence selected from the group consisting of SEQ ID NOs: 117-174 reduces the level of activity by a protein or polypeptide encoded by the nucleic acid sequence as compared to activity of a protein or polypeptide encoded by the endogenous nucleic acid sequence in a control tobacco plant when grown under comparable conditions, where the nucleic acid sequence lacks the non-natural mutation in the control tobacco plant.

As used herein, when referring to a protein or polypeptide, "activity" refers to the ability to carry out an enzymatic function.

Increased Expression/Activity

In an aspect, a non-natural mutation results in increased expression of a nucleic acid sequence. In an aspect, a non-natural mutation results in an increased level of expression of said nucleic acid sequence as compared to expression of said nucleic acid sequence in the same tissue of a control tobacco plant when grown under comparable conditions, wherein said nucleic acid sequence lacks the at least one non-natural mutation in said control tobacco plant.

In an aspect, an increased level of expression comprises an increase of at least 5% as compared to expression in the same tissue of a control plant grown under comparable conditions. In another aspect, an increased level of expression comprises an increase of at least 10% as compared to expression in the same tissue of a control plant grown under comparable conditions. In another aspect, an increased level of expression comprises an increase of at least 25% as compared to expression in the same tissue of a control plant grown under comparable conditions. In another aspect, an increased level of expression comprises an increase of at least 50% as compared to expression in the same tissue of a control plant grown under comparable conditions. In another aspect, an increased level of expression comprises an increase of at least 75% as compared to expression in the same tissue of a control plant grown under comparable conditions. In another aspect, an increased level of expression comprises an increase of at least 100% as compared to expression in the same tissue of a control plant grown under comparable conditions. In another aspect, an increased level of expression comprises an increase of at least 200% as compared to expression in the same tissue of a control plant grown under comparable conditions. In another aspect, an increased level of expression comprises an increase of at least 500% as compared to expression in the same tissue of a control plant grown under comparable conditions.

In an aspect, a non-natural mutation results in an increased level of activity by a protein or polypeptide encoded by said nucleic acid sequence as compared to activity of a protein or polypeptide encoded by said nucleic acid sequence in a control tobacco plant when grown under comparable conditions, wherein said nucleic acid sequence lacks the at least one non-natural mutation in said control tobacco plant.

Alkaloids

As used herein, "alkaloid" refers to a complex, nitrogen-containing compound that naturally occurs in tobacco, and has pharmacological effects in humans or other animals. Non-limiting examples of alkaloids include nicotine, anabasine, anatabine, and nornicotine.

Nicotine is the primary natural alkaloid in commercialized cigarette tobacco, and it accounts for approximately 90% of the alkaloid content in *Nicotiana tabacum*. Without being limiting, other major alkaloids in tobacco include cotinine, nornicotine, myosmine, nicotyrine, anabasine and anatabine. Without being limiting, minor tobacco alkaloids include nicotine-n-oxide, N-methyl anatabine, N-methyl anabasine, pseudooxynicotine, 2,3 dipyridyl and others.

In an aspect, an alkaloid is selected from the group consisting of anabasine, anatabine, nicotine, and nornicotine.

Alkaloid levels can be assayed by methods known in the art, for example by quantification based on gas-liquid chromatography, high performance liquid chromatography, radio-immunoassays, enzyme-linked immunosorbent assays, and mass spectrometry. For example, nicotinic alkaloid levels can be measured by a GC-FID method based on CORESTA Recommended Method No. 7, 1987 and ISO Standards (ISO TC 126N 394 E. See also Hibi et al., Plant Physiology 100: 826-35 (1992) for a method using gas-liquid chromatography equipped with a capillary column and an FID detector.

Alkaloid levels can be assayed from any plant tissue. Non-limiting examples include leaf and hairy root cultures. Additionally, alkaloid levels can be assayed in cured plant materials or in plant materials that have not been cured.

Alternatively, tobacco total alkaloids can be measured using a segmented-flow colorimetric method developed for analysis of tobacco samples as adapted by Skalar Instrument Co. (West Chester, PA) and described by Collins et al., Tobacco Science 13:79-81 (1969). In short, samples of tobacco are dried, ground, and extracted prior to analysis of total alkaloids and reducing sugars. The method then employs an acetic acid/methanol/water extraction and charcoal for decolorization. Determination of total alkaloids was based on the reaction of cyanogen chloride with nicotine alkaloids in the presence of an aromatic amine to form a colored complex which is measured at 460 nm.

In an aspect, the level of an individual alkaloid is measured based on a freeze-dried cured leaf sample using liquid chromatography with tandem mass spectrometry (LC/MS/MS). In an aspect, the level of an individual alkaloid is measured based on a freeze-dried hairy root culture sample using liquid chromatography with tandem mass spectrometry (LC/MS/MS).

Unless specified otherwise, the nicotine or alkaloid level (or another leaf chemistry or property characterization) of a tobacco plant is measured after topping in a pooled leaf sample collected from leaf number 3, 4, and 5 after topping. As used herein, whenever a comparison between leaves from two plants (e.g., a mutant plant versus a control plant) is mentioned, leaves from the same or comparable stalk position(s) and developmental stage(s) are intended so that the comparison can demonstrate effects due to genotype differences, not from other factors. As a non-limiting illustration, leaf 3 of a control plant is intended as a reference point for comparing with leaf 3 of a modified plant comprising a non-natural mutation or recombinant DNA construct.

As used herein, leaf numbering is based on the leaf position on a tobacco stalk with leaf number 1 being the youngest leaf (at the top) after topping and the highest leaf number assigned to the oldest leaf (at the bottom).

As used herein, "topping" refers to the removal of the stalk apex, including the shoot apical meristem, flowers, and up to several adjacent leaves, when a tobacco plant is near vegetative maturity and around the start of reproductive growth. Typically, tobacco plants are topped in the button stage (soon after the flower begins to appear). For example, greenhouse or field-grown tobacco plants can be topped when 50% of the plants have at least one open flower. Topping a tobacco plant results in the loss of apical dominance and also induce increased alkaloid production.

Typically, the alkaloid level (or another leaf chemistry or property characterization; e.g., polyamines) of a tobacco plant is measured about 2 weeks after topping. Other time points can also be used. In an aspect, alkaloid level (or another leaf chemistry or property characterization) of a tobacco plant is measured about 1, 2, 3, 4, or 5 weeks after topping. In another aspect, the nicotine, alkaloid, or polyamine level (or another leaf chemistry or property characterization; e.g., polyamines) of a tobacco plant is measured about 3, 5, 7, 10, 12, 14, 17, 19, or 21 days after topping.

In an aspect, a modified tobacco plant, or part thereof, comprising at least one non-natural mutation in an endogenous nucleic acid produces at least one leaf comprising a reduced amount of at least one alkaloid as compared to the amount of the alkaloid in a control tobacco plant lacking the at least one non-natural mutation in the endogenous nucleic acid when grown under comparable conditions.

In an aspect, a modified tobacco plant, or part thereof, comprising a recombinant DNA construct provided herein produces at least one leaf comprising a reduced amount of at least one alkaloid as compared to the amount of the alkaloid in a control tobacco plant lacking the recombinant DNA construct when grown under comparable conditions.

In an aspect, a reduced level of at least one alkaloid comprises a reduction of at least 0.5% as compared to a control tobacco plant when grown under comparable conditions. In an aspect, a reduced level of at least one alkaloid comprises a reduction of at least 1% as compared to a control tobacco plant when grown under comparable conditions. In an aspect, a reduced level of at least one alkaloid comprises a reduction of at least 2% as compared to a control tobacco plant when grown under comparable conditions. In an aspect, a reduced level of at least one alkaloid comprises a reduction of at least 3% as compared to a control tobacco plant when grown under comparable conditions. In an aspect, a reduced level of at least one alkaloid comprises a reduction of at least 4% as compared to a control tobacco plant when grown under comparable conditions. In an aspect, a reduced level of at least one alkaloid comprises a reduction of at least 5% as compared to a control tobacco plant when grown under comparable conditions. In an aspect, a reduced level of at least one alkaloid comprises a reduction of at least 10% as compared to a control tobacco plant when grown under comparable conditions. In an aspect, a reduced level of at least one alkaloid comprises a reduction of at least 15% as compared to a control tobacco plant when grown under comparable conditions. In an aspect, a reduced level of at least one alkaloid comprises a reduction of at least 20% as compared to a control tobacco plant when grown under comparable conditions. In an aspect, a reduced level of at least one alkaloid comprises a reduction of at least 25% as compared to a control tobacco plant when grown under comparable conditions. In an aspect, a reduced level of at least one alkaloid comprises a reduction of at least 35% as compared to a control tobacco plant when grown under comparable conditions. In an aspect, a reduced level of at least one alkaloid comprises a reduction of at least 50% as compared to a control tobacco plant when grown under comparable conditions. In an aspect, a reduced level of at least one alkaloid comprises a reduction of at least 75% as compared to a control tobacco plant when grown under comparable conditions. In an aspect, a reduced level of at least one alkaloid comprises a reduction of at least 90% as compared to a control tobacco plant when grown under comparable conditions.

In an aspect, a reduced level of at least one alkaloid comprises a reduction of at between 1% and 99% as compared to a control tobacco plant when grown under comparable conditions. In an aspect, a reduced level of at least one alkaloid comprises a reduction of at between 1% and 90% as compared to a control tobacco plant when grown under comparable conditions. In an aspect, a reduced level of at least one alkaloid comprises a reduction of at between 1% and 80% as compared to a control tobacco plant when grown under comparable conditions. In an aspect, a reduced level of at least one alkaloid comprises a reduction of at between 1% and 70% as compared to a control tobacco plant when grown under comparable conditions. In an aspect, a reduced level of at least one alkaloid comprises a reduction of at between 1% and 60% as compared to a control tobacco plant when grown under comparable conditions. In an aspect, a reduced level of at least one alkaloid comprises a reduction of at between 1% and 50% as compared to a control tobacco plant when grown under comparable conditions. In an aspect, a reduced level of at least one alkaloid comprises a reduction of at between 1% and 40% as compared to a control tobacco plant when grown under comparable conditions. In an aspect, a reduced level of at least one alkaloid comprises a reduction of at between 1% and 30% as compared to a control tobacco plant when grown under comparable conditions. In an aspect, a reduced level of at least one alkaloid comprises a reduction of at between 1% and 20% as compared to a control tobacco plant when grown under comparable conditions. In an aspect, a reduced level of at least one alkaloid comprises a reduction of at between 1% and 10% as compared to a control tobacco plant when grown under comparable conditions. In an aspect, a reduced level of at least one alkaloid comprises a reduction of at between 1% and 5% as compared to a control tobacco plant when grown under comparable conditions. In an aspect, a reduced level of at least one alkaloid comprises a reduction of at between 10% and 75% as compared to a control tobacco plant when grown under comparable conditions. In an aspect, a reduced level of at least one alkaloid comprises a reduction of at between 10% and 50% as compared to a control tobacco plant when grown under comparable conditions. In an aspect, a reduced level of at least one alkaloid comprises a reduction of at between 10% and 25% as compared to a control tobacco plant when grown under comparable conditions.

In an aspect, a reduced level of at least one alkaloid comprises a reduction of nicotine by at least 0.5% as compared to a control tobacco plant when grown under comparable conditions. In an aspect, a reduced level of at least one alkaloid comprises a reduction of nicotine by at least 1% as compared to a control tobacco plant when grown under comparable conditions. In an aspect, a reduced level of at least one alkaloid comprises a reduction of nicotine by at least 2% as compared to a control tobacco plant when grown under comparable conditions. In an aspect, a reduced level of at least one alkaloid comprises a reduction of nicotine by at least 3% as compared to a control tobacco plant when grown under comparable conditions. In an aspect, a reduced level of at least one alkaloid comprises a reduction of nicotine by at least 4% as compared to a control tobacco plant when grown under comparable conditions. In an aspect, a reduced level of at least one alkaloid comprises a reduction of nicotine by at least 5% as compared to a control tobacco plant when grown under comparable conditions. In an aspect, a reduced level of at least one alkaloid comprises a reduction of nicotine by at least 10% as compared to a control tobacco plant when grown under comparable conditions. In an aspect, a reduced level of at least one alkaloid comprises a reduction of nicotine by at least 15% as compared to a control tobacco plant when grown under comparable conditions. In an aspect, a reduced level of at least one alkaloid comprises a reduction of nicotine by at least 20% as compared to a control tobacco plant when grown under comparable conditions. In an aspect, a reduced level of at least one alkaloid comprises a reduction of nicotine by at least 25% as compared to a control tobacco plant when grown under comparable conditions. In an aspect, a reduced level of at least one alkaloid comprises a reduction of nicotine by at least 35% as compared to a control tobacco plant when grown under comparable conditions. In an aspect, a reduced level of at least one alkaloid comprises a reduction of nicotine by at least 50% as compared to a control tobacco plant when grown under comparable conditions. In an aspect, a reduced level of at least one alkaloid comprises a reduction of nicotine by at least 75% as compared to a control tobacco plant when grown under comparable conditions. In an aspect, a reduced level of at least one alkaloid comprises a reduction of nicotine by at least 90% as compared to a control tobacco plant when grown under comparable conditions.

In an aspect, a reduced level of at least one alkaloid comprises a reduction of nicotine by between 1% and 99% as compared to a control tobacco plant when grown under comparable conditions. In an aspect, a reduced level of at least one alkaloid comprises a reduction of nicotine by between 1% and 90% as compared to a control tobacco plant when grown under comparable conditions. In an aspect, a reduced level of at least one alkaloid comprises a reduction of nicotine by between 1% and 80% as compared to a control tobacco plant when grown under comparable conditions. In an aspect, a reduced level of at least one alkaloid comprises a reduction of nicotine by between 1% and 70% as compared to a control tobacco plant when grown under comparable conditions. In an aspect, a reduced level of at least one alkaloid comprises a reduction of nicotine by between 1% and 60% as compared to a control tobacco plant when grown under comparable conditions. In an aspect, a reduced level of at least one alkaloid comprises a reduction of nicotine by between 1% and 50% as compared to a control tobacco plant when grown under comparable conditions. In an aspect, a reduced level of at least one alkaloid comprises a reduction of nicotine by between 1% and 40% as compared to a control tobacco plant when grown under comparable conditions. In an aspect, a reduced level of at least one alkaloid comprises a reduction of nicotine by between 1% and 30% as compared to a control tobacco plant when grown under comparable conditions. In an aspect, a reduced level of at least one alkaloid comprises a reduction of nicotine by between 1% and 20% as compared to a control tobacco plant when grown under comparable conditions. In an aspect, a reduced level of at least one alkaloid comprises a reduction of nicotine by between 1% and 10% as compared to a control tobacco plant when grown under comparable conditions. In an aspect, a reduced level of at least one alkaloid comprises a reduction of nicotine by between 1% and 5% as compared to a control tobacco plant when grown under comparable conditions. In an aspect, a reduced level of at least one alkaloid comprises a reduction of nicotine by between 10% and 75% as compared to a control tobacco plant when grown under comparable conditions. In an aspect, a reduced level of at least one alkaloid comprises a reduction of nicotine by between 10% and 50% as compared to a control tobacco plant when grown under comparable conditions. In an aspect, a reduced level of at least one alkaloid comprises a reduction of nicotine by between 10% and 25% as compared to a control tobacco plant when grown under comparable conditions.

In an aspect, a modified tobacco plant comprises a nicotine level of less than or equal to 17 milligrams per gram (mg/g) of dry weight. In an aspect, a modified tobacco plant comprises a nicotine level of less than or equal to 16 mg/g of dry weight. In an aspect, a modified tobacco plant comprises a nicotine level of less than or equal to 15 mg/g of dry weight. In an aspect, a modified tobacco plant comprises a nicotine level of less than or equal to 14 mg/g of dry weight. In an aspect, a modified tobacco plant comprises a nicotine level of less than or equal to 13 mg/g of dry weight. In an aspect, a modified tobacco plant comprises a nicotine level of less than or equal to 12 mg/g of dry weight. In an aspect, a modified tobacco plant comprises a nicotine level of less than or equal to 11 mg/g of dry weight. In an aspect, a modified tobacco plant comprises a nicotine level of less than or equal to 10 mg/g of dry weight. In an aspect, a modified tobacco plant comprises a nicotine level of less than or equal to 9 mg/g of dry weight. In an aspect, a modified tobacco plant comprises a nicotine level of less than or equal to 8 mg/g of dry weight. In an aspect, a modified tobacco plant comprises a nicotine level of less than or equal to 7 mg/g of dry weight. In an aspect, a modified tobacco plant comprises a nicotine level of less than or equal to 6 mg/g of dry weight. In an aspect, a modified tobacco plant comprises a nicotine level of less than or equal to 5 mg/g of dry weight. In an aspect, a modified tobacco plant comprises a nicotine level of less than or equal to 4 mg/g of dry weight. In an aspect, a modified tobacco plant comprises a nicotine level of less than or equal to 3 mg/g of dry weight. In an aspect, a modified tobacco plant comprises a nicotine level of less than or equal to 2 mg/g of dry weight. In an aspect, a modified tobacco plant comprises a nicotine level of less than or equal to 1.5 mg/g of dry weight. In an aspect, a modified tobacco plant comprises a nicotine level of less than or equal to 1 mg/g of dry weight.

In an aspect, a reduced level of at least one alkaloid comprises a reduction of anatabine by at least 0.5% as compared to a control tobacco plant when grown under comparable conditions. In an aspect, a reduced level of at least one alkaloid comprises a reduction of anatabine by at least 1% as compared to a control tobacco plant when grown under comparable conditions. In an aspect, a reduced level of at least one alkaloid comprises a reduction of anatabine by at least 2% as compared to a control tobacco plant when grown under comparable conditions. In an aspect, a reduced level of at least one alkaloid comprises a reduction of anatabine by at least 3% as compared to a control tobacco plant when grown under comparable conditions. In an aspect, a reduced level of at least one alkaloid comprises a reduction of anatabine by at least 4% as compared to a control tobacco plant when grown under comparable conditions. In an aspect, a reduced level of at least one alkaloid comprises a reduction of anatabine by at least 5% as compared to a control tobacco plant when grown under comparable conditions. In an aspect, a reduced level of at least one alkaloid comprises a reduction of anatabine by at least 10% as compared to a control tobacco plant when grown under comparable conditions. In an aspect, a reduced level of at least one alkaloid comprises a reduction of anatabine by at least 15% as compared to a control tobacco plant when grown under comparable conditions. In an aspect, a reduced level of at least one alkaloid comprises a reduction of anatabine by at least 20% as compared to a control tobacco plant when grown under comparable conditions. In an aspect, a reduced level of at least one alkaloid comprises a reduction of anatabine by at least 25% as compared to a control tobacco plant when grown under comparable conditions. In an aspect, a reduced level of at least one alkaloid comprises a reduction of anatabine by at least 35% as compared to a control tobacco plant when grown under comparable conditions. In an aspect, a reduced level of at least one alkaloid comprises a reduction of anatabine by at least 50% as compared to a control tobacco plant when grown under comparable conditions. In an aspect, a reduced level of at least one alkaloid comprises a reduction of anatabine by at least 75% as compared to a control tobacco plant when grown under comparable conditions. In an aspect, a reduced level of at least one alkaloid comprises a reduction of anatabine by at least 90% as compared to a control tobacco plant when grown under comparable conditions.

In an aspect, a reduced level of at least one alkaloid comprises a reduction of anatabine by between 1% and 99% as compared to a control tobacco plant when grown under comparable conditions. In an aspect, a reduced level of at least one alkaloid comprises a reduction of anatabine by between 1% and 90% as compared to a control tobacco plant when grown under comparable conditions. In an aspect, a reduced level of at least one alkaloid comprises a reduction of anatabine by between 1% and 80% as compared to a control tobacco plant when grown under comparable conditions. In an aspect, a reduced level of at least one alkaloid comprises a reduction of anatabine by between 1% and 70% as compared to a control tobacco plant when grown under comparable conditions. In an aspect, a reduced level of at least one alkaloid comprises a reduction of anatabine by between 1% and 60% as compared to a control tobacco plant when grown under comparable conditions. In an aspect, a reduced level of at least one alkaloid comprises a reduction of anatabine by between 1% and 50% as compared to a control tobacco plant when grown under comparable conditions. In an aspect, a reduced level of at least one alkaloid comprises a reduction of anatabine by between 1% and 40% as compared to a control tobacco plant when grown under comparable conditions. In an aspect, a reduced level of at least one alkaloid comprises a reduction of anatabine by between 1% and 30% as compared to a control tobacco plant when grown under comparable conditions. In an aspect, a reduced level of at least one alkaloid comprises a reduction of anatabine by between 1% and 20% as compared to a control tobacco plant when grown under comparable conditions. In an aspect, a reduced level of at least one alkaloid comprises a reduction of anatabine by between 1% and 10% as compared to a control tobacco plant when grown under comparable conditions. In an aspect, a reduced level of at least one alkaloid comprises a reduction of anatabine by between 1% and 5% as compared to a control tobacco plant when grown under comparable conditions. In an aspect, a reduced level of at least one alkaloid comprises a reduction of anatabine by between 10% and 75% as compared to a control tobacco plant when grown under comparable conditions. In an aspect, a reduced level of at least one alkaloid comprises a reduction of anatabine by between 10% and 50% as compared to a control tobacco plant when grown under comparable conditions. In an aspect, a reduced level of at least one alkaloid comprises a reduction of anatabine by between 10% and 25% as compared to a control tobacco plant when grown under comparable conditions.

In an aspect, a modified tobacco plant comprises an anatabine level of less than or equal to 1.5 mg/g of dry weight. In an aspect, a modified tobacco plant comprises an anatabine level of less than or equal to 1.4 mg/g of dry weight. In an aspect, a modified tobacco plant comprises an anatabine level of less than or equal to 1.3 mg/g of dry weight. In an aspect, a modified tobacco plant comprises an anatabine level of less than or equal to 1.2 mg/g of dry weight. In an aspect, a modified tobacco plant comprises an anatabine level of less than or equal to 1.1 mg/g of dry weight. In an aspect, a modified tobacco plant comprises an anatabine level of less than or equal to 1.0 mg/g of dry weight. In an aspect, a modified tobacco plant comprises an anatabine level of less than or equal to 0.9 mg/g of dry weight. In an aspect, a modified tobacco plant comprises an anatabine level of less than or equal to 0.8 mg/g of dry weight. In an aspect, a modified tobacco plant comprises an anatabine level of less than or equal to 0.7 mg/g of dry weight. In an aspect, a modified tobacco plant comprises an anatabine level of less than or equal to 0.6 mg/g of dry weight. In an aspect, a modified tobacco plant comprises an anatabine level of less than or equal to 0.5 mg/g of dry weight. In an aspect, a modified tobacco plant comprises an anatabine level of less than or equal to 0.4 mg/g of dry weight. In an aspect, a modified tobacco plant comprises an anatabine level of less than or equal to 0.3 mg/g of dry weight. In an aspect, a modified tobacco plant comprises an anatabine level of less than or equal to 0.25 mg/g of dry weight. In an aspect, a modified tobacco plant comprises an anatabine level of less than or equal to 0.2 mg/g of dry weight.

In an aspect, a reduced level of at least one alkaloid comprises a reduction of anabasine by at least 0.5% as compared to a control tobacco plant when grown under comparable conditions. In an aspect, a reduced level of at least one alkaloid comprises a reduction of anabasine by at least 1% as compared to a control tobacco plant when grown under comparable conditions. In an aspect, a reduced level of at least one alkaloid comprises a reduction of anabasine by at least 2% as compared to a control tobacco plant when grown under comparable conditions. In an aspect, a reduced level of at least one alkaloid comprises a reduction of anabasine by at least 3% as compared to a control tobacco plant when grown under comparable conditions. In an aspect, a reduced level of at least one alkaloid comprises a reduction of anabasine by at least 4% as compared to a control tobacco plant when grown under comparable conditions. In an aspect, a reduced level of at least one alkaloid comprises a reduction of anabasine by at least 5% as compared to a control tobacco plant when grown under comparable conditions. In an aspect, a reduced level of at least one alkaloid comprises a reduction of anabasine by at least 10% as compared to a control tobacco plant when grown under comparable conditions. In an aspect, a reduced level of at least one alkaloid comprises a reduction of anabasine by at least 15% as compared to a control tobacco plant when grown under comparable conditions. In an aspect, a reduced level of at least one alkaloid comprises a reduction of anabasine by at least 20% as compared to a control tobacco plant when grown under comparable conditions. In an aspect, a reduced level of at least one alkaloid comprises a reduction of anabasine by at least 25% as compared to a control tobacco plant when grown under comparable conditions. In an aspect, a reduced level of at least one alkaloid comprises a reduction of anabasine by at least 35% as compared to a control tobacco plant when grown under comparable conditions. In an aspect, a reduced level of at least one alkaloid comprises a reduction of anabasine by at least 50% as compared to a control tobacco plant when grown under comparable conditions. In an aspect, a reduced level of at least one alkaloid comprises a reduction of anabasine by at least 75% as compared to a control tobacco plant when grown under comparable conditions. In an aspect, a reduced level of at least one alkaloid comprises a reduction of anabasine by at least 90% as compared to a control tobacco plant when grown under comparable conditions.

In an aspect, a reduced level of at least one alkaloid comprises a reduction of anabasine by between 1% and 99% as compared to a control tobacco plant when grown under comparable conditions. In an aspect, a reduced level of at least one alkaloid comprises a reduction of anabasine by between 1% and 90% as compared to a control tobacco plant when grown under comparable conditions. In an aspect, a reduced level of at least one alkaloid comprises a reduction of anabasine by between 1% and 80% as compared to a control tobacco plant when grown under comparable conditions. In an aspect, a reduced level of at least one alkaloid comprises a reduction of anabasine by between 1% and 70% as compared to a control tobacco plant when grown under comparable conditions. In an aspect, a reduced level of at least one alkaloid comprises a reduction of anabasine by between 1% and 60% as compared to a control tobacco plant when grown under comparable conditions. In an aspect, a reduced level of at least one alkaloid comprises a reduction of anabasine by between 1% and 50% as compared to a control tobacco plant when grown under comparable conditions. In an aspect, a reduced level of at least one alkaloid comprises a reduction of anabasine by between 1% and 40% as compared to a control tobacco plant when grown under comparable conditions. In an aspect, a reduced level of at least one alkaloid comprises a reduction of anabasine by between 1% and 30% as compared to a control tobacco plant when grown under comparable conditions. In an aspect, a reduced level of at least one alkaloid comprises a reduction of anabasine by between 1% and 20% as compared to a control tobacco plant when grown under comparable conditions. In an aspect, a reduced level of at least one alkaloid comprises a reduction of anabasine by between 1% and 10% as compared to a control tobacco plant when grown under comparable conditions. In an aspect, a reduced level of at least one alkaloid comprises a reduction of anabasine by between 1% and 5% as compared to a control tobacco plant when grown under comparable conditions. In an aspect, a reduced level of at least one alkaloid comprises a reduction of anabasine by between 10% and 75% as compared to a control tobacco plant when grown under comparable conditions. In an aspect, a reduced level of at least one alkaloid comprises a reduction of anabasine by between 10% and 50% as compared to a control tobacco plant when grown under comparable conditions. In an aspect, a reduced level of at least one alkaloid comprises a reduction of anabasine by between 10% and 25% as compared to a control tobacco plant when grown under comparable conditions.

In an aspect, a modified tobacco plant comprises an anabasine level of less than or equal to 0.6 mg/g of dry weight. In an aspect, a modified tobacco plant comprises an anabasine level of less than or equal to 0.5 mg/g of dry weight. In an aspect, a modified tobacco plant comprises an anabasine level of less than or equal to 0.4 mg/g of dry weight. In an aspect, a modified tobacco plant comprises an anabasine level of less than or equal to 0.3 mg/g of dry weight. In an aspect, a modified tobacco plant comprises an anabasine level of less than or equal to 0.25 mg/g of dry weight. In an aspect, a modified tobacco plant comprises an anabasine level of less than or equal to 0.2 mg/g of dry weight. In an aspect, a modified tobacco plant comprises an anabasine level of less than or equal to 0.15 mg/g of dry weight. In an aspect, a modified tobacco plant comprises an anabasine level of less than or equal to 0.1 mg/g of dry weight.

In an aspect, a reduced level of at least one alkaloid comprises a reduction of nornicotine by at least 0.5% as compared to a control tobacco plant when grown under comparable conditions. In an aspect, a reduced level of at least one alkaloid comprises a reduction of nornicotine by at least 1% as compared to a control tobacco plant when grown under comparable conditions. In an aspect, a reduced level of at least one alkaloid comprises a reduction of nornicotine by at least 2% as compared to a control tobacco plant when grown under comparable conditions. In an aspect, a reduced level of at least one alkaloid comprises a reduction of nornicotine by at least 3% as compared to a control tobacco plant when grown under comparable conditions. In an aspect, a reduced level of at least one alkaloid comprises a reduction of nornicotine by at least 4% as compared to a control tobacco plant when grown under comparable conditions. In an aspect, a reduced level of at least one alkaloid comprises a reduction of nornicotine by at least 5% as compared to a control tobacco plant when grown under comparable conditions. In an aspect, a reduced level of at least one alkaloid comprises a reduction of nornicotine by at least 10% as compared to a control tobacco plant when grown under comparable conditions. In an aspect, a reduced level of at least one alkaloid comprises a reduction of nornicotine by at least 15% as compared to a control tobacco plant when grown under comparable conditions. In an aspect, a reduced level of at least one alkaloid comprises a reduction of nornicotine by at least 20% as compared to a control tobacco plant when grown under comparable conditions. In an aspect, a reduced level of at least one alkaloid comprises a reduction of nornicotine by at least 25% as compared to a control tobacco plant when grown under comparable conditions. In an aspect, a reduced level of at least one alkaloid comprises a reduction of nornicotine by at least 35% as compared to a control tobacco plant when grown under comparable conditions. In an aspect, a reduced level of at least one alkaloid comprises a reduction of nornicotine by at least 50% as compared to a control tobacco plant when grown under comparable conditions. In an aspect, a reduced level of at least one alkaloid comprises a reduction of nornicotine by at least 75% as compared to a control tobacco plant when grown under comparable conditions. In an aspect, a reduced level of at least one alkaloid comprises a reduction of nornicotine by at least 90% as compared to a control tobacco plant when grown under comparable conditions.

In an aspect, a reduced level of at least one alkaloid comprises a reduction of nornicotine by between 1% and 99% as compared to a control tobacco plant when grown under comparable conditions. In an aspect, a reduced level of at least one alkaloid comprises a reduction of nornicotine by between 1% and 90% as compared to a control tobacco plant when grown under comparable conditions. In an aspect, a reduced level of at least one alkaloid comprises a reduction of nornicotine by between 1% and 80% as compared to a control tobacco plant when grown under comparable conditions. In an aspect, a reduced level of at least one alkaloid comprises a reduction of nornicotine by between 1% and 70% as compared to a control tobacco plant when grown under comparable conditions. In an aspect, a reduced level of at least one alkaloid comprises a reduction of nornicotine by between 1% and 60% as compared to a control tobacco plant when grown under comparable conditions. In an aspect, a reduced level of at least one alkaloid comprises a reduction of nornicotine by between 1% and 50% as compared to a control tobacco plant when grown under comparable conditions. In an aspect, a reduced level of at least one alkaloid comprises a reduction of nornicotine by between 1% and 40% as compared to a control tobacco plant when grown under comparable conditions. In an aspect, a reduced level of at least one alkaloid comprises a reduction of nornicotine by between 1% and 30% as compared to a control tobacco plant when grown under comparable conditions. In an aspect, a reduced level of at least one alkaloid comprises a reduction of nornicotine by between 1% and 20% as compared to a control tobacco plant when grown under comparable conditions. In an aspect, a reduced level of at least one alkaloid comprises a reduction of nornicotine by between 1% and 10% as compared to a control tobacco plant when grown under comparable conditions. In an aspect, a reduced level of at least one alkaloid comprises a reduction of nornicotine by between 1% and 5% as compared to a control tobacco plant when grown under comparable conditions. In an aspect, a reduced level of at least one alkaloid comprises a reduction of nornicotine by between 10% and 75% as compared to a control tobacco plant when grown under comparable conditions. In an aspect, a reduced level of at least one alkaloid comprises a reduction of nornicotine by between 10% and 50% as compared to a control tobacco plant when grown under comparable conditions. In an aspect, a reduced level of at least one alkaloid comprises a reduction of nornicotine by between 10% and 25% as compared to a control tobacco plant when grown under comparable conditions.

In an aspect, a modified tobacco plant comprises a nornicotine level of less than or equal to 1.0 mg/g of dry weight. In an aspect, a modified tobacco plant comprises a nornicotine level of less than or equal to 0.9 mg/g of dry weight. In an aspect, a modified tobacco plant comprises a nornicotine level of less than or equal to 0.8 mg/g of dry weight. In an aspect, a modified tobacco plant comprises a nornicotine level of less than or equal to 0.7 mg/g of dry weight. In an aspect, a modified tobacco plant comprises a nornicotine level of less than or equal to 0.6 mg/g of dry weight. In an aspect, a modified tobacco plant comprises a nornicotine level of less than or equal to 0.5 mg/g of dry weight. In an aspect, a modified tobacco plant comprises a nornicotine level of less than or equal to 0.4 mg/g of dry weight. In an aspect, a modified tobacco plant comprises a nornicotine level of less than or equal to 0.3 mg/g of dry weight. In an aspect, a modified tobacco plant comprises a nornicotine level of less than or equal to 0.2 mg/g of dry weight.

Plants

As used herein, a tobacco plant can be from any plant from the *Nicotiana* genus including, but not limited to *Nicotiana tabacum, Nicotiana amplexicaulis* PI 271989; *Nicotiana benthamiana* PI 555478; *Nicotiana bigelovii* PI 555485; *Nicotiana debneyi; Nicotiana excelsior* PI 224063; *Nicotiana glutinosa* PI 555507; *Nicotiana goodspeedii* PI 241012; *Nicotiana gossei* PI 230953; *Nicotiana hesperis* PI 271991; *Nicotiana knightiana* PI 555527; *Nicotiana maritima* PI 555535; *Nicotiana megalosiphon* PI 555536; *Nicotiana nudicaulis* PI 555540; *Nicotiana paniculata* PI 555545; *Nicotiana plumbaginifolia* PI 555548; *Nicotiana repanda* PI 555552; *Nicotiana rustica; Nicotiana suaveolens* PI 230960; *Nicotiana sylvestris* PI 555569; *Nicotiana tomentosa* PI 266379; *Nicotiana tomentosiformis*; and *Nicotiana trigonophylla* PI 555572. In an aspect, a tobacco plant described here is a *Nicotiana tabacum* plant.

In an aspect, tobacco parts provided include, but are not limited to, a leaf, a stem, a root, a trichome, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In an aspect, tobacco part provided does not include seed. In an aspect, this disclosure provides tobacco plant cells, tissues, and organs that are not reproductive material and do not mediate the natural reproduction of the plant. In another aspect, this disclosure also provides tobacco plant cells, tissues, and organs that are reproductive material and mediate the natural reproduction of the plant. In another aspect, this disclosure provides tobacco plant cells, tissues, and organs that cannot maintain themselves via photosynthesis. In another aspect, this disclosure provides somatic tobacco plant cells. Somatic cells, contrary to germline cells, do not mediate plant reproduction.

Cells, tissues and organs can be from seed, fruit, leaf, cotyledon, hypocotyl, meristem, embryos, endosperm, root, shoot, stem, trichome, pod, flower, inflorescence, stalk, pedicel, style, stigma, receptacle, petal, sepal, pollen, anther, filament, ovary, ovule, pericarp, phloem, vascular tissue. In another aspect, this disclosure provides a tobacco plant chloroplast. In a further aspect, this disclosure provides epidermal cells, stomata cell, leaf or root hairs, a storage root, or a tuber. In another aspect, this disclosure provides a tobacco protoplast.

Skilled artisans understand that tobacco plants naturally reproduce via seeds, not via asexual reproduction or vegetative propagation. In an aspect, this disclosure provides tobacco endosperm.

This disclosure provides cells from tobacco plants provided herein.

As used herein, a "progeny tobacco plant" or "progeny tobacco seed" can be from any filial generation, e.g., $F_1$, $F_2$, $F_3$, $F_4$, $F_5$, $F_6$, $F_7$, etc.

In an aspect, a tobacco plant, or part thereof, is of a tobacco variety selected from the group consisting of a flue-cured variety, a bright variety, a Burley variety, a Virginia variety, a Maryland variety, a dark variety, a Galpio variety, an Oriental variety, and a Turkish variety. In one aspect, a modified tobacco plant, or part thereof, provided herein is of a tobacco variety selected from the group consisting of a flue-cured variety, a bright variety, a Burley variety, a Virginia variety, a Maryland variety, a dark variety, a Galpio variety, an Oriental variety, and a Turkish variety.

In an aspect, a tobacco cell is of a tobacco variety selected from the group consisting of a flue cured variety, a bright variety, a Burley variety, a Virginia variety, a Maryland variety, a dark variety, a Galpio variety, an Oriental variety, and a Turkish variety. In an aspect, a modified tobacco cell is of a tobacco variety selected from the group consisting of a flue cured variety, a bright variety, a Burley variety, a Virginia variety, a Maryland variety, a dark variety, a Galpio variety, an Oriental variety, and a Turkish variety.

In an aspect, a tobacco leaf is of a tobacco variety selected from the group consisting of a flue cured variety, a bright variety, a Burley variety, a Virginia variety, a Maryland variety, a dark variety, a Galpio variety, an Oriental variety, and a Turkish variety.

In an aspect, a cured tobacco leaf or plant part is of a tobacco variety selected from the group consisting of a flue cured variety, a bright variety, a Burley variety, a Virginia variety, a Maryland variety, a dark variety, a Galpio variety, an Oriental variety, and a Turkish variety. Skilled artisans further understand that cured tobacco does not constitute a living organism and is not capable of growth or reproduction Flue-cured tobaccos (also called "Virginia" or "bright" tobaccos) amount to approximately 40% of world tobacco production. Flue-cured tobaccos are often also referred to as "bright tobacco" because of the golden-yellow to deep-orange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the United States of America. In one aspect, tobacco plants or seeds or modified tobacco plants or seeds provided herein are of a flue-cured tobacco variety selected from the group consisting of the varieties listed in Table 2, and any variety essentially derived from any one of the foregoing varieties. See WO 2004/041006 A1. In a further aspect, modified tobacco plants or seeds provided herein are in a flue-cured variety selected from the group consisting of K326, K346, and NC 196.

TABLE 2

| Flue-cured Tobacco Varieties | | |
| --- | --- | --- |
| 400 (TC 225) | K 346 | Reams 134 |
| 401 (TC 226) | K 346 (TC 569) | Reams 158 |
| 401 Cherry Red (TC 227) | K 358 | Reams 713 |
| 401 Cherry Red Free (TC 228) | K 394 (TC 321) | Reams 744 |
| Cash (TC 250) | K 399 | Reams M1 |
| Cash (TI 278) | K 399 (TC 322) | RG 11 (TC 600) |
| CC 101 | K 730 | RG 13 (TC 601) |
| CC 1063 | Lonibow (TI 1573) | RG 17 (TC 627) |
| CC 13 | Lonibow (TI 1613) | RG 22 (TC 584) |
| CC 143 | McNair 10 (TC 330) | RG 8 (TC 585) |
| CC 200 | McNair 135 (TC 337) | RG 81 (TC 618) |
| CC 27 | McNair 30 (TC 334) | RG H51 |
| CC 301 | McNair 373 (TC 338) | RG4H 217 |
| CC 33 | McNair 944 (TC 339) | RGH 12 |
| CC 35 | MK94 (TI 1512) | RGH 4 |
| CC 37 | MS K 326 | RGH 51 |
| CC 400 | MS NC 71 | RGH 61 |
| CC 500 | MS NC 72 | SC 58 (TC 400) |
| CC 600 | NC 100 | SC 72 (TC 403) |
| CC 65 | NC 102 | Sp. G-168 |
| CC 67 | NC 1071 (TC 364) | SPEIGHT 168 |
| CC 700 | NC 1125-2 | Speight 168 (TC 633) |
| CC 800 | NC 12 (TC 346) | Speight 172 (TC 634) |
| CC 900 | NC 1226 | Speight 178 |
| Coker 139 (TC 259) | NC 196 | Speight 179 |
| Coker 139 yb1, yb2 | NC 2326 (TC 365) | Speight 190 |
| Coker 140 (TC 260) | NC 27 NF (TC 349) | Speight 196 |
| Coker 176 (TC 262) | NC 291 | SPEIGHT 220 |
| Coker 187 (TC 263) | NC 297 | SPEIGHT 225 |
| Coker 187-Hicks (TC 265) | NC 299 | SPEIGHT 227 |
| Coker 209 (TC 267) | NC 37 NF (TC 350) | SPEIGHT 236 |
| Coker 258 (TC 270) | NC 471 | Speight G-10 (TC 416) |
| Coker 298 (TC 272) | NC 55 | Speight G-102 |
| Coker 316 (TC 273) | NC 567 (TC 362) | Speight G-108 |
| Coker 319 (TC 274) | NC 60 (TC 352) | Speight G-111 |
| Coker 347 (TC 275) | NC 606 | Speight G-117 |
| Coker 371-Gold (TC 276) | NC 6140 | Speight G-126 |
| Coker 411 (TC 277) | NC 71 | Speight G-15 (TC 418) |
| Coker 48 (TC 253) | NC 72 | Speight G-23 |
| Coker 51 (TC 254) | NC 729 (TC 557) | Speight G-28 (TC 420) |
| Coker 86 (TC 256) | NC 810 (TC 659) | Speight G-33 |

TABLE 2-continued

| Flue-cured Tobacco Varieties | | |
|---|---|---|
| CU 263 (TC 619) | NC 82 (TC 356) | Speight G-41 |
| CU 561 | NC 8640 | Speight G-5 |
| DH95-1562-1 | NC 89 (TC 359) | Speight G-52 |
| Dixie Bright 101 (TC 290) | NC 92 | Speight G-58 |
| Dixie Bright 102 (TC 291) | NC 925 | Speight G-70 |
| Dixie Bright 244 (TC 292) | NC 95 (TC 360) | Speight G-70 (TC 426) |
| Dixie Bright 27 (TC 288) | NC 98 (TC 361) | Speight G-80 (TC 427) |
| Dixie Bright 28 (TC 289) | NC EX 24 | Speight NF3 (TC 629) |
| GF 157 | NC PY 10 (TC 367) | STNCB |
| GF 318 | NC TG 61 | VA 182 |
| GL 26H | Oxford 1 (TC 369) | VA 45 (TC 559) |
| GL 338 | Oxford 1-181 (TC 370) | Vesta 30 (TC 439) |
| GL 350 | Oxford 2 (TC 371) | Vesta 33 (TC 440) |
| GL 368 | Oxford 207 (TC 632) | Vesta 5 (TC 438) |
| GL 395 | Oxford 26 (TC 373) | Vesta 62 (TC 441) |
| GL 600 | Oxford 3 (TC 372) | Virginia (TI 220) |
| GL 737 | Oxford 414 NF | Virginia (TI 273) |
| GL 939 | PD 611 (TC 387) | Virginia (TI 877) |
| GL 939 (TC 628) | PVH 03 | Virginia 115 (TC 444) |
| Hicks (TC 310) | PVH 09 | Virginia 21 (TC 443) |
| Hicks Broadleaf (TC 311) | PVH 1118 | Virginia Bright (TI 964) |
| K 149 (TC 568) | PVH 1452 | Virginia Bright Leaf (TC 446) |
| K 317 | PVH 1600 | Virginia Gold (TC 447) |
| K 326 | PVH 2110 | White Stem Orinoco (TC 451) |
| K 326 (TC 319) | PVH 2275 | |
| K 340 (TC 320) | R 83 (Line 256-1) (TI 1400) | |

Air-cured tobaccos include "Burley," "Maryland," and "dark" tobaccos. The common factor linking air-cured tobaccos is that curing occurs primarily without artificial sources of heat and humidity. Burley tobaccos are light to dark brown in color, high in oil, and low in sugar. Burley tobaccos are typically air-cured in barns. Major Burley growing countries include Argentina, Brazil, Italy, Malawi, and the United States of America.

Maryland tobaccos are extremely fluffy, have good burning properties, low nicotine and a neutral aroma. Major Maryland growing countries include the United States of America and Italy.

In one aspect, tobacco plants or seeds or modified tobacco plants or seeds provided herein are of a Burley tobacco variety selected from the group consisting of the tobacco varieties listed in Table 3, and any variety essentially derived from any one of the foregoing varieties. In a further aspect, modified tobacco plants or seeds provided herein are in a Burley variety selected from the group consisting of TN 90, KT 209, KT 206, KT212, and HB 4488.

TABLE 3

| Burley Tobacco Varieties | | |
|---|---|---|
| 4407 LC | HB 4108P | KY 54 (TC 71) |
| AA-37-1 | HB 4151P | KY 56 (TC 72) |
| Burley 21 (TC 7) | HB 4192P | KY 56 (TC 72) |
| Burley 49 (TC 10) | HB 4194P | KY 57 (TC 73) |
| Burley 64 (TC 11) | HB 4196 | KY 58 (TC 74) |
| Burley Mammoth KY | HB 4488 | KY 8654 (TC 77) |
| 16 (TC 12) | | |
| Clay 402 | HB 4488P | KY 8959 |
| Clay 403 | HB04P | KY 9 (TC 54) |
| Clay 502 | HB 4488 LC | KY 907 LC |
| Clays 403 | HIB 21 | KY 908 (TC 630) |
| GR 10 (TC 19) | HPB 21 | NBH 98 (Screened) |
| GR 10 (TC 19) | HY 403 | NC 1206 |
| GR 10A (TC 20) | Hybrid 403 LC | NC 129 |
| GR 13 (TC 21) | Hybrid 404 LC | NC 2000 LC |
| GR 14 (TC 22) | Hybrid 501 LC | NC 2002 LC |
| GR 149 LC | KDH-959 (TC 576) | NC 3 LC |
| GR 153 | KDH-960 (TC 577) | NC 5 LC |

TABLE 3-continued

| Burley Tobacco Varieties | | |
|---|---|---|
| GR 17 (TC 23) | KT 200 LC | NC 6 LC |
| GR 17B (TC 24) | KT 204 LC | NC 7 LC |
| GR 18 (TC 25) | KT 206 LC | NC BH 129 LC |
| GR 19 (TC 26) | KT 209 LC | NC03-42-2 |
| GR 2 (TC 15) | KT 210 LC | Newton 98 |
| GR 24 (TC 27) | KT 212 LC | R 610 LC |
| GR 36 (TC 28) | KT 215 LC | R 630 LC |
| GR 38 (TC 29) | KY 1 (TC 52) | R 7-11 |
| GR 38A (TC 30) | KY 10 (TC 55) | R 59-116 LC |
| GR 40 (TC 31) | KY 12 (TC 56) | RG 17 |
| GR 42 (TC 32) | KY 14 (TC 57) | TKF 1801 LC |
| GR 42C (TC 33) | KY 14 × L8 LC | TKF 2002 LC |
| GR 43 (TC 34) | KY 15 (TC 58) | TKF 4024 LC |
| GR 44 (TC 35) | KY 16 (TC 59) | TKF 4028 LC |
| GR 45 (TC 36) | KY 17 (TC 60) | TKF 6400 LC |
| GR 46 (TC 37) | KY 19 (TC 61) | TKF 7002 LC |
| GR 48 (TC 38) | KY 21 (TC 62) | TKS 2002 LC |
| GR 5 (TC 16) | KY 22 (TC 63) | TN 86 (TC 82) |
| GR 53 (TC 39) | KY 24 (TC 64) | TN 90 LC |
| GR 6 (TC 17) | KY 26 (TC 65) | TN 97 Hybrid LC |
| GR 9 (TC 18) | KY 33 (TC 66) | TN 97 LC |
| GR139 NS | KY 34 (TC 67) | VA 116 |
| GR139 S | KY 35 (TC 68) | VA 119 |
| HB 04P | KY 41A (TC 69) | Virgin A |
| | | Mutante (TI 1406) |
| HB 04P LC | KY 5 (TC 53) | Virginia 509 (TC 84) |
| HB 3307P LC | KY 52 (TC 70) | |

In another aspect, tobacco plants or seeds or modified tobacco plants or seeds provided herein are of a Maryland tobacco variety selected from the group consisting of the tobacco varieties listed in Table 4, and any variety essentially derived from any one of the foregoing varieties.

TABLE 4

| Maryland Tobacco Varieties |
|---|
| Maryland 10 (TC 498) |
| Maryland 14 D2 (TC 499) |
| Maryland 201 (TC 503) |
| Maryland 21 (TC 500) |

TABLE 4-continued

| Maryland Tobacco Varieties |
| --- |
| Maryland 341 (TC 504) |
| Maryland 40 |
| Maryland 402 |
| Maryland 59 (TC 501) |
| Maryland 601 |
| Maryland 609 (TC 505) |
| Maryland 64 (TC 502) |
| Maryland 872 (TC 506) |
| Maryland Mammoth (TC 507) |

Dark air-cured tobaccos are distinguished from other tobacco types primarily by its curing process, which gives dark air-cured tobacco its medium-brown to dark-brown color and a distinct aroma. Dark air-cured tobaccos are mainly used in the production of chewing tobacco and snuff.

In one aspect, modified tobacco plants or seeds provided herein are of a dark air-cured tobacco variety selected from the group consisting of Sumatra, Jatim, Dominican Cubano, Besuki, One sucker, Green River, Virginia sun-cured, and Paraguan Passado, and any variety essentially derived from any one of the foregoing varieties.

Dark fire-cured tobaccos are generally cured with low-burning wood fires on the floors of closed curing barns. Dark fire-cured tobaccos are typically used for making pipe blends, cigarettes, chewing tobacco, snuff, and strong-tasting cigars. Major growing regions for dark fire-cured tobaccos are Tennessee, Kentucky, and Virginia in the United States of America. In one aspect, tobacco plants or seeds or modified tobacco plants or seeds provided herein are of a dark fire-cured tobacco variety selected from the group consisting of the tobacco varieties listed in Table 5, and any variety essentially derived from any one of the foregoing varieties.

TABLE 5

| Dark Tobacco Varieties | | |
| --- | --- | --- |
| Black Mammoth (TC 461) | KY 171 (TC 475) | PD 7309 LC |
| Black Mammoth Small Stalk (TC 641) | KY 171 LC | PD 7312 LC |
| Certified Madole (TC 463) | KY 171 NS | PD 7318 LC |
| D-534-A-1 (TC 464) | KY 180 (TC 573) | PD 7319 LC |
| DAC ULT 302 | KY 190 (TC 574) | Petico M PG04 |
| DAC ULT 303 | Little Crittenden | PY KY 160 (TC 612) |
| DAC ULT 306 | Little Crittenden (TC 476) | PY KY 171 (TC 613) |
| DAC ULT 308 | Little Crittenden LC (certified) | Shirey |
| DAC ULT 312 | Little Crittenden PhPh | TI 1372 |
| DF 300 (TC 465) | Lizard Tail Turtle Foot | TN D94 |
| DF 485 (TC 466) | Madole (TC 478) | TN D94 (TC 621) |
| DF 516 (TC 467) | Madole (TC 479) | TN D950 |
| DF 911 (TC 468) | MS KY 171 | TN D950 (PhPh) |
| DT 508 | MS NL Madole LC | TN D950 |
| DT 518 (Screened) | MS TN D950 LC | TN D950 (TC 622) |
| DT 538 LC | Nance (TC 616) | TR Madole (TC 486) |
| DT 592 | Narrow Leaf Madole LC (certified) | VA 309 |
| Improved Madole (TC 471) | Neal Smith Madole (TC 646) | VA 309 (TC 560) |
| Jernigan's Madole (TC 472) | Newtons VH Madole | VA 309 LC (certified) |
| KT 14LC | NL Madole | VA 310 (TC 487) |
| KT D17LC | NL Madole (PhPh) | VA 331 (TC 592) |
| KT D4 LC | NL Madole (TC 484) | VA 355 (TC 638) |
| KT D6 LC | NL Madole LC | VA 359 |
| KT D8 LC | NL Madole LC (PhPh) | VA 359 (Screened) |
| KY 153 (TC 216) | NL Madole NS | VA 359 (TC 639) |
| KY 157 (TC 217) | One Sucker (TC 224) | VA 359 LC (certified) |
| KY 160 | OS 400 | VA 403 (TC 580) |
| KY 160 (TC 218) | PD 302H | VA 405 (TC 581) |
| KY 163 (TC 219) | PD 312H | VA 409 (TC 562) |
| KY 165 (TC 220) | PD 318H | VA 510 (TC 572) |
| KY 170 (TC 474) | PD 7302 LC | |
| KY 171 (PhPh) | PD 7305 | |

Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant size, small leaf size, and unique aroma properties of Oriental tobacco varieties are a result of their adaptation to the poor soil and stressful climatic conditions in which they have been developed. In one aspect, tobacco plants or seeds or modified tobacco plants or seeds provided herein are of an Oriental tobacco variety selected from the group consisting of the tobacco varieties listed in Table 6, and any variety essentially derived from any one of the foregoing varieties.

TABLE 6

| Oriental Tobacco Varieties | | |
|---|---|---|
| Bafra (TI 1641) | Edirne (TI 1671) | Samsun (TC 536) |
| Bahce (TI 1730) | Ege (TI 1642) | Samsun 959 (TI 1570) |
| Bahia (TI 1416) | Ege-64 (TI 1672) | Samsun Evkaf (TI 1723) |
| Bahia (TI 1455) | Izmir (Akhisar) (TI 1729) | Samsun Holmes NN (TC 540) |
| Baiano (TI 128) | Izmir (Gavurkoy) (TI 1727) | Samsun Maden (TI 1647) |
| Basma | Izmir Ege 64 | Samsun NO 15 (TC 541) |
| Basma (TI 1666) | Izmir-Incekara (TI 1674) | Samsun-BLK SHK Tol (TC 542) |
| Basma Drama | Izmir-Ozbas (TI 1675) | Samsun-Canik (TI 1678) |
| Basma Hybrid (PhPh) | Jaka Dzebel (TI 1326) | Samsun-Maden (TI 1679) |
| Basma Zihna I | Kaba-Kulak | Saribaptar 407 - Izmir Region |
| Bitlis (TI 1667) | Kagoshima Maruba (TI 158) | Smyrna (TC 543) |
| Bitlis (TI 1725) | Katerini | Smyrna No. 23 (TC 545) |
| Bubalovac (TI 1282) | Katerini S53 | Smyrna No. 9 (TC 544) |
| Bursa (TI 1650) | Krumovgrad 58 | Smyrna-Blk Shk Tol (TC 546) |
| Bursa (TI 1668) | MS Basma | Trabzon (TI 1649) |
| Canik (TI 1644) | MS Katerini S53 | Trabzon (TI 1682) |
| Djebel 174 (TI 1492) | Nevrokop 1146 | Trapezund 161 (TI 1407) |
| Djebel 359 (TI 1493) | Ozbas (TI 1645) | Turkish (TC 548) |
| Djebel 81 | Perustitza (TI 980) | Turkish Angshit (TI 90) |
| Dubec 566 (TI 1409) | Prilep (TI 1291) | Turkish Samsum (TI 92) |
| Dubec 7 (TI 1410) | Prilep (TI 1325) | Turkish Tropizoid (TI 93) |
| Dubek 566 (TI 1567) | Prilep 12-2/1 | Turkish Varotic (TI 89) |
| Duzce (TI 1670) | Prilep 23 | Xanthi (TI 1662) |

In an aspect, tobacco plants or seeds or modified tobacco plants or seeds provided herein are of an cigar tobacco variety selected from the group consisting of the tobacco varieties listed in Table 7, and any variety essentially derived from any one of the foregoing varieties.

TABLE 7

| Cigar Tobacco Varieties | | |
|---|---|---|
| Bahai (TI 62) | Castillo Negro, Blanco, Pina (TI 449) | Enshu (TI 1586) |
| Beinhart 1000 | Caujaro (TI 893) | Florida 301 |
| Beinhart 1000 (TI 1562) | Chocoa (TI 289) | Florida 301 (TC 195) |
| Beinhart 1000-1 (TI 1561) | Chocoa (TI 313) | PA Broadleaf (TC 119) |
| Bergerac C | Connecticut 15 (TC 183) | Pennsylvania Broadleaf |
| Bergerac C (TI 1529) | Connecticut Broadleaf | Pennsylvania Broadleaf (TC 119) |
| Big Cuban (TI 1565) | Connecticut Broadleaf (TC 186) | Petite Havana SR1 |
| Castillo Negro, Blanco, Pina (TI 448) | Connecticut Shade (TC 188) | Petite Havana SR1 (TC 105) |
| Castillo Negro, Blanco, Pina (TI 448A) | Criollo, Colorado (TI 1093) | |

In an aspect, tobacco plants or seeds or modified tobacco plants or seeds provided herein are of a tobacco variety selected from the group consisting of the tobacco varieties listed in Table 8, and any variety essentially derived from any one of the foregoing varieties.

TABLE 8

| Other Tobacco Varieties |
| --- |
| Chocoa (TI 319) |
| Hoja Parada (TI 1089) |
| Hoja Parado (Galpoa) (TI 1068) |
| Perique (St. James Parrish) |
| Perique (TC 556) |
| Perique (TI 1374) |
| Sylvestris (TI 984) |
| TI 179 |

In an aspect, a tobacco plant, or part thereof, is from a variety selected from the group consisting of the tobacco varieties listed in Table 2, Table 3, Table 4, Table 5, Table 6, Table 7, and Table 8. In another aspect, a tobacco plant, or part thereof, is from a variety listed in Table 2. In another aspect, a tobacco plant, or part thereof, is from a variety listed in Table 3. In another aspect, a tobacco plant, or part thereof, is from a variety listed in Table 4. In another aspect, a tobacco plant, or part thereof, is from a variety listed in Table 5. In another aspect, a tobacco plant, or part thereof, is from a variety listed in Table 6. In another aspect, a tobacco plant, or part thereof, is from a variety listed in Table 7. In another aspect, a tobacco plant, or part thereof, is from a variety listed in Table 8.

In an aspect, a modified tobacco plant, or part thereof, is from a variety selected from the group consisting of the tobacco varieties listed in Table 2, Table 3, Table 4, Table 5, Table 6, Table 7, and Table 8. In an aspect, a modified tobacco plant, or part thereof, is from a variety listed in Table 2. In another aspect, a modified tobacco plant, or part thereof, is from a variety listed in Table 3. In another aspect, a modified tobacco plant, or part thereof, is from a variety listed in Table 4. In another aspect, a modified tobacco plant, or part thereof, is from a variety listed in Table 5. In another aspect, a modified tobacco plant, or part thereof, is from a variety listed in Table 6. In another aspect, a modified tobacco plant, or part thereof, is from a variety listed in Table 7. In another aspect, a modified tobacco plant, or part thereof, is from a variety listed in Table 8.

In an aspect, a tobacco seed is from a variety selected from the group consisting of the tobacco varieties listed in Table 2, Table 3, Table 4, Table 5, Table 6, Table 7, and Table 8. In another aspect, a tobacco seed is from a variety listed in Table 2. In another aspect, a tobacco seed is from a variety listed in Table 3. In another aspect, a tobacco seed is from a variety listed in Table 4. In another aspect, a tobacco seed is from a variety listed in Table 5. In another aspect, a tobacco seed is from a variety listed in Table 6. In another aspect, a tobacco seed is from a variety listed in Table 7. In another aspect, a tobacco seed is from a variety listed in Table 8.

In an aspect, a tobacco cell is from a variety selected from the group consisting of the tobacco varieties listed in Table 2, Table 3, Table 4, Table 5, Table 6, Table 7, and Table 8. In another aspect, a tobacco cell is from a variety listed in Table 2. In another aspect, a tobacco cell is from a variety listed in Table 3. In another aspect, a tobacco cell is from a variety listed in Table 4. In another aspect, a tobacco cell is from a variety listed in Table 5. In another aspect, a tobacco cell is from a variety listed in Table 6. In another aspect, a tobacco cell is from a variety listed in Table 7. In another aspect, a tobacco cell is from a variety listed in Table 8.

All foregoing mentioned specific varieties of flue-cured, dark air-cured, Burley, Maryland, dark fire-cured, cigar, or Oriental type are listed only for exemplary purposes. Any additional flue-cured, dark air-cured, Burley, Maryland, dark fire-cured, cigar, or Oriental varieties are also contemplated in the present application.

In an aspect, a tobacco plant or variety provided herein is an inbred tobacco plant or variety. As used herein, an "inbred" tobacco variety is a variety that has been bred for genetic homogeneity.

As used herein, a "hybrid" is created by crossing two plants from different varieties or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an E×F hybrid. The first and second hybrids can be further crossed to create the higher order hybrid (C×D)×(E×F) comprising genetic information from all four parent varieties. In an aspect, a modified tobacco plant provided herein is a hybrid tobacco plant. In another aspect, a modified tobacco seed provided herein is a hybrid tobacco seed. In an aspect, a tobacco plant or variety provided herein is a hybrid tobacco plant or variety. In another aspect, a modified tobacco plant provided herein is a hybrid tobacco plant.

In an aspect, this disclosure provides a method for producing a modified tobacco plant comprising: (a) crossing at least one tobacco plant of a first tobacco variety with at least one tobacco plant of a second tobacco variety to produce at least one progeny tobacco seed, where the at least one tobacco plant of the first tobacco variety comprises a non-natural mutation in an endogenous nucleic acid sequence, where the endogenous nucleic acid sequence encodes a polypeptide comprising an amino acid sequence at least 80% identical or similar to an amino acid sequence selected from the group consisting of SEQ ID NOs: 117-174, where the non-natural mutation is not present in the endogenous nucleic acid sequence in a control tobacco plant of the first tobacco variety; and (b) selecting for at least one progeny tobacco seed, or a plant germinated therefrom, wherein the at least one tobacco seed or plant germinated therefrom comprises the non-natural mutation. In another aspect, this disclosure provides a method for producing a modified tobacco plant comprising: (a) crossing at least one tobacco plant of a first tobacco variety with at least one tobacco plant of a second tobacco variety to produce at least one progeny tobacco seed, where the at least one tobacco plant of the first tobacco variety comprises a non-natural mutation in an endogenous nucleic acid sequence at least 80% identical to a nucleic acid sequence selected from the group consisting of SEQ ID NOs: 1-58, where the non-natural mutation is not present in the endogenous nucleic acid sequence in a control tobacco plant of the first tobacco variety; and (b) selecting for at least one progeny tobacco seed, or a plant germinated therefrom, wherein the at least one tobacco seed or plant germinated therefrom comprises the non-natural mutation. In another aspect, this disclosure provides a method for producing a modified tobacco plant comprising: (a) crossing at least one tobacco plant of a first tobacco variety with at least one tobacco plant of a second tobacco variety to produce at least one progeny tobacco seed, where the at least one tobacco plant of the first tobacco variety comprises a non-natural mutation in an endogenous nucleic acid sequence at least 80% identical to a nucleic acid sequence selected from the group consisting of SEQ ID NOs: 59-116, where the non-natural mutation is not present in the endogenous nucleic acid sequence in a control tobacco plant of the first tobacco variety; and (b) selecting for at least one progeny tobacco seed, or a plant germinated therefrom, wherein the at least one tobacco seed or plant germinated therefrom comprises the non-natural mutation. In another aspect, this disclosure provides a method for producing a modified tobacco plant comprising: (a) crossing at least one tobacco plant of a first tobacco variety with at least one tobacco plant of a second tobacco variety to produce at least one progeny tobacco seed, where the at least one tobacco plant of the first tobacco variety comprises a non-natural mutation in an endogenous nucleic acid sequence selected from the group consisting of SEQ ID NOs: 1-116, where the non-natural mutation is not present in the endogenous nucleic acid sequence in a control tobacco plant of the first tobacco variety; and (b) selecting for at least one progeny tobacco seed, or a plant germinated therefrom, wherein the at least one tobacco seed or plant germinated therefrom comprises the non-natural mutation. In an aspect, in any of the foregoing methods, the first tobacco variety and second tobacco variety are the same tobacco variety. In another aspect, in any of the foregoing methods, the first tobacco variety and second tobacco variety are two different tobacco varieties.

In an aspect, this disclosure provides a method for producing a modified tobacco plant comprising: (a) crossing at least one tobacco plant of a first tobacco variety with at least one tobacco plant of a second tobacco variety to produce at least one progeny tobacco seed, where the at least one tobacco plant of the first tobacco variety comprises a recombinant DNA construct, where the recombinant DNA construct comprises a heterologous promoter operably linked to a nucleic acid sequence encoding at least one small RNA molecule capable of binding to and reducing the expression of an endogenous nucleic acid sequence encoding a polypeptide at least 80% identical or similar to an amino acid sequence selected from the group consisting of SEQ ID NOs: 117-174, were the recombinant DNA construct is not present in a control tobacco plant of the first tobacco variety; and (b) selecting for at least one progeny tobacco seed, or a plant germinated therefrom, wherein the at least one progeny tobacco seed or plant germinated therefrom comprises the recombinant DNA construct. In another aspect, this disclosure provides a method for producing a modified tobacco plant comprising: (a) crossing at least one tobacco plant of a first tobacco variety with at least one tobacco plant of a second tobacco variety to produce at least one progeny tobacco seed, where the at least one tobacco plant of the first tobacco variety comprises a recombinant DNA construct, where the recombinant DNA construct comprises a heterologous promoter operably linked to a nucleic acid sequence encoding at least one small RNA molecule capable of binding to and reducing the expression of an endogenous nucleic acid sequence at least 80% identical or similar to a nucleic acid sequence selected from the group consisting of SEQ ID NOs: 1-58, were the recombinant DNA construct is not present in a control tobacco plant of the first tobacco variety; and (b) selecting for at least one progeny tobacco seed, or a plant germinated therefrom, wherein the at least one progeny tobacco seed or plant germinated therefrom comprises the recombinant DNA construct. In another aspect, this disclosure provides a method for producing a modified tobacco plant comprising: (a) crossing at least one tobacco plant of a first tobacco variety with at least one tobacco plant of a second tobacco variety to produce at least one progeny tobacco seed, where the at least one tobacco plant of the first tobacco variety comprises a recombinant DNA construct, where the recombinant DNA construct comprises a heterologous promoter operably linked to a nucleic acid sequence encoding at least one small RNA molecule capable of binding to and reducing the expression of an endogenous nucleic acid sequence at least 80% identical or similar to a nucleic acid sequence selected from the group consisting of SEQ ID NOs: 59-116, were the recombinant DNA construct is not present in a control tobacco plant of the first tobacco variety; and (b) selecting for at least one progeny tobacco seed, or a plant germinated therefrom, where the at least one progeny tobacco seed or plant germinated therefrom comprises the recombinant DNA construct. In an aspect, in any of the foregoing methods, the first tobacco variety and second tobacco variety are the same tobacco variety. In another aspect, in any of the foregoing methods, the first tobacco variety and second tobacco variety are two different tobacco varieties.

In an aspect, this disclosure provides a method for producing a modified tobacco plant comprising: (a) crossing at least one tobacco plant of a first tobacco variety with at least one tobacco plant of a second tobacco variety to produce at least one progeny tobacco seed, where the at least one tobacco plant of the first tobacco variety comprises a recombinant DNA construct, where the recombinant DNA construct comprises a heterologous promoter operably linked to a nucleic acid sequence encoding a polypeptide comprising an amino acid sequence at least 80% identical or similar to an amino acid sequence selected from the group consisting of SEQ ID NOs: 117-174, where the recombinant DNA construct is not present in a control tobacco plant of the first tobacco variety; and (b) selecting for at least one progeny tobacco seed, or a plant germinated therefrom, where the at least one progeny tobacco seed or plant germinated therefrom comprises the recombinant DNA construct. In another aspect, this disclosure provides a method for producing a modified tobacco plant comprising: (a) crossing at least one tobacco plant of a first tobacco variety with at least one tobacco plant of a second tobacco variety to produce at least one progeny tobacco seed, where the at least one tobacco plant of the first tobacco variety comprises a recombinant DNA construct, where the recombinant DNA construct comprises a heterologous promoter operably linked to a nucleic acid sequence at least 80% identical to a nucleic acid sequence selected from the group consisting of SEQ ID NOs: 1-58, where the recombinant DNA construct is not present in a control tobacco plant of the first tobacco variety; and (b) selecting for at least one progeny tobacco seed, or a plant germinated therefrom, where the at least one progeny tobacco seed or plant germinated therefrom comprises the recombinant DNA construct. In another aspect, this disclosure provides a method for producing a modified tobacco plant comprising: (a) crossing at least one tobacco plant of a first tobacco variety with at least one tobacco plant of a second tobacco variety to produce at least one progeny tobacco seed, where the at least one tobacco plant of the first tobacco variety comprises a recombinant DNA construct, where the recombinant DNA construct comprises a heterologous promoter operably linked to a nucleic acid sequence at least 80% identical to a nucleic acid sequence selected from the group consisting of SEQ ID NOs: 59-116, where the recombinant DNA construct is not present in a control tobacco plant of the first tobacco variety; and (b) selecting for at least one progeny tobacco seed, or a plant germinated therefrom, where the at least one progeny tobacco seed or plant germinated therefrom comprises the recombinant DNA construct. In an aspect, in any of the foregoing methods, the first tobacco variety and second tobacco variety are the same tobacco variety. In another aspect, in any of the foregoing methods, the first tobacco variety and second tobacco variety are two different tobacco varieties.

As used herein, the term "crossing" refers to the deliberate mating of two plants. In an aspect, crossing comprises pollination and/or fertilization of a first tobacco plant by a second tobacco plant. The two tobacco plants being crossed can be distantly related, closely related, or identical. In an aspect, the two tobacco plants being crossed are both modified tobacco plants. In an aspect, the two tobacco plants being crossed are of the same tobacco variety. In an aspect, the two tobacco plants being crossed are of two different tobacco varieties. In an aspect, one of the two tobacco plants being crossed is male sterile. In an aspect, one of the two tobacco plants being crossed is female sterile. In an aspect, at least one of the two tobacco plants being crossed is a hybrid tobacco plant. In an aspect, at least one of the two tobacco plants being crossed is a modified tobacco plant.

In an aspect, a tobacco plant or variety provided herein is male sterile. In another aspect, a tobacco plant or variety provided herein is cytoplasmic male sterile (CMS). In an aspect, a modified tobacco plant or variety provided herein is male sterile. In another aspect, a modified tobacco plant or variety provided herein is cytoplasmic male sterile (CMS). Male sterile tobacco plants can be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y. 761 pp.

In another aspect, a tobacco plant or variety provided herein is female sterile. In another aspect, a modified tobacco plant or variety provided herein is female sterile. As a non-limiting example, female sterile plants can be made by mutating the STIG1 gene. See, for example, Goldman et al. 1994, *EMBO Journal* 13:2976-2984. In an aspect, a modified tobacco plant provided herein is female sterile.

Unless specified otherwise, all comparisons to control plants require similar growth conditions or comparable growth conditions for the two plants being compared. As used herein, "grown under comparable conditions," "similar growth conditions" or "comparable growth conditions" refer to similar environmental conditions and/or agronomic practices for growing and making meaningful comparisons between two or more plant genotypes so that neither environmental conditions nor agronomic practices would contribute to or explain any difference observed between the two or more plant genotypes. Environmental conditions include, for example, light, temperature, water (humidity), and nutrition (e.g., nitrogen and phosphorus). Agronomic practices include, for example, seeding, clipping, undercutting, transplanting, topping, and suckering. See Chapters 4B and 4C of Tobacco, Production, Chemistry and Technology, Davis & Nielsen, eds., Blackwell Publishing, Oxford (1999), pp 70-103. As used herein, a "control plant" refers to a plant of identical, or nearly identical, genetic makeup as the modified plant being compared, except for the non-natural mutation or recombinant DNA construct provided herein that was introduced to the modified plant.

In an aspect, a modified tobacco plant described herein is a low-alkaloid variety or low-alkaloid plant. As a non-limiting example, LA Burley 21 (LA BU21) is a low-alkaloid variety of tobacco. LA BU21 is produced by incorporation of a low alkaloid gene(s) from a Cuban cigar variety into Burley 21 through several backcrosses. It has approximately 0.2% total alkaloids (dry weight) compared to the about 3.5% (dry weight) of its parent, Burley 21. LA BU21 has a leaf grade well below commercially acceptable standards. LA BU21 also exhibits other unfavorable leaf phenotypes characterized by lower yields, delayed ripening and senescence, higher susceptibility to insect herbivory, and poor end-product quality after curing. LA BU21 leaves further exhibit traits such as higher polyamine content, higher chlorophyll content and more mesophyll cells per unit leaf area. See US2019/0271000 for more characterization of LA BU21 leaf phenotypes.

In an aspect, the present disclosure provides tobacco plants, or part thereof, comprising a low nicotine or low alkaloid-conferring mutation or transgene (e.g., a genetic modification in or targeting one or more ADC, AO, or ODC) and capable of producing a leaf comprising a comparable level of one or more polyamines relative to a comparable leaf of a control plant not comprising the same mutation or transgene. In one aspect, a comparable level of one or more polyamines is within 20%, 17.5%, 15%, 12.5%, 10%, 7.5%, 5%, 2.5%, or 1% of the level in a comparable leaf of a control plant not comprising the same mutation or transgene. In an aspect, a comparable level of one or more polyamines is between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, or between 19% and 20% of the level in a comparable leaf of a control plant not comprising the same mutation or transgene. In a further aspect, a comparable level of one or more polyamines is between 0.5% and 5%, between 5% and 10%, or between 10% and 20% of the level in a comparable leaf of a control plant not comprising the same mutation or transgene.

In an aspect, the present disclosure provides ADC mutant or transgenic tobacco plants or parts thereof, AO mutant or transgenic tobacco plants or parts thereof, or ODC mutant or transgenic tobacco plants or parts thereof, capable of producing a leaf comprising a comparable chlorophyll level relative to a comparable leaf of a control plant not comprising the same mutation or transgene. In one aspect, a comparable chlorophyll level is within 20%, 17.5%, 15%, 12.5%, 10%, 7.5%, 5%, 2.5%, or 1% of the level in a comparable leaf of a control plant not comprising the same mutation or transgene. In an aspect, a comparable chlorophyll level is between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, or between 19% and 20% of the level in a comparable leaf of a control plant not comprising the same mutation or transgene. In a further aspect, a comparable chlorophyll level is between 0.5% and 5%, between 5% and 10%, or between 10% and 20% of the level in a comparable leaf of a control plant not comprising the same mutation or transgene.

In an aspect, the present disclosure provides ADC mutant or transgenic tobacco plants or parts thereof, AO mutant or transgenic tobacco plants or parts thereof, or ODC mutant or transgenic tobacco plants or parts thereof, capable of producing a leaf comprising a comparable number of mesophyll cell per unit of leaf area relative to a comparable leaf of a control plant not comprising the same mutation or transgene. In one aspect, a comparable number of mesophyll cell per unit of leaf area is within 20%, 17.5%, 15%, 12.5%, 10%, 7.5%, 5%, 2.5%, or 1% of the level in a comparable leaf of a control plant not comprising the same mutation or transgene. In an aspect, a comparable number of mesophyll cell per unit of leaf area is between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, or between 19% and 20% of the level in a comparable leaf of a control plant not comprising the same mutation or transgene. In a further aspect, a comparable number of mesophyll cell per unit of leaf area is between 0.5% and 5%, between 5% and 10%, or between 10% and 20% of the level in a comparable leaf of a control plant not comprising the same mutation or transgene.

In an aspect, the present disclosure provides ADC mutant or transgenic tobacco plants or parts thereof, AO mutant or transgenic tobacco plants or parts thereof, or ODC mutant or transgenic tobacco plants or parts thereof, capable of producing a leaf comprising a comparable epidermal cell size relative to a comparable leaf of a control plant not comprising the same mutation or transgene. In one aspect, a comparable epidermal cell size is within 20%, 17.5%, 15%, 12.5%, 10%, 7.5%, 5%, 2.5%, or 1% of the level in a comparable leaf of a control plant not comprising the same mutation or transgene. In an aspect, a comparable epidermal cell size is between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, or between 19% and 20% of the level in a comparable leaf of a control plant not comprising the same mutation or transgene. In a further aspect, a comparable epidermal cell size is between 0.5% and 5%, between 5% and 10%, or between 10% and 20% of the level in a comparable leaf of a control plant not comprising the same mutation or transgene.

In an aspect, the present disclosure provides ADC mutant or transgenic tobacco plants or parts thereof, AO mutant or transgenic tobacco plants or parts thereof, or ODC mutant or transgenic tobacco plants or parts thereof, capable of producing a leaf comprising a comparable leaf yield relative to a comparable leaf of a control plant not comprising the same mutation or transgene. In one aspect, a comparable leaf yield is within 20%, 17.5%, 15%, 12.5%, 10%, 7.5%, 5%, 2.5%, or 1% of the level in a comparable leaf of a control plant not comprising the same mutation or transgene. In an aspect, a comparable leaf yield is between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, or between 19% and 20% of the level in a comparable leaf of a control plant not comprising the same mutation or transgene. In a further aspect, a comparable leaf yield is between 0.5% and 5%, between 5% and 10%, or between 10% and 20% of the level in a comparable leaf of a control plant not comprising the same mutation or transgene.

In an aspect, the present disclosure provides ADC mutant or transgenic tobacco plants or parts thereof, AO mutant or transgenic tobacco plants or parts thereof, or ODC mutant or transgenic tobacco plants or parts thereof, exhibiting a comparable insect herbivory susceptibility relative to a comparable leaf of a control plant not comprising the same mutation or transgene. In one aspect, a comparable insect herbivory susceptibility is within 20%, 17.5%, 15%, 12.5%, 10%, 7.5%, 5%, 2.5%, or 1% of the level in a comparable leaf of a control plant not comprising the same mutation or transgene. In an aspect, a comparable insect herbivory susceptibility is between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, or between 19% and 20% of the level in a comparable leaf of a control plant not comprising the same mutation or transgene. In a further aspect, a comparable insect herbivory susceptibility is between 0.5% and 5%, between 5% and 10%, or between 10% and 20% of the level in a comparable leaf of a control plant not comprising the same mutation or transgene.

Any genetic modification provided herein can be introduced into any ADC mutant or transgenic tobacco plants or parts thereof, AO mutant or transgenic tobacco plants or parts thereof, or ODC mutant or transgenic tobacco plants or parts thereof.

Insect herbivory susceptibility level can be assayed by methods known in the art, for example, in an insect feeding assay. In short, a quarter inch layer of 0.7% agar in water is added to a 100 mm Petri dish and allowed to solidify. Leaf discs are cut from the petri dish lid, placed in the plates and pushed gently into the agar. Leaf discs are taken from plants at the 4-5 leaf stage. Discs were taken from lamina only to exclude major midribs. A single disc is taken from each of the four largest leaves of the plant generating 4 replicates per plant. Four plants are sampled for a total of 16 biological replicates test line. A single budworm (e.g., *Heliothis* sp., *Helicoverpa* sp.) at the second instar stage is added to the leaf and allowed to feed for 48 hours at ambient temperature. After 48 hours the budworm larvae are weighed and final larval weights are recorded.

In an aspect, a tobacco plant, or part thereof, comprises relative to a control tobacco plant: a first genome modification providing a lower level of nicotine or total alkaloid (e.g., in or targeting one or more ADC, AO, or ODC genes), and a second genome modification providing a comparable level of one or more traits selected from the group consisting of total leaf polyamine level, total root polyamine level, total leaf chlorophyll level, mesophyll cell number per leaf area unit, and leaf epidermal cell size; and where the control plant does not have both the first and the second genome modifications. In one aspect, a tobacco plant, or part thereof, comprises relative to a control tobacco plant: a first genome modification providing a lower level of nicotine or total alkaloid (e.g., in or targeting one or more ADC, AO, or ODC genes), and a second genome modification providing a comparable level of total leaf polyamine level, where the control plant does not have both the first and the second genome modifications. In an aspect, a tobacco plant, or part thereof, comprises relative to a control tobacco plant: a first genome modification providing a lower level of nicotine or total alkaloid (e.g., in or targeting one or more ADC, AO, or ODC genes), and a second genome modification providing a comparable level of total root polyamine level, where the control plant does not have both the first and the second genome modifications. In one aspect, a tobacco plant, or part thereof, comprises relative to a control tobacco plant: a first genome modification providing a lower level of nicotine or total alkaloid (e.g., in or targeting one or more ADC, AO, or ODC genes), and a second genome modification providing a comparable level of total leaf chlorophyll level, where the control plant does not have both the first and the second genome modifications. In an aspect, a tobacco plant, or part thereof, comprises relative to a control tobacco plant: a first genome modification providing a lower level of nicotine or total alkaloid (e.g., in or targeting one or more ADC, AO, or ODC genes), and a second genome modification providing a comparable level of mesophyll cell number per leaf area unit, where the control plant does not have both the first and the second genome modifications. In one aspect, a tobacco plant, or part thereof, comprises relative to a control tobacco plant: a first genome modification providing a lower level of nicotine or total alkaloid (e.g., in or targeting one or more ADC, AO, or ODC genes), and a second genome modification providing a comparable level of leaf epidermal cell size, where the control plant does not have both the first and the second genome modifications. In an aspect, a second genome modification is in or targeting an ADC, AO, or ODC gene.

In an aspect, a first genome modification, a second genome modification, or both comprise a transgene, a mutation, or both. In one aspect, a genome modification, a second genome modification, or both comprise a transgene. In an aspect, a first genome modification, a second genome modification, or both comprise a mutation. In one aspect, a first genome modification, a second genome modification, or both are not transgene-based. In an aspect, a first genome modification, a second genome modification, or both are not mutation-based.

In an aspect, tobacco plants provided herein comprise a reduced amount of total conjugated polyamines in leaves relative to the control tobacco plant. In one aspect, tobacco plants provided herein comprise a reduced amount of total conjugated polyamines in roots relative to the control tobacco plant. Used here, conjugated polyamines include, but are not limited to, soluble conjugated polyamines such as phenolamides containing a backbone consisting of a free polyamine (e.g., putrescine, spermine, and/or spermidine) conjugated with one or more phenylpropanoids such as ferulic, caffeic and courmaric acids. Conjugated polyamines also include, but are not limited to, insoluble conjugated polyamines incorporated into structural polymers such as lignin. In an aspect, tobacco plants provided herein comprise a reduced amount of total free polyamines (e.g., putrescine, spermine, and spermidine) in leaves relative to the control tobacco plant. In one aspect, tobacco plants provided herein comprise a reduced amount of total conjugated polyamines in roots relative to the control tobacco plant. In an aspect, tobacco plants provided herein comprise a reduced amount of total conjugated form of one or more polyamines selected from the group consisting of putrescine, spermidine and spermine in leaves relative to the control tobacco plant. In one aspect, tobacco plants provided herein comprise a reduced amount of total conjugated form of one or more polyamines selected from the group consisting of putrescine, spermidine and spermine in roots relative to the control tobacco plant. In an aspect, tobacco plants provided herein comprise a reduced amount of total free form of one or more polyamines selected from the group consisting of putrescine, spermidine and spermine in leaves relative to the control tobacco plant. In one aspect, tobacco plants provided herein comprise a reduced amount of total conjugated form of one or more polyamines selected from the group consisting of putrescine, spermidine and spermine in roots relative to the control tobacco plant.

In an aspect, a characteristic or a trait of a tobacco plant described here are measured at a time selected from the group consisting of immediately before flowering, at topping, 1 week-post-topping (WPT), 2 WPT, 3 WPT, 4 WPT, 5 WPT, 6 WPT, 7 WPT, 8 WPT, and at harvest. In one aspect, tobacco plants provided herein comprising a first and a second genome modification are capable of producing a leaf with a leaf grade comparable to that of a leaf from a control plant. In an aspect, tobacco plants provided herein comprising a first and a second genome modification have a total leaf yield comparable to a control plant.

In one aspect, a tobacco plant of the present disclosure comprises a nic1 mutation, a nic2 mutation, or both.

In an aspect, a modified tobacco plant provided herein further comprises a transgene or mutation directly suppressing the expression or activity of one or more, two or more, three or more, four or more, five or more, six or more, seven or more, eight or more, nine or more, ten or more, eleven or more, twelve or more, thirteen or more, fourteen or more, fifteen or more, sixteen or more, or seventeen or more genes or loci encoding a protein selected from the group consisting of agmatine deiminase (AIC), arginase, diamine oxidase, methylputrescine oxidase (MPO), NADH dehydrogenase, phosphoribosylanthranilate isomerase (PRAI), putrescine N-methyltransferase (PMT), quinolate phosphoribosyl transferase (QPT), S-adenosyl-methionine synthetase (SAMS), A622, NBB1, berberine bridge enzyme-like (BBL), MYC2, Nic1_ERF, Nic2_ERF, ethylene response factor (ERF) transcription factor, nicotine uptake permease (NUP), and MATE transporter. See Dewey and Xie, Molecular genetics of alkaloid biosynthesis in *Nicotiana tabacum*, Phytochemistry 94 (2013) 10-27.

In an aspect, a modified tobacco plant provided herein further comprises a mutation in an ERF gene of Nic2 locus (Nic2_ERF). In an aspect, a modified tobacco plant provided herein further comprises one or more mutations in one or more, two or more, three or more, four or more, five or more, six or more, seven or more, eight or more, nine or more, or all ten genes selected from the group consisting of ERF32, ERF34, ERF39, ERF189, ERF115, ERF221, ERF104, ERF179, ERF17, and ERF168. See Shoji et al., *Plant Cell*, (10):3390-409 (2010); and Kajikawa et al., *Plant physiol.* 2017, 174:999-1011. In one aspect, a modified tobacco plant provided herein further comprises one or more mutations in ERF189, ERF115, or both. In an aspect, a modified tobacco plant provided herein further comprises one or more transgenes targeting and suppressing a gene encoding one or more, two or more, three or more, four or more, five or more, six or more, seven or more, eight or more, nine or more, or all ten proteins selected from the group consisting of ERF32, ERF34, ERF39, ERF189, ERF115, ERF221, ERF104, ERF179, ERF17, and ERF168.

In an aspect, a modified tobacco plant provided herein further comprises a mutation in an ERF gene of Nic1 locus (Nic1_ERF) (or Nic1b locus as in WO/2019/140297). See also WO/2018/237107. In an aspect, a modified tobacco plant provided herein further comprises one or more mutations in two or more, three or more, four or more, five or more, six or more, or seven or more genes selected from the group consisting of ERF101, ERF110, ERFnew, ERF199, ERF19, ERF130, ERF16, ERF29, ERF210, and ERF91L2. See WO/2019/140297 and Kajikawa et al., *Plant physiol.* 2017, 174:999-1011. In an aspect, a modified tobacco plant provided herein further comprises one or more mutations in one or more, two or more, three or more, four or more, five or more, or all six genes selected from the group consisting of ERFnew, ERF199, ERF19, ERF29, ERF210, and ERF91L2. In an aspect, a modified tobacco plant provided herein further comprises one or more transgenes targeting and suppressing a gene encoding one or more, two or more, three or more, four or more, five or more, six or more, or seven or more genes selected from the group consisting of ERF101, ERF110, ERFnew, ERF199, ERF19, ERF130, ERF16, ERF29, ERF210, and ERF91L2.

In an aspect, a modified tobacco plant provided herein further comprise a first genetic modification comprising a mutation in a gene or locus encoding a protein selected from the group consisting of aspartate oxidase, agmatine deiminase (AIC), arginase, diamine oxidase, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), and S-adenosyl-methionine synthetase (SAMS), A622, NBB1, BBL, MYC2, Nic1_ERF, Nic2_ERF, ethylene response factor (ERF) transcription factor, nicotine uptake permease (NUP), and MATE transporter, and further comprises a second genetic modification targeting one or more amino acid sequences at least 80% identical or similar to an amino acid sequence selected from the group consisting of SEQ ID NOs: 117-174. In one aspect, a modified tobacco plant provided herein comprises a first genetic modification comprises a transgene targeting and suppressing a gene or locus encoding a protein selected from the group consisting of aspartate oxidase, agmatine deiminase (AIC), arginase, diamine oxidase, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), and S-adenosyl-methionine synthetase (SAMS), A622, NBB1, BBL, MYC2, Nic1, Nic2, ethylene response factor (ERF) transcription factor, nicotine uptake permease (NUP), and MATE transporter, and further comprises a second genetic modification targeting one or more amino acid sequences at least 80% identical or similar to an amino acid sequence selected from the group consisting of SEQ ID NOs: 117-174.

Cured Tobacco/Tobacco Products

In an aspect, this disclosure provides a method comprising preparing a tobacco product using cured tobacco material from a modified tobacco plant, where the modified tobacco plant comprises a non-natural mutation in an endogenous nucleic acid sequence encoding a polypeptide comprising an amino acid sequence at least 80% identical or similar to an amino acid sequence selected from the group consisting of SEQ ID NOs: 117-174. In another aspect, this disclosure provides a method comprising preparing a tobacco product using cured tobacco material from a modified tobacco plant, where the modified tobacco plant comprises a non-natural mutation in an endogenous nucleic acid sequence at least 80% identical to a nucleic acid sequence selected from the group consisting of SEQ ID NOs: 1-58. In another aspect, this disclosure provides a method comprising preparing a tobacco product using cured tobacco material from a modified tobacco plant, where the modified tobacco plant comprises a non-natural mutation in an endogenous nucleic acid sequence at least 80% identical to a nucleic acid sequence selected from the group consisting of SEQ ID NOs: 59-116.

In an aspect, this disclosure provides a method comprising preparing a tobacco product using cured tobacco material from a modified tobacco plant, where the modified tobacco plant comprises a recombinant DNA construct, where the recombinant DNA construct comprises a heterologous promoter operably linked to a nucleic acid sequence encoding at least one small RNA molecule capable of binding to and reducing the expression of an endogenous nucleic acid sequence encoding a polypeptide at least 80% identical or similar to an amino acid sequence selected from the group consisting of SEQ ID NOs: 117-174. In another aspect, this disclosure provides a method comprising preparing a tobacco product using cured tobacco material from a modified tobacco plant, where the modified tobacco plant comprises a recombinant DNA construct, and where the recombinant DNA construct comprises a heterologous promoter operably linked to a nucleic acid sequence encoding at least one small RNA molecule capable of binding to and reducing the expression of an endogenous nucleic acid sequence at least 80% identical to a nucleic acid sequence selected from the group consisting of SEQ ID NOs: 1-58. In another aspect, this disclosure provides a method comprising preparing a tobacco product using cured tobacco material from a modified tobacco plant, where the modified tobacco plant comprises a recombinant DNA construct, and where the recombinant DNA construct comprises a heterologous promoter operably linked to a nucleic acid sequence encoding at least one small RNA molecule capable of binding to and reducing the expression of an endogenous nucleic acid sequence at least 80% identical to a nucleic acid sequence selected from the group consisting of SEQ ID NOs: 59-116.

In an aspect, this disclosure provides a method comprising preparing a tobacco plant using cured tobacco material from a modified tobacco plant, where the modified tobacco plant comprises a recombinant DNA construct, and where the recombinant DNA construct comprises a heterologous promoter operably linked to a nucleic acid sequence encoding a polypeptide comprising an amino acid sequence at least 80% identical or similar to an amino acid sequence selected from the group consisting of SEQ ID NOs: 117-174. In another aspect, this disclosure provides a method comprising preparing a tobacco plant using cured tobacco material from a modified tobacco plant, where the modified tobacco plant comprises a recombinant DNA construct, and where the recombinant DNA construct comprises a heterologous promoter operably linked to a nucleic acid sequence at least 80% identical to a nucleic acid sequence selected from the group consisting of SEQ ID NOs: 1-58. In another aspect, this disclosure provides a method comprising preparing a tobacco plant using cured tobacco material from a modified tobacco plant, where the modified tobacco plant comprises a recombinant DNA construct, and where the recombinant DNA construct comprises a heterologous promoter operably linked to a nucleic acid sequence at least 80% identical to a nucleic acid sequence selected from the group consisting of SEQ ID NOs: 59-116.

"Curing" is the aging process that reduces moisture and brings about the destruction of chlorophyll giving tobacco leaves a golden color and by which starch is converted to sugar. Cured tobacco therefore has a higher reducing sugar content and a lower starch content compared to harvested green leaf. In one aspect, tobacco plants or plant components provided herein can be cured using conventional means, e.g., flue-cured, barn-cured, fire-cured, air-cured or sun-cured. See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (e.g., a hogshead) or cardboard cartons in compressed conditions for several years (e.g., two to five years), at a moisture content ranging from 10% to about 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation.

Information regarding the harvesting of burley and dark tobacco varieties can be found in the 2019-2020 *Burley and Dark Tobacco Production Guide* (December 2018) published by the University of Kentucky, The University of Tennessee, Virginia Polytechnic Institute and State University, and North Carolina State University, which is incorporated herein by reference in its entirety.

In an aspect, this disclosure provides cured tobacco material from any tobacco plant, or part thereof, provided herein. In an aspect, this disclosure provides cured tobacco material from any modified tobacco plant, or part thereof, provided herein.

In an aspect, cured tobacco material comprises tobacco material selected from the group selected from cured leaf material, cured stem material, cured bud material, cured flower material, and cured root material. In another aspect, cured tobacco material comprises cured leaf material, cured stem material, or both. In a further aspect, cured tobacco material comprises cured leaf material. In yet another aspect, cured tobacco material comprises cured stem material.

In an aspect, cured tobacco material comprises flue-cured tobacco material. In another aspect, cured tobacco material comprises air-cured tobacco material. In another aspect, cured tobacco material comprises fire-cured tobacco material. In another aspect, cured tobacco material comprises sun-cured tobacco material. In another aspect, cured tobacco material provided herein is selected from the group consisting of air-cured tobacco material, fire-cured tobacco material, sun-cured tobacco material, and flue-cured tobacco material. In another aspect, cured tobacco material is from a tobacco variety selected from the group consisting of a flue-cured variety, a bright variety, a Burley variety, a Virginia variety, a Maryland variety, a dark variety, an Oriental variety, and a Turkish variety.

In an aspect, cured tobacco leaf provided herein is selected from the group consisting of air-cured tobacco leaf, fire-cured tobacco leaf, sun-cured tobacco leaf, and flue-cured tobacco leaf. In an aspect, cured tobacco leaf is from a tobacco variety selected from the group consisting of a flue-cured variety, a bright variety, a Burley variety, a Virginia variety, a Maryland variety, a dark variety, an Oriental variety, and a Turkish variety.

Fermentation typically is characterized by high initial moisture content, heat generation, and a 10 to 20% loss of dry weight. See, for example, U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cured, aged, and fermented tobacco can be further processed (e.g., cut, shredded, expanded, or blended). See, for example, U.S. Pat. Nos.

4,528,993; 4,660,577; and 4,987,907. In an aspect, this disclosure provides fermented tobacco material from any tobacco plant, or part thereof, provided herein. In another aspect, this disclosure provides fermented tobacco material from any modified tobacco plant, or part thereof, provided herein.

Tobacco material obtained from the tobacco lines, varieties or hybrids of the present disclosure can be used to make tobacco products. As used herein, "tobacco product" is defined as any product made or derived from tobacco that is intended for human use or consumption. In an aspect, this disclosure provides a tobacco product comprising plant material from a tobacco plant provided herein. In another aspect, this disclosure provides a tobacco product comprising plant material from a modified tobacco plant provided herein. In another aspect, this disclosure provides a tobacco product comprising cured tobacco material. In another aspect, this disclosure provides a tobacco product comprising fermented tobacco material. In another aspect, this disclosure provides a tobacco product comprising a tobacco blend.

Tobacco products include, without limitation, cigarette products (e.g., cigarettes and bidi cigarettes), cigar products (e.g., cigar wrapping tobacco and cigarillos), pipe tobacco products, products derived from tobacco, tobacco-derived nicotine products, oral nicotine products, smokeless tobacco products (e.g., moist snuff, dry snuff, and chewing tobacco), films, chewables, tabs, shaped parts, gels, consumable units, insoluble matrices, hollow shapes, reconstituted tobacco, expanded tobacco, and the like. See, e.g., U.S. Patent Publication No. US 2006/0191548.

As used herein, "cigarette" refers a tobacco product having a "rod" and "filler". The cigarette "rod" includes the cigarette paper, filter, plug wrap (used to contain filtration materials), tipping paper that holds the cigarette paper (including the filler) to the filter, and all glues that hold these components together. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette).

In an aspect, a tobacco product comprises reconstituted tobacco. In another aspect, this disclosure provides reconstituted tobacco comprising cured tobacco material. As used herein, "reconstituted tobacco" refers to a part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars.

In an aspect, a tobacco product comprises expanded tobacco. As used herein, "expanded tobacco" refers to a part of tobacco filler which is processed through expansion of suitable gases so that the tobacco is "puffed" resulting in reduced density and greater filling capacity. It reduces the weight of tobacco used in cigarettes.

Tobacco products derived from plants of the present disclosure also include cigarettes and other smoking articles, particularly those smoking articles including filter elements, where the rod of smokable material includes cured tobacco within a tobacco blend. In an aspect, a tobacco product of the present disclosure is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, and cut tobacco. In another aspect, a tobacco product of the present disclosure is selected from the group consisting of a cigarette, a heated tobacco product, a kretek, a bidi cigarette, a cigar, a cigarillo, a non-ventilated cigarette, a vented recess filter cigarette, pipe tobacco, snuff, snus, chewing tobacco, moist smokeless tobacco, fine cut chewing tobacco, long cut chewing tobacco, pouched chewing tobacco product, gum, a tablet, a lozenge, and a dissolving strip.

In another aspect, a tobacco product of the present disclosure is a smokeless tobacco product. In an aspect, a smokeless tobacco product is selected from the group consisting of loose leaf chewing tobacco, plug chewing tobacco, moist snuff, nasal snuff, dry snuff, and snus.

Smokeless tobacco products are not combusted and include, but not limited to, chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat-treated smokeless tobacco. Dry snuff is finely ground tobacco that is placed in the mouth or used nasally.

In yet another aspect, a tobacco product of the present disclosure is selected from the group consisting of an electronically heated cigarette, an e-cigarette, an electronic vaporing device, and an inhalable nicotine product.

In an aspect, a tobacco product of the present disclosure can be a blended tobacco product.

In another aspect, this disclosure provides a tobacco blend comprising cured tobacco material. A tobacco blend can comprise any combination of cured tobacco, uncured tobacco, fermented tobacco, unfermented tobacco, expanded tobacco, and reconstituted tobacco.

In an aspect, a tobacco blend comprises at least 5% cured tobacco by weight. In an aspect, a tobacco blend comprises at least 10% cured tobacco by weight. In an aspect, a tobacco blend comprises at least 15% cured tobacco by weight. In an aspect, a tobacco blend comprises at least 20% cured tobacco by weight. In an aspect, a tobacco blend comprises at least 25% cured tobacco by weight. In an aspect, a tobacco blend comprises at least 30% cured tobacco by weight. In an aspect, a tobacco blend comprises at least 35% cured tobacco by weight. In an aspect, a tobacco blend comprises at least 40% cured tobacco by weight. In an aspect, a tobacco blend comprises at least 45% cured tobacco by weight. In an aspect, a tobacco blend comprises at least 50% cured tobacco by weight. In an aspect, a tobacco blend comprises at least 55% cured tobacco by weight. In an aspect, a tobacco blend comprises at least 60% cured tobacco by weight. In an aspect, a tobacco blend comprises at least 65% cured tobacco by weight. In an aspect, a tobacco blend comprises at least 70% cured tobacco by weight. In an aspect, a tobacco blend comprises at least 75% cured tobacco by weight. In an aspect, a tobacco blend comprises at least 80% cured tobacco by weight. In an aspect, a tobacco blend comprises at least 85% cured tobacco by weight. In an aspect, a tobacco blend comprises at least 90% cured tobacco by weight. In an aspect, a tobacco blend comprises at least 95% cured tobacco by weight.

In an aspect, a tobacco blend comprises at least 5% cured tobacco by volume. In an aspect, a tobacco blend comprises at least 10% cured tobacco by volume. In an aspect, a tobacco blend comprises at least 15% cured tobacco by volume. In an aspect, a tobacco blend comprises at least 20% cured tobacco by volume. In an aspect, a tobacco blend comprises at least 25% cured tobacco by volume. In an aspect, a tobacco blend comprises at least 30% cured tobacco by volume. In an aspect, a tobacco blend comprises at least 35% cured tobacco by volume. In an aspect, a tobacco blend comprises at least 40% cured tobacco by volume. In an aspect, a tobacco blend comprises at least 45% cured tobacco by volume. In an aspect, a tobacco blend comprises at least 50% cured tobacco by volume. In an aspect, a tobacco blend comprises at least 55% cured tobacco by volume. In an aspect, a tobacco blend comprises at least 60% cured tobacco by volume. In an aspect, a tobacco blend comprises at least 65% cured tobacco by volume. In an aspect, a tobacco blend comprises at least 70% cured tobacco by volume. In an aspect, a tobacco blend comprises at least 75% cured tobacco by volume. In an aspect, a tobacco blend comprises at least 80% cured tobacco by volume. In an aspect, a tobacco blend comprises at least 85% cured tobacco by volume. In an aspect, a tobacco blend comprises at least 90% cured tobacco by volume. In an aspect, a tobacco blend comprises at least 95% cured tobacco by volume.

Transformation

In an aspect, this disclosure provides a method of producing a modified tobacco plant comprising: (a) inducing a non-natural mutation in at least one tobacco cell in an endogenous nucleic acid sequence encoding a polypeptide comprising an amino acid sequence at least 80% identical or similar to an amino acid sequence selected from the group consisting of SEQ ID NOs: 117-174; (b) selecting at least one tobacco cell comprising the non-natural mutation from step (a); and (c) regenerating at least one modified tobacco plant from the at least one tobacco cell selected in step (b). In another aspect, this disclosure provides a method of producing a modified tobacco plant comprising: (a) inducing a non-natural mutation in at least one tobacco cell in an endogenous nucleic acid sequence at least 80% identical to a nucleic acid sequence selected from the group consisting of SEQ ID NOs: 1-58; (b) selecting at least one tobacco cell comprising the non-natural mutation from step (a); and (c) regenerating at least one modified tobacco plant from the at least one tobacco cell selected in step (b). In another aspect, this disclosure provides a method of producing a modified tobacco plant comprising: (a) inducing a non-natural mutation in at least one tobacco cell in an endogenous nucleic acid sequence at least 80% identical to a nucleic acid sequence selected from the group consisting of SEQ ID NOs: 59-116; (b) selecting at least one tobacco cell comprising the non-natural mutation from step (a); and (c) regenerating at least one modified tobacco plant from the at least one tobacco cell selected in step (b). In another aspect, this disclosure provides a method of producing a modified tobacco plant comprising: (a) inducing a non-natural mutation in at least one tobacco cell in an endogenous nucleic acid sequence selected from the group consisting of SEQ ID NOs: 1-116; (b) selecting at least one tobacco cell comprising the non-natural mutation from step (a); and (c) regenerating at least one modified tobacco plant from the at least one tobacco cell selected in step (b). In an aspect, any of the foregoing methods further comprises (d) growing the modified tobacco plant regenerated in step (c). In another aspect, any of the foregoing methods further comprises: (e) crossing the modified tobacco plant grown in step (d) with a second tobacco plant; and (f) obtaining at least one seed from the crossing in step (e).

In an aspect, this disclosure provides a method of producing a modified tobacco plant comprising: (a) introducing a recombinant DNA construct to at least one tobacco cell, where the recombinant DNA construct comprises a heterologous promoter operably linked to a nucleic acid encoding at least one small RNA molecule capable of binding to and reducing the expression of an endogenous nucleic acid sequence encoding a polypeptide at least 80% identical or similar to an amino acid sequence selected from the group consisting of SEQ ID NOs: 117-174; (b) selecting at least one tobacco cell comprising the recombinant DNA construct; and (c) regenerating at least one modified tobacco plant from the at least one tobacco cell selected in step (b). In another aspect, this disclosure provides a method of producing a modified tobacco plant comprising: (a) introducing a recombinant DNA construct to at least one tobacco cell, where the recombinant DNA construct comprises a heterologous promoter operably linked to a nucleic acid encoding at least one small RNA molecule capable of binding to and reducing the expression of an endogenous nucleic acid sequence at least 80% identical to a nucleic acid sequence selected from the group consisting of SEQ ID NOs: 1-58; (b) selecting at least one tobacco cell comprising the recombinant DNA construct; and (c) regenerating at least one modified tobacco plant from the at least one tobacco cell selected in step (b). In another aspect, this disclosure provides a method of producing a modified tobacco plant comprising: (a) introducing a recombinant DNA construct to at least one tobacco cell, where the recombinant DNA construct comprises a heterologous promoter operably linked to a nucleic acid encoding at least one small RNA molecule capable of binding to and reducing the expression of an endogenous nucleic acid sequence at least 80% identical to a nucleic acid sequence selected from the group consisting of SEQ ID NOs: 59-116; (b) selecting at least one tobacco cell comprising the recombinant DNA construct; and (c) regenerating at least one modified tobacco plant from the at least one tobacco cell selected in step (b). In an aspect, any of the foregoing methods further comprises (d) growing the modified tobacco plant regenerated in step (c). In another aspect, any of the foregoing methods further comprises: (e) crossing the modified tobacco plant grown in step (d) with a second tobacco plant; and (f) obtaining at least one seed from the crossing in step (e).

In an aspect, this disclosure provides a method of producing a modified tobacco plant comprising: (a) introducing a recombinant DNA construct to at least one tobacco cell, where the recombinant DNA construct comprises a heterologous promoter operably linked to a nucleic acid sequence encoding a polypeptide comprising an amino acid sequence at least 80% identical or similar to an amino acid sequence selected from the group consisting of SEQ ID NOs: 117-174; (b) selecting at least one tobacco cell comprising the recombinant DNA construct; and (c) regenerating at least one modified tobacco plant from the at least one tobacco cell selected in step (b). In another aspect, this disclosure provides a method of producing a modified tobacco plant comprising: (a) introducing a recombinant DNA construct to at least one tobacco cell, where the recombinant DNA construct comprises a heterologous promoter operably linked to a nucleic acid sequence selected from the group consisting of SEQ ID NOs: 1-58; (b) selecting at least one tobacco cell comprising the recombinant DNA construct; and (c) regenerating at least one modified tobacco plant from the at least one tobacco cell selected in step (b). In another aspect, this disclosure provides a method of producing a modified tobacco plant comprising: (a) introducing a recombinant DNA construct to at least one tobacco cell, where the recombinant DNA construct comprises a heterologous promoter operably linked to a nucleic acid sequence at least 80% identical to a nucleic acid sequence selected from the group consisting of SEQ ID NOs: 59-116; (b) selecting at least one tobacco cell comprising the recombinant DNA construct; and (c) regenerating at least one modified tobacco plant from the at least one tobacco cell selected in step (b). In an aspect, any of the foregoing methods further comprises (d) growing the modified tobacco plant regenerated in step (c). In another aspect, any of the foregoing methods further comprises: (e) crossing the modified tobacco plant grown in step (d) with a second tobacco plant; and (f) obtaining at least one seed from the crossing in step (e).

In an aspect, this disclosure provides a method comprising transforming a tobacco cell with a recombinant DNA construct, where the recombinant DNA construct comprises a heterologous promoter operably linked to a nucleic acid sequence encoding at least one small RNA molecule capable of binding to and reducing the expression of an endogenous nucleic acid sequence encoding a polypeptide at least 80% identical or similar to an amino acid sequence selected from the group consisting of SEQ ID NOs: 117-174. In another aspect, this disclosure provides a method comprising transforming a tobacco cell with a recombinant DNA construct, where the recombinant DNA construct comprises a heterologous promoter operably linked to a nucleic acid sequence encoding at least one small RNA molecule capable of binding to and reducing the expression of an endogenous nucleic acid sequence at least 80% identical a nucleic acid sequence selected from the group consisting of SEQ ID NOs: 1-58. In another aspect, this disclosure provides a method comprising transforming a tobacco cell with a recombinant DNA construct, where the recombinant DNA construct comprises a heterologous promoter operably linked to a nucleic acid sequence encoding at least one small RNA molecule capable of binding to and reducing the expression of an endogenous nucleic acid sequence at least 80% identical a nucleic acid sequence selected from the group consisting of SEQ ID NOs: 59-116. In another aspect, the foregoing methods further comprise regenerating a modified tobacco plant from the transformed tobacco cell.

In an aspect, this disclosure provides a method comprising transforming a tobacco cell with a recombinant DNA construct, where the recombinant DNA construct comprises a heterologous promoter operably linked to a nucleic acid sequence encoding a polypeptide comprising an amino acid sequence at least 80% identical or similar to an amino acid sequence selected from the group consisting of SEQ ID NOs: 117-174. In another aspect, this disclosure provides a method comprising transforming a tobacco cell with a recombinant DNA construct, where the recombinant DNA construct comprises a heterologous promoter operably linked to a nucleic acid sequence at least 80% identical to a nucleic acid sequence selected from the group consisting of SEQ ID NOs: 1-58. In another aspect, this disclosure provides a method comprising transforming a tobacco cell with a recombinant DNA construct, where the recombinant DNA construct comprises a heterologous promoter operably linked to a nucleic acid sequence at least 80% identical to a nucleic acid sequence selected from the group consisting of SEQ ID NOs: 59-116. In another aspect, the foregoing methods further comprise regenerating a modified tobacco plant from the transformed tobacco cell.

Numerous methods for introducing a recombinant DNA construct to a plant cell are known in the art, which can be used according to methods of the present application to produce a transgenic plant cell and plant. Any suitable method or technique for transformation of a plant cell known in the art can be used according to present methods. Effective methods for transformation of plants include bacterially mediated transformation, such as *Agrobacterium*-mediated or *Rhizobium*-mediated transformation and microprojectile bombardment-mediated transformation. A variety of methods are known in the art for transforming explants with a transformation vector via bacterially mediated transformation or microprojectile bombardment and then subsequently culturing, etc., those explants to regenerate or develop transgenic plants. Other methods for plant transformation, such as microinjection, electroporation, vacuum infiltration, pressure, sonication, silicon carbide fiber agitation, polyethylene glycol (PEG)-mediated transformation, etc., are also known in the art. Transgenic plants produced by these transformation methods can be chimeric or non-chimeric for the transformation event depending on the methods and explants used.

Methods of transforming plant cells are well known by persons of ordinary skill in the art. For instance, specific instructions for transforming plant cells by microprojectile bombardment with particles coated with recombinant DNA (e.g., biolistic transformation) are found in U.S. Pat. Nos. 5,550,318; 5,538,880 6,160,208; 6,399,861; and 6,153,812 and *Agrobacterium*-mediated transformation is described in U.S. Pat. Nos. 5,159,135; 5,824,877; 5,591,616; 6,384,301; 5,750,871; 5,463,174; and 5,188,958, all of which are incorporated herein by reference. Additional methods for transforming plants can be found in, for example, Compendium of Transgenic Crop Plants (2009) Blackwell Publishing. Any appropriate method known to those skilled in the art can be used to transform a tobacco cell with any of the nucleic acid molecules provided herein.

In an aspect, a method of introducing a nucleic acid molecule to a tobacco cell comprises *Agrobacterium*-mediated transformation. In another aspect, a method of introducing a nucleic acid molecule to a cell comprises PEG-mediated transformation. In another aspect, a method of introducing a nucleic acid molecule to a cell comprises biolistic transformation. In another aspect, a method of introducing a nucleic acid molecule to a cell comprises liposome-mediated transfection (lipofection). In another aspect, a method of introducing a nucleic acid molecule to a cell comprises lentiviral transfection.

Lipofection is described in e.g., U.S. Pat. Nos. 5,049,386, 4,946,787; and 4,897,355) and lipofection reagents are sold commercially (e.g., Transfectam™ and Lipofectin™) Cationic and neutral lipids that are suitable for efficient receptor-recognition lipofection of polynucleotides include those of WO 91/17424 and WO 91/16024. Delivery can be to cells (e.g. in vitro or ex vivo administration) or target tissues (e.g. in vivo administration).

Any tobacco cell from which a fertile tobacco plant can be regenerated is contemplated as a useful recipient cell for practice of this disclosure. In an aspect, a recombinant DNA construct is introduced to a tobacco cell. In an aspect, a recombinant DNA construct is introduced to a tobacco protoplast cell. In another aspect, a recombinant DNA construct is introduced to a tobacco callus cell. In an aspect, a recombinant DNA construct is introduced to a tobacco cell selected from the group consisting of a seed cell, a fruit cell, a leaf cell, a cotyledon cell, a hypocotyl cell, a meristem cell, an embryo cell, an endosperm cell, a root cell, a shoot cell, a stem cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, and a phloem cell.

Callus can be initiated from various tissue sources, including, but not limited to, immature embryos or parts of embryos, seedling apical meristems, microspores, and the like. Those cells which are capable of proliferating as callus can serve as recipient cells for transformation. Practical transformation methods and materials for making transgenic plants of this disclosure (e.g., various media and recipient target cells, transformation of immature embryos, and subsequent regeneration of fertile transgenic plants) are disclosed, for example, in U.S. Pat. Nos. 6,194,636 and 6,232,526 and U. S. Patent Application Publication 2004/0216189, all of which are incorporated herein by reference.

Leaf Grade

As used herein, "USDA leaf grade index" refers to a subdivision of a leaf type according to group, quality, and color. In one aspect, a USDA grade quality score is quantified as a 0-100 numerical representation of the grade as determined by a certified tobacco leaf grader, and is a weighted average of all stalk positions. A higher grade index indicates higher quality. As used below, a "point" refers to each whole number numerical representation of the USDA leaf grade score. For example, the difference between a USDA leaf grade index score of 90 and a score of 85 is 5 points.

Alternatively, leaf grade can be determined via hyperspectral imaging. See e.g., WO 2011/027315 (published on Mar. 10, 2011, and incorporated by reference in its entirety).

As used herein, a "certified tobacco leaf grader" refers to a person trained to grade tobacco leaves in accordance with USDA Official Standards Grades defined by the United States Department of Agriculture (USDA), Agricultural Marketing Systems as published in 7 CFR § 29. A USDA leaf grade index score may be assigned by an employee, a past employee, or a person otherwise trained to grade tobacco leaves in accordance with USDA Official Standards Grades. Exemplary steps of a standard operation for commercial inspection service begins with a grower delivering tobacco to market after which the tobacco is arranged on flat baskets as lots. Each lot is weighed and then inspected by a certified tobacco leaf grader. After examination, the grader assigns a grade to each lot which becomes a certificate of grade indicating group, quality, and color. The steps for grading experimental lots is similar; however, experimental tobacco is not taken to market or otherwise used for commercial purposes.

Tobacco grades are evaluated based on factors including, but not limited to, the leaf stalk position, leaf size, leaf color, leaf uniformity and integrity, ripeness, texture, elasticity, sheen (related with the intensity and the depth of coloration of the leaf as well as the shine), hygroscopicity (the faculty of the tobacco leaves to absorb and to retain the ambient moisture), and green nuance or cast. Leaf grade can be determined, for example, using an Official Standard Grade published by the Agricultural Marketing Service of the US Department of Agriculture (7 U.S.C. § 511). See, e.g., Official Standard Grades for Burley Tobacco (U.S. Type 31 and Foreign Type 93), effective Nov. 5, 1990 (55 F.R. 40645); Official Standard Grades for Flue-Cured Tobacco (U.S. Types 11, 12, 13, 14 and Foreign Type 92), effective Mar. 27, 1989 (54 F.R. 7925); Official Standard Grades for Pennsylvania Seedleaf Tobacco (U.S. Type 41), effective Jan. 8, 1965 (29 F.R. 16854); Official Standard Grades for Ohio Cigar-Leaf Tobacco (U.S. Types 42, 43, and 44), effective Dec. 8, 1963 (28 F.R. 11719 and 28 F.R. 11926); Official Standard Grades for Wisconsin Cigar-Binder Tobacco (U.S. Types 54 and 55), effective Nov. 20, 1969 (34 F.R. 17061); Official Standard Grades for Wisconsin Cigar-Binder Tobacco (U.S. Types 54 and 55), effective Nov. 20, 1969 (34 F.R. 17061); Official Standard Grades for Georgia and Florida Shade-Grown Cigar-Wrapper Tobacco (U.S. Type 62), Effective April 1971. A USDA grade index value can be determined according to an industry accepted grade index. See, e.g., Bowman et al, *Tobacco Science,* 32:39-40 (1988); Legacy Tobacco Document Library (Bates Document #523267826-523267833, Jul. 1, 1988, Memorandum on the Proposed Burley Tobacco Grade Index); and Miller et al., 1990, Tobacco Intern., 192:55-57 (all foregoing references are incorporated by reference in their entirety).

Unless specified otherwise, measurements of leaf grade index values, alkaloid, or nicotine levels mentioned herein for a tobacco plant, variety, cultivar, or line refer to average measurements, including, for example, an average of multiple leaves of a single plant or an average measurement from a population of tobacco plants from a single variety, cultivar, or line. A population of tobacco plants or a collection of tobacco leaves for determining an average measurement (e.g., leaf grading or alkaloid or nicotine level) can be of any size, for example, 2, 5, 10, 15, 20, 25, 30, 35, 40, 50, or more. A population of at least 5 or more tobacco plants is used to determine standard deviation. Industry-accepted standard protocols are followed for determining average measurements or grade index values.

As used herein, "USDA graded leaf group", "leaf group", or "group" is a division of a type covering closely related grades based on certain characteristics which are related to stalk position, body, or general quality. Group is the first factor of a USDA grade. Group determination is part of the grading procedure and is assigned by a certified tobacco leaf grader.

In an aspect, a modified tobacco plant comprising a non-natural mutation comprises a comparable or higher USDA leaf grade index as compared to a control tobacco plant lacking the non-natural mutation when grown under comparable conditions. In another aspect, a modified tobacco plant comprising a recombinant DNA construct comprises a comparable or higher USDA leaf grade index as compared to a control tobacco plant lacking the recombinant DNA construct when grown under comparable conditions.

As used herein, a "comparable" USDA leaf grade index refers to within 15%. For example, if a control plant has a USDA leaf grade index of 100, a comparable USDA leaf grade index would be between 85 and 100.

In an aspect, a modified tobacco plant comprises a USDA leaf grade index at least 1% higher than the USDA leaf grade index of a control tobacco plant when grown under comparable conditions. In another aspect, a modified tobacco plant comprises a USDA leaf grade index at least 5% higher than the USDA leaf grade index of a control tobacco plant when grown under comparable conditions. In another aspect, a modified tobacco plant comprises a USDA leaf grade index at least 10% higher than the USDA leaf grade index of a control tobacco plant when grown under comparable conditions. In another aspect, a modified tobacco plant comprises a USDA leaf grade index at least 20% higher than the USDA leaf grade index of a control tobacco plant when grown under comparable conditions. In another aspect, a modified tobacco plant comprises a USDA leaf grade index at least 30% higher than the USDA leaf grade index of a control tobacco plant when grown under comparable conditions. In another aspect, a modified tobacco plant comprises a USDA leaf grade index at least 40% higher than the USDA leaf grade index of a control tobacco plant when grown under comparable conditions. In another aspect, a modified tobacco plant comprises a USDA leaf grade index at least 50% higher than the USDA leaf grade index of a control tobacco plant when grown under comparable conditions. In another aspect, a modified tobacco plant comprises a USDA leaf grade index at least 75% higher than the USDA leaf grade index of a control tobacco plant when grown under comparable conditions. In another aspect, a modified tobacco plant comprises a USDA leaf grade index at least 100% higher than the USDA leaf grade index of a control tobacco plant when grown under comparable conditions.

In an aspect, a modified tobacco plant comprises a USDA leaf grade index between 1% higher and 100% higher than the USDA leaf grade index of a control tobacco plant when grown under comparable conditions. In an aspect, a modified tobacco plant comprises a USDA leaf grade index between 1% higher and 75% higher than the USDA leaf grade index of a control tobacco plant when grown under comparable conditions. In an aspect, a modified tobacco plant comprises a USDA leaf grade index between 1% higher and 50% higher than the USDA leaf grade index of a control tobacco plant when grown under comparable conditions. In an aspect, a modified tobacco plant comprises a USDA leaf grade index between 1% higher and 40% higher than the USDA leaf grade index of a control tobacco plant when grown under comparable conditions. In an aspect, a modified tobacco plant comprises a USDA leaf grade index between 1% higher and 30% higher than the USDA leaf grade index of a control tobacco plant when grown under comparable conditions. In an aspect, a modified tobacco plant comprises a USDA leaf grade index between 1% higher and 20% higher than the USDA leaf grade index of a control tobacco plant when grown under comparable conditions. In an aspect, a modified tobacco plant comprises a USDA leaf grade index between 1% higher and 10% higher than the USDA leaf grade index of a control tobacco plant when grown under comparable conditions. In an aspect, a modified tobacco plant comprises a USDA leaf grade index between 10% higher and 75% higher than the USDA leaf grade index of a control tobacco plant when grown under comparable conditions. In an aspect, a modified tobacco plant comprises a USDA leaf grade index between 10% higher and 50% higher than the USDA leaf grade index of a control tobacco plant when grown under comparable conditions. In an aspect, a modified tobacco plant comprises a USDA leaf grade index between 1% higher and 30% higher than the USDA leaf grade index of a control tobacco plant when grown under comparable conditions.

In an aspect, a modified tobacco plant comprises a USDA leaf grade index at least 1 point higher than the USDA leaf grade index of a control tobacco plant when grown under comparable conditions. In another aspect, a modified tobacco plant comprises a USDA leaf grade index at least 2 points higher than the USDA leaf grade index of a control tobacco plant when grown under comparable conditions. In another aspect, a modified tobacco plant comprises a USDA leaf grade index at least 3 points higher than the USDA leaf grade index of a control tobacco plant when grown under comparable conditions. In another aspect, a modified tobacco plant comprises a USDA leaf grade index at least 4 points higher than the USDA leaf grade index of a control tobacco plant when grown under comparable conditions. In another aspect, a modified tobacco plant comprises a USDA leaf grade index at least 5 points higher than the USDA leaf grade index of a control tobacco plant when grown under comparable conditions. In another aspect, a modified tobacco plant comprises a USDA leaf grade index at least 6 points higher than the USDA leaf grade index of a control tobacco plant when grown under comparable conditions. In another aspect, a modified tobacco plant comprises a USDA leaf grade index at least 7 points higher than the USDA leaf grade index of a control tobacco plant when grown under comparable conditions. In another aspect, a modified tobacco plant comprises a USDA leaf grade index at least 8 points higher than the USDA leaf grade index of a control tobacco plant when grown under comparable conditions. In another aspect, a modified tobacco plant comprises a USDA leaf grade index at least 9 points higher than the USDA leaf grade index of a control tobacco plant when grown under comparable conditions. In another aspect, a modified tobacco plant comprises a USDA leaf grade index at least 10 points higher than the USDA leaf grade index of a control tobacco plant when grown under comparable conditions. In another aspect, a modified tobacco plant comprises a USDA leaf grade index at least 11 points higher than the USDA leaf grade index of a control tobacco plant when grown under comparable conditions. In another aspect, a modified tobacco plant comprises a USDA leaf grade index at least 12 points higher than the USDA leaf grade index of a control tobacco plant when grown under comparable conditions. In another aspect, a modified tobacco plant comprises a USDA leaf grade index at least 13 points higher than the USDA leaf grade index of a control tobacco plant when grown under comparable conditions. In another aspect, a modified tobacco plant comprises a USDA leaf grade index at least 14 points higher than the USDA leaf grade index of a control tobacco plant when grown under comparable conditions. In another aspect, a modified tobacco plant comprises a USDA leaf grade index at least 15 points higher than the USDA leaf grade index of a control tobacco plant when grown under comparable conditions. In another aspect, a modified tobacco plant comprises a USDA leaf grade index at least 16 points higher than the USDA leaf grade index of a control tobacco plant when grown under comparable conditions. In another aspect, a modified tobacco plant comprises a USDA leaf grade index at least 17 points higher than the USDA leaf grade index of a control tobacco plant when grown under comparable conditions. In another aspect, a modified tobacco plant comprises a USDA leaf grade index at least 18 points higher than the USDA leaf grade index of a control tobacco plant when grown under comparable conditions. In another aspect, a modified tobacco plant comprises a USDA leaf grade index at least 19 points higher than the USDA leaf grade index of a control tobacco plant when grown under comparable conditions. In another aspect, a modified tobacco plant comprises a USDA leaf grade index at least 20 points higher than the USDA leaf grade index of a control tobacco plant when grown under comparable conditions. In another aspect, a modified tobacco plant comprises a USDA leaf grade index at least 25 points higher than the USDA leaf grade index of a control tobacco plant when grown under comparable conditions. In another aspect, a modified tobacco plant comprises a USDA leaf grade index at least 30 points higher than the USDA leaf grade index of a control tobacco plant when grown under comparable conditions. In another aspect, a modified tobacco plant comprises a USDA leaf grade index at least 35 points higher than the USDA leaf grade index of a control tobacco plant when grown under comparable conditions. In another aspect, a modified tobacco plant comprises a USDA leaf grade index at least 40 points higher than the USDA leaf grade index of a control tobacco plant when grown under comparable conditions. In another aspect, a modified tobacco plant comprises a USDA leaf grade index at least 50 points higher than the USDA leaf grade index of a control tobacco plant when grown under comparable conditions.

In an aspect, a modified tobacco plant comprises a USDA leaf grade index between 1 point higher and 100 points higher than the USDA leaf grade index of a control tobacco plant when grown under comparable conditions. In another aspect, a modified tobacco plant comprises a USDA leaf grade index between 1 point higher and 75 points higher than the USDA leaf grade index of a control tobacco plant when grown under comparable conditions. In another aspect, a modified tobacco plant comprises a USDA leaf grade index between 1 point higher and 50 points higher than the USDA leaf grade index of a control tobacco plant when grown under comparable conditions. In another aspect, a modified tobacco plant comprises a USDA leaf grade index between 1 point higher and 25 points higher than the USDA leaf grade index of a control tobacco plant when grown under comparable conditions. In another aspect, a modified tobacco plant comprises a USDA leaf grade index between 1 point higher and 10 points higher than the USDA leaf grade index of a control tobacco plant when grown under comparable conditions. In another aspect, a modified tobacco plant comprises a USDA leaf grade index between 1 point higher and 5 points higher than the USDA leaf grade index of a control tobacco plant when grown under comparable conditions. In another aspect, a modified tobacco plant comprises a USDA leaf grade index between 10 points higher and 50 points higher than the USDA leaf grade index of a control tobacco plant when grown under comparable conditions. In another aspect, a modified tobacco plant comprises a USDA leaf grade index between 10 points higher and 25 points higher than the USDA leaf grade index of a control tobacco plant when grown under comparable conditions.

In an aspect, a comparable USDA leaf grade index between a modified tobacco plant and a control tobacco plant grown under comparable conditions is within 1 point. In another aspect, a comparable USDA leaf grade index between a modified tobacco plant and a control tobacco plant grown under comparable conditions is within 2 points. In another aspect, a comparable USDA leaf grade index between a modified tobacco plant and a control tobacco plant grown under comparable conditions is within 3 points. In another aspect, a comparable USDA leaf grade index between a modified tobacco plant and a control tobacco plant grown under comparable conditions is within 4 points. In another aspect, a comparable USDA leaf grade index between a modified tobacco plant and a control tobacco plant grown under comparable conditions is within 5 points. In another aspect, a comparable USDA leaf grade index between a modified tobacco plant and a control tobacco plant grown under comparable conditions is within 6 points. In another aspect, a comparable USDA leaf grade index between a modified tobacco plant and a control tobacco plant grown under comparable conditions is within 7 points. In another aspect, a comparable USDA leaf grade index between a modified tobacco plant and a control tobacco plant grown under comparable conditions is within 8 points. In another aspect, a comparable USDA leaf grade index between a modified tobacco plant and a control tobacco plant grown under comparable conditions is within 9 points. In another aspect, a comparable USDA leaf grade index between a modified tobacco plant and a control tobacco plant grown under comparable conditions is within 10 points. In another aspect, a comparable USDA leaf grade index between a modified tobacco plant and a control tobacco plant grown under comparable conditions is within 11 points. In another aspect, a comparable USDA leaf grade index between a modified tobacco plant and a control tobacco plant grown under comparable conditions is within 12 points. In another aspect, a comparable USDA leaf grade index between a modified tobacco plant and a control tobacco plant grown under comparable conditions is within 13 points. In another aspect, a comparable USDA leaf grade index between a modified tobacco plant and a control tobacco plant grown under comparable conditions is within 14 points. In another aspect, a comparable USDA leaf grade index between a modified tobacco plant and a control tobacco plant grown under comparable conditions is within 15 points.

Aroma/Flavor

In an aspect, a modified tobacco plant provided herein comprises a similar level of one or more tobacco aroma compounds selected from the group consisting of 3-methylvaleric acid, valeric acid, isovaleric acid, a labdenoid, a cembrenoid, a sugar ester, and a reducing sugar, compared to a control tobacco plant when grown under comparable conditions. As used herein, a "similar" level refers to within 20%.

As used herein, "tobacco aroma compounds" are compounds associated with the flavor and aroma of tobacco smoke. These compounds include, but are not limited to, 3-methylvaleric acid, valeric acid, isovaleric acid, cembrenoid and labdenoid diterpenes, and sugar esters. Concentrations of tobacco aroma compounds can be measured by any known metabolite profiling methods in the art including, without limitation, gas chromatography mass spectrometry (GC-MS), Nuclear Magnetic Resonance Spectroscopy, liquid chromatography-linked mass spectrometry. See The Handbook of Plant Metabolomics, edited by Weckwerth and Kahl, (Wiley-Blackwell) (May 28, 2013).

As used herein, "reducing sugar(s)" are any sugar (monosaccharide or polysaccharide) that has a free or potentially free aldehyde or ketone group. Glucose and fructose act as nicotine buffers in cigarette smoke by reducing smoke pH and effectively reducing the amount of "free" unprotonated nicotine. Reducing sugars balances smoke flavor, for example, by modifying the sensory impact of nicotine and other tobacco alkaloids. An inverse relationship between sugar content and alkaloid content has been reported across tobacco varieties, within the same variety, and within the same plant line caused by planting conditions. Reducing sugar levels can be measured using a segmented-flow colorimetric method developed for analysis of tobacco samples as adapted by Skalar Instrument Co (West Chester, PA) and described by Davis, *Tobacco Science* 20:139-144 (1976). For example, a sample is dialyzed against a sodium carbonate solution. Copper neocuproin is added to the sample and the solution is heated. The copper neocuproin chelate is reduced in the presence of sugars resulting in a colored complex which is measured at 460 nm.

TSNAs

In an aspect, a modified tobacco plant provided further comprises one or more mutations in one or more loci encoding a nicotine demethylase (e.g., CYP82E4, CYP82E5, CYP82E10) that confer reduced amounts of nornicotine (See U.S. Pat. Nos. 8,319,011; 8,124,851; 9,187, 759; 9,228,194; 9,228,195; 9,247,706) compared to a control tobacco plant lacking one or more mutations in one or more loci encoding a nicotine demethylase when grown under comparable conditions. In an aspect, a modified tobacco plant described further comprises reduced nicotine demethylase activity compared to a control plant when grown and cured under comparable conditions. In a further aspect, a tobacco plant provided further comprises one or more mutations or transgenes providing an elevated level of one or more antioxidants (See U.S. Patent Application Publication No. 2018/0119163 and WO 2018/067985). In another aspect, a tobacco plant provided further comprises one or more mutations or transgenes providing a reduced level of one or more tobacco-specific nitrosamines (TSNAs). In an aspect, a TSNA is selected from the group consisting of N'-nitrosonornicotine (NNN), 4-methylnitrosoamino-1-(3-pyridyl)-1-butanone (NNK), N'-nitrosoanatabine (NAT), and N'-nitrosoanabasine (NAB).

EMBODIMENTS

The following non-limiting embodiments are envisioned:

1. A modified tobacco plant, or part thereof, comprising at least one non-natural mutation in an endogenous nucleic acid sequence, wherein the endogenous nucleic acid sequence encodes a polypeptide comprising an amino acid sequence at least 80% identical or similar to an amino acid sequence selected from the group consisting of SEQ ID NOs: 117-174.

2. A modified tobacco plant, or part thereof, comprising a recombinant DNA construct comprising a heterologous promoter operably linked to a nucleic acid encoding at least one small RNA molecule capable of binding to and reducing the expression of an endogenous nucleic acid sequence encoding a polypeptide at least 80% identical or similar to an amino acid sequence selected from the group consisting of SEQ ID NOs: 117-174.

3. A modified tobacco plant, or part thereof, comprising a recombinant DNA construct comprising a heterologous promoter operably linked to a nucleic acid sequence encoding a polypeptide comprising an amino acid sequence at least 80% identical or similar to an amino acid sequence selected from the group consisting of SEQ ID NOs: 117-174.

4. The modified tobacco plant, or part thereof, of embodiment 1, wherein said tobacco plant produces at least one leaf comprising a reduced amount of at least one alkaloid as compared to the amount of said alkaloid in a control tobacco plant lacking said at least one non-natural mutation in said endogenous nucleic acid sequence when grown under comparable conditions.

5. The modified tobacco plant, or part thereof, of embodiment 2 or 3, wherein said tobacco plant produces at least one leaf comprising a reduced amount of at least one alkaloid as compared to the amount of said alkaloid in a control tobacco plant lacking said recombinant DNA construct when grown under comparable conditions.

6. The modified tobacco plant, or part thereof, of any one of embodiments 1, 2, or 4, wherein said endogenous nucleic acid sequence comprises a nucleic acid sequence at least 80% identical or complementary to a sequence selected from the group consisting of SEQ ID NOs: 1-58.

7. The modified tobacco plant, or part thereof, of embodiment 3, wherein said nucleic acid sequence comprises a nucleic acid sequence at least 80% identical or complementary to a sequence selected from the group consisting of SEQ ID NOs: 1-58.

8. The modified tobacco plant, or part thereof, of any one of embodiments 1, 2, or 4, wherein said endogenous nucleic acid sequence comprises a nucleic acid sequence at least 80% identical or complementary to a sequence selected from the group consisting of SEQ ID NOs: 59-116.

9. The modified tobacco plant, or part thereof, of embodiment 3, wherein said nucleic acid sequence comprises a nucleic acid sequence at least 80% identical or complementary to a sequence selected from the group consisting of SEQ ID NOs: 59-116.

10. The modified tobacco plant, or part thereof, of embodiment 1 or 4, wherein said tobacco plant is homozygous for said at least one non-natural mutation.

11. The modified tobacco plant, or part thereof, of embodiment 1 or 4, wherein said tobacco plant is heterozygous for said at least one non-natural mutation.

12. The modified tobacco plant, or part thereof, of any one of embodiments 4-6, 8, 10, or 11, wherein said at least one alkaloid is selected from the group consisting of anabasine, anatabine, nicotine, and nornicotine.

13. The modified tobacco plant, or part thereof, of any one of embodiments 4-6, 8, or 10-12, wherein said reduced amount of at least one alkaloid comprises a reduction of at least 1%.

14. The modified tobacco plant, or part thereof, of any one of embodiments 1, 4, 10, or 11, wherein said at least one non-natural mutation comprises a mutation selected from the group consisting of an insertion, a deletion, a substitution, a duplication, and an inversion.

15. The modified tobacco plant, or part thereof, of any one of embodiments 1, 4, 10, or 11, wherein said at least one non-natural mutation comprises at least one mutation selected from the group consisting of a nonsense mutation, a missense mutation, a frameshift mutation, and a splice-site mutation.

16. The modified tobacco plant, or part thereof, of any one of embodiments 1, 4, 10, 11, 14, or 15, wherein said at least one non-natural mutation comprises a null mutation.

17. The modified tobacco plant, or part thereof, of any one of embodiments 1, 4, 10, 11, or 14-16, wherein said at least one non-natural mutation results in a truncation of said polypeptide.

18. The modified tobacco plant, or part thereof, of any one of embodiments 1, 4, 10, 11, or 14-17, wherein said at least one non-natural mutation comprises a mutation in a sequence region selected from the group consisting of a promoter, a 5'-untranslated region (UTR), an exon, an intron, a 3'-UTR, and a terminator.

19. The modified tobacco plant, or part thereof, or part thereof, of any one of embodiments 1, 4, 10, 11, or 14-18, wherein said at least one non-natural mutation results in a reduced level of expression of said nucleic acid sequence as compared to expression of said nucleic acid sequence in the same tissue of a control tobacco plant when grown under comparable conditions, wherein said nucleic acid sequence lacks the at least one non-natural mutation in said control tobacco plant.

20. The modified tobacco plant, or part thereof, of any one of embodiments 1, 4, 10, 11, or 14-19, wherein said at least one non-natural mutation results in a reduced level of activity by a protein or polypeptide encoded by said nucleic acid sequence as compared to activity of a protein or polypeptide encoded by said nucleic acid sequence in a control tobacco plant when grown under comparable conditions, wherein said nucleic acid sequence lacks the at least one non-natural mutation in said control tobacco plant.

21. The modified tobacco plant, or part thereof, of any one of embodiments 2, 3, 5, 7, or 9, wherein said promoter comprises a promoter selected from the group consisting of a constitutive promoter, a tissue-preferred promoter, a tissue-specific promoter, and an inducible promoter.

22. The modified tobacco plant, or part thereof, of embodiment 21, wherein said tissue-preferred promoter comprises a root-preferred promoter.

23. The modified tobacco plant, or part thereof, of embodiment 21, wherein said tissue-specific promoter comprises a root-specific promoter.

24. The modified tobacco plant, or part thereof, of embodiment 21, wherein said constitutive promoter is selected from the group consisting of a Cauliflower Mosaic Virus (CaMV) 35S promoter, a ubiquitin promoter, an actin promoter, an opine promoter, and an alcohol dehydrogenase promoter.

25. The modified tobacco plant, or part thereof, of embodiment 2, wherein the at least one small RNA molecule is selected from the group consisting of a double-stranded RNA, a small interfering RNA (siRNA), a trans-acting siRNA, and a microRNA.

26. The modified tobacco plant, or part thereof, of embodiment 2, wherein said at least one small RNA molecule comprises between 18 nucleotides and 30 nucleotides.

27. The modified tobacco plant, or part thereof, of embodiment 2, wherein said at least one small RNA molecule comprises a nucleic acid sequence at least 90% complementary to a sequence selected from the group consisting of SEQ ID NOs: 59-116.

28. The modified tobacco plant, or part thereof, of any one of embodiments 1-27, wherein the modified tobacco plant is of a tobacco variety selected from the group consisting of a flue-cured variety, a bright variety, a Burley variety, a Virginia variety, a Maryland variety, a dark variety, a Galpio variety, an Oriental variety, and a Turkish variety.

29. The modified tobacco plant, or part thereof, of any one of embodiments 1-116, wherein the modified tobacco plant is of a variety selected from the group consisting of the tobacco varieties listed in Tables 2-8.

30. The modified tobacco plant, or part thereof, of any one of embodiments 1-29, wherein the modified tobacco plant is a hybrid.

31. The modified tobacco plant, or part thereof, of any one of embodiments 1-30, wherein the modified tobacco plant is male sterile or cytoplasmically male sterile.

32. The modified tobacco plant, or part thereof, of any one of embodiments 1-30, wherein the modified tobacco plant is female sterile.

33. Cured tobacco material from the modified tobacco plant, or part thereof, of any one of embodiments 1-32.

34. The cured tobacco material of embodiment 33, wherein said cured tobacco material comprises cured leaf material, cured stem material, or both.

35. The cured tobacco material of embodiment 33 or 34, wherein said cured tobacco material comprises flue-cured tobacco material, air-cured tobacco material, fire-cured tobacco material, and sun-cured tobacco material.

36. A tobacco blend comprising the cured tobacco material of any one of embodiments 33-35.

37. The tobacco blend of embodiment 36, wherein said tobacco blend comprises at least 10% cured tobacco by weight.

38. The tobacco blend of embodiment 36, wherein said tobacco blend comprises at least 10% cured tobacco by volume.

39. A tobacco product comprising the tobacco blend of any one of embodiments 36-38.

40. A tobacco product comprising the cured tobacco material of any one of embodiments 33-35.

41. The tobacco product of embodiment 39 or 40, wherein said tobacco product is selected from the group consisting of a cigarette, a heated tobacco product, a kretek, a bidi cigarette, a cigar, a cigarillo, a non-ventilated cigarette, a vented recess filter cigarette, pipe tobacco, snuff, snus, chewing tobacco, moist smokeless tobacco, fine cut chewing tobacco, long cut chewing tobacco, pouched chewing tobacco product, gum, a tablet, a lozenge, and a dissolving strip.

42. The tobacco product of embodiment 39 or 40, wherein said tobacco product is a smokeless tobacco product.

43. The tobacco product of embodiment 42, wherein said smokeless tobacco product is selected from the group consisting of loose leaf chewing tobacco, plug chewing tobacco, moist snuff, nasal snuff, dry snuff, and snus.

44. A reconstituted tobacco comprising the cured tobacco material of any one of embodiments 33-35.

45. A method of producing a modified tobacco plant comprising:
(a) inducing a non-natural mutation in at least one tobacco cell in an endogenous nucleic acid sequence encoding a polypeptide comprising an amino acid sequence at least 80% identical or similar to an amino acid sequence selected from the group consisting of SEQ ID NOs: 117-174;
(b) selecting at least one tobacco cell comprising said non-natural mutation from step (a); and
(c) regenerating at least one modified tobacco plant from said at least one tobacco cell selected in step (b).

46. A method of producing a modified tobacco plant comprising:
(a) introducing a recombinant DNA construct to at least one tobacco cell, wherein said recombinant DNA construct comprises a heterologous promoter operably linked to a nucleic acid encoding at least one small RNA molecule capable of binding to and reducing the expression of an endogenous nucleic acid sequence encoding a polypeptide at least 80% identical or similar to an amino acid sequence selected from the group consisting of SEQ ID NOs: 117-174;
(b) selecting at least one tobacco cell comprising said recombinant DNA construct; and
(c) regenerating at least one modified tobacco plant from said at least one tobacco cell selected in step (b).

47. A method of producing a modified tobacco plant comprising:
(a) introducing a recombinant DNA construct to at least one tobacco cell, wherein said recombinant DNA construct comprises a heterologous promoter operably linked to a nucleic acid sequence encoding a polypeptide comprising an amino acid sequence at least 80% identical or similar to an amino acid sequence selected from the group consisting of SEQ ID NOs: 117-174;
(b) selecting at least one tobacco cell comprising said recombinant DNA construct; and
(c) regenerating at least one modified tobacco plant from said at least one tobacco cell selected in step (b).

48. The method of embodiment 45, wherein said at least one modified tobacco plant comprises a reduced amount of at least one alkaloid as compared to a control tobacco plant lacking said mutation when grown under comparable conditions.

49. The method of embodiment 46 or 47, wherein said at least one modified tobacco plant comprises a reduced amount of at least one alkaloid as compared to a control tobacco plant lacking said recombinant DNA construct when grown under comparable conditions.

50. The method of any one of embodiments 45, 46, 48, or 49, wherein said endogenous nucleic acid sequence is at least 80% identical to a sequence selected from the group consisting of SEQ ID NOs: 1-58.

51. The method of embodiment 47 or 49, wherein said nucleic acid sequence is at least 80% identical to a sequence selected from the group consisting of SEQ ID NOs: 1-58.

52. The method of any one of embodiments 45, 46, 48, or 49, wherein said endogenous nucleic acid sequence is at least 80% identical to a sequence selected from the group consisting of SEQ ID NOs: 59-116.

53. The method of embodiment 47 or 49, wherein said nucleic acid sequence is at least 80% identical to a sequence selected from the group consisting of SEQ ID NOs: 59-116.

54. The method of any one of embodiments 48-53, wherein said at least one alkaloid is selected from the group consisting of anabasine, anatabine, nicotine, and nornicotine.

55. The method of any one of embodiments 48-53, wherein said reduced amount of at least one alkaloid comprises a reduction of at least 1%.

56. The method of any one of embodiments 45, 48, 50, 52, 54, or 55, wherein said non-natural mutation comprises a mutation selected from the group consisting of an insertion, a deletion, a substitution, a duplication, and an inversion.

57. The method of any one of embodiments 45, 48, 50, 52, or 54-56, wherein said non-natural mutation comprises a mutation selected from the group consisting of a nonsense mutation, a missense mutation, a frameshift mutation, and a splice-site mutation.

58. The method of any one of embodiments 45, 48, 50, 52, or 54-57, wherein said non-natural mutation comprises a null mutation.

59. The method of any one of embodiments 45, 48, 50, 52, or 54-58, wherein said non-natural mutation results in a truncation of said polypeptide.

60. The method of any one of embodiments 45, 48, 50, 52, or 54-59, wherein said non-natural mutation comprises a mutation in a sequence region selected from the group consisting of a promoter, a 5'-untranslated region (UTR), an exon, an intron, a 3'-UTR, and a terminator.

61. The method of any one of embodiments 45, 48, 50, 52, or 54-60, wherein said inducing comprises the use of an agent selected from the group consisting of: a chemical mutagen, irradiation, a transposon, *Agrobacterium*, and a nuclease.

62. The method of embodiment 61, wherein said nuclease is selected from the group consisting of a meganuclease, a zinc-finger nuclease, a transcription activator-like effector nuclease, a CRISPR/Cas9 nuclease, a CRISPR/Cpf1 nuclease, a CRISPR/CasX nuclease, a CRISPR/CasY nuclease, a Csm1 nuclease, or any combination thereof.

63. The method of embodiment 61, wherein said chemical mutagen comprises ethyl methanesulfonate.

64. The method of embodiment 61, wherein said irradiation comprises gamma rays, X-rays, ionizing radiation, or fast neutrons.

65. The method of embodiment 46, wherein said small RNA molecule is selected from the group consisting of a double-stranded RNA, a small interfering RNA (siRNA), a trans-acting siRNA, and a microRNA.

66. The method of embodiment 46, wherein said at least one small RNA molecule comprises between 18 nucleotides and 30 nucleotides.

67. The method of embodiment 46, wherein said at least one small RNA molecule comprises a nucleic acid sequence at least 90% complementary to a sequence selected from the group consisting of SEQ ID NOs: 59-116.

68. The method of any one of embodiments 46, 47, or 49-53, wherein said promoter comprises a promoter selected from the group consisting of a constitutive promoter, a tissue-preferred promoter, a tissue-specific promoter, and an inducible promoter.

69. The method of embodiment 68, wherein said tissue-preferred promoter comprises a root-preferred promoter.

70. The method of embodiment 68, wherein said tissue-specific promoter comprises a root-specific promoter.

71. The method of embodiment 68, wherein said constitutive promoter is selected from the group consisting of a Cauliflower Mosaic Virus (CaMV) 35S promoter, a ubiquitin promoter, an actin promoter, an opine promoter, and an alcohol dehydrogenase promoter.

72. The method of any one of embodiments 45-71, wherein said at least one tobacco cell is a tobacco protoplast cell.

73. The method of any one of embodiments 45-71, wherein said at least one tobacco cell is a tobacco callus cell.

74. The method of any one of embodiments 45-71, wherein said at least one tobacco cell is selected from the group consisting of a seed cell, a fruit cell, a leaf cell, a cotyledon cell, a hypocotyl cell, a meristem cell, an embryo cell, an endosperm cell, a root cell, a shoot cell, a stem cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, and a phloem cell.

75. The method of any one of embodiments 45-47, wherein said method further comprises:
(d) growing said modified tobacco plant regenerated in step (c).

76. The method of embodiment 75, wherein said method further comprises:
(e) crossing said modified tobacco plant grown in step (d) with a second tobacco plant; and
(f) obtaining at least one seed from said crossing in step (e).

77. The method of embodiment 45 or 48, wherein said at least one non-natural mutation results in a reduced level of expression of said nucleic acid sequence as compared to expression of said nucleic acid sequence in the same tissue of a control tobacco plant when grown under comparable conditions, wherein said nucleic acid sequence lacks the at least one non-natural mutation in said control tobacco plant.

78. The method of embodiment 77, wherein said reduced level of expression comprises a reduction of at least 5%.

79. The method of embodiment 45 or 48, wherein said at least one non-natural mutation results in an increased level of expression of said nucleic acid sequence as compared to expression of said nucleic acid sequence in the same tissue of a control tobacco plant when grown under comparable conditions, wherein said nucleic acid sequence lacks the at least one non-natural mutation in said control tobacco plant.

80. The method of embodiment 79, wherein said increased level of expression comprises an increase of at least 5%.

81. The method of embodiment 45 or 48, wherein said at least one non-natural mutation results in a reduced level of activity by a protein or polypeptide encoded by said nucleic acid sequence as compared to activity of a protein or polypeptide encoded by said nucleic acid sequence in a control tobacco plant when grown under comparable conditions, wherein said nucleic acid sequence lacks the at least one non-natural mutation in said control tobacco plant.

82. The method of embodiment 45 or 48, wherein said at least one non-natural mutation results in an increased level of activity by a protein or polypeptide encoded by said nucleic acid sequence as compared to activity of a protein or polypeptide encoded by said nucleic acid sequence in a control tobacco plant when grown under comparable conditions, wherein said nucleic acid sequence lacks the at least one non-natural mutation in said control tobacco plant.

83. The method of any one of embodiments 45-82, wherein said modified tobacco plant is of a tobacco variety selected from the group consisting of a flue-cured variety, a bright variety, a Burley variety, a Virginia variety, a Maryland variety, a dark variety, a Galpio variety, an Oriental variety, and a Turkish variety.

84. The method of any one of embodiments 45-83, wherein said modified tobacco plant is of a variety selected from the group consisting of the varieties listed in Tables 2-8.

85. The method of any one of embodiments 45-84, wherein said modified tobacco plant is a hybrid.

86. The method of any one of embodiments 45-85, wherein said modified tobacco plant is male sterile or cytoplasmically male sterile.

87. The method of any one of embodiments 45-85, wherein said modified tobacco plant is female sterile.

88. The method of embodiment 45 or 48, wherein said modified tobacco plant comprises a comparable or higher USDA leaf grade index as compared to a control tobacco plant lacking said non-natural mutation when grown under comparable conditions.

89. The method of embodiment 46 or 47, wherein said modified tobacco plant comprises a comparable or higher USDA leaf grade index as compared to a control tobacco plant lacking said recombinant DNA construct when grown under comparable conditions.

90. A method comprising preparing a tobacco product using cured tobacco material from a modified tobacco plant, wherein said modified tobacco plant comprises a non-natural mutation in an endogenous nucleic acid sequence, wherein the endogenous nucleic acid sequence encodes a polypeptide comprising an amino acid sequence at least 80% identical or similar to an amino acid sequence selected from the group consisting of SEQ ID NOs: 117-174.

91. A method comprising preparing a tobacco product using cured tobacco material from a modified tobacco plant, wherein said modified tobacco plant comprises a recombinant DNA construct, and wherein said recombinant DNA construct comprises a heterologous promoter operably linked to a nucleic acid sequence encoding at least one small RNA molecule capable of binding to and reducing the expression of an endogenous nucleic acid sequence encoding a polypeptide at least 80% identical or similar to an amino acid sequence selected from the group consisting of SEQ ID NOs: 117-174.

92. A method comprising preparing a tobacco product using cured tobacco material from a modified tobacco plant, wherein said modified tobacco plant comprises a recombinant DNA construct, and wherein said recombinant DNA construct comprises a heterologous promoter operably linked to a nucleic acid sequence encoding a polypeptide comprising an amino acid sequence at least 80% identical or similar to an amino acid sequence selected from the group consisting of SEQ ID NOs: 117-174.

93. The method of any one of embodiments 90-92, wherein said cured tobacco material comprises cured leaf material, cured stem material, or both.

94. The method of any one of embodiments 90-92, wherein said cured tobacco material comprises flue-cured tobacco material, air-cured tobacco material, fire-cured tobacco material, and sun-cured tobacco material.

95. The method of any one of embodiments 90-92, wherein said tobacco product is selected from the group consisting of a cigarette, a kretek, a bidi cigarette, a cigar, a cigarillo, a non-ventilated cigarette, a vented recess filter cigarette, pipe tobacco, snuff, snus, chewing tobacco, moist smokeless tobacco, fine cut chewing tobacco, long cut chewing tobacco, pouched chewing tobacco product, gum, a tablet, a lozenge, and a dissolving strip.

96. The method of any one of embodiments 90-92, wherein said tobacco product is a smokeless tobacco product.

97. The method of embodiment 96, wherein said smokeless tobacco product is selected from the group consisting of loose leaf chewing tobacco, plug chewing tobacco, moist snuff, nasal snuff, dry snuff, and snus.

98. The method of any one of embodiments 90-92, wherein said cured tobacco material is of a tobacco variety selected from the group consisting of a flue-cured variety, a bright variety, a Burley variety, a Virginia variety, a Maryland variety, a dark variety, a Galpão variety, an Oriental variety, and a Turkish variety.

99. The method of any one of embodiments 90-98, wherein said endogenous nucleic acid sequence comprises a sequence at least 80% identical to a sequence selected from the group consisting of SEQ ID NOs: 1-116.

100. The method of any one of embodiments 92-98, wherein said nucleic acid sequence comprises a sequence at least 80% identical to a sequence selected from the group consisting of SEQ ID NOs: 1-116.

101. A method comprising transforming a tobacco cell with a recombinant DNA construct, wherein said recombinant DNA construct comprises a heterologous promoter operably linked to a nucleic acid sequence encoding at least one small RNA molecule capable of binding to and reducing the expression of an endogenous nucleic acid sequence encoding a polypeptide at least 80% identical or similar to an amino acid sequence selected from the group consisting of SEQ ID NOs: 117-174.

102. A method comprising transforming a tobacco cell with a recombinant DNA construct, wherein said recombinant DNA construct comprises a heterologous promoter operably linked to a nucleic acid sequence encoding a polypeptide comprising an amino acid sequence at least 80% identical or similar to an amino acid sequence selected from the group consisting of SEQ ID NOs: 117-174.

103. A method for producing a modified tobacco plant comprising:

(a) crossing at least one tobacco plant of a first tobacco variety with at least one tobacco plant of a second tobacco variety to produce at least one progeny tobacco seed, wherein said at least one tobacco plant of said first tobacco variety comprises a non-natural mutation in an endogenous nucleic acid sequence, where the endogenous nucleic acid sequence encodes a polypeptide comprising an amino acid sequence at least 80% identical or similar to an amino acid sequence selected from the group consisting of SEQ ID NOs: 117-174, wherein said non-natural mutation is not present in said endogenous nucleic acid sequence in a control tobacco plant of said first tobacco variety; and (b) selecting for at least one progeny tobacco seed, or a plant germinated therefrom, wherein said at least one tobacco seed or plant germinated therefrom comprises said non-natural mutation.

104. A method for producing a modified tobacco plant comprising:

(a) crossing at least one tobacco plant of a first tobacco variety with at least one tobacco plant of a second tobacco variety to produce at least one progeny tobacco seed, wherein said at least one tobacco plant of said first tobacco variety comprises a recombinant DNA construct, wherein said recombinant DNA construct comprises a heterologous promoter operably linked to a nucleic acid sequence encoding at least one small RNA molecule capable of binding to and reducing the expression of an endogenous nucleic acid sequence encoding a polypeptide at least 80% identical or similar to an amino acid sequence selected from the group consisting of SEQ ID NOs: 117-174, wherein said recombinant DNA construct is not present in said endogenous nucleic acid sequence in a control tobacco plant of the same variety; and (b) selecting for at least one progeny tobacco seed, or a plant germinated therefrom, wherein said at least one tobacco seed or plant germinated therefrom comprises said recombinant DNA construct.

105. A method for producing a modified tobacco plant comprising:
  (a) crossing at least one tobacco plant of a first tobacco variety with at least one tobacco plant of a second tobacco variety to produce at least one progeny tobacco seed, wherein said at least one tobacco plant of said first tobacco variety comprises a recombinant DNA construct, wherein said recombinant DNA construct comprises a heterologous promoter operably linked to a nucleic acid sequence encoding a polypeptide comprising an amino acid sequence at least 80% identical or similar to an amino acid sequence selected from the group consisting of SEQ ID NOs: 117-174, wherein said recombinant DNA construct is not present in said nucleic acid sequence in a control tobacco plant of the first tobacco variety; and
  (b) selecting for at least one progeny tobacco seed, or a plant germinated therefrom, wherein said at least one tobacco seed or plant germinated therefrom comprises said recombinant DNA construct.

106. The method of any one of embodiments 103-105, wherein said plant germinated in step
  (b) comprises a reduced amount of at least one alkaloid as compared to said control tobacco plant when grown under comparable conditions.

107. The method of embodiment 106, wherein said at least one alkaloid is selected from the group consisting of anabasine, anatabine, nicotine, and nornicotine.

108. The method of embodiment 106 or 107, wherein said reduced amount of at least one alkaloid comprises a reduction of at least 1%.

109. The method of embodiment 103 or 104, wherein said endogenous nucleic acid sequence comprises a sequence at least 80% identical to a sequence selected from the group consisting of SEQ ID NOs: 1-116.

110. The method of embodiment 105, wherein said nucleic acid sequence comprises a sequence at least 80% identical to a sequence selected from the group consisting of SEQ ID NOs: 1-116.

111. A modified tobacco plant, or part thereof, comprising at least one non-natural mutation in an endogenous nucleic acid sequence that modulates the expression or functional activity of a gene, wherein said gene encodes a polypeptide comprising an amino acid sequence at least 80% identical or similar to an amino acid sequence selected from the group consisting of SEQ ID NOs: 117-174.

112. The modified tobacco plant, or part thereof, of embodiment 111, wherein said endogenous nucleic acid sequence encodes a transcription factor that is capable of binding to a nucleic acid sequence encoding said gene.

113. The modified tobacco plant, or part thereof, of embodiment 111, wherein said endogenous nucleic acid sequence encodes a repressor that is capable of binding to a nucleic acid sequence encoding said gene.

114. The modified tobacco plant, or part thereof, of embodiment 111, wherein said endogenous nucleic acid sequence encodes a protein that generates a precursor or substrate required for said polypeptide to function.

115. The modified tobacco plant, or part thereof, of any one of embodiments 111-114, wherein said expression or functional activity is increased expression or activity as compared to a control tobacco plant lacking said at least one non-natural mutation when grown under comparable conditions.

116. The modified tobacco plant, or part thereof, of any one of embodiments 111-114, wherein said expression or functional activity is decreased expression or activity as compared to a control tobacco plant lacking said at least one non-natural mutation when grown under comparable conditions.

117. The modified tobacco plant, or part thereof, of any one of embodiments 111-116, wherein said tobacco plant produces a leaf comprising a reduced amount of at least one alkaloid as compared to the amount of said alkaloid in a control tobacco plant lacking said at least one non-natural mutation in said endogenous nucleic acid sequence when grown under comparable conditions.

118. Cured tobacco material from the modified tobacco plant, or part thereof, of any one of embodiments 111-117.

119. A tobacco blend comprising the cured tobacco material of embodiment 118.

120. A tobacco product comprising the tobacco blend of embodiment 119.

121. A tobacco product comprising the cured tobacco material of embodiment 118.

122. A reconstituted tobacco comprising the cured tobacco material of embodiment 118.

123. A modified tobacco plant, or part thereof, comprising: (a) a genetic modification in a gene; or (b) a genetic modification targeting said gene; wherein said genetic modification downregulates the expression or activity of said gene, wherein said gene encodes a nucleic acid sequence having at least 80% identity to a polynucleotide sequence selected from the group consisting of SEQ ID NOs: 1-116.

Having now generally described the disclosure, the same will be more readily understood through reference to the following examples that are provided by way of illustration, and are not intended to be limiting of the present disclosure, unless specified.

EXAMPLES

Example 1. RNA Sequencing

RNA is isolated from TN90 tobacco roots at three time points: before topping, three-days after topping, one-week after topping, and two-weeks after topping. Three technical replicates from three biological replicates are collected for each time point. The isolated RNA is sequenced using Illumina® technology.

Sequenced reads are assessed for quality, and then mapped to a proprietary tobacco reference genome using CLC Genomics Workbench version 11.0.1 software (QIAGEN) using default parameter settings. A read count matrix including all samples is generating by aggregating the raw counts of the mapped reads for each gene in each sample against a total of 98,753 tobacco genes using the Expression Browser Tool in CLC Genomics Workbench.

RNA sequences are mapped to 57,595 tobacco genes. The 41,158 tobacco genes that do not exhibit expression are removed from further consideration. For the tobacco genes that exhibit expression, gene expression values are normalized by library size in terms of reads mapped per kilobase per million reads (RPKM). In order to reduce noise from tobacco genes with consistent expression across all four time points, or that have consistently low expression, tobacco genes that exhibit a fold change in expression across all samples of less than two log are removed. Following the removal of these tobacco genes, a total of 21,025 tobacco genes exhibit dynamic expression across the three measured time points.

Example 2. WGCNA Analysis

The R package wgcna is used to perform weighted gene co-expression network analysis (WGCNA) on the 21,025 genes exhibiting dynamic expression. See Langfelder & Horvath, "WGCNA: an R package for weighted correlation network analysis," *BMC Bioinformatics,* 9:559 (2008). A matrix of all tobacco genes with their RPKM values across nine samples (all technical and biological replicates) is used as input for WGCNA. An adjacency matrix is generated to determine similarity (e.g., correlation for every tobacco gene pair across the nine samples) between tobacco genes. Next, the results are transformed through a soft thresholding procedure in wgcna using the function pickSoftThreshold, where a soft power of 10 is chosen for module detection.

A topological overlap measure (TOM) is calculated from the adjacency matrix to estimate network interconnectedness. The dissimilarity of TOM (1-TOM) is used as the input for average linkage hierarchical clustering to identify co-expression modules. The clustering identifies 54 gene modules, and the 34 known nicotine biosynthetic pathway genes are present among these modules. See FIG. 1.

wgcna is also used to determine the interconnectedness of genes within, and between, modules. A strength value (e.g., weight) is assigned to the connection (edge) between each gene (node) and every other gene in the network. An integrated co-expression network is generating after filtering gene-to-gene connections having connectivity (edge weight >0.02).

Figure 2:
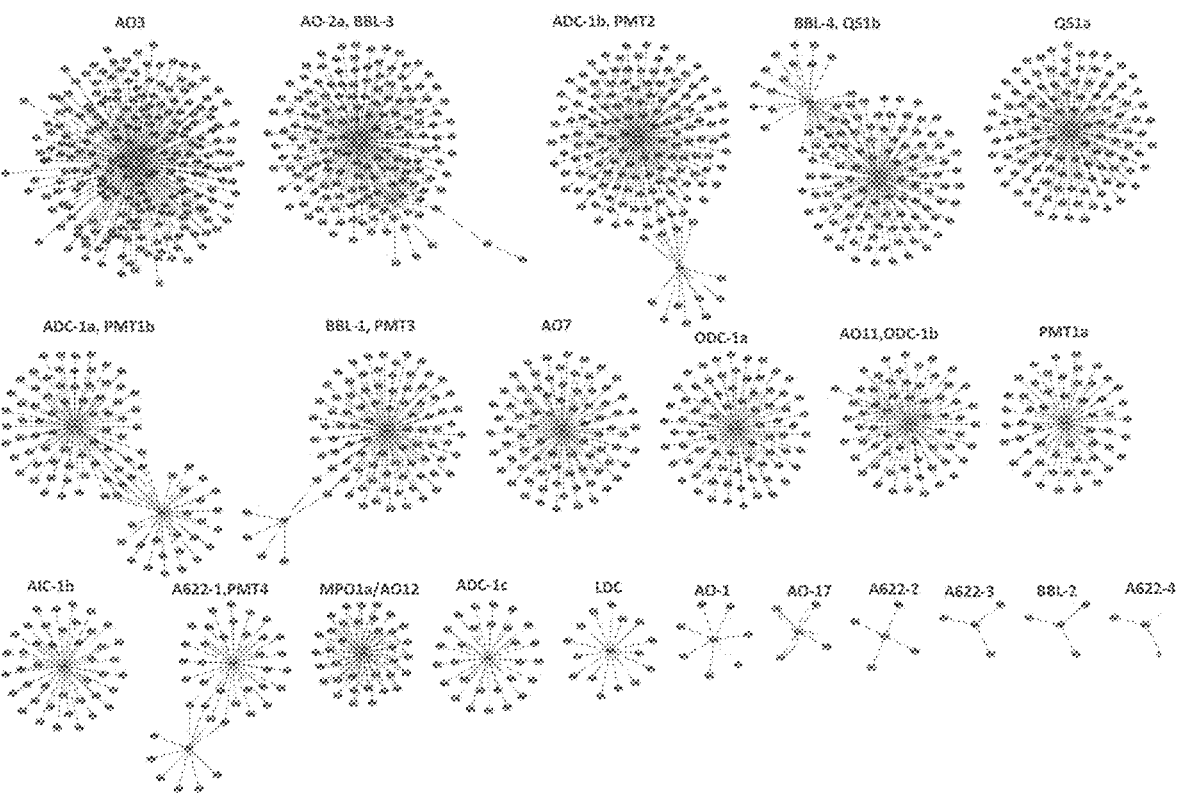
FIG. 2 depicts subnetworks extracted from wgcna and visualized in Cytoscape. Genes (nodes) labelled in the center of each subnetwork are known nicotine biosynthetic genes. Abbreviations: AO3 (L-ascorbate oxidase 3); AO-2a (L-ascorbate oxidase 2a); BBL-3 (berberine bridge enzyme-like 3); ADC-1b (arginine decarboxylase 1b); BBL-4 (berberine bridge enzyme-like 4); QS1b (quinolinate synthase 1b); QS1a (quinolinate synthase 1a); ADC-1a (arginine decarboxylase 1a); PMT1b (putrescine methyltransferase 1b); BBL-1 (berberine bridge enzyme-like 1); PMT3 (putrescine methyltransferase 3); AO7 (L-ascorbate oxidase 7); ODC-1a (ornithine decarboxylase 1a); AO11 (L-ascorbate oxidase 11); ODC-1b (ornithine decarboxylase 1b); PMT1a (putrescine methyltransferase 1a); AIC-1b (agmatine deiminase 1b); A622-1 (isoflavone reductase homolog A622 1); PMT4 (putrescine methyltransferase 4); MPO1a (N-methylputrescine oxidase 1a); AO12 (L-ascorbate oxidase 12); ADC-1c (arginine decarboxylase 1c); LDC (lysine decarboxylase); AO4 (L-ascorbate oxidase 4); AO17 (L-ascorbate oxidase 17); A622-2 (isoflavone reductase homolog A622 2); A622-3 (isoflavone reductase homolog A622 3); BBL-2 (berberine bridge enzyme-like 2); and A622-4 (isoflavone reductase homolog A622 4).

In order to define sub-networks related to specific developmental processes, and to identify novel regulatory factors, the co-expression networks are filtered for genes having strong connects to known genes of interest within a module. Co-expression modules are extracted for all of the known genes in the nicotine biosynthetic pathway and used to construct sub-networks. Gene-to-gene connections are filtered using an edge weight parameter of >0.08 to reduce complexity, and the edge weight parameter is subjected to increased stringency within sub-networks as necessary. See FIG. 2.

The sub-networks comprise 1452 tobacco genes, of which 1394 are annotated. The genes in the sub-networks include 30 nicotine biosynthesis-related genes and their homologs, plus an 58 unknown tobacco genes. The 58 unknown tobacco genes are candidates for further study. See Table 9.

TABLE 9

Candidate gene nucleic acid and amino acid sequences.

| Gene Identifier | Genomic DNA SEQ ID NO | cDNA SEQ ID NO | Amino Acid SEQ ID NO |
|---|---|---|---|
| g12941 | 1 | 59 | 117 |
| g14663 | 2 | 60 | 118 |
| g20986 | 3 | 61 | 119 |
| g20989a | 4 | 62 | 120 |
| g20989b | 5 | 63 | 121 |
| g22648 | 6 | 64 | 122 |
| g23499 | 7 | 65 | 123 |
| g26597 | 8 | 66 | 124 |
| g31004 | 9 | 67 | 125 |

92

TABLE 9-continued

Candidate gene nucleic acid and amino acid sequences.

| Gene Identifier | Genomic DNA SEQ ID NO | cDNA SEQ ID NO | Amino Acid SEQ ID NO |
|---|---|---|---|
| g31698 | 10 | 68 | 126 |
| g31724 | 11 | 69 | 127 |
| g44455 | 12 | 70 | 128 |
| g44587 | 13 | 71 | 129 |
| g47147 | 14 | 72 | 130 |
| g49713 | 15 | 73 | 131 |
| g52130 | 16 | 74 | 132 |
| g57292 | 17 | 75 | 133 |
| g59464 | 18 | 76 | 134 |
| g59465 | 19 | 77 | 135 |
| g60786 | 20 | 78 | 136 |
| g62380 | 21 | 79 | 137 |
| g62763 | 22 | 80 | 138 |
| g66085 | 23 | 81 | 139 |
| g66301 | 24 | 82 | 140 |
| g68242 | 25 | 83 | 141 |
| g69182 | 26 | 84 | 142 |
| g69391 | 27 | 85 | 143 |
| g71598 | 28 | 86 | 144 |
| g74738 | 29 | 87 | 145 |
| g74782 | 30 | 88 | 146 |
| g74912 | 31 | 89 | 147 |
| g75157 | 32 | 90 | 148 |
| g75446 | 33 | 91 | 149 |
| g75500 | 34 | 92 | 150 |
| g76096 | 35 | 93 | 151 |
| g77018 | 36 | 94 | 152 |
| g77780 | 37 | 95 | 153 |
| g78265 | 38 | 96 | 154 |
| g78408 | 39 | 97 | 155 |
| g79607 | 40 | 98 | 156 |
| g79774 | 41 | 99 | 157 |
| g82124 | 42 | 100 | 158 |
| g82252 | 43 | 101 | 159 |
| g82744 | 44 | 102 | 160 |
| g83936 | 45 | 103 | 161 |
| g86315 | 46 | 104 | 162 |
| g86407 | 47 | 105 | 163 |
| g86563 | 48 | 106 | 164 |
| g89013 | 49 | 107 | 165 |
| g91123 | 50 | 108 | 166 |
| g91334 | 51 | 109 | 167 |
| g91336 | 52 | 110 | 168 |
| g91411 | 53 | 111 | 169 |
| g92376 | 54 | 112 | 170 |
| g92662 | 55 | 113 | 171 |
| g93191 | 56 | 114 | 172 |
| g95317 | 57 | 115 | 173 |
| g95400 | 58 | 116 | 174 |

Example 3. Candidate Gene Expression

Figure 3:
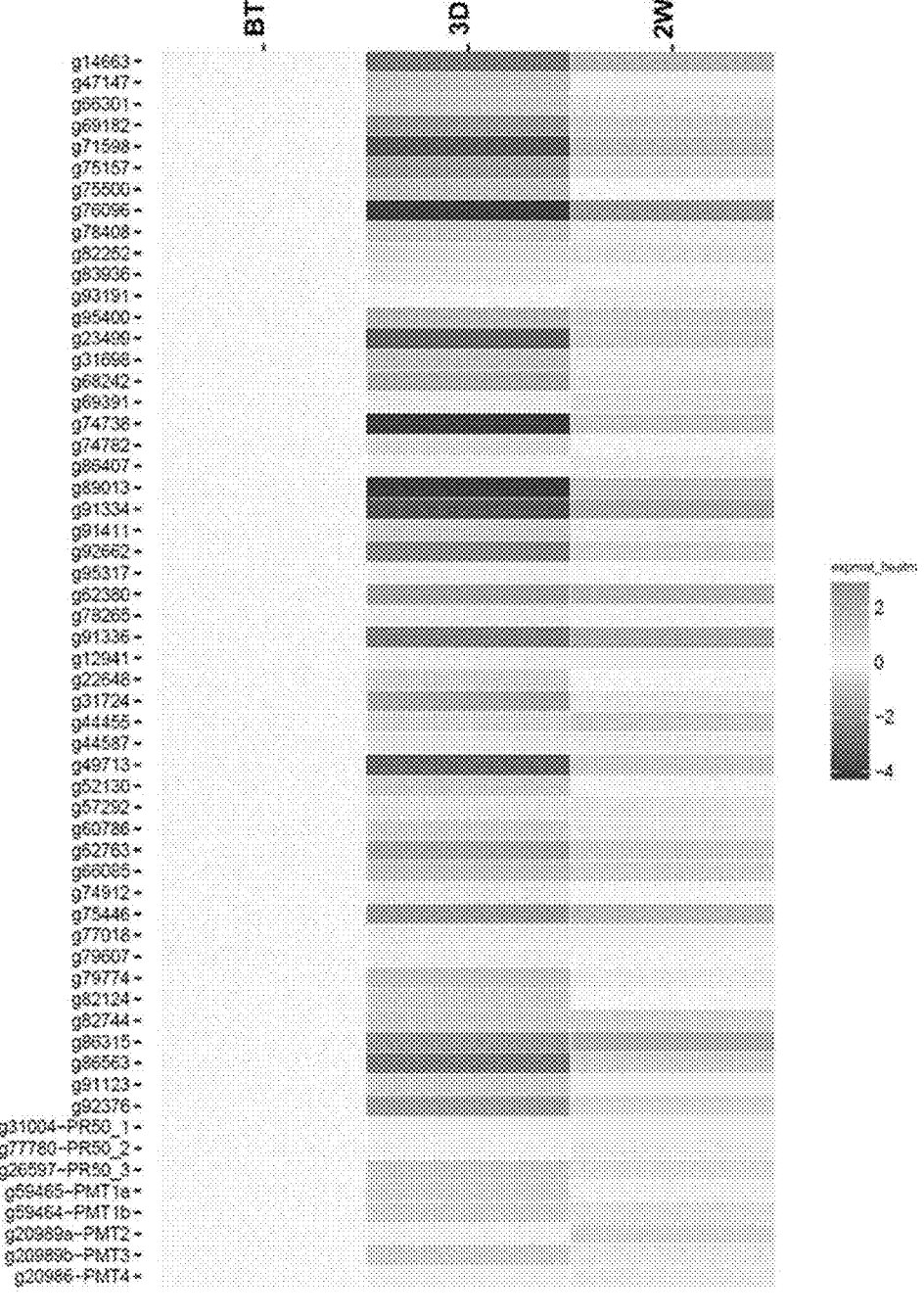
FIG. 3 depicts a heat map showing the expression in terms of log 2 fold-change between before topping (BT), three-days post-topping (3 D), and two-weeks post-topping (2 W) in TN90 tobacco root samples.
Figure 4:
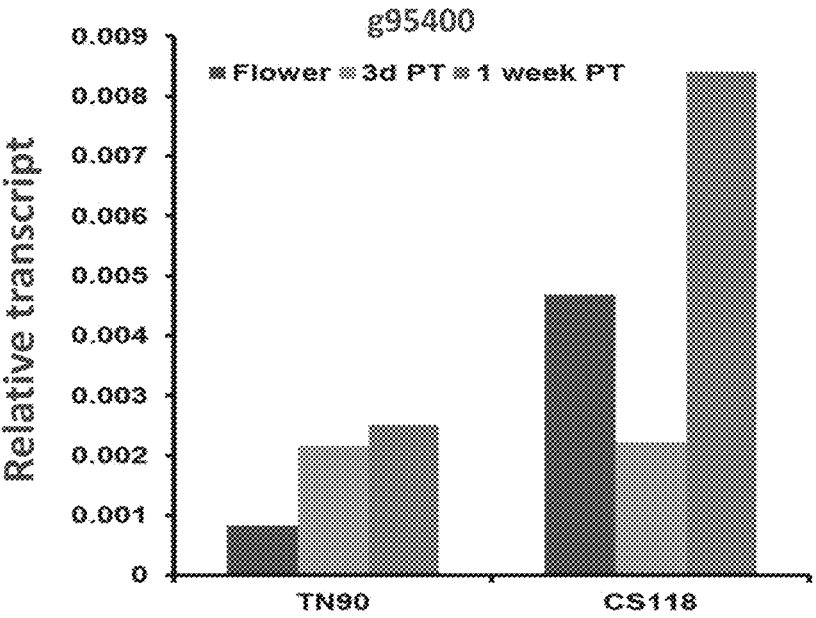
FIGS. 4 to 16 depict the relative expression (as compared to tobacco eukaryotic translation elongation factor 1 alpha (EF1α)) of fourteen novel tobacco genes in root tissue of the tobacco lines TN90 and CS118. Expression is examined before topping (BT), three days after topping (3 d) and one week after topping (1 w). Error bars, if present, represent one standard deviation.
Figure 5:
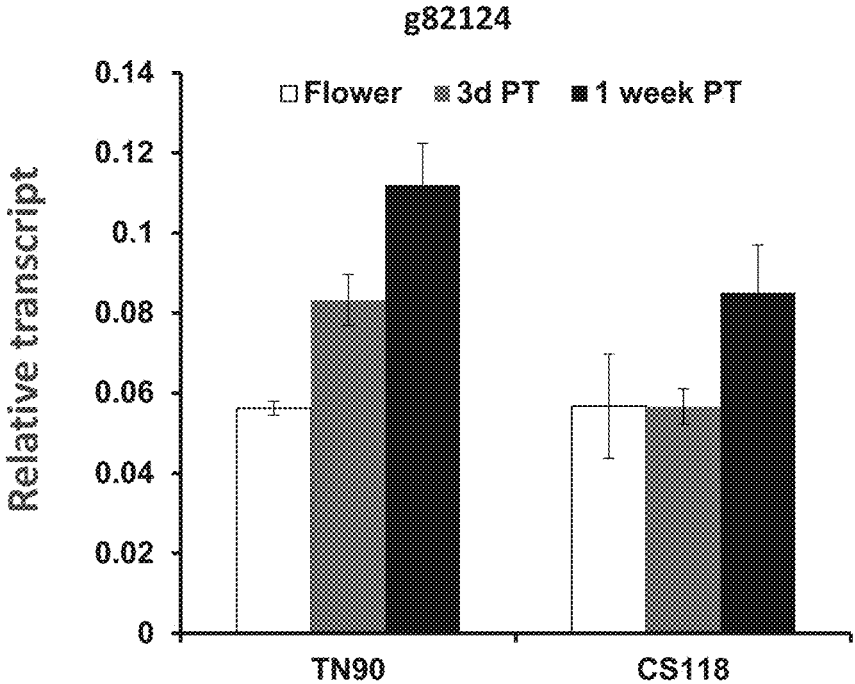
Figure 6:
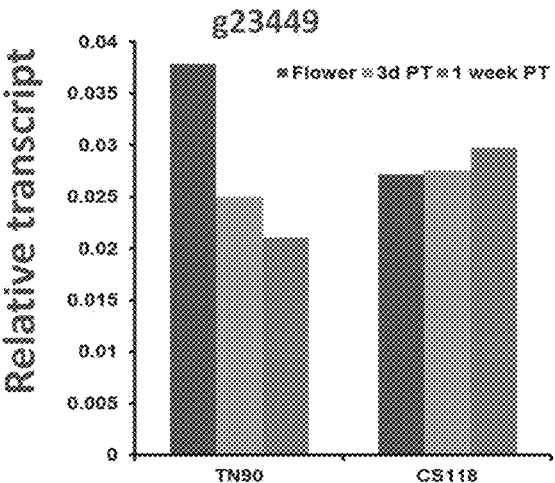
Figure 7:
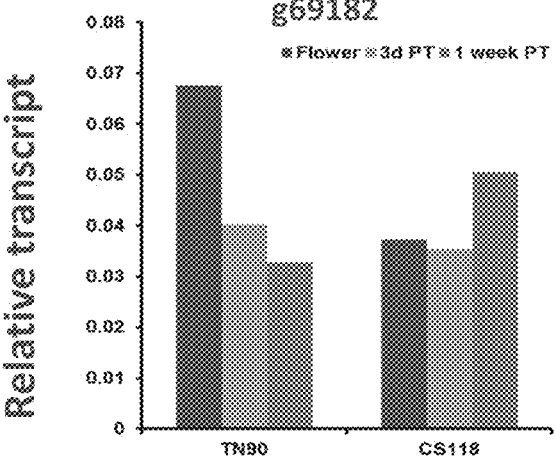
Figure 8:
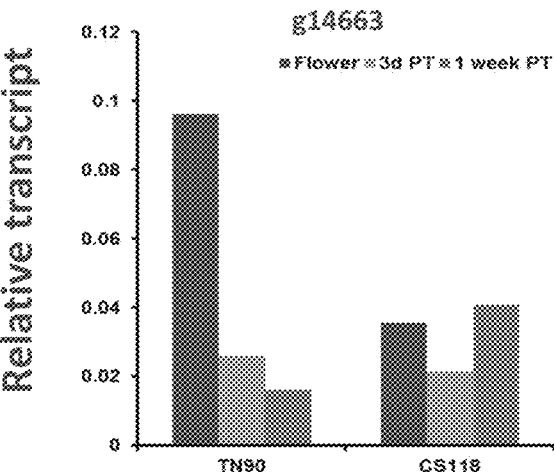
Figure 9:
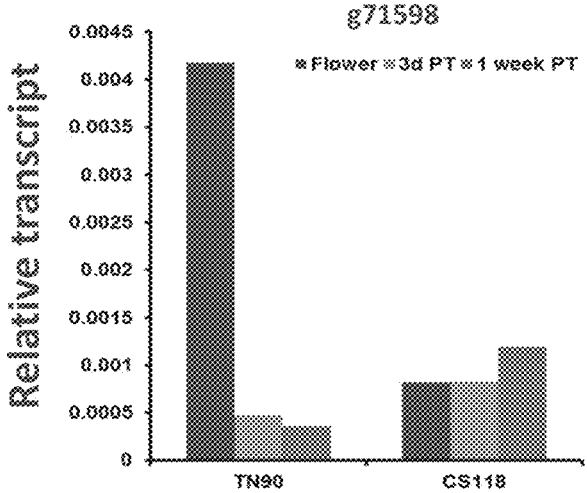
Figure 10:
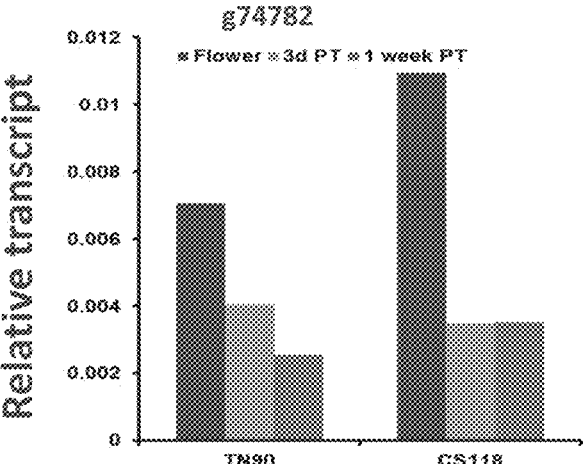
Figure 11:
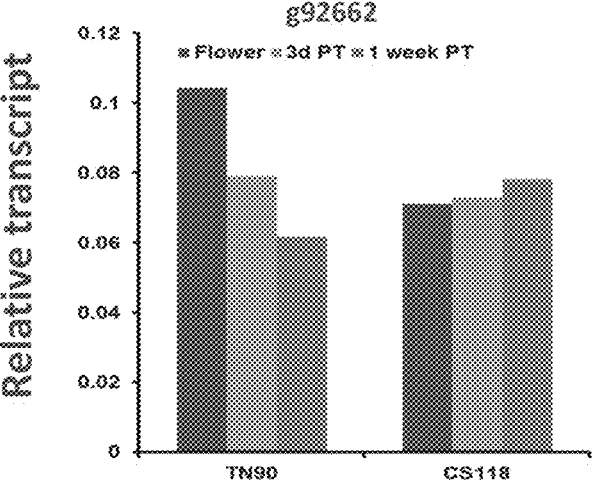
Figure 12:
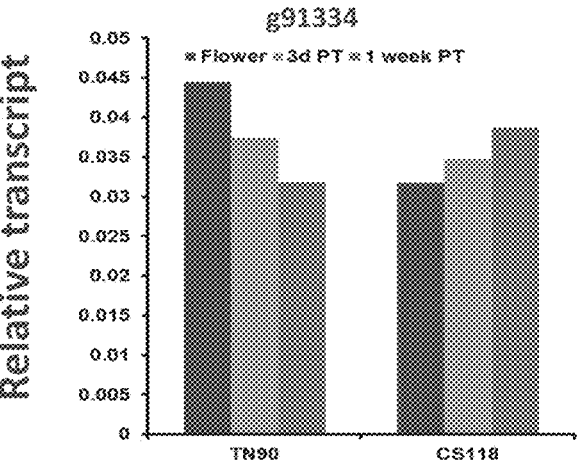
Figure 13:
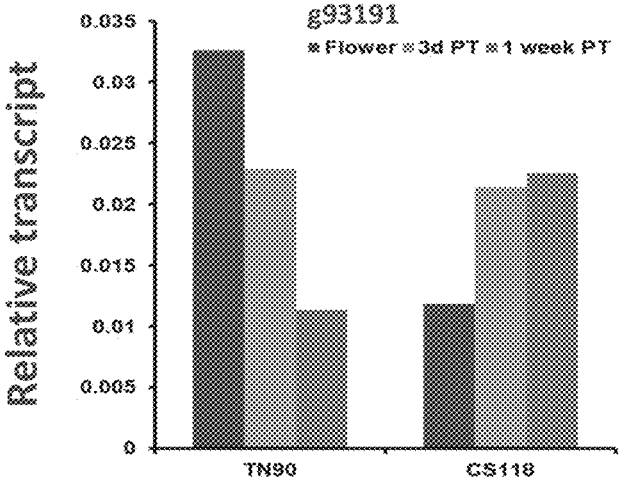
Figure 14:
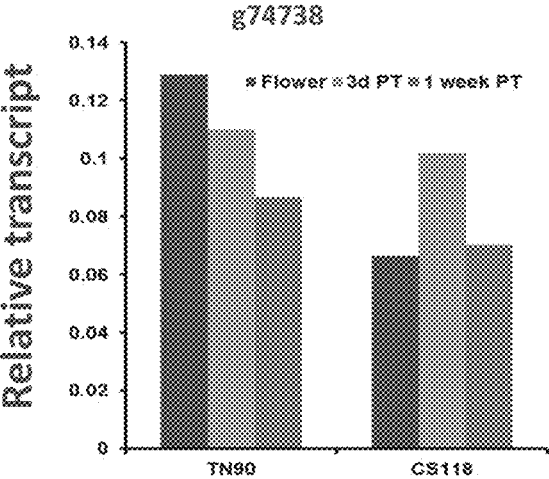
Figure 15:
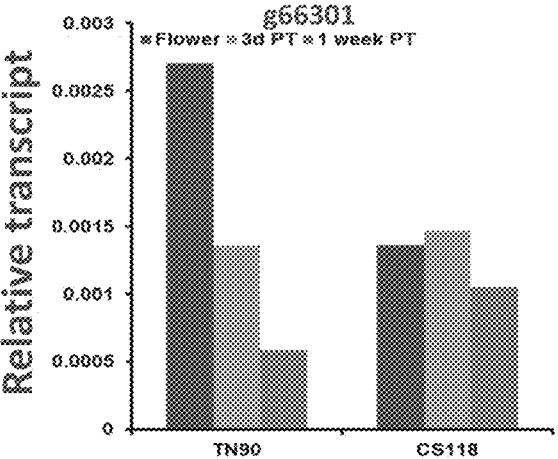
Figure 16:
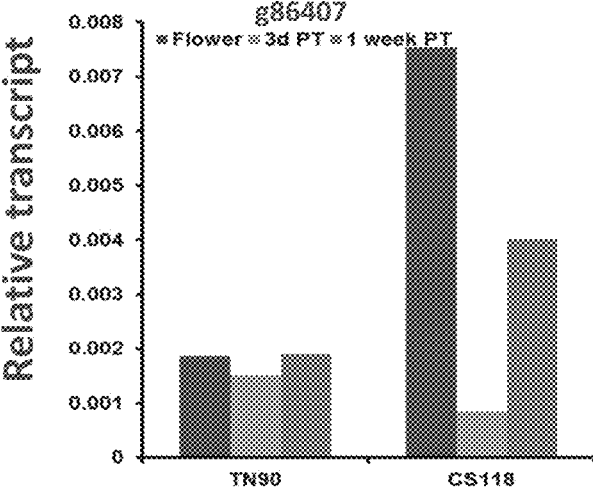

Of the 58 unknown tobacco genes ultimately identified in Example 2, 50 are considered for further evaluation. RNA expression data from Example 1 are used to compare the expression of the 50 candidate genes against the expression of known genes (e.g., PR50_1, PR50_2, PR50_3, PMT1a, PMT1b, PMT2, PMT3, PMT4). See FIG. 3.

To validate the RNA sequencing data from Example 1, expression of the candidate genes listed in Table 9 is examined in root samples from two tobacco lines: TN90 and CS118 (e.g., a PMT knockout line). See U.S. Patent Application Publication No. 2020/0029522 for additional information about CS118. Three independently collected samples are obtained at three time points: before topping (e.g., at flowering stage), three days after topping, and one week after topping.

RNA is extracted from the root samples, and cDNA transcripts are generated from the RNA samples, using methods standard in the art. The resulting cDNA is used to measure the relative expression of each candidate gene with quantitative RT-PCR (qRT-PCR) using gene-specific primers.

Relative expression of each candidate gene, as compared to a control (tobacco EF1α; SEQ ID NO: 176) is measured. See, e.g., FIGS. 4-16.

Example 4. Transformation and Regeneration of Modified Tobacco Plants

An expression vector is used as a backbone to generate multiple transformation vectors comprising recombinant DNA constructs (SEQ ID NO: 175). The expression vector contains a Cassava Vein Mosaic Virus (CsVMV) promoter, a NOS terminator, and a cassette comprising a kanamycin selection marker (NPT II) operably linked to an Actin2 promoter and a NOS terminator. Nucleic acid vectors comprising transgenes of interest (e.g., SEQ ID NOs: 1-116) are introduced into tobacco leaf discs via *Agrobacterium* transformation. See, for example, Mayo et al., 2006, *Nat Protoc.* 1:1105-11 and Horsch et al., 1985, *Science* 227:1229-1231.

TN90 tobacco plants are grown in Magenta™ GA-7 boxes and leaf discs are cut and placed into Petri plates. *Agrobacterium tumefaciens* cells comprising a transformation vector are collected by centrifuging a 20 mL cell suspension in a 50 mL centrifuge tube at 3500 RPM for 10 minutes. The supernatant is removed and the *Agrobacterium tumefaciens* cell pellet is re-suspended in 40 mL liquid re-suspension medium. Tobacco leaves, avoiding the midrib, are cut into eight 0.6 cm discs with a #15 razor blade and placed upside down in a Petri plate. A thin layer of Murashige & Skoog (MS) with B5 vitamin liquid re-suspension medium is added to the Petri plate and the leaf discs are poked uniformly with a fine point needle. About 25 mL of the *Agrobacterium tumefaciens* suspension is added to the Petri plate and the leaf discs are incubated in the suspension for 10 minutes.

Leaf discs are transferred to co-cultivation Petri plates (½ MS medium) and discs are placed upside down in contact with filter paper overlaid on the co-cultivation TOM medium (MS medium with 20 g/L sucrose; 1 mg/L indole-3-acetic acid; and 2.5 mg/L 6-benzyl aminopurine (BAP)). The Petri plate is sealed with parafilm prior to incubation in dim light (60-80 mE/ms) with 18 hours on, 6 hours off photoperiods at 24° C. for three days. After incubation, leaf discs are transferred to regeneration/selection TOM K medium Petri plates (TOM medium plus 300 mg/L kanamycin). Leaf discs are sub-cultured bi-weekly to fresh TOM K medium in dim light with 18 hours on, 6 hours off photoperiods at 24° C. until shoots become excisable. Shoots from leaves are removed with forceps and inserted in MS basal medium with 100 mg/L kanamycin. Shoots on MS basal medium with 100 mg/L kanamycin are incubated at 24° C. with 18 hours on, 6 hours off photoperiods with high intensity lighting (6080 mE/ms) to induce rooting.

When plantlets comprising both shoots and roots grow large enough (e.g., over half the height of a Magenta™ GA-7 box), they are transferred to soil for acclimatization. Once established, seedlings are transferred to a greenhouse for further growth, breeding, and analysis.

Example 5. Measuring Alkaloid Levels in Tobacco

Modified tobacco plants from Example 4, along with controls, are grown in 25 centimeter pots in a greenhouse with 75 parts per million fertilizer. At flowering stage, plants are topped. Two weeks after topping, lamina samples are collected from the third, fourth, and fifth leaves from the top of the plant, and alkaloid levels are measured using a method in accordance with CORESTA Method No 62, *Determination of Nicotine in Tobacco and Tobacco Products by Gas Chromatographic Analysis*, February 2005, and those defined in the Centers for Disease Control and Prevention's *Protocol for Analysis of Nicotine, Total Moisture and pH in Smokeless Tobacco Products*, as published in the Federal Register Vol. 64, No. 55 Mar. 23, 1999 (and as amended in Vol. 74, No. 4, Jan. 7, 2009).

Briefly, approximately 0.5 grams (g) of tobacco is extracted using liquid/liquid extraction into an organic solvent containing an internal standard and analyzed using gas chromatography (GC) with flame ionization detection (FID). Results can be reported as weight percent (Wt %) on either an "as is" or a "dry weight" basis. Reporting data on a dry weight basis requires an oven volatiles (OV) determination. Unless specified otherwise, total or individual alkaloid levels or nicotine levels provided herein are on a milligrams/gram dry weight basis.

Plants are also planted in the field, harvested, and tested for alkaloids and TSNA levels in cured tobacco. Both leaf yield and leaf grade are also assessed for modified plants.

Example 6. Overexpression of Candidate Genes in Tobacco Hairy Root Cultures or Tobacco Plants Separate transformation vectors comprising one each of SEQ ID NOs: 59-116 under the control of a CsVMV promoter are constructed using the vector described in Example 4. The vectors are used to (a) transform dark tobacco hairy root cultures using the *Agrobacterium rhizogenes* line ATCC15834 and/or (b) generate modified tobacco plants as described in Example 4. Control hairy root cultures and control modified tobacco plants are transformed with an "empty" vector that lacks the overexpressed gene (termed "vector controls" or "VC"). Alkaloid levels of tobacco plants are measured as described in Example 5. Alkaloid levels of tobacco root cultures are measured as described in Example 7.

Hairy root cultures can serve as an alternative to plant cell suspensions and serve as useful proxies for whole plants when studying secondary metabolites. See, for example, Zhou et al., *Appl. Microbiol Biotechnol.*, 90:1229-1239 (2011) and Hidalgo et al., Scientific Reports, 7:45331 (2017) for additional information regarding hairy root cultures.

Transformation and hairy root induction is performed as described in Hidalgo et al., *Scientific Reports*, 7:17976 (2017). Briefly, leaf discs from tobacco plantlets are grown in vitro on MS medium. The leaf discs are co-infected with *Agrobacterium rhizogenes* line ATCC15834 to introduce the transformation vectors described above and to induce hairy root formation. Approximately two to four weeks after transformation, hairy roots appear in leaf discs grown on solid MS medium comprising 30 grams per liter (g/L) sucrose and 500 milligrams per liter (mg/L) cefotaxime. Hairy roots are then excised and individually cultured on solid MS medium comprising 30 g/L sucrose, 500 mg/L cefotaxime, and 50 mg/L kanamycin to select for hairy root cultures that are successfully transformed. Transformed hairy root cultures are grown in the dark at 25° C. Approximately two to three weeks later, liquid cultures are inoculated with transgenic roots and are grown at 25° C. until they are used in further analyses.

FIGS. 17, 29, 41, and 45 depict the relative expression of g22648, g12941, g14663, and g71598, respectively, as compared to the expression of EF1α (SEQ ID NO: 176) in dark tobacco hairy root cultures in lines over-expressing each gene. FIGS. 18, 30, 42, and 46 depict relative expression of the tobacco quinolinate phosphoribosyltransferase (QPT) and putrescine N-methyltransferase (PMT) gene families as compared to EF1α in the hairy root culture lines overexpressing g22648, g12941, g14663, and g71598, respectively.

Example 8. Measuring Alkaloid Content in Transformed Tobacco Hairy Root Cultures Overexpressing Candidate Genes Alkaloid levels are also measured in the hairy root cultures that are overexpressing a candidate gene discussed above in Example 6 and control hairy root cultures comprising an empty vector.

Briefly, to measure alkaloids, hairy root culture tissues are frozen in liquid nitrogen and ground to a fine powder. Approximately 50 mg of the fine powder (per sample) is extracted twice with two volumes of 100% methanol, sonicated for 30 minutes, and then the supernatant is collected and evaporated. Alkaloid levels are quantified via gas chromatography-mass spectrometry (GC/MS) using a QP2010SE quadrupole mass spectrometer (Shimadzu, Japan) following separation using a Zebron ZB-5 (Phenomenex, USA) 30 m stationary phase column with 0.25 mm internal diameter and 0.25 μm film thickness. For each sample, 1 μL of sample is injected into a column with the following settings: split mode 1:10, injection port temperature 250° C. The ZB5 column is maintained at 45° C. for one minute followed by a gradient of 10° C. per minute until the temperature reaches 300° C., which is held for a further seven minutes. Helium inlet pressure is checked by electronic pressure control to achieve a constant column flow rate of 1.0 milliliter per minute. Alkaloids are identified by comparison with reference spectra and the NIST library. Quantities of alkaloids detected are provided as milligrams per gram (mg/g).

FIGS. 19, 31, 43, and 47 depict average nicotine levels (using three biological replicates per line) in hairy root culture lines overexpressing g22648, g12941, g14663, and g71598, respectively, and corresponding vector controls. FIGS. 20, 32, 44, and 48 depict average nornicotine, anatabine, and anabasine levels (using three biological replicates per line) in hairy root culture lines overexpressing g22648, g12941, g14663, and g71598, respectively, and corresponding vector controls. Table 10 provides average alkaloid levels as shown in FIGS. 19, 20, 31, 32, 43, 44, 47, and 48. Table 11 provides percentage change for each overexpression line as compared to the vector control average (or single vector control if only one vector control is available) for each alkaloid. Percent change compared to control in Table 11 is calculated by using the formula: ((Overexpression Line Level−Control Level)/(Control Level))×100 for each measured alkaloid.

TABLE 10

Alkaloid levels in tobacco plants overexpressing genes of interest.

| Gene | | Alkaloids (mg/g dry weight) | | | |
|---|---|---|---|---|---|
| ID | Expression | Nicotine | Nornicotine | Anatabine | Anabasine |
| g22648 | OX-1 | 14.66 | 1.002 | 0.789 | 0.735 |
| | OX-2 | 11.75 | 0.956 | 0.419 | 0.294 |
| | VC | 10.88 | 0.796 | 0.408 | 0.252 |
| | VC | 9.60 | 0.751 | 0.517 | 0.370 |

TABLE 10-continued

Alkaloid levels in tobacco plants overexpressing genes of interest.

| Gene | | Alkaloids (mg/g dry weight) | | | |
|---|---|---|---|---|---|
| ID | Expression | Nicotine | Nornicotine | Anatabine | Anabasine |
| | VC | 7.05 | 0.378 | 0.536 | 0.297 |
| | OX Average | 13.2 | 0.979 | 0.604 | 0.515 |
| | VC Average | 9.17 | 0.642 | 0.487 | 0.306 |
| g12941 | OX-1 | 8.41 | 0.488 | 0.750 | 0.397 |
| | OX-2 | 13.24 | 0.855 | 0.753 | 0.582 |
| | VC | 9.80 | 0.501 | 0.735 | 0.155 |
| | VC | 12.61 | 0.746 | 0.803 | 0.194 |
| | VC | 7.05 | 0.378 | 1.205 | 0.132 |
| | OX Average | 10.825 | 0.672 | 0.752 | 0.49 |
| | VC Average | 9.82 | 0.542 | 0.914 | 0.16 |
| g14663 | OX-1 | 4.70 | 0.264 | 0.766 | 0.072 |
| | OX-2 | 5.80 | 0.360 | 0.303 | 0.163 |
| | VC | 7.05 | 0.378 | 0.536 | 0.297 |
| | OX Average | 5.25 | 0.312 | 0.535 | 0.118 |
| g71958 | OX-1 | 7.99 | 0.544 | 0.450 | 0.227 |
| | OX-2 | 7.78 | 0.520 | 0.352 | 0.308 |
| | VC | 9.80 | 0.501 | 0.735 | 0.155 |
| | OX Average | 7.89 | 0.532 | 0.401 | 0.268 |

OX = overexpression line; VC = vector control.

TABLE 11

Percent change in alkaloids as compared to controls.

| Gene | | Alkaloids (% change compared to control) | | | |
|---|---|---|---|---|---|
| ID | Expression | Nicotine | Nornicotine | Anatabine | Anabasine |
| g22648 | OX-1 | +59.87% | +56.07% | +62.01% | +140.2% |
| | OX-2 | +28.14% | +48.91% | −13.96% | −3.92% |
| g12941 | OX-1 | −14.36% | −9.96% | −17.94% | +148.1% |
| | OX-2 | +34.83% | +57.75% | −17.61% | +263.8% |
| g14663 | OX-1 | −33.33% | −30.16% | +42.91% | −75.76% |
| | OX-2 | −17.73% | −4.76% | −43.47% | −45.12% |
| g71958 | OX-1 | −18.47% | +8.58% | −38.78% | +46.45% |
| | OX-2 | −20.61% | +3.79% | −52.11% | +98.71% |

OX = overexpression line.

Example 9. Knockdown of Candidate Genes Using Small RNA Molecules in Tobacco Reducing the expression of genes identified in Table 9 is tested for their effect on the levels of specific alkaloids such as nicotine, nornicotine, anatabine, and anabasine.

Separate transformation vectors comprising an artificial miRNA designed to reduce the transcription or translation of one each of SEQ ID NOs: 59-116 driven by CsVMV are constructed using the vector described in Example 4. Tobacco lines (plants or hairy root cultures) expressing these RNAi constructs can be collectively referred to as "knockdown lines."

The vectors are used to (a) transform dark tobacco hairy root cultures using the *Agrobacterium rhizogenes* line ATCC15834 as described in Example 6 and/or (b) generate modified tobacco plants as described in Example 4. Control hairy root cultures and control modified tobacco plants are transformed with an "empty" vector that lacks the miRNA constructs (referred to as "vector controls" or "VC"). Alkaloid levels of transformed tobacco hairy root cultures are measured as described in Example 8. Alkaloid levels of transformed tobacco plants are measured as described in Example 5.

Figure 17:
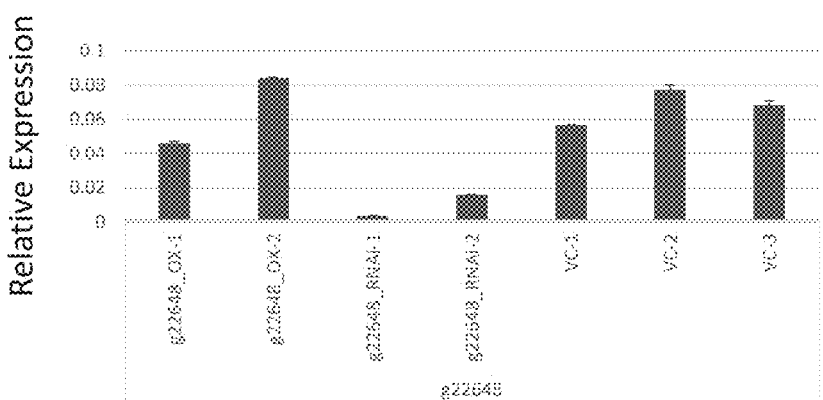
FIG. 17 depicts relative expression (as compared to EF1α) of g22648 in over-expression (OX) and knockdown (RNAi) lines as compared to three vector control lines (VC-1, VC-2, and VC-3).
Figure 21:
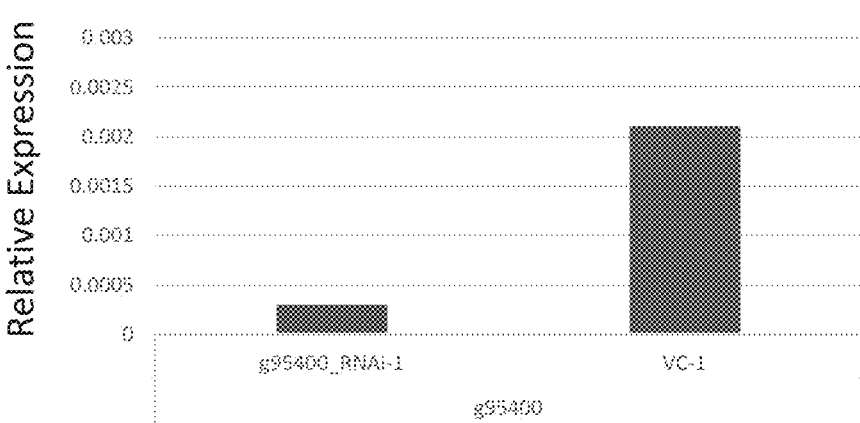
FIG. 21 depicts relative expression (as compared to EF1α) of g95400 in an RNAi knockdown tobacco line as compared to a vector control line (VC).
Figure 25:
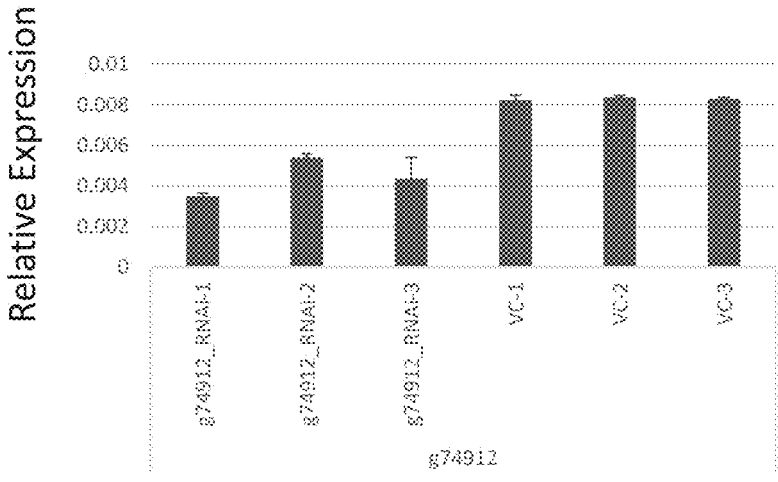
FIG. 25 depicts relative expression (as compared to EF1α) of g74912 in RNAi knockdown tobacco line as compared to three vector control lines (VC).
Figure 29:
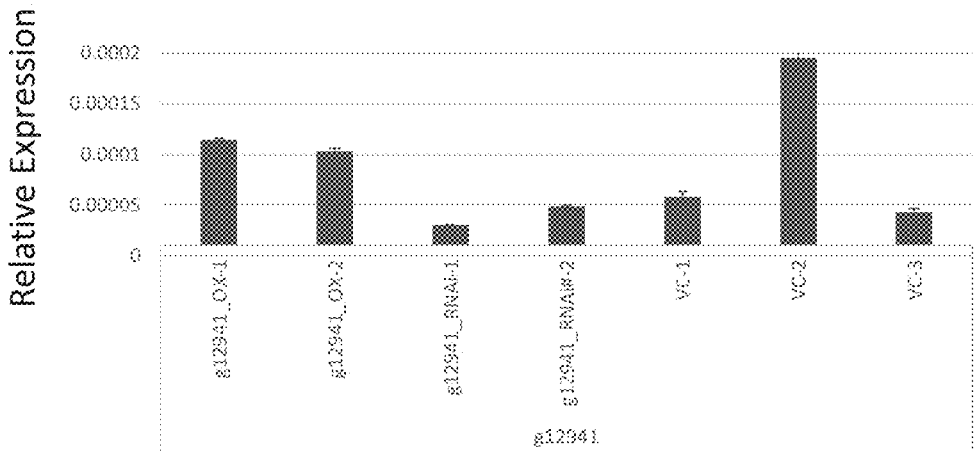
FIG. 29 depicts relative expression (as compared to EF1α) of g12941 in over-expression (OX) and knockdown (RNAi) lines as compared to three vector control lines (VC-1, VC-2, and VC-3).
Figure 33:
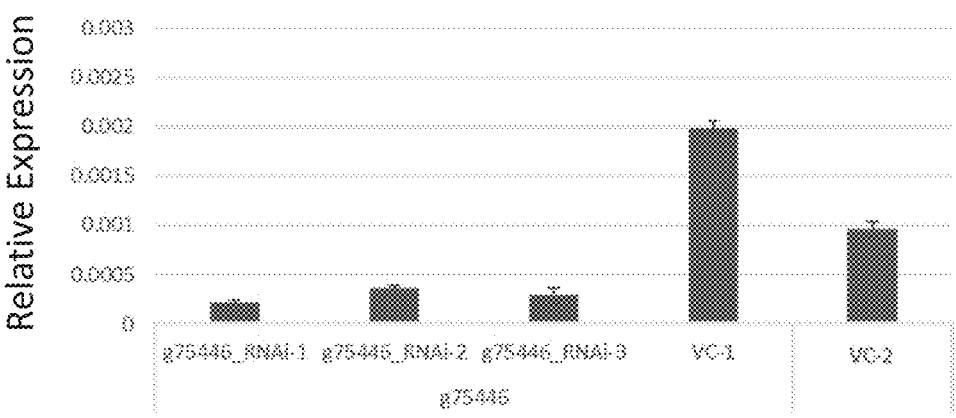
FIG. 33 depicts relative expression (as compared to EF1α) of g75446 in RNAi knockdown tobacco lines as compared to two vector control lines (VC).
Figure 37:
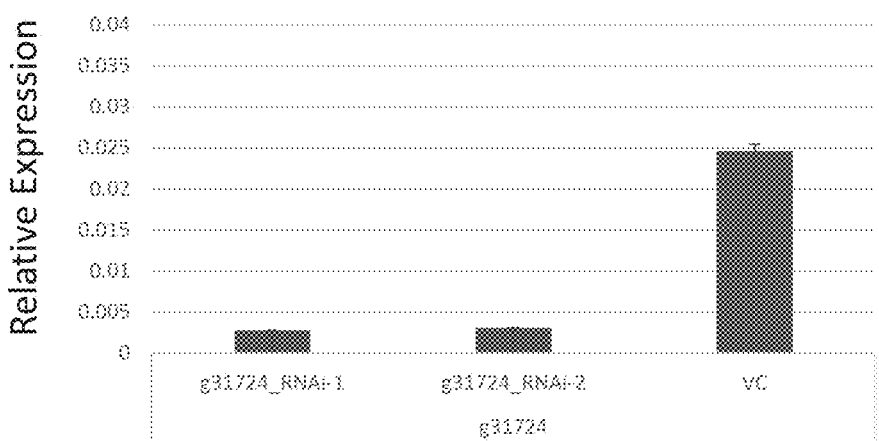
FIG. 37 depicts relative expression (as compared to EF1α) of g31724 in two RNAi knockdown tobacco lines as compared to a vector control line (VC).
Figure 49:
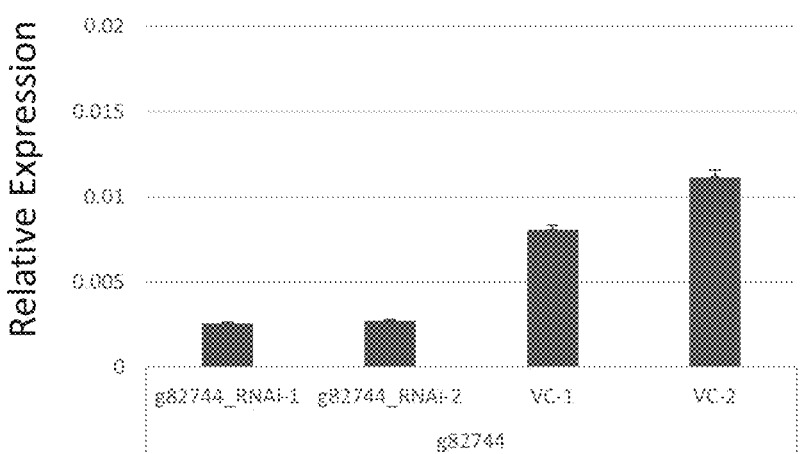
FIG. 49 depicts relative expression (as compared to EF1α) of g82744 in two RNAi knockdown tobacco lines as compared to two vector control lines (VC).
Figure 53:
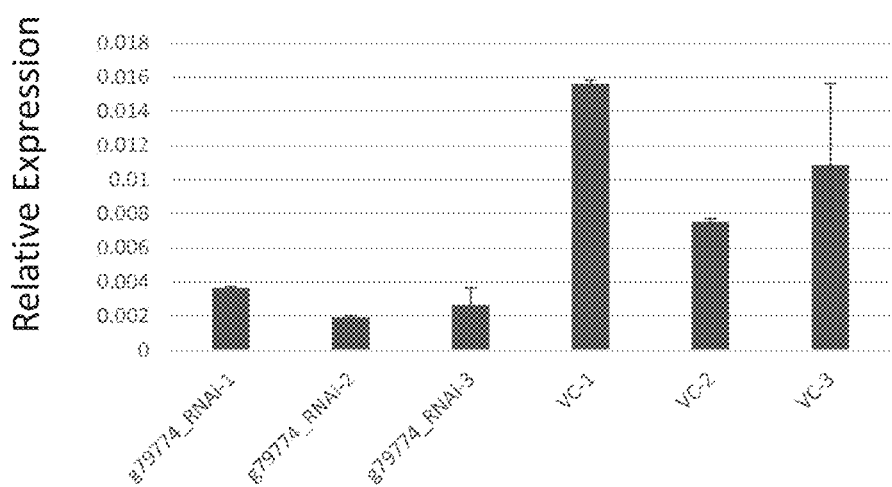
FIG. 53 depicts relative expression (as compared to EF1α) of g79774 in three RNAi knockdown tobacco lines as compared to two vector control lines (VC).
Figure 57:
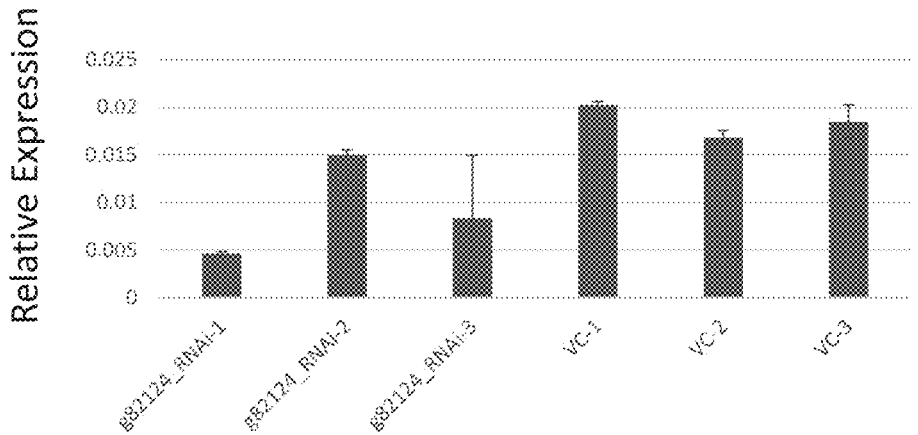
FIG. 57 depicts relative expression (as compared to EF1α) of g82124 in three RNAi knockdown tobacco lines as compared to three vector control lines (VC).

FIG. 17 depicts relative expression of g22648 relative to EF1α in hairy root culture knockdown lines as compared to vector control lines. FIG. 21 depicts relative expression of g95400 relative to EF1α in a hairy root culture knockdown line as compared to a vector control line. FIG. 25 depicts relative expression of g74912 relative to EF1α in hairy root culture knockdown lines as compared to vector control lines. FIG. 29 depicts relative expression of g12941 relative to EF1α in hairy root culture knockdown lines as compared to vector control lines. FIG. 33 depicts relative expression of g75446 relative to EF1α in hairy root culture knockdown lines as compared to vector control lines. FIG. 37 depicts relative expression of g31724 relative to EF1α in hairy root culture knockdown lines as compared to vector control lines. FIG. 49 depicts relative expression of g82744 relative to EF1α in hairy root culture knockdown lines as compared to vector control lines. FIG. 53 depicts relative expression of g79774 relative to EF1α in hairy root culture knockdown lines as compared to vector control lines. FIG. 57 depicts relative expression of g82124 relative to EF1α in hairy root culture knockdown lines as compared to vector control lines.

Figure 18:
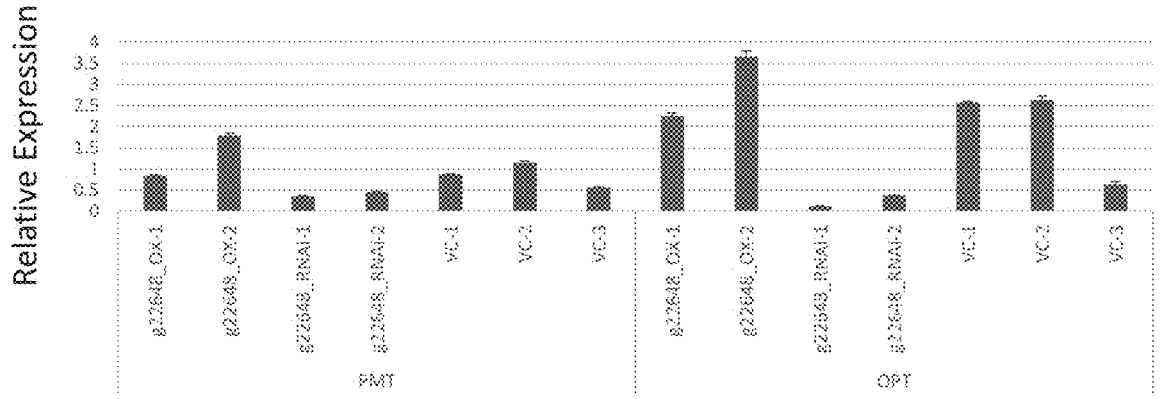
FIG. 18 depicts the relative expression (as compared to EF1α) of putrescine N-methyltransferase (PMT) and quinolinate phosphoribosyltransferase (QPT) gene families in g22648 overexpression (OX) and knockdown (RNAi) tobacco lines, as compared to three vector control lines (VC-1, VC-2, and VC-3).
Figure 22:
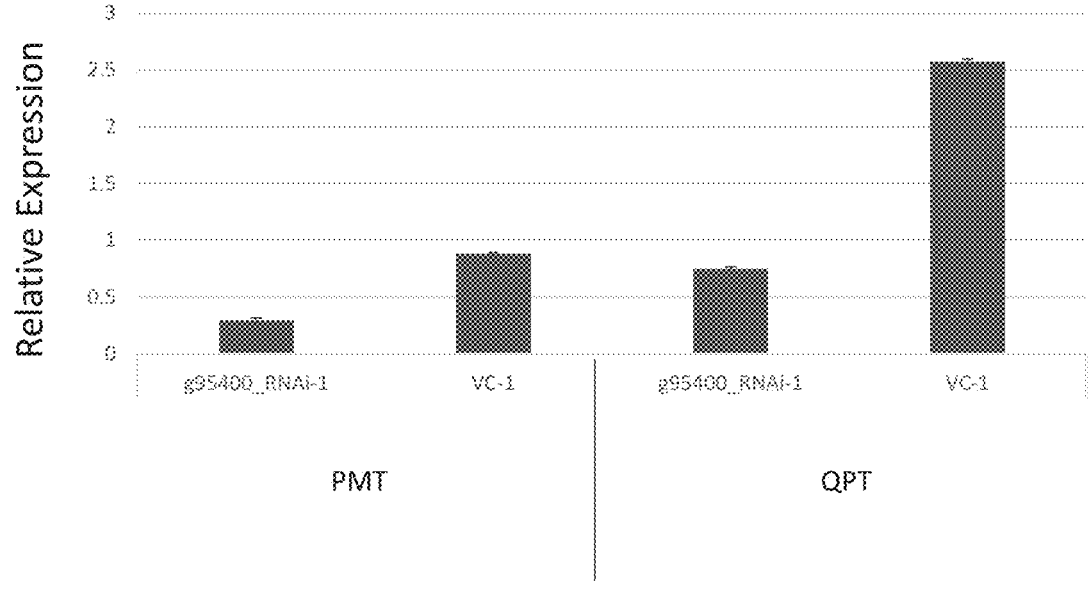
FIG. 22 depicts relative expression (as compared to EF1α) of PMT and QPT gene families in a g95400 RNAi knockdown tobacco line as compared to a vector control line (VC).
Figure 26:
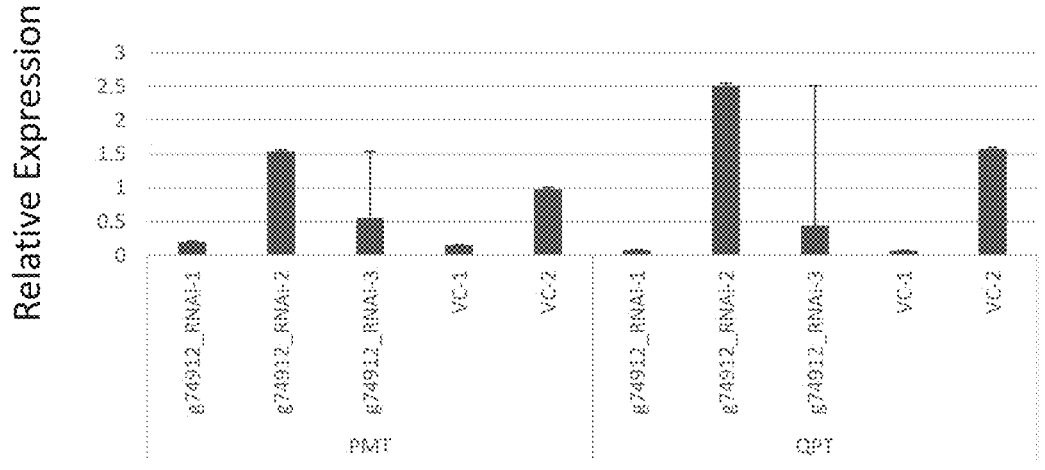
FIG. 26 depicts relative expression (as compared to EF1α) of PMT and QPT gene families in g74912 RNAi knockdown tobacco lines as compared to two vector control lines (VC).
Figure 30:
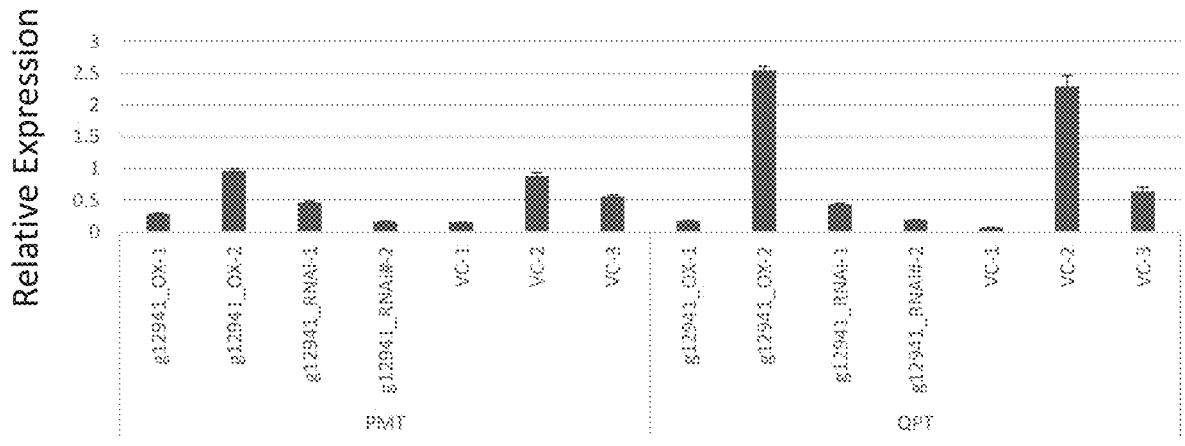
FIG. 30 depicts relative expression (as compared to EF1α) of putrescine N-methyltransferase (PMT) and quinolinate phosphoribosyltransferase (QPT) in g12941 over-expression (OX) and knockdown (RNAi) tobacco lines, as compared to three vector control lines (VC-1, VC-2, and VC-3).
Figure 34:
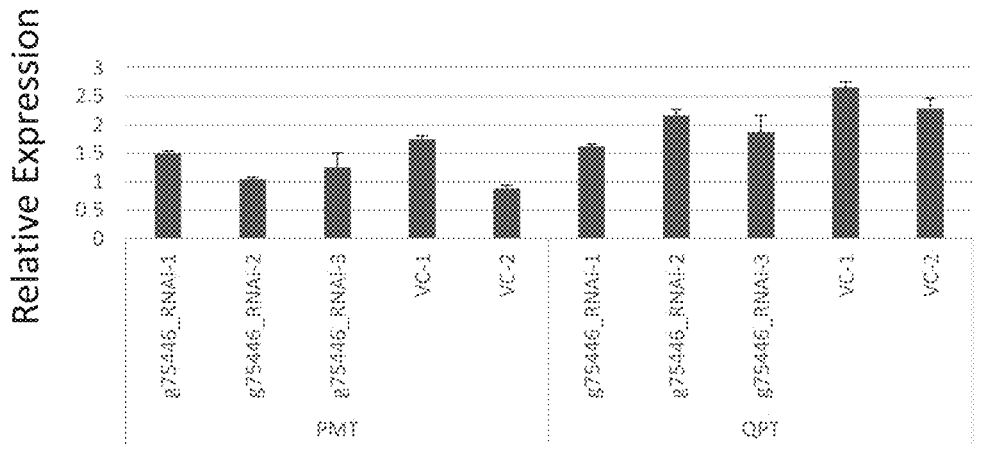
FIG. 34 depicts relative expression (as compared to EF1α) of PMT and QPT gene families gene families in g75446 RNAi knockdown tobacco lines as compared to two vector control lines (VC).
Figure 38:
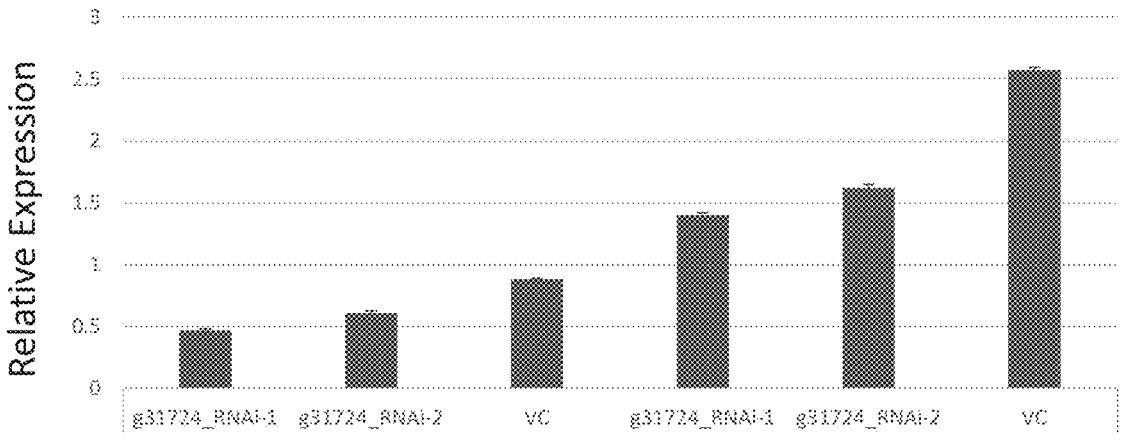
FIG. 38 depicts relative expression (as compared to EF1α) of PMT and QPT gene families gene families in two g31724 RNAi knockdown tobacco lines as compared to a vector control line (VC).
Figure 50:
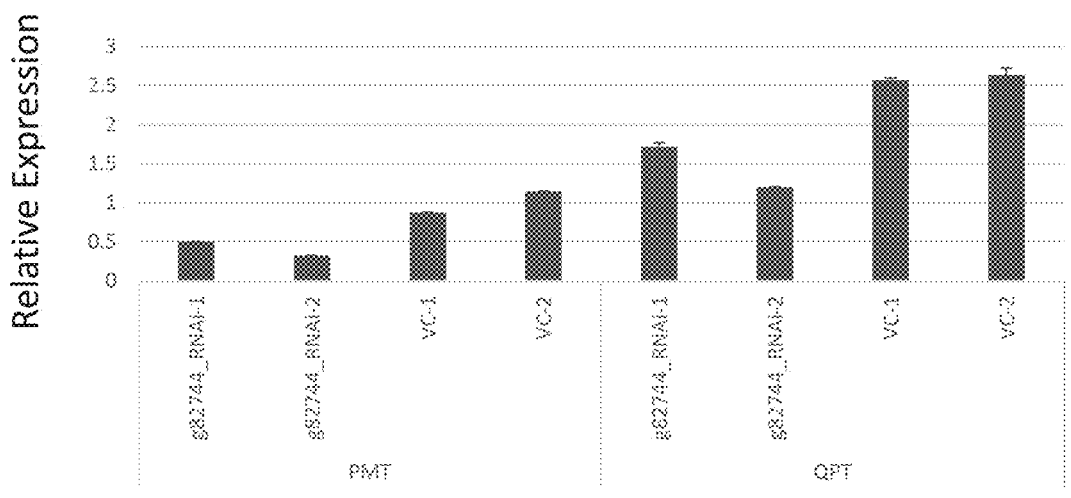
FIG. 50 depicts relative expression (as compared to EF1α) of PMT and QPT gene families in two g82744 RNAi knockdown tobacco lines as compared to two vector control lines (VC).
Figure 54:
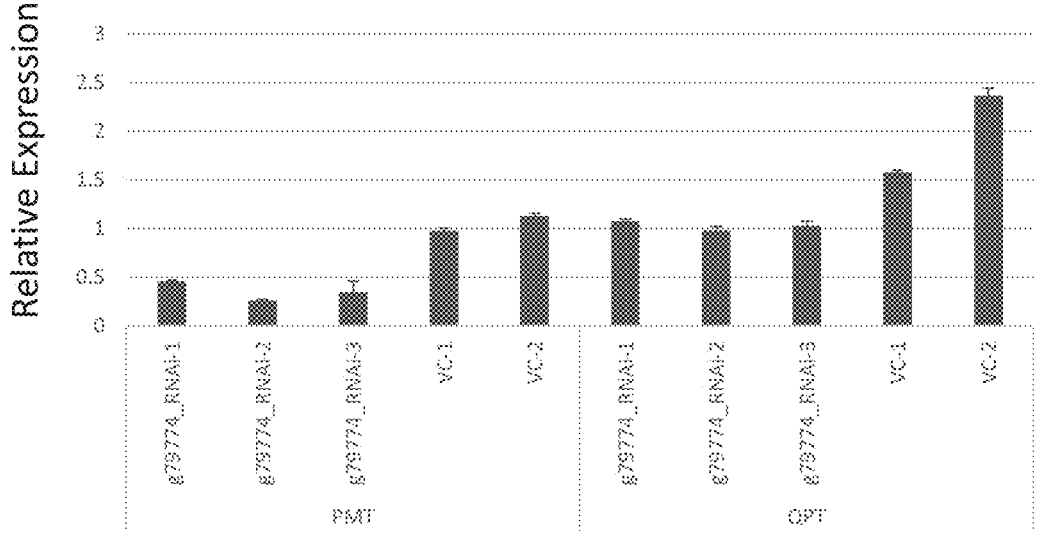
FIG. 54 depicts relative expression (as compared to EF1α) of PMT and QPT gene families in three g79774 RNAi knockdown tobacco lines as compared to two vector control lines (VC).
Figure 58:
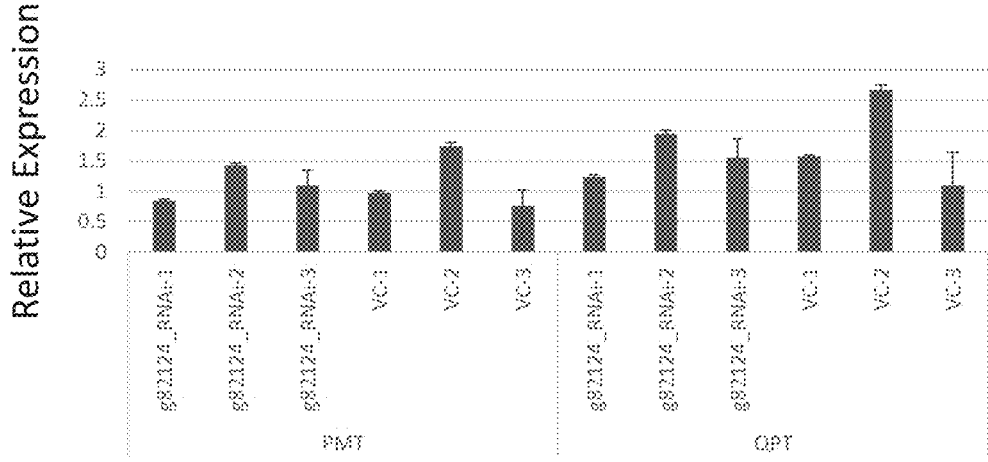
FIG. 58 depicts relative expression (as compared to EF1α) of PMT and QPT gene families in three g82124 RNAi knockdown tobacco lines as compared to three vector control lines (VC).

The relative expression of both PMT and QPT gene families is also measured in each of the knockdown lines. FIG. 18 depicts relative expression of PMT and QPT gene families relative to EF1α in hairy root culture g22648 knockdown lines as compared to vector control lines. FIG. 22 depicts relative expression of PMT and QPT gene families relative to EF1α in a hairy root culture g25400 knockdown line as compared to a vector control line. FIG. 26 depicts relative expression of PMT and QPT gene families relative to EF1α in hairy root culture g74912 knockdown lines as compared to vector control lines. FIG. 30 depicts relative expression of PMT and QPT gene families relative to EF1α in hairy root culture g12941 knockdown lines as compared to vector control lines. FIG. 34 depicts relative expression of PMT and QPT gene families relative to EF1α in hairy root culture g75446 knockdown lines as compared to vector control lines. FIG. 38 depicts relative expression of PMT and QPT gene families relative to EF1α in hairy root culture g31724 knockdown lines as compared to vector control lines. FIG. 50 depicts relative expression of PMT and QPT gene families relative to EF1α in hairy root culture g82744 knockdown lines as compared to vector control lines. FIG. 54 depicts relative expression of PMT and QPT gene families relative to EF1α in hairy root culture g79774 knockdown lines as compared to vector control lines. FIG. 58 depicts relative expression of PMT and QPT gene families relative to EF1α in hairy root culture g82124 knockdown lines as compared to vector control lines.

Figure 19:
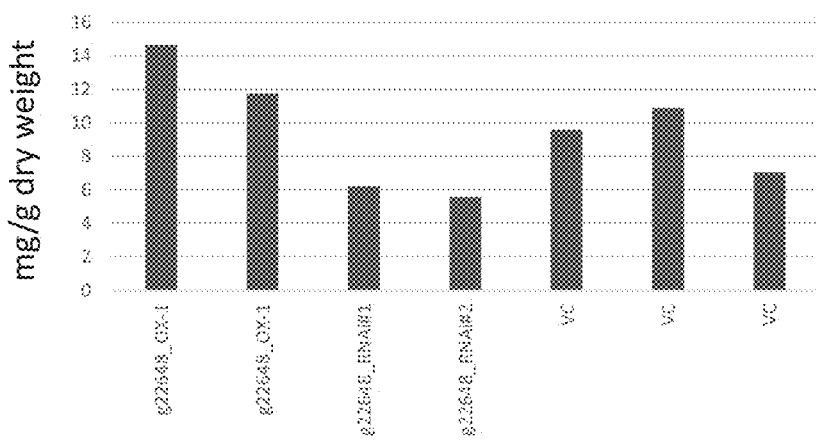
FIG. 19 depicts nicotine levels in g22648 overexpression (OX) and knockdown (RNAi) tobacco lines, as compared to three vector control lines (VC).
Figure 20:
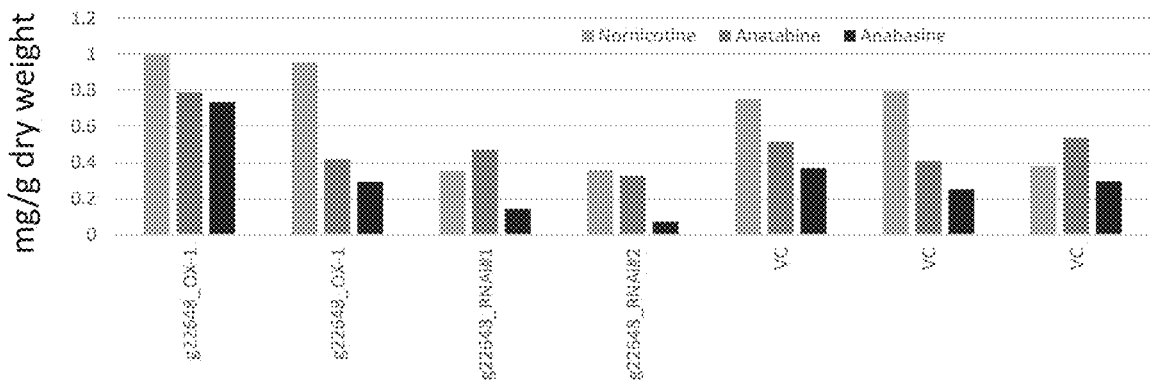
FIG. 20 depicts nornicotine, anatabine, and anabasine levels in g22648 overexpression (OX) and knockdown (RNAi) tobacco lines, as compared to three vector control lines (VC).
Figure 23:
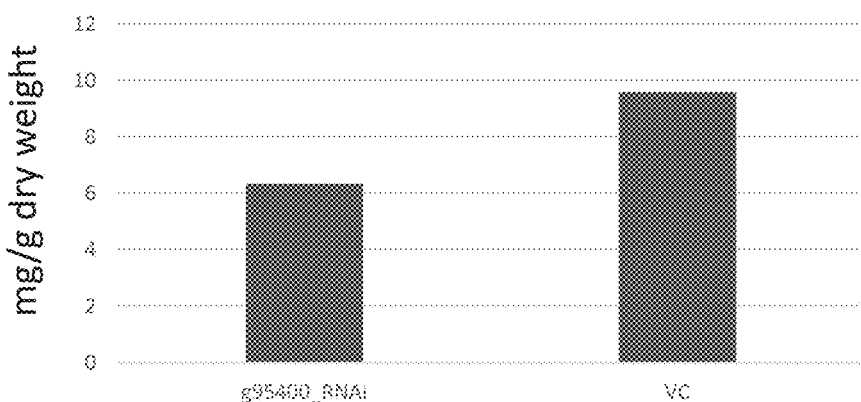
FIG. 23 depicts nicotine levels in a g95400 RNAi knockdown line as compared to a vector control line (VC).
Figure 24:
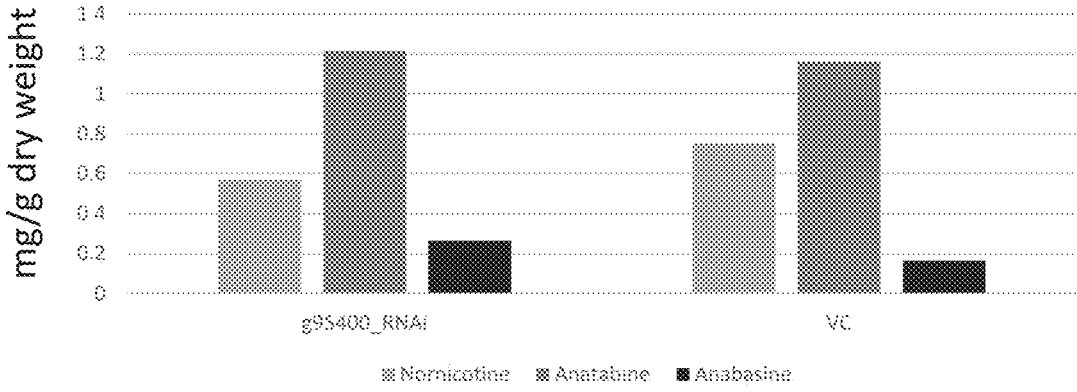
FIG. 24 depicts nornicotine, anatabine, and anabasine levels in a g95400 RNAi knockdown tobacco line as compared to a vector control line (VC).
Figure 27:
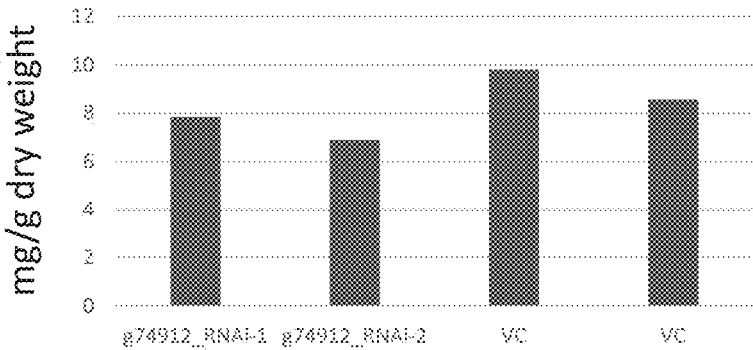
FIG. 27 depicts nicotine levels in g74912 RNAi knockdown tobacco lines as compared to two vector control lines (VC).
Figure 28:
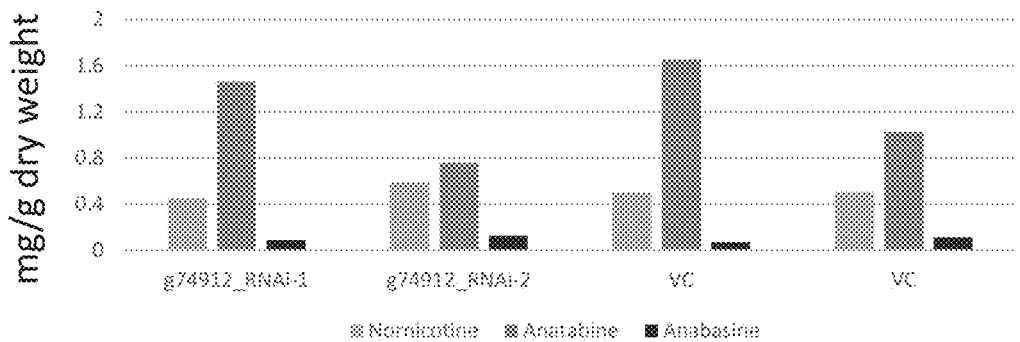
FIG. 28 depicts nornicotine, anatabine, and anabasine levels in g74912 RNAi knockdown tobacco lines as compared to two vector control lines (VC).
Figure 31:
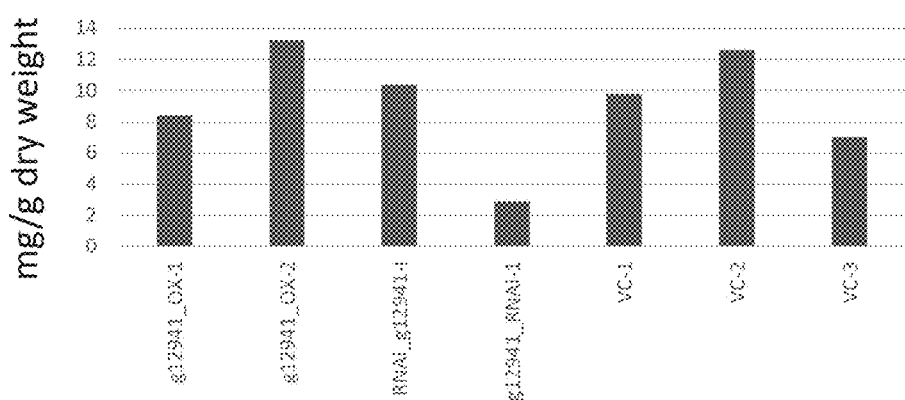
FIG. 31 depicts nicotine levels in g12941 overexpression (OX) and knockdown (RNAi) tobacco lines, as compared to three vector control lines (VC-1, VC-2, and VC-3).
Figure 32:
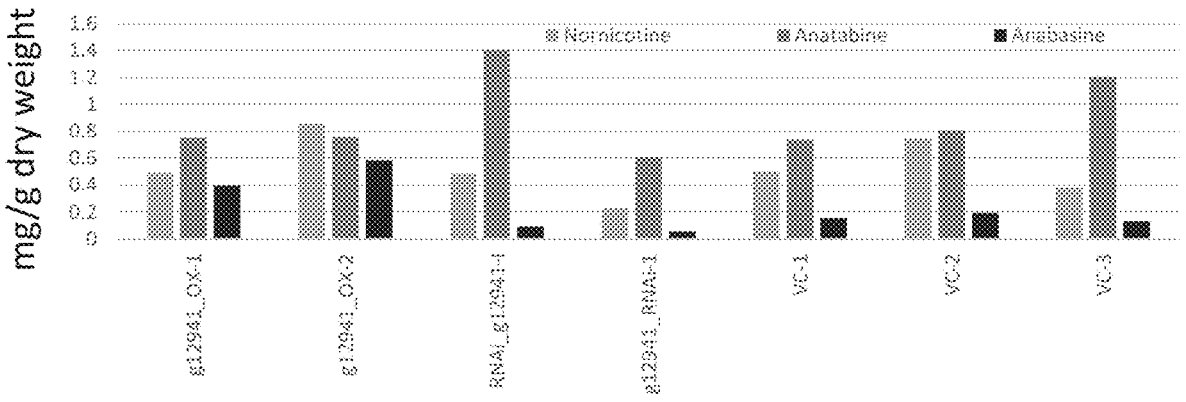
FIG. 32 depicts nornicotine, anatabine, and anabasine levels in g12941 overexpression (OX) and knockdown (RNAi) tobacco lines, as compared to three vector control lines (VC-1, VC-2, and VC-3).
Figure 35:
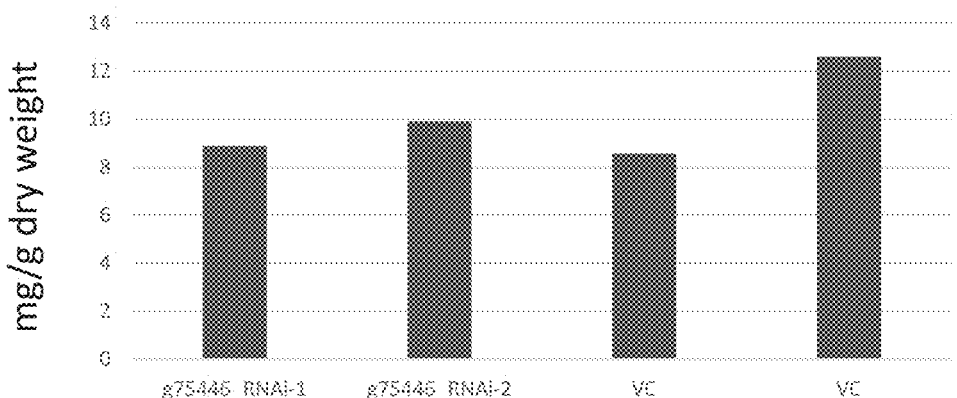
FIG. 35 depicts nicotine levels in g75446 RNAi knockdown tobacco lines as compared to two vector control lines (VC).
Figure 36:
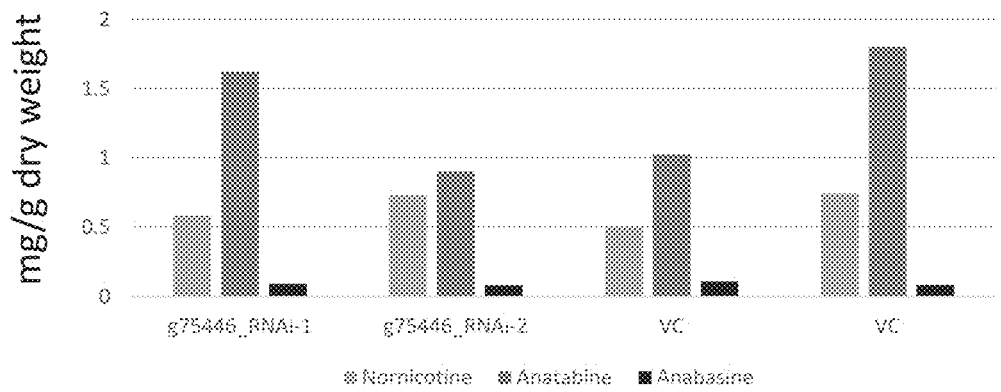
FIG. 36 depicts nornicotine, anatabine, and anabasine levels in g75446 RNAi knockdown tobacco lines as compared to two vector control lines (VC).
Figure 39:
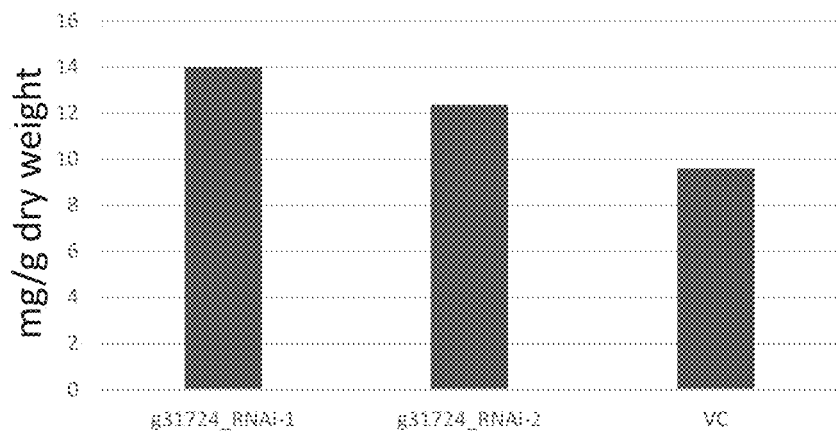
FIG. 39 depicts nicotine levels in two g31724 RNAi knockdown tobacco lines as compared to a vector control line (VC).
Figure 40:
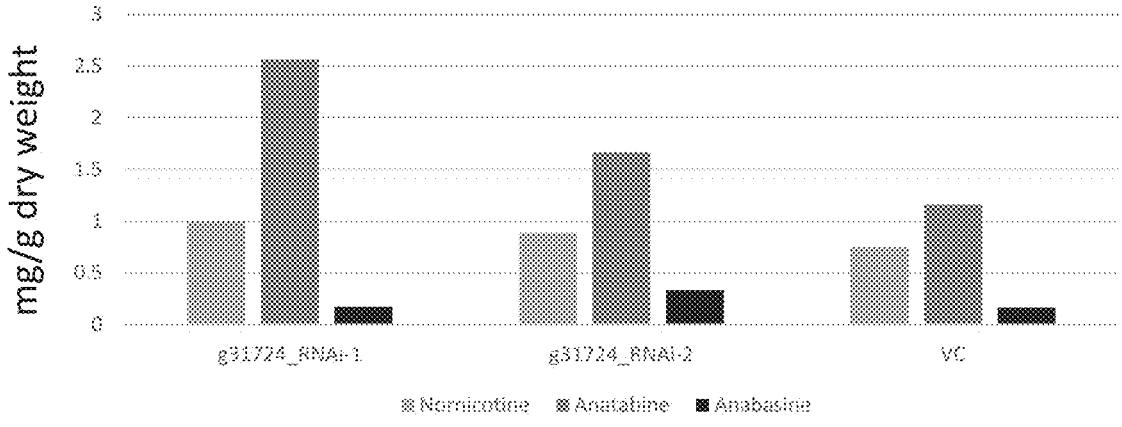
FIG. 40 depicts nornicotine, anatabine, and anabasine levels in two g31724 RNAi knockdown tobacco lines as compared to a vector control line (VC).
Figure 41:
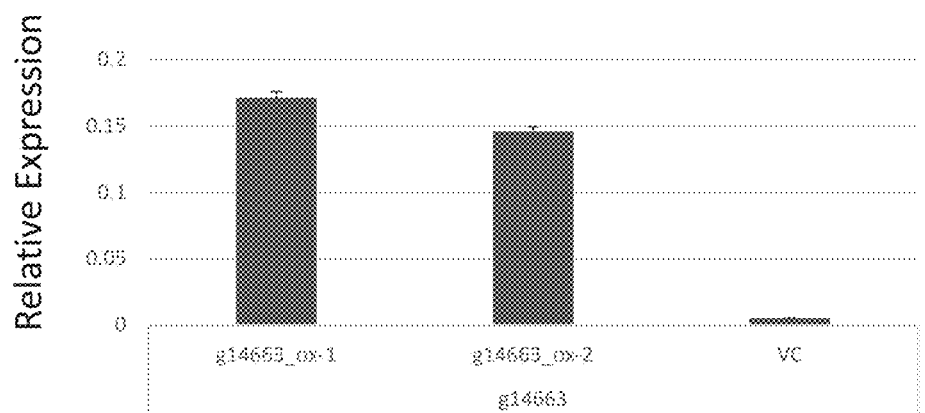
FIG. 41 depicts relative expression (as compared to EF1α) of g14663 overexpression (OX) in two tobacco lines as compared to a vector control line (VC).
Figure 42:
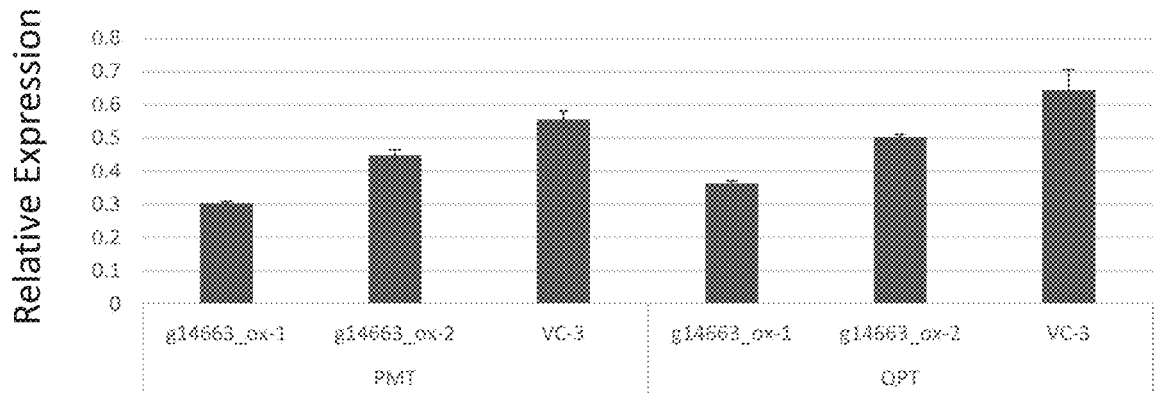
FIG. 42 depicts relative expression (as compared to EF1α) of PMT and QPT gene families in two g14663 overexpression (OX) tobacco lines as compared to a vector control line (VC).
Figure 43:
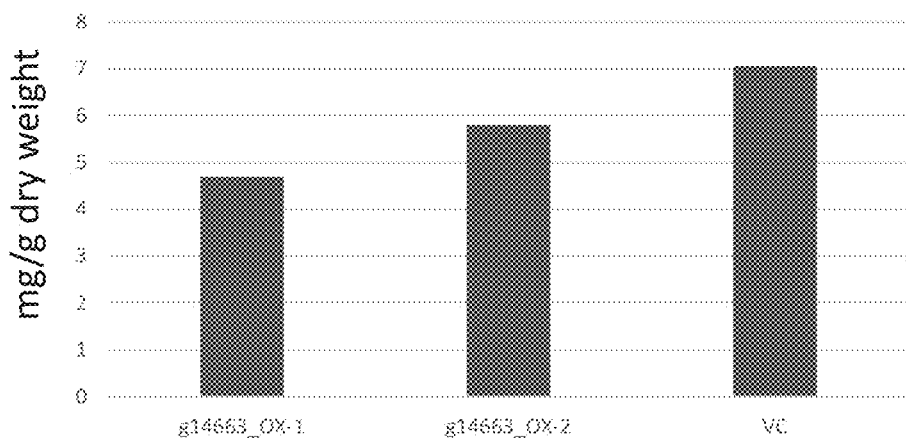
FIG. 43 depicts nicotine levels in two g14663 overexpression (OX) tobacco lines as compared to a vector control line (VC).
Figure 44:
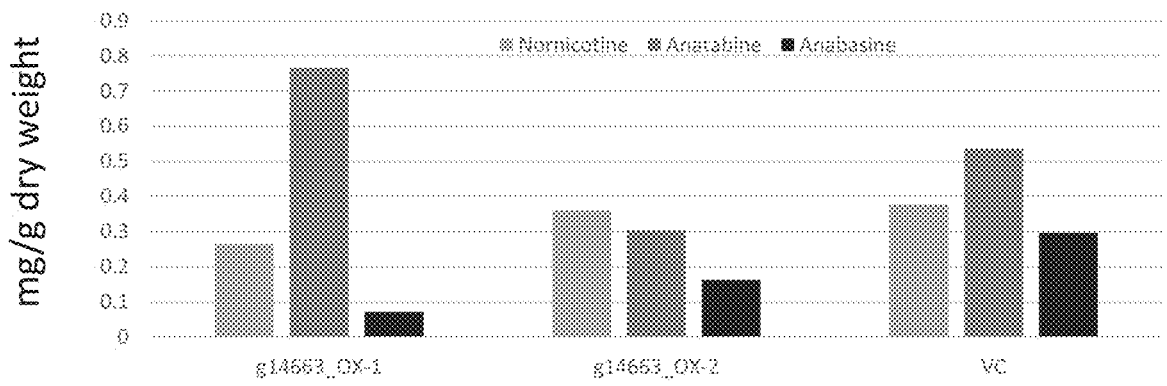
FIG. 44 depicts nornicotine, anatabine, and anabasine levels in two g14663 overexpression (OX) tobacco lines as compared to a vector control line (VC).
Figure 45:
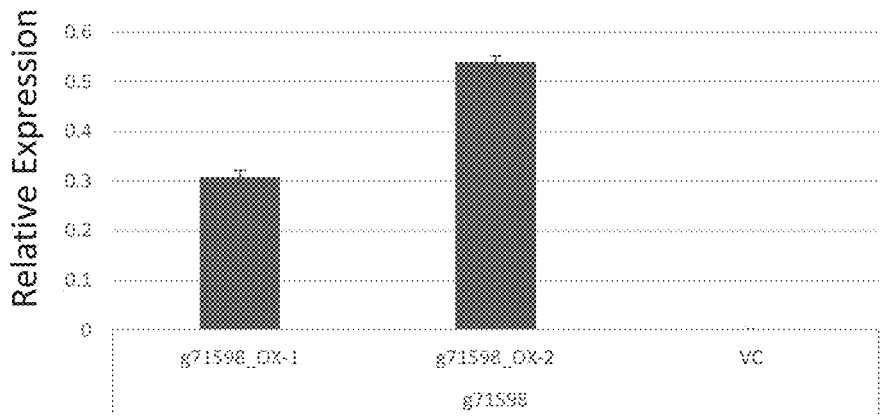
FIG. 45 depicts relative expression (as compared to EF1α) of g71598 overexpression (OX) in two tobacco lines as compared to a vector control line (VC).
Figure 46:
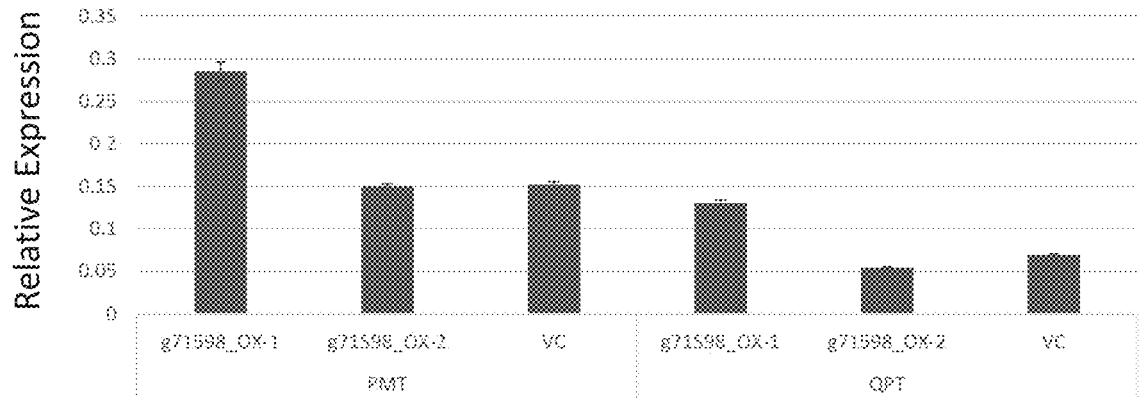
FIG. 46 depicts relative expression (as compared to EF1α) of PMT and QPT gene families in two g71598 overexpression (OX) tobacco lines as compared to a vector control line (VC).
Figure 47:
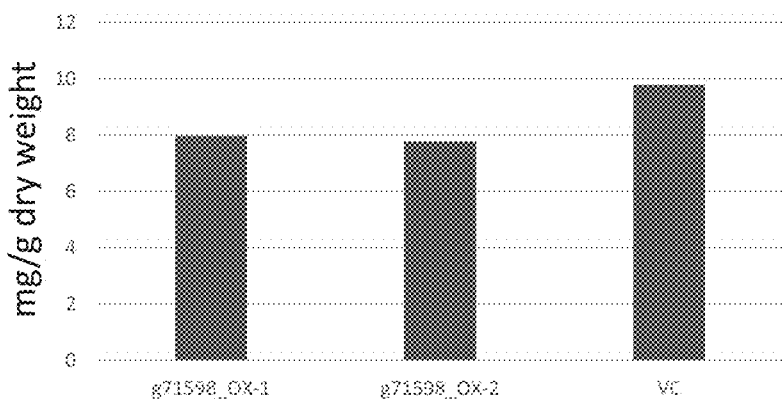
FIG. 47 depicts nicotine levels in two g71598 overexpression (OX) tobacco lines as compared to a vector control line (VC).
Figure 48:
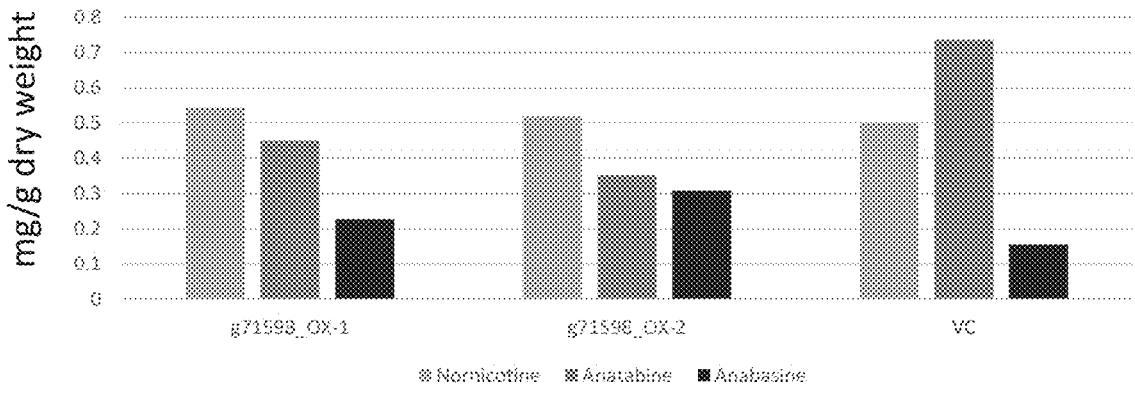
FIG. 48 depicts nornicotine, anatabine, and anabasine levels in two g71598 overexpression (OX) tobacco lines as compared to a vector control line (VC).
Figure 51:
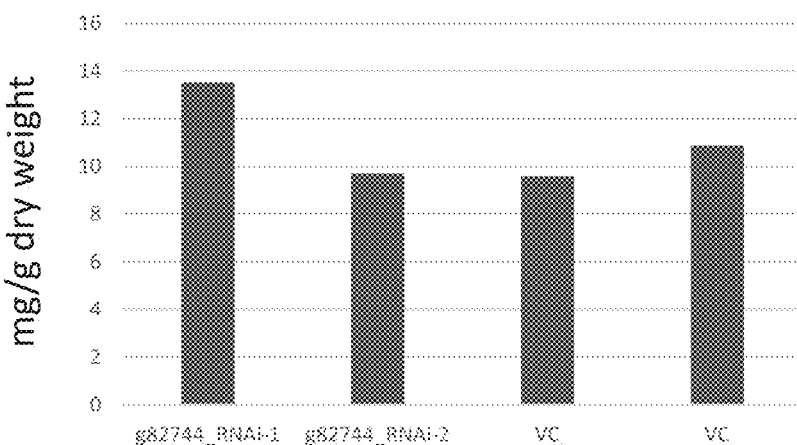
FIG. 51 depicts nicotine levels in two g82744 RNAi knockdown tobacco lines as compared to two vector control lines (VC).
Figure 52:
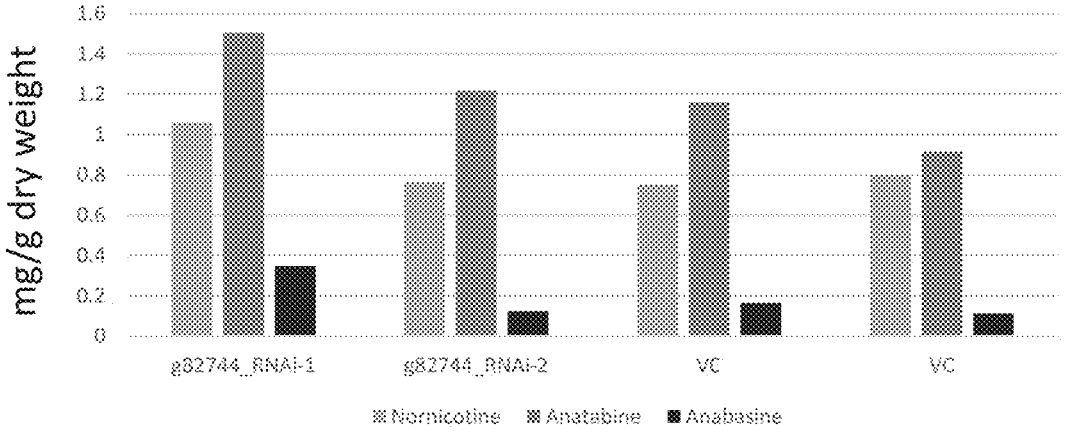
FIG. 52 depicts nornicotine, anatabine, and anabasine levels in two g82744 RNAi knockdown tobacco lines as compared to two vector control lines (VC).
Figure 55:
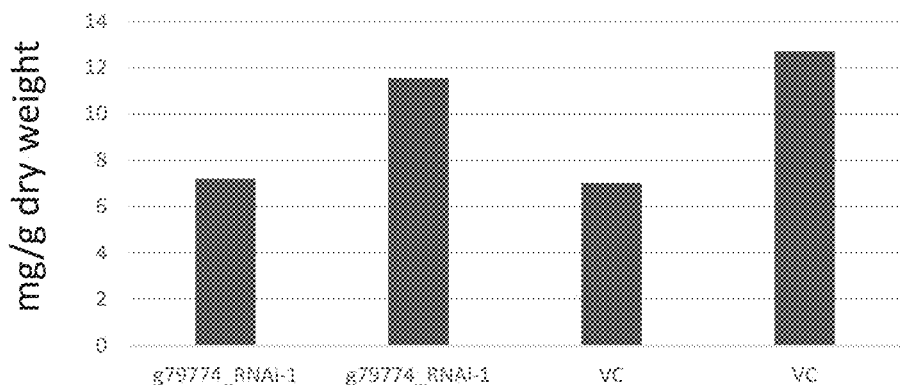
FIG. 55 depicts nicotine levels in three g79774 RNAi knockdown tobacco lines as compared to two vector control lines (VC).
Figure 56:
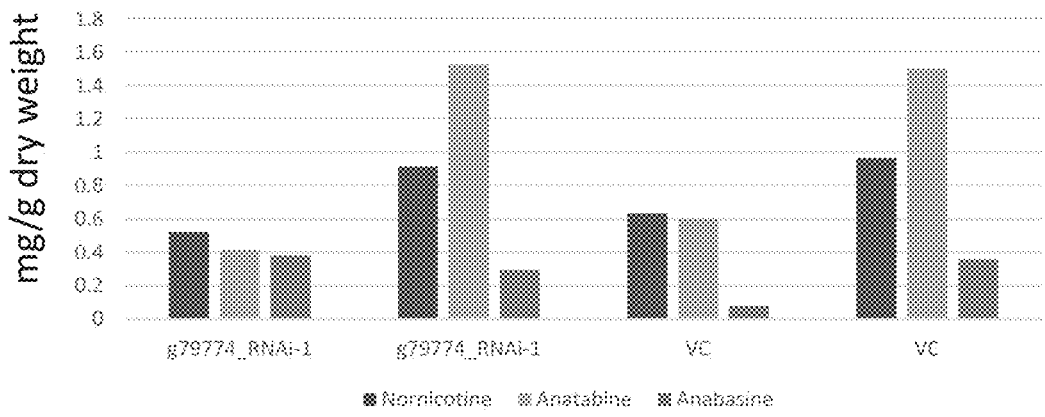
FIG. 56 depicts nornicotine, anatabine, and anabasine levels in three g79774 RNAi knockdown tobacco lines as compared to two vector control lines (VC).
Figure 59:
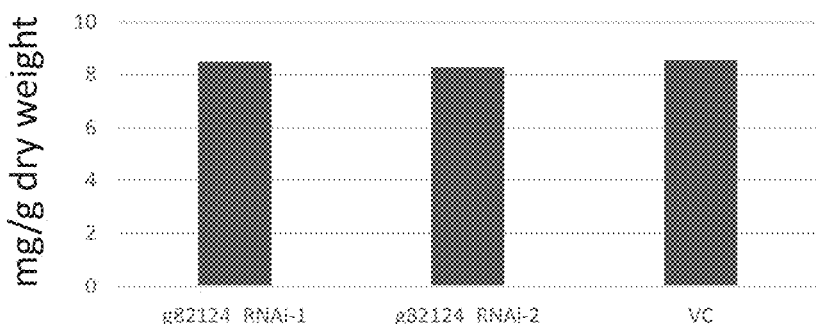
FIG. 59 depicts nicotine levels in three g82124 RNAi knockdown tobacco lines as compared to a vector control line (VC).
Figure 60:
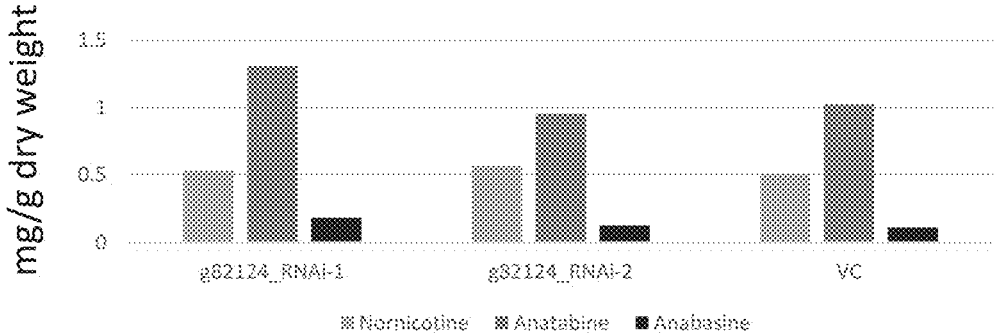
FIG. 60 depicts nornicotine, anatabine, and anabasine levels in three g82124 RNAi knockdown tobacco lines as compared to a vector control line (VC).

Alkaloid levels (e.g., nicotine, nornicotine, anatabine, anabasine) are measured in hairy root culture knockdown lines as described in Example 8. FIG. 19 depicts nicotine levels in hairy root culture g22648 knockdown lines as compared to vector control lines, and FIG. 20 depicts nornicotine, anatabine, and anabasine levels in hairy root culture g22648 knockdown lines as compared to vector control lines. FIG. 23 depicts nicotine levels in a hairy root culture g95400 knockdown line as compared to a vector control line, and FIG. 24 depicts nornicotine, anatabine, and anabasine levels in a hairy root culture g95400 knockdown line as compared to a vector control line. FIG. 27 depicts nicotine levels in hairy root culture g74912 knockdown lines as compared to vector control lines, and FIG. 28 depicts nornicotine, anatabine, and anabasine levels in hairy root culture g74912 knockdown lines as compared to vector control lines. FIG. 31 depicts nicotine levels in hairy root culture g12941 knockdown lines as compared to vector control lines, and FIG. 32 depicts nornicotine, anatabine, and anabasine levels in hairy root culture g12941 knockdown lines as compared to vector control lines. FIG. 35 depicts nicotine levels in hairy root culture g75446 knockdown lines as compared to vector control lines, and FIG. 36 depicts nornicotine, anatabine, and anabasine levels in hairy root culture g75446 knockdown lines as compared to vector control lines. FIG. 39 depicts nicotine levels in hairy root culture g31724 knockdown lines as compared to vector control lines, and FIG. 40 depicts nornicotine, anatabine, and anabasine levels in hairy root culture g31724 knockdown lines as compared to vector control lines. FIG. 51 depicts nicotine levels in hairy root culture g82744 knockdown lines as compared to vector control lines, and FIG. 52 depicts nornicotine, anatabine, and anabasine levels in hairy root culture g82744 knockdown lines as compared to vector control lines. FIG. 55 depicts nicotine levels in hairy root culture g79774 knockdown lines as compared to vector control lines, and FIG. 56 depicts nornicotine, anatabine, and anabasine levels in hairy root culture g79774 knockdown lines as compared to vector control lines. FIG. 59 depicts nicotine levels in hairy root culture g82124 knockdown lines as compared to vector control lines, and FIG. 60 depicts nornicotine, anatabine, and anabasine levels in hairy root culture g82124 knockdown lines as compared to vector control lines.

Table 12 provides average alkaloid levels as shown in FIGS. 19, 20, 23, 24, 27, 28, 31, 32, 35, 36, 39, 40, 51, 52, 55, 56, 59, and 60. Table 13 provides percentage change for each overexpression line as compared to the vector control average (or single vector control if only one vector control is available) for each alkaloid. Percent change compared to control in Table 13 is calculated by using the formula: ((Overexpression Line Level–Control Level)/(Control Level))×100 for each measured alkaloid.

TABLE 12

| Gene | | Alkaloids (mg/g dry weight) | | | |
|---|---|---|---|---|---|
| ID | Expression | Nicotine | Nornicotine | Anatabine | Anabasine |
| g22648 | RNAi-1 | 6.22 | 0.351 | 0.471 | 0.144 |
| | RNAi-2 | 5.57 | 0.357 | 0.327 | 0.073 |
| | VC | 10.88 | 0.796 | 0.408 | 0.252 |
| | VC | 9.60 | 0.751 | 0.517 | 0.370 |
| | VC | 7.05 | 0.378 | 0.536 | 0.297 |
| | RNAi Average | 5.9 | 0.354 | 0.399 | 0.109 |
| | VC Average | 9.17 | 0.642 | 0.487 | 0.306 |
| g95400 | RNAi-1 | 6.35 | 0.568 | 1.215 | 0.266 |
| | VC | 9.60 | 0.751 | 1.161 | 0.165 |
| g74912 | RNAi-1 | 7.84 | 0.448 | 1.460 | 0.087 |
| | RNAi-2 | 6.89 | 0.589 | 0.759 | 0.126 |
| | VC | 9.80 | 0.501 | 1.652 | 0.069 |
| | VC | 8.57 | 0.505 | 1.026 | 0.111 |
| | RNAi Average | 7.365 | 0.519 | 1.11 | 0.107 |
| | VC Average | 9.19 | 0.503 | 1.339 | 0.09 |
| g12941 | RNAi-1 | 10.38 | 0.484 | 1.401 | 0.093 |
| | RNAi-2 | 2.90 | 0.227 | 0.606 | 0.057 |
| | VC | 9.80 | 0.501 | 0.735 | 0.155 |
| | VC | 12.61 | 0.746 | 0.803 | 0.194 |

TABLE 12-continued

| Alkaloid levels in tobacco knockdown lines. | | | | | |
|---|---|---|---|---|---|
| Gene | | Alkaloids (mg/g dry weight) | | | |
| ID | Expression | Nicotine | Nornicotine | Anatabine | Anabasine |
| | VC | 7.05 | 0.378 | 1.205 | 0.132 |
| | RNAi | 6.64 | 0.356 | 1.00 | 0.075 |
| | Average | | | | |
| | VC Average | 9.82 | 0.542 | 1.248 | 0.16 |
| g75446 | RNAi-1 | 8.89 | 0.584 | 1.625 | 0.094 |
| | RNAi-2 | 9.92 | 0.733 | 0.905 | 0.082 |
| | VC | 8.57 | 0.505 | 1.026 | 0.111 |
| | VC | 12.61 | 0.746 | 1.804 | 0.086 |
| | RNAi | 9.405 | 0.659 | 1.265 | 0.088 |
| | Average | | | | |
| | VC Average | 10.59 | 0.626 | 1.415 | 0.099 |
| g31724 | RNAi-1 | 13.98 | 1.001 | 2.565 | 0.172 |
| | RNAi-2 | 12.36 | 0.890 | 1.666 | 0.335 |
| | VC | 9.60 | 0.751 | 1.161 | 0.165 |
| | RNAi | 13.17 | 0.946 | 2.116 | 0.254 |
| | Average | | | | |
| g82744 | RNAi-1 | 13.53 | 1.060 | 1.505 | 0.348 |
| | RNAi-2 | 9.71 | 0.764 | 1.218 | 0.123 |
| | VC | 9.60 | 0.751 | 1.161 | 0.165 |
| | VC | 10.88 | 0.796 | 0.915 | 0.112 |
| | RNAi | 11.62 | 0.912 | 1.362 | 0.236 |
| | Average | | | | |
| | VC Average | 10.24 | 0.774 | 1.038 | 0.139 |
| g79774 | RNAi-1 | 7.20 | 0.523 | 0.416 | 0.381 |
| | RNAi-2 | 11.55 | 0.915 | 1.528 | 0.296 |
| | VC | 7.02 | 0.633 | 0.601 | 0.078 |
| | VC | 12.71 | 0.965 | 1.502 | 0.358 |
| | RNAi | 9.375 | 0.719 | 0.972 | 0.339 |
| | Average | | | | |
| | VC Average | 9.865 | 0.799 | 1.052 | 0.218 |
| g82124 | RNAi-1 | 8.50 | 0.533 | 1.308 | 0.183 |
| | RNAi-2 | 8.30 | 0.567 | 0.957 | 0.125 |
| | VC | 8.57 | 0.505 | 1.026 | 0.111 |
| | RNAi | 8.40 | 0.55 | 1.133 | 0.154 |
| | Average | | | | |

RNAi = knockdown line; VC = vector control.

TABLE 13

| Percent change in alkaloids as compared to controls. | | | | | |
|---|---|---|---|---|---|
| Gene | Expres- | Alkaloids (% change compared to control) | | | |
| ID | sion | Nicotine | Nornicotine | Anatabine | Anabasine |
| g22648 | RNAi-1 | −32.17% | −45.33% | −3.29% | −52.94% |
| | RNAi-2 | −39.26% | −44.39% | −32.85% | −76.14% |
| g95400 | RNAi-1 | −33.85% | −24.37% | +4.65% | +61.21% |
| g74912 | RNAi-1 | −14.69% | −10.93% | +9.04% | −3.33% |
| | RNAi-2 | −25.03% | +17.10% | −43.32% | +40% |
| g12941 | RNAi-1 | +8.76% | −10.70% | +12.26% | −41.88% |
| | RNAi-2 | −70.47% | −58.12% | −51.44% | −64.38% |
| g75446 | RNAi-1 | −16.05% | −6.71% | +14.84% | −5.05% |
| | RNAi-2 | −6.33% | −17.09% | −36.04% | −17.17% |
| g31724 | RNAi-1 | +45.63% | +33.29% | +120.93% | +4.24% |
| | RNAi-2 | +28.75% | +18.51% | +43.50% | +103.03% |
| g82744 | RNAi-1 | +32.13% | +36.95% | +44.99% | +150.36% |
| | RNAi-2 | −5.18% | −1.29% | +17.34% | −11.51% |
| g79774 | RNAi-1 | −27.01% | −34.54% | −60.46% | +74.77% |
| | RNAi-2 | +17.08% | +14.52% | +45.25% | +35.78% |
| g82124 | RNAi-1 | −0.82% | +5.54% | +27.49% | +64.86% |
| | RNAi-2 | −3.15% | +12.28% | −6.73% | +12.61% |

RNAi = knockdown line.

Example 10. Generating Mutations in Candidate Genes

Mutations are produced in each of the genes identified in Table 9 by specifically editing SEQ ID NOs: 1-58, separately and individually, in the tobacco genome. Tobacco protoplasts are transfected using polyethylene glycol (PEG) with plasmids encoding a CRISPR protein or a CRISPR protein and specific guide RNA (gRNA) targeting individual genes at desired positions.

Transfected protoplasts are then immobilized in 1% agarose beads and subjected to tissue culture. When calli grow to approximately 1 millimeter in diameter, they are spread on TOM2 plates. Calli are screened for mutations (e.g., insertions or deletions (indels)) at the target positions using fragment analysis. Candidates, showing size shifts compared to wildtype control, are selected for further culture and the consequent shoots are tested by fragment analysis again to confirm the presence of mutations.

Modified tobacco plants (TO generation) are grown as described in Example 4. Then, plants are topped, and alkaloid levels are measured as described in Example 5.

The invention claimed is:

1. A modified tobacco plant, or part thereof, comprising at least one non-natural mutation in an endogenous nucleic acid sequence, wherein the endogenous nucleic acid sequence encodes a polypeptide comprising an amino acid sequence at least 95% identical to SEQ ID NO: 122, and wherein the at least one non-natural mutation results in a reduced level of activity by the polypeptide as compared to a control tobacco plant lacking the at least one non-natural mutation when grown under comparable conditions.

2. The modified tobacco plant, or part thereof, of claim 1, wherein the tobacco plant produces at least one leaf comprising a reduced amount of at least one alkaloid as compared to the amount of the alkaloid in the control tobacco plant when grown under comparable conditions.

3. The modified tobacco plant, or part thereof, of claim 1, wherein the endogenous nucleic acid sequence comprises a nucleic acid sequence identical or complementary to SEQ ID NO: 6.

4. The modified tobacco plant, or part thereof, of claim 1, wherein the endogenous nucleic acid sequence comprises a nucleic acid sequence identical or complementary to SEQ ID NO: 64.

5. The modified tobacco plant, or part thereof, of claim 2, wherein the at least one alkaloid is selected from the group consisting of anabasine, anatabine, nicotine, and nornicotine.

6. The modified tobacco plant, or part thereof, or part thereof, of claim 1, wherein the at least one non-natural mutation results in a reduced level of expression of the nucleic acid sequence as compared to expression of the nucleic acid sequence in the same tissue of the control tobacco plant when grown under comparable conditions.

7. The modified tobacco plant, or part thereof, of claim 1, wherein the modified tobacco plant is of a tobacco variety selected from the group consisting of a flue-cured variety, a bright variety, a Burley variety, a Virginia variety, a Maryland variety, a dark variety, a Galpão variety, an Oriental variety, and a Turkish variety.

8. Cured tobacco material from the modified tobacco plant, or part thereof, of claim 1, wherein the cured tobacco material comprises the at least one non-natural mutation.

9. The cured tobacco material of claim 8, wherein said cured tobacco material comprises cured tobacco material selected from the group consisting of flue-cured tobacco material, air-cured tobacco material, fire-cured tobacco material, and sun-cured tobacco material.

10. A tobacco blend comprising the cured tobacco material of claim 8.

11. A tobacco product comprising the tobacco blend of claim 10.

12. A tobacco product comprising the cured tobacco material of claim 8.

13. The tobacco product of claim 12, wherein the tobacco product is selected from the group consisting of a cigarette, a heated tobacco product, a kretek, a bidi cigarette, a cigar, a cigarillo, a non-ventilated cigarette, a vented recess filter cigarette, pipe tobacco, snuff, snus, chewing tobacco, moist smokeless tobacco, fine cut chewing tobacco, long cut chewing tobacco, pouched chewing tobacco product, gum, a tablet, a lozenge, and a dissolving strip.

14. The tobacco product of claim 12, wherein the tobacco product is a smokeless tobacco product.

15. The tobacco product of claim 14, wherein the smokeless tobacco product is selected from the group consisting of loose leaf chewing tobacco, plug chewing tobacco, moist snuff, nasal snuff, dry snuff, and snus.

16. The modified tobacco plant, or part thereof, of claim 1, wherein the polypeptide is at least 99% identical to SEQ ID NO: 122.

17. The modified tobacco plant, or part thereof, of claim 1, wherein the polypeptide is identical to SEQ ID NO: 122.

18. The modified tobacco plant, or part thereof, of claim 1, wherein the non-natural mutation results in a truncation of the polypeptide as compared to the polypeptide encoded by the endogenous nucleic acid sequence.

19. The modified tobacco plant, or part thereof, of claim 1, wherein the at least one non-natural mutation comprises a mutation selected from the group consisting of an insertion and a deletion.

20. The modified tobacco plant, or part thereof, of claim 1, wherein the at least one non-natural mutation comprises a substitution.

* * * * *